US009388396B2

(12) United States Patent
Faurholm et al.

(10) Patent No.: US 9,388,396 B2
(45) **Date of Patent: *Jul. 12, 2016**

(54) CHIMERIC DNA POLYMERASES

(71) Applicant: KAPA BIOSYSTEMS, INC., Wilmington, MA (US)

(72) Inventors: Bjarne Faurholm, Western Cape (ZA); Paul McEwan, Western Cape (ZA); William Bourn, Western Cape (ZA); Gavin Rush, Western Cape (ZA)

(73) Assignee: Kapa Biosystems, Inc., Wilmington, MA (US)

( * ) Notice: Subject to any disclaimer, the term of this patent is extended or adjusted under 35 U.S.C. 154(b) by 58 days.

This patent is subject to a terminal disclaimer.

(21) Appl. No.: 14/270,304

(22) Filed: May 5, 2014

(65) Prior Publication Data

US 2014/0363848 A1 Dec. 11, 2014

Related U.S. Application Data

(63) Continuation of application No. 13/127,420, filed as application No. PCT/US2009/063166 on Nov. 3, 2009, now Pat. No. 9,023,633.

(60) Provisional application No. 61/110,862, filed on Nov. 3, 2008.

(51) Int. Cl.
*C12N 9/12* (2006.01)
*C12P 19/34* (2006.01)

(52) U.S. Cl.
CPC ............ *C12N 9/1252* (2013.01); *C12N 9/1241* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 5,948,663 | A | 9/1999 | Mathur |
| 6,225,065 | B1 | 5/2001 | Kitabayashi et al. |
| 7,690,157 | B2 | 4/2010 | Blumberg |
| 8,481,685 | B2 | 7/2013 | Bourn et al. |
| 9,023,633 | B2 | 5/2015 | Faurholm et al. |
| 2002/0076768 | A1 | 6/2002 | Kuroita et al. |
| 2002/0119461 | A1 | 8/2002 | Chatterjee |
| 2004/0058362 | A1 | 3/2004 | Frey et al. |
| 2004/0197800 | A1 | 10/2004 | Borns |
| 2005/0048530 | A1 | 3/2005 | Borns |
| 2005/0127554 | A1 | 6/2005 | Smith |
| 2007/0196846 | A1 | 8/2007 | Hanzel et al. |
| 2008/0108082 | A1 | 5/2008 | Rank et al. |
| 2011/0269211 | A1 | 11/2011 | Bourn et al. |
| 2012/0115188 | A1 | 5/2012 | Faurholm et al. |

FOREIGN PATENT DOCUMENTS

| | | | |
|---|---|---|---|
| EP | 0547359 | A1 | 6/1993 |
| JP | H07-298879 | A | 11/1995 |
| WO | WO 98/33900 | A1 | 8/1998 |
| WO | WO-98/33900 | A1 | 8/1998 |
| WO | WO-01/18213 | A1 | 3/2001 |
| WO | WO 01/61015 | A2 | 8/2001 |
| WO | WO-01/61015 | A2 | 8/2001 |
| WO | WO-2004/058942 | A2 | 7/2004 |
| WO | WO-2005/113760 | A2 | 12/2005 |
| WO | WO 2005/113760 | A2 | 12/2005 |
| WO | WO 2005/118866 | A2 | 12/2005 |
| WO | WO-2005/118866 | A2 | 12/2005 |
| WO | WO-2008/046612 | A1 | 4/2008 |

OTHER PUBLICATIONS

Database Geneseq [Online] DNA Polymerase SEQ ID No. 5, AEE87102, Feb. 23, 2006.
Database Geneseq [Online] Heat-resistant Pfu DNA synthetase I, AAW77017, Nov. 19, 1998.
Elshawadfy, A.M. et al., DNA polymerase hybrids derived from the family-B enzymes of Pyrococcus furiosus and Thermococcus kodakarensis: improving performance in the polymerase chain reaction, Frontiers in Microbiology, 5: 1-14 (2014).
European Search Report for 15160891.6, 9 pages (Jul. 20, 2015).
International Search Report for PCT/US2009/063169, 5 pages (Jul. 1, 2010).
International Search Report for PCT/US2009/63166, 4 pages (Jul. 1, 2010).
NCBI database 1WNS_A (Aug. 9, 2004).
NCBI database NP_577941 (Feb. 26, 2002).
Ngo, J.T. et al., Computational Complexity, Protein Structure Prediction, and the Levinthal Paradox, The Protein Folding Problem and Tertiary Structure Prediction, Birkhauser, Boston (1994).
Pavlov, A.R. et al., Helix-hairpin-helix motifs confer salt resistance and processivity on chimeric DNA polymerases, Proceedings of the National Academy of Sciences of the United States of America, 99(21):13510-13515 (2002).
Supplementary European Search Report for EP 09829689, 12 pages (Apr. 24, 2012).
Written Opinion for PCT/US2009/063166, 5 pages (Jul. 1, 2010).
Written Opinion for PCT/US2009/063169, 5 pages (Jul. 1, 2010).
"DNA Polymerase SEQ ID No. 5," Feb. 23, 2006.
"Heat-resistant Pfu DNA synthetase I," Nov. 19, 1998.
Pavlov A. R. et al., "Helix-hairpin-helix motifs confer salt resistance and processivity on chimeric DNA polymerases," Proceedings of the National Academy of Sciences, National Academy of Sciences, Washington, CD; US, vol. 99, No. 21, Oct. 15, 2002, pp. 13510-13515.
Supplementary European Search Report, EP 09829689, published as EP 2352818 on Aug. 10, 2011, mailed on Apr. 24, 2012.

*Primary Examiner* — Richard Hutson
(74) *Attorney, Agent, or Firm* — Choate Hall & Stewart LLP; Brenda Herschbach Jarrell; Maria C. Smith

(57) ABSTRACT

The present invention provides, among other things, chimeric DNA polymerases containing heterologous domains having sequences derived from at least two DNA polymerases that have at least one distinct functional characteristics (e.g., elongation rate, processivity, error rate or fidelity, salt tolerance or resistance) and methods of making and using the same. In some embodiments, the present invention can combine desired functional characteristics (e.g., high processivity; high elongation rate; thermostability; resistance to salt, PCR additives (e.g., PCR enhancers) and other impurities; and high fidelity) of different DNA polymerases in a chimeric polymerase.

4 Claims, 7 Drawing Sheets

SEQUENCE LISTING

```
<160> NUMBER OF SEQ ID NOS: 46

<210> SEQ ID NO 1
<211> LENGTH: 2328
<212> TYPE: DNA
<213> ORGANISM: Pyrococcus furiosus

<400> SEQUENCE: 1

atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga   180

aagattgtga gaattgttga tgtagagaag gttgagaaaa agtttctcgg caagcctatt    240

accgtgtgga aactttattt ggaacatccc caagatgttc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gatatagaaa ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgacttccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140
```

ctcagggaga gctacacagg tggattcgtt aaagagccag aaaaggggtt gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg ggaagaaag 1560 tacatcgagt tagtatggaa ggagctcgaa gaaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca ttgagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328

<210> SEQ ID NO 2
<211> LENGTH: 2325
<212> TYPE: DNA
<213> ORGANISM: Thermococcus sp.

<400> SEQUENCE: 2
atgatcctcg acactgacta cataaccgag gatggaaagc ctgtcataag aattttcaag 60
aaggaaaacg gcgagtttaa gattgagtac gaccggactt ttgaacccta cttctacgcc 120
ctcctgaagg acgattctgc cattgaggaa gtcaagaaga taaccgccga gaggcacggg 180
acggttgtaa cggttaagcg ggttgaaaag gttcagaaga agttcctcgg gagaccagtt 240
gaggtctgga aactctactt tactcatccg caggacgtcc cagcgataag ggacaagata 300
cgagagcatc cagcagttat tgacatctac gagtacgaca tacccttcgc caagcgctac 360
ctcatagaca agggattagt gccaatggaa ggcgacgagg agctgaaaat gctcgccttc 420
gacattgaaa ctctctacca tgagggcgag gagttcgccg aggggccaat ccttatgata 480
agctacgccg acgaggaagg ggccagggtg ataacttgga agaacgtgga tctcccctac 540
gttgacgtcg tctcgacgga gagggagatg ataaagcgct tcctccgtgt tgtgaaggag 600
aaagacccgg acgttctcat aacctacaac ggcgacaact tcgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960

```
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg gagacctcct agaggagagg   1380
cagaagataa agaagaagat gaaggccacg attgacccga tcgagaggaa gctcctcgat   1440
tacaggcaga gggccatcaa gatcctggca aacagctact acggttacta cggctatgca   1500
agggcgcgct ggtactgcaa ggagtgtgca gagagcgtaa cggcctgggg aagggagtac   1560
ataacgatga ccatcaagga gatagaggaa aagtacggct ttaaggtaat ctacagcgac   1620
accgacggat tttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca aacgcggctt cttcgtcacg aagaagaagt atgcggtgat agacgaggaa   1800
ggcaagataa caacgcgcgg acttgagatt gtgaggcgtg actggagcga gatagcgaaa   1860
gagacgcagg cgagggttct tgaagctttg ctaaaggacg gtgacgtcga gaaggccgtg   1920
aggatagtca aagaagttac cgaaaagctg agcaagtacg aggttccgcc ggagaagctg   1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                   2325
```

<210> SEQ ID NO 3
<211> LENGTH: 2328
<212> TYPE: DNA
<213> ORGANISM: Artificial Sequence
<220> FEATURE:
<223> OTHER INFORMATION: Pfu codon optimized nucleotide sequence

<400> SEQUENCE: 3

```
atgattctgg atgtggacta tatcaccgaa gagggcaaac cggttatacg tttatttaag     60
aaagagaatg gtaaattcaa gatcgagcat gaccgcacgt tccgtccata catttacgcg    120
ttgcttcggg atgatagcaa aattgaggaa gtcaaaaaga tcaccgggga acgtcatgga    180
aaaatagtaa gaattgtgga cgttgaaaaa gtcgaaaaga aatttctggg caaaccgatc    240
actgtatgga agctctatct ggaacatcct caggatgtgc ccacaattcg agaaaaagtt    300
cgtgagcacc cagccgtcgt ggatatattt gaatatgaca tcccttttgc aaaacgctac    360
ttaattgata aaggcctgat cccgatggag ggggaagaag aacttaaaat tctggctttt    420
gacatagaaa cgctctatca tgagggagaa gaatttggca aaggtcccat cattatgatt    480
tcttacgcgg atgagaacga agccaaggta atcacttgga aaaatattga cctgccgtac    540
gttgaagtgg tcagttcaga gcgggaaatg attaaacgtt ttttacgcat cattagagag    600
aaagatccag atataatcgt tacatataac ggcgactcct tcgattttcc ttacctggca    660
```

```
aaacgagctg aaaaattggg tattaaactt accatcgggc gtgacggatc ggaaccgaaa    720

atgcaacgca ttggcgatat gacggcggta gaggtgaaag gtcggataca ctttgatctg    780

tatcatgtca tcacccgtac tattaatctc cccacataca cgttagaagc cgtttatgag    840

gcaatattcg gcaagccgaa agaaaaagtg tacgctgacg aaatcgcgaa ggcatgggag    900

agcggcgaaa acctggagcg cgtagcaaaa tattctatgg aagatgctaa agcgacctac    960

gaattgggga aagaatttct tccaatggaa attcagctga gtcgtttagt cggacaacct   1020

ctgtgggacg tttcacgctc ctcgactggc aatctcgtgg agtggttcct gttgagaaaa   1080

gcctatgaac gaaacgaagt agcaccgaat aaaccaagcg aggaagaata tcagcgtcgc   1140

cttcgcgagt cttacacagg tgggtttgtt aaggaaccgg agaaaggtct ttgggaaaac   1200

atcgtgtatt tagatttccg tgcgctgtac cccagtatta taatcaccca caatgtctca   1260

cctgacacgc tcaacttgga aggttgcaaa aattatgata ttgctccgca agttggacat   1320

aagttttgta aagatattcc gggcttcatc ccgtccctgc ttggtcactt actggaagag   1380

cgccaaaaaa ttaagaccaa aatgaaagag actcaggatc ccattgaaaa gatcctgctc   1440

gattaccggc aaaaagccat taaattgctt gcaaactcgt tttatgggta ctatggctat   1500

gcgaaggctc gttggtactg caaagaatgt gccgagagcg tgacagcatg ggtcgcaaa   1560

tatatagaat tagtatggaa ggagctggaa gaaaaattcg gattcaaagt cctgtacatc   1620

gatacggatg gcctctatgc gaccattcct ggtggggagt ctgaagaaat caagaaaaaa   1680

gccttggaat tcgttaagta cattaatagt aaattaccgg gactgcttga actggagtat   1740

gaaggcttct acaaaagagg tttttcgtt actaagaaac gatatgccgt aatagatgaa   1800

gaggggaaag tcatcacacg tggcctcgag attgttcgcc gggactggtc agagatagca   1860

aaggaaacgc aggcgcgcgt gctcgaaacc atcttgaaac atggtgatgt agaggaagcc   1920

gtccgcattg ttaaagaggt gatccagaag ttagcaaact atgaaattcc accggaaaaa   1980

ctggcgatat acgagcaaat cactcgtccc cttcacgaat ataaagctat tggacctcat   2040

gtagccgtcg cgaagaaact ggctgcaaaa ggcgttaaga taaaaccagg tatggtgatc   2100

gggtacattg tactccgcgg cgacggtccg atttccaata gagccatctt ggcggaggaa   2160

tatgatccta aaaagcataa atacgacgct gaatattaca ttgagaacca ggtcttgccg   2220

gcagttctgc ggatacttga aggatttggc tatcgtaaag aagatctgcg ctatcaaaag   2280

acgcgacagg tgggtctgac tagctggttg aatatcaaaa aatcgtaa                2328
```

<210> SEQ ID NO 4
<211> LENGTH: 2337
<212> TYPE: DNA
<213> ORGANISM: Artificial Sequence
<220> FEATURE:
<223> OTHER INFORMATION: Pfu codon optimized nucleotide sequence, extra 9 nt in 5' area

<400> SEQUENCE: 4

```
atggctagcg ccattctgga tgtggactat atcaccgaag agggcaaacc ggttatacgt     60

ttatttaaga aagagaatgg taaattcaag atcgagcatg accgcacgtt ccgtccatac    120

atttacgcgt tgcttcggga tgatagcaaa attgaggaag tcaaaaagat caccggggaa    180

cgtcatggaa aaatagtaag aattgtggac gttgaaaaag tcgaaaagaa atttctgggc    240

aaaccgatca ctgtatggaa gctctatctg gaacatcctc aggatgtgcc cacaattcga    300

gaaaaagttc gtgagcaccc agccgtcgtg gatatatttg aatatgacat ccctttgca    360
```

-continued

```
aaacgctact taattgataa aggcctgatc ccgatggagg gggaagaaga acttaaaatt    420

ctggcttttg acatagaaac gctctatcat gagggagaag aatttggcaa aggtcccatc    480

attatgattt cttacgcgga tgagaacgaa gccaaggtaa tcacttggaa aaatattgac    540

ctgccgtacg ttgaagtggt cagttcagag cgggaaatga ttaaacgttt tttacgcatc    600

attagagaga aagatccaga tataatcgtt acatataacg gcgactcctt cgattttcct    660

tacctggcaa aacgagctga aaaattgggt attaaactta ccatcgggcg tgacggatcg    720

gaaccgaaaa tgcaacgcat tggcgatatg acggcggtag aggtgaaagg tcggatacac    780

tttgatctgt atcatgtcat cacccgtact attaatctcc ccacatacac gttagaagcc    840

gtttatgagg caatattcgg caagccgaaa gaaaaagtgt acgctgacga aatcgcgaag    900

gcatgggaga gcggcgaaaa cctggagcgc gtagcaaaat attctatgga agatgctaaa    960

gcgacctacg aattggggaa agaatttctt ccaatggaaa ttcagctgag tcgtttagtc   1020

ggacaacctc tgtgggacgt ttcacgctcc tcgactggca atctcgtgga gtggttcctg   1080

ttgagaaaag cctatgaacg aaacgaagta gcaccgaata aaccaagcga ggaagaatat   1140

cagcgtcgcc ttcgcgagtc ttacacaggt gggtttgtta aggaaccgga gaaaggtctt   1200

tgggaaaaca tcgtgtattt agatttccgt gcgctgtacc ccagtattat aatcacccac   1260

aatgtctcac ctgacacgct caacttggaa ggttgcaaaa attatgatat tgctccgcaa   1320

gttggacata agttttgtaa agatattccg ggcttcatcc cgtccctgct tggtcactta   1380

ctggaagagc gccaaaaaat taagaccaaa atgaaagaga ctcaggatcc cattgaaaag   1440

atcctgctcg attaccggca aaaagccatt aaattgcttg caaactcgtt ttatgggtac   1500

tatggctatg cgaaggctcg ttggtactgc aaagaatgtg ccgagagcgt gacagcatgg   1560

ggtcgcaaat atatagaatt agtatggaag gagctggaag aaaaattcgg attcaaagtc   1620

ctgtacatcg atacggatgg cctctatgcg accattcctg gtggggagtc tgaagaaatc   1680

aagaaaaaag ccttggaatt cgttaagtac attaatagta aattaccggg actgcttgaa   1740

ctggagtatg aaggcttcta caaaagaggt tttttcgtta ctaagaaacg atatgccgta   1800

atagatgaag aggggaaagt catcacacgt ggcctcgaga ttgttcgccg ggactggtca   1860

gagatagcaa aggaaacgca ggcgcgcgtg ctcgaaacca tcttgaaaca tggtgatgta   1920

gaggaagccg tccgcattgt taaagaggtg atccagaagt tagcaaacta tgaaattcca   1980

ccggaaaaac tggcgatata cgagcaaatc actcgtcccc ttcacgaata taaagctatt   2040

ggacctcatg tagccgtcgc gaagaaactg gctgcaaaag gcgttaagat aaaaccaggt   2100

atggtgatcg ggtacattgt actccgcggc gacggtccga tttccaatag agccatcttg   2160

gcggaggaat atgatcctaa aaagcataaa tacgacgctg aatattacat tgagaaccag   2220

gtcttgccgg cagttctgcg gatacttgaa ggatttggct atcgtaaaga agatctgcgc   2280

tatcaaaaga cgcgacaggt gggtctgact agctggttga atatcaaaaa atcgtaa      2337
```

```
<210> SEQ ID NO 5
<211> LENGTH: 2325
<212> TYPE: DNA
<213> ORGANISM: Artificial Sequence
<220> FEATURE:
<223> OTHER INFORMATION: KOD codon optimized nucleotide sequence

<400> SEQUENCE: 5

atgattctgg ataccgacta tatcacggaa gatggcaaac cggtgatacg tatttttaag     60

aaagagaatg gtgagttcaa aatcgagtac gaccgcactt ttgagccata tttctacgcg    120
```

-continued

```
ttactgaagg acgatagcgc cattgaagaa gttaaaaaaa tcaccgcaga gcggcatggg    180
acagtggtaa ccgtgaagag agttgaaaaa gtccagaaaa aatttttggg acgacctgta    240
gaagtgtgga aactttattt cactcacccc caagatgttc cggctatacg tgataaaatt    300
cgcgaacatc cagcggtcat tgatatttac gaatatgata taccttttgc caagcgttac    360
ctcatcgaca aaggcctggt gccgatggaa ggtgatgaag aattaaaaat gttggcattc    420
gacattgaaa cactttatca cgagggggaa gagtttgctg agggtcccat cctgatgatt    480
tcttatgcgg atgaagaggg tgcccgcgta ataacctgga agaacgttga tctcccgtac    540
gtggacgtcg ttagtacgga acgggaaatg atcaaacgtt tcctgcgcgt agtgaaagag    600
aaagatccag acgtcttaat tacctataat ggtgataact ttgattttgc atacctgaaa    660
aaaagatgcg aaaagttggg cataaatttc gctcttggtc gagacgggtc agagcctaaa    720
atccagcgta tgggagatcg ctttgcggtt gaagtgaaag gccggattca tttcgacctg    780
tatccggtaa ttcgtcgcac tatcaacctc cccacataca cgttagaagc cgtctatgag    840
gcagtttttg gtcaaccgaa ggaaaaagtt tacgctgagg aaattaccac tgcgtgggaa    900
acaggcgaga atctggaacg tgtagcccgc tattctatgg aggatgcaaa agttacctat    960
gaattgggta aggaatttct tccaatggag gcgcagctgt cgagattaat agggcagagc   1020
ctgtgggacg tgtctcgaag ttcaacggga aacctcgtcg aatggtttct gttgcggaaa   1080
gcatacgagc gtaatgaact tgcccctaac aaaccggatg aaaaggagct ggcacgccgt   1140
cgccaatcct atgaaggcgg ttacgttaaa gaaccagagc gggggttatg ggaaaatatc   1200
gtgtatctgg atttccgttc gctctacccg agcattatca ttacccacaa cgtatctccc   1260
gacactttga atcgcgaggg ctgtaaagaa tatgatgtcg cgccgcaggt tggtcataga   1320
ttttgcaagg acttcccggg atttatacca agtctgcttg gcgatttact ggaagagcga   1380
caaaaaatca aaaagaaaat gaaagctaca atcgatccga tagaacgtaa gctgctcgac   1440
taccgccagc gggccatcaa aattttggca aactcatatt atggttacta tgggtacgcg   1500
cgtgctcgct ggtattgtaa agagtgcgcc gaatccgtga cggcatgggg ccgtgaatac   1560
atcaccatga ctattaagga gatagaagag aaatatggtt tcaaagtaat ctactcggat   1620
acagacggat tctttgcgac gattcccggt gccgatgcag aaaccgtcaa gaaaaaagcg   1680
atggaattcc ttaagtatat aaatgctaaa ttacctggtg ccctggagct ggaatacgaa   1740
gggttttaca aacgcggatt ctttgttact aagaaaaaat atgcggtgat cgacgaggaa   1800
ggcaagatta cgaccagagg cctcgagatt gtacggcgtg attggagcga aatcgctaaa   1860
gaaacacagg cacgtgtctt ggaggcatta ctgaaagatg gggacgttga aaaggcggtg   1920
cgaattgtaa aagaagtcac cgaaaaactt tctaagtacg aagttccgcc agagaaactg   1980
gtgatacacg aacaaatcac tcgtgatctg aaagactata aggctacagg cccgcatgta   2040
gcagtcgcca aacgcctcgc ggctcggggt gttaaaattc gtcccggaac ggtgatcagt   2100
tacattgtat tgaagggctc aggtcgcata ggggatagag caatcccttt cgacgagttt   2160
gatccaacca aacacaaata tgatgccgaa tactatattg aaaaccaggt cttgccggcg   2220
gttgagcgta tactgcgcgc tttcggctat cgaaaggaag atcttcgtta ccaaaaaact   2280
agacaggtgg gtctgtccgc atggctcaaa cctaagggaa cgtaa                    2325
```

<210> SEQ ID NO 6
<211> LENGTH: 2334
<212> TYPE: DNA

```
<213> ORGANISM: Artificial Sequence
<220> FEATURE:
<223> OTHER INFORMATION: KOD codon optimized nucleotide sequence, extra
      9 nt in 5' area.

<400> SEQUENCE: 6

atggctagcg ccattctgga taccgactat atcacggaag atggcaaacc ggtgatacgt     60

atttttaaga aagagaatgg tgagttcaaa atcgagtacg accgcacttt tgagccatat    120

ttctacgcgt tactgaagga cgatagcgcc attgaagaag ttaaaaaaat caccgcagag    180

cggcatggga cagtggtaac cgtgaagaga gttgaaaaag tccagaaaaa atttttggga    240

cgacctgtag aagtgtggaa actttatttc actcaccccc aagatgttcc ggctatacgt    300

gataaaattc gcgaacatcc agcggtcatt gatatttacg aatatgatat accttttgcc    360

aagcgttacc tcatcgacaa aggcctggtg ccgatggaag gtgatgaaga attaaaaatg    420

ttggcattcg acattgaaac actttatcac gagggggaag agtttgctga gggtcccatc    480

ctgatgattt cttatgcgga tgaagagggt gcccgcgtaa taacctggaa gaacgttgat    540

ctcccgtacg tggacgtcgt tagtacggaa cgggaaatga tcaaacgttt cctgcgcgta    600

gtgaaagaga aagatccaga cgtcttaatt acctataatg gtgataactt tgattttgca    660

tacctgaaaa aaagatgcga aaagttgggc ataaatttcg ctcttggtcg agacgggtca    720

gagcctaaaa tccagcgtat gggagatcgc tttgcggttg aagtgaaagg ccggattcat    780

ttcgacctgt atccggtaat tcgtcgcact atcaacctcc ccacatacac gttagaagcc    840

gtctatgagg cagtttttgg tcaaccgaag gaaaaagttt acgctgagga aattaccact    900

gcgtgggaaa caggcgagaa tctggaacgt gtagcccgct attctatgga ggatgcaaaa    960

gttacctatg aattgggtaa ggaatttctt ccaatggagg cgcagctgtc gagattaata   1020

gggcagagcc tgtgggacgt gtctcgaagt tcaacgggaa acctcgtcga atggtttctg   1080

ttgcggaaag catacgagcg taatgaactt gcccctaaca aaccggatga aaaggagctg   1140

gcacgccgtc gccaatccta tgaaggcggt tacgttaaag aaccagagcg ggggttatgg   1200

gaaaatatcg tgtatctgga tttccgttcg ctctacccga gcattatcat tacccacaac   1260

gtatctcccg acactttgaa tcgcgagggc tgtaaagaat atgatgtcgc gccgcaggtt   1320

ggtcatagat tttgcaagga cttcccggga tttataccaa gtctgcttgg cgatttactg   1380

gaagagcgac aaaaaatcaa aaagaaaatg aaagctacaa tcgatccgat agaacgtaag   1440

ctgctcgact accgccagcg ggccatcaaa attttggcaa actcatatta tggttactat   1500

gggtacgcgc gtgctcgctg gtattgtaaa gagtgcgccg aatccgtgac ggcatggggc   1560

cgtgaataca tcaccatgac tattaaggag atagaagaga aatatggttt caaagtaatc   1620

tactcggata cagacggatt ctttgcgacg attcccggtg ccgatgcaga aaccgtcaag   1680

aaaaaagcga tggaattcct taagtatata aatgctaaat tacctggtgc cctggagctg   1740

gaatacgaag ggttttacaa acgcggattc tttgttacta agaaaaaata tgcggtgatc   1800

gacgaggaag gcaagattac gaccagaggc ctcgagattg tacggcgtga ttggagcgaa   1860

atcgctaaag aaacacaggc acgtgtcttg gaggcattac tgaaagatgg ggacgttgaa   1920

aaggcggtgc gaattgtaaa agaagtcacc gaaaaacttt ctaagtacga agttccgcca   1980

gagaaactgg tgatacacga acaaatcact cgtgatctga aagactataa ggctacaggc   2040

ccgcatgtag cagtcgccaa acgcctcgcg gctcggggtg ttaaaattcg tcccggaacg   2100

gtgatcagtt acattgtatt gaagggctca ggtcgcatag gggatagagc aatccctttc   2160
```

-continued gacgagtttg atccaaccaa acacaaatat gatgccgaat actatattga aaaccaggtc 2220
ttgccggcgg ttgagcgtat actgcgcgct ttcggctatc gaaaggaaga tcttcgttac 2280
caaaaaacta gacaggtggg tctgtccgca tggctcaaac ctaagggaac gtaa 2334

<210> SEQ ID NO 7
<211> LENGTH: 5017
<212> TYPE: DNA
<213> ORGANISM: Artificial Sequence
<220> FEATURE:
<223> OTHER INFORMATION: pKB13 - Pfu codon optimized nucleotide sequence
in pUC19 vector

<400> SEQUENCE: 7
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cggtctcagc gccattctgg 420
ataccgacta tatcacggaa gatggcaaac cggtgatacg tatttttaag aaagagaatg 480
gtgagttcaa aatcgagtac gaccgcactt ttgagccata tttctacgcg ttactgaagg 540
acgatagcgc cattgaagaa gttaaaaaaa tcaccgcaga gcggcatggg acagtggtaa 600
ccgtgaagag agttgaaaaa gtccagaaaa aatttttggg acgacctgta gaagtgtgga 660
aactttattt cactcacccc caagatgttc cggctatacg tgataaaatt cgcgaacatc 720
cagcggtcat tgatatttac gaatatgata tacctttttgc caagcgttac ctcatcgaca 780
aaggcctggt gccgatggaa ggtgatgaag aattaaaaat gttggcattc gacattgaaa 840
cactttatca cgagggggaa gagtttgctg agggtcccat cctgatgatt tcttatgcgg 900
atgaagaggg tgcccgcgta ataacctgga agaacgttga tctcccgtac gtggacgtcg 960
ttagtacgga acgggaaatg atcaaacgtt tcctgcgcgt agtgaaagag aaagatccag 1020
acgtcttaat tacctataat ggtgataact ttgattttgc atacctgaaa aaaagatgcg 1080
aaaagttggg cataaatttc gctcttggtc gagacgggtc agagcctaaa atccagcgta 1140
tgggagatcg ctttgcggtt gaagtgaaag gccggattca tttcgacctg tatccggtaa 1200
ttcgtcgcac tatcaacctc cccacataca cgttagaagc cgtctatgag gcagtttttg 1260
gtcaaccgaa ggaaaaagtt tacgctgagg aaattaccac tgcgtgggaa acaggcgaga 1320
atctggaacg tgtagcccgc tattctatgg aggatgcaaa agttacctat gaattgggta 1380
aggaatttct tccaatggag gcgcagctgt cgagattaat agggcagagc ctgtgggacg 1440
tgtctcgaag ttcaacggga aacctcgtcg aatggtttct gttgcggaaa gcatacgagc 1500
gtaatgaact tgcccctaac aaaccggatg aaaaggagct ggcacgccgt cgccaatcct 1560
atgaaggcgg ttacgttaaa gaaccagagc gggggttatg ggaaaatatc gtgtatctgg 1620
atttccgttc gctctacccg agcattatca ttacccacaa cgtatctccc gacactttga 1680
atcgcgaggg ctgtaaagaa tatgatgtcg cgccgcaggt tggtcataga ttttgcaagg 1740
acttcccggg atttatacca agtctgcttg gcgatttact ggaagagcga caaaaaatca 1800
aaaagaaaat gaaagctaca atcgatccga tagaacgtaa gctgctcgac taccgccagc 1860

-continued

```
gggccatcaa aattttggca aactcatatt atggttacta tgggtacgcg cgtgctcgct   1920
ggtattgtaa agagtgcgcc gaatccgtga cggcatgggg ccgtgaatac atcaccatga   1980
ctattaagga gatagaagag aaatatggtt tcaaagtaat ctactcggat acagacggat   2040
tctttgcgac gattcccggt gccgatgcag aaaccgtcaa gaaaaaagcg atggaattcc   2100
ttaagtatat aaatgctaaa ttacctggtg ccctggagct ggaatacgaa gggttttaca   2160
aacgcggatt ctttgttact aagaaaaaat atgcggtgat cgacgaggaa ggcaagatta   2220
cgaccagagg cctcgagatt gtacggcgtg attggagcga aatcgctaaa gaaacacagg   2280
cacgtgtctt ggaggcatta ctgaaagatg gggacgttga aaaggcggtg cgaattgtaa   2340
aagaagtcac cgaaaaactt tctaagtacg aagttccgcc agagaaactg gtgatacacg   2400
aacaaatcac tcgtgatctg aaagactata aggctacagg cccgcatgta gcagtcgcca   2460
aacgcctcgc ggctcggggt gttaaaattc gtcccggaac ggtgatcagt tacattgtat   2520
tgaagggctc aggtcgcata ggggatagag caatcccttt cgacgagttt gatccaacca   2580
aacacaaata tgatgccgaa tactatattg aaaaccaggt cttgccggcg gttgagcgta   2640
tactgcgcgc tttcggctat cgaaaggaag atcttcgtta ccaaaaaact agacaggtgg   2700
gtctgtccgc atggctcaaa cctaagggaa cgtaatgata tgagaccgga tcctctagag   2760
tcgacctgca ggcatgcaag cttggcgtaa tcatggtcat agctgtttcc tgtgtgaaat   2820
tgttatccgc tcacaattcc acacaacata cgagccggaa gcataaagtg taaagcctgg   2880
ggtgcctaat gagtgagcta actcacatta attgcgttgc gctcactgcc cgctttccag   2940
tcgggaaacc tgtcgtgcca gctgcattaa tgaatcggcc aacgcgcggg gagaggcggt   3000
ttgcgtattg ggcgctcttc cgcttcctcg ctcactgact cgctgcgctc ggtcgttcgg   3060
ctgcggcgag cggtatcagc tcactcaaag gcggtaatac ggttatccac agaatcaggg   3120
gataacgcag gaaagaacat gtgagcaaaa ggccagcaaa aggccaggaa ccgtaaaaag   3180
gccgcgttgc tggcgttttt ccataggctc cgcccccctg acgagcatca caaaaatcga   3240
cgctcaagtc agaggtggcg aaacccgaca ggactataaa gataccaggc gtttccccct   3300
ggaagctccc tcgtgcgctc tcctgttccg accctgccgc ttaccggata cctgtccgcc   3360
tttctccctt cgggaagcgt ggcgctttct catagctcac gctgtaggta tctcagttcg   3420
gtgtaggtcg ttcgctccaa gctgggctgt gtgcacgaac cccccgttca gcccgaccgc   3480
tgcgccttat ccggtaacta tcgtcttgag tccaacccgg taagacacga cttatcgcca   3540
ctggcagcag ccactggtaa caggattagc agagcgaggt atgtaggcgg tgctacagag   3600
ttcttgaagt ggtggcctaa ctacggctac actagaagaa cagtatttgg tatctgcgct   3660
ctgctgaagc cagttacctt cggaaaaaga gttggtagct cttgatccgg caaacaaacc   3720
accgctggta gcggtggttt ttttgtttgc aagcagcaga ttacgcgcag aaaaaaagga   3780
tctcaagaag atcctttgat cttttctacg gggtctgacg ctcagtggaa cgaaaactca   3840
cgttaaggga ttttggtcat gagattatca aaaaggatct tcacctagat ccttttaaat   3900
taaaaatgaa gttttaaatc aatctaaagt atatatgagt aaacttggtc tgacagttac   3960
caatgcttaa tcagtgaggc acctatctca gcgatctgtc tatttcgttc atccatagtt   4020
gcctgactcc ccgtcgtgta gataactacg atacgggagg gcttaccatc tggccccagt   4080
gctgcaatga taccgcgaga cccacgctca ccggctccag atttatcagc aataaaccag   4140
ccagccggaa gggccgagcg cagaagtggt cctgcaactt tatccgcctc catccagtct   4200
attaattgtt gccgggaagc tagagtaagt agttcgccag ttaatagttt gcgcaacgtt   4260
```

-continued

```
gttgccattg ctacaggcat cgtggtgtca cgctcgtcgt ttggtatggc ttcattcagc   4320

tccggttccc aacgatcaag gcgagttaca tgatccccca tgttgtgcaa aaaagcggtt   4380

agctccttcg gtcctccgat cgttgtcaga agtaagttgg ccgcagtgtt atcactcatg   4440

gttatggcag cactgcataa ttctcttact gtcatgccat ccgtaagatg cttttctgtg   4500

actggtgagt actcaaccaa gtcattctga gaatagtgta tgcggcgacc gagttgctct   4560

tgcccggcgt caatacggga taataccgcg ccacatagca gaactttaaa agtgctcatc   4620

attggaaaac gttcttcggg gcgaaaactc tcaaggatct taccgctgtt gagatccagt   4680

tcgatgtaac ccactcgtgc acccaactga tcttcagcat cttttacttt caccagcgtt   4740

tctgggtgag caaaaacagg aaggcaaaat gccgcaaaaa agggaataag ggcgacacgg   4800

aaatgttgaa tactcatact cttccttttt caatattatt gaagcattta tcagggttat   4860

tgtctcatga gcggatacat atttgaatgt atttagaaaa ataaacaaat aggggttccg   4920

cgcacatttc cccgaaaagt gccacctgac gtctaagaaa ccattattat catgacatta   4980

acctataaaa ataggcgtat cacgaggccc tttcgtc                            5017
```

<210> SEQ ID NO 8
<211> LENGTH: 5017
<212> TYPE: DNA
<213> ORGANISM: Artificial Sequence
<220> FEATURE:
<223> OTHER INFORMATION: pKB8 - KOD codon optimized nucleotide sequence
      in pUC19 vector

<400> SEQUENCE: 8

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cggtctcagc gccattctgg    420

ataccgacta tatcacggaa gatggcaaac cggtgatacg tatttttaag aaagagaatg    480

gtgagttcaa aatcgagtac gaccgcactt ttgagccata tttctacgcg ttactgaagg    540

acgatagcgc cattgaagaa gttaaaaaaa tcaccgcaga gcggcatggg acagtggtaa    600

ccgtgaagag agttgaaaaa gtccagaaaa aatttttggg acgacctgta gaagtgtgga    660

aactttattt cactcacccc caagatgttc cggctatacg tgataaaatt cgcgaacatc    720

cagcggtcat tgatatttac gaatatgata taccttttgc caagcgttac ctcatcgaca    780

aaggcctggt gccgatggaa ggtgatgaag aattaaaaat gttggcattc gacattgaaa    840

cactttatca cgagggggaa gagtttgctg agggtcccat cctgatgatt tcttatgcgg    900

atgaagaggg tgcccgcgta ataacctgga agaacgttga tctcccgtac gtggacgtcg    960

ttagtacgga acgggaaatg atcaaacgtt tcctgcgcgt agtgaaagag aaagatccag   1020

acgtcttaat tacctataat ggtgataact ttgattttgc atacctgaaa aaaagatgcg   1080

aaaagttggg cataaatttc gctcttggtc gagacgggtc agagcctaaa atccagcgta   1140

tgggagatcg ctttgcggtt gaagtgaaag gccggattca tttcgacctg tatccggtaa   1200

ttcgtcgcac tatcaacctc cccacataca cgttagaagc cgtctatgag gcagtttttg   1260
```

-continued

```
gtcaaccgaa ggaaaaagtt tacgctgagg aaattaccac tgcgtgggaa acaggcgaga   1320
atctggaacg tgtagcccgc tattctatgg aggatgcaaa agttacctat gaattgggta   1380
aggaatttct tccaatggag gcgcagctgt cgagattaat agggcagagc ctgtgggacg   1440
tgtctcgaag ttcaacggga aacctcgtcg aatggtttct gttgcggaaa gcatacgagc   1500
gtaatgaact tgcccctaac aaaccggatg aaaaggagct ggcacgccgt cgccaatcct   1560
atgaaggcgg ttacgttaaa gaaccagagc gggggttatg ggaaaatatc gtgtatctgg   1620
atttccgttc gctctacccg agcattatca ttacccacaa cgtatctccc gacactttga   1680
atcgcgaggg ctgtaaagaa tatgatgtcg cgccgcaggt tggtcataga ttttgcaagg   1740
acttcccggg atttatacca agtctgcttg gcgatttact ggaagagcga caaaaaatca   1800
aaaagaaaat gaaagctaca atcgatccga tagaacgtaa gctgctcgac taccgccagc   1860
gggccatcaa aattttggca aactcatatt atggttacta tgggtacgcg cgtgctcgct   1920
ggtattgtaa agagtgcgcc gaatccgtga cggcatgggg ccgtgaatac atcaccatga   1980
ctattaagga gatagaagag aaatatggtt tcaaagtaat ctactcggat acagacggat   2040
tctttgcgac gattcccggt gccgatgcag aaaccgtcaa gaaaaaagcg atggaattcc   2100
ttaagtatat aaatgctaaa ttacctggtg ccctggagct ggaatacgaa gggttttaca   2160
aacgcggatt ctttgttact aagaaaaaat atgcggtgat cgacgaggaa ggcaagatta   2220
cgaccagagg cctcgagatt gtacggcgtg attggagcga aatcgctaaa gaaacacagg   2280
cacgtgtctt ggaggcatta ctgaaagatg gggacgttga aaaggcggtg cgaattgtaa   2340
aagaagtcac cgaaaaactt tctaagtacg aagttccgcc agagaaactg gtgatacacg   2400
aacaaatcac tcgtgatctg aaagactata aggctacagg cccgcatgta gcagtcgcca   2460
aacgcctcgc ggctcggggt gttaaaattc gtcccggaac ggtgatcagt tacattgtat   2520
tgaagggctc aggtcgcata ggggatagag caatcccttt cgacgagttt gatccaacca   2580
aacacaaata tgatgccgaa tactatattg aaaaccaggt cttgccggcg gttgagcgta   2640
tactgcgcgc tttcggctat cgaaaggaag atcttcgtta ccaaaaaact agacaggtgg   2700
gtctgtccgc atggctcaaa cctaagggaa cgtaatgata tgagaccgga tcctctagag   2760
tcgacctgca ggcatgcaag cttggcgtaa tcatggtcat agctgtttcc tgtgtgaaat   2820
tgttatccgc tcacaattcc acacaacata cgagccggaa gcataaagtg taaagcctgg   2880
ggtgcctaat gagtgagcta actcacatta attgcgttgc gctcactgcc cgctttccag   2940
tcgggaaacc tgtcgtgcca gctgcattaa tgaatcggcc aacgcgcggg gagaggcggt   3000
ttgcgtattg ggcgctcttc cgcttcctcg ctcactgact cgctgcgctc ggtcgttcgg   3060
ctgcggcgag cggtatcagc tcactcaaag gcggtaatac ggttatccac agaatcaggg   3120
gataacgcag gaaagaacat gtgagcaaaa ggccagcaaa aggccaggaa ccgtaaaaag   3180
gccgcgttgc tggcgttttt ccataggctc cgcccccctg acgagcatca caaaaatcga   3240
cgctcaagtc agaggtggcg aaacccgaca ggactataaa gataccaggc gtttccccct   3300
ggaagctccc tcgtgcgctc tcctgttccg accctgccgc ttaccggata cctgtccgcc   3360
tttctccctt cgggaagcgt ggcgctttct catagctcac gctgtaggta tctcagttcg   3420
gtgtaggtcg ttcgctccaa gctgggctgt gtgcacgaac cccccgttca gcccgaccgc   3480
tgcgccttat ccggtaacta tcgtcttgag tccaacccgg taagacacga cttatcgcca   3540
ctggcagcag ccactggtaa caggattagc agagcgaggt atgtaggcgg tgctacagag   3600
```

-continued

```
ttcttgaagt ggtggcctaa ctacggctac actagaagaa cagtatttgg tatctgcgct   3660

ctgctgaagc cagttacctt cggaaaaaga gttggtagct cttgatccgg caaacaaacc   3720

accgctggta gcggtggttt ttttgtttgc aagcagcaga ttacgcgcag aaaaaaagga   3780

tctcaagaag atcctttgat cttttctacg gggtctgacg ctcagtggaa cgaaaactca   3840

cgttaaggga ttttggtcat gagattatca aaaaggatct tcacctagat ccttttaaat   3900

taaaaatgaa gttttaaatc aatctaaagt atatatgagt aaacttggtc tgacagttac   3960

caatgcttaa tcagtgaggc acctatctca gcgatctgtc tatttcgttc atccatagtt   4020

gcctgactcc ccgtcgtgta gataactacg atacgggagg gcttaccatc tggccccagt   4080

gctgcaatga taccgcgaga cccacgctca ccggctccag atttatcagc aataaaccag   4140

ccagccggaa gggccgagcg cagaagtggt cctgcaactt tatccgcctc catccagtct   4200

attaattgtt gccgggaagc tagagtaagt agttcgccag ttaatagttt gcgcaacgtt   4260

gttgccattg ctacaggcat cgtggtgtca cgctcgtcgt ttggtatggc ttcattcagc   4320

tccggttccc aacgatcaag gcgagttaca tgatccccca tgttgtgcaa aaaagcggtt   4380

agctccttcg gtcctccgat cgttgtcaga agtaagttgg ccgcagtgtt atcactcatg   4440

gttatggcag cactgcataa ttctcttact gtcatgccat ccgtaagatg cttttctgtg   4500

actggtgagt actcaaccaa gtcattctga gaatagtgta tgcggcgacc gagttgctct   4560

tgcccggcgt caatacggga taataccgcg ccacatagca gaactttaaa agtgctcatc   4620

attggaaaac gttcttcggg gcgaaaactc tcaaggatct taccgctgtt gagatccagt   4680

tcgatgtaac ccactcgtgc acccaactga tcttcagcat cttttacttt caccagcgtt   4740

tctgggtgag caaaaacagg aaggcaaaat gccgcaaaaa agggaataag ggcgacacgg   4800

aaatgttgaa tactcatact cttccttttt caatattatt gaagcattta tcagggttat   4860

tgtctcatga gcggatacat atttgaatgt atttagaaaa ataaacaaat aggggttccg   4920

cgcacatttc cccgaaaagt gccacctgac gtctaagaaa ccattattat catgacatta   4980

acctataaaa ataggcgtat cacgaggccc tttcgtc                            5017
```

<210> SEQ ID NO 9
<211> LENGTH: 775
<212> TYPE: PRT
<213> ORGANISM: Pyrococcus furiosus

<400> SEQUENCE: 9

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125
```

-continued

```
Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540
```

Leu Tyr Ala Thr Ile Pro Gly Gly Glu Ser Glu Glu Ile Lys Lys Lys
545 550 555 560

Ala Leu Glu Phe Val Lys Tyr Ile Asn Ser Lys Leu Pro Gly Leu Leu
565 570 575

Glu Leu Glu Tyr Glu Gly Phe Tyr Lys Arg Gly Phe Phe Val Thr Lys
580 585 590

Lys Arg Tyr Ala Val Ile Asp Glu Glu Gly Lys Val Ile Thr Arg Gly
595 600 605

Leu Glu Ile Val Arg Arg Asp Trp Ser Glu Ile Ala Lys Glu Thr Gln
610 615 620

Ala Arg Val Leu Glu Thr Ile Leu Lys His Gly Asp Val Glu Glu Ala
625 630 635 640

Val Arg Ile Val Lys Glu Val Ile Gln Lys Leu Ala Asn Tyr Glu Ile
645 650 655

Pro Pro Glu Lys Leu Ala Ile Tyr Glu Gln Ile Thr Arg Pro Leu His
660 665 670

Glu Tyr Lys Ala Ile Gly Pro His Val Ala Val Ala Lys Lys Leu Ala
675 680 685

Ala Lys Gly Val Lys Ile Lys Pro Gly Met Val Ile Gly Tyr Ile Val
690 695 700

Leu Arg Gly Asp Gly Pro Ile Ser Asn Arg Ala Ile Leu Ala Glu Glu
705 710 715 720

Tyr Asp Pro Lys Lys His Lys Tyr Asp Ala Glu Tyr Tyr Ile Glu Asn
725 730 735

Gln Val Leu Pro Ala Val Leu Arg Ile Leu Glu Gly Phe Gly Tyr Arg
740 745 750

Lys Glu Asp Leu Arg Tyr Gln Lys Thr Arg Gln Val Gly Leu Thr Ser
755 760 765

Trp Leu Asn Ile Lys Lys Ser
770 775

<210> SEQ ID NO 10
<211> LENGTH: 778
<212> TYPE: PRT
<213> ORGANISM: Artificial Sequence
<220> FEATURE:
<223> OTHER INFORMATION: Pfu amino acid sequence, extra 3 aa in 5' area.

<400> SEQUENCE: 10

Met Ala Ser Ala Ile Leu Asp Val Asp Tyr Ile Thr Glu Glu Gly Lys
1 5 10 15

Pro Val Ile Arg Leu Phe Lys Lys Glu Asn Gly Lys Phe Lys Ile Glu
20 25 30

His Asp Arg Thr Phe Arg Pro Tyr Ile Tyr Ala Leu Leu Arg Asp Asp
35 40 45

Ser Lys Ile Glu Glu Val Lys Lys Ile Thr Gly Glu Arg His Gly Lys
50 55 60

Ile Val Arg Ile Val Asp Val Glu Lys Val Glu Lys Lys Phe Leu Gly
65 70 75 80

Lys Pro Ile Thr Val Trp Lys Leu Tyr Leu Glu His Pro Gln Asp Val
85 90 95

Pro Thr Ile Arg Glu Lys Val Arg Glu His Pro Ala Val Val Asp Ile
100 105 110

Phe Glu Tyr Asp Ile Pro Phe Ala Lys Arg Tyr Leu Ile Asp Lys Gly
115 120 125

-continued

```
Leu Ile Pro Met Glu Gly Glu Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270

Leu Pro Thr Tyr Thr Leu Glu Ala Val Tyr Glu Ala Ile Phe Gly Lys
        275                 280                 285

Pro Lys Glu Lys Val Tyr Ala Asp Glu Ile Ala Lys Ala Trp Glu Ser
    290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Val Gly Gln Pro Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Val Ala Pro Asn Lys Pro Ser Glu Glu Glu Tyr Gln Arg Arg Leu
    370                 375                 380

Arg Glu Ser Tyr Thr Gly Gly Phe Val Lys Glu Pro Glu Lys Gly Leu
385                 390                 395                 400

Trp Glu Asn Ile Val Tyr Leu Asp Phe Arg Ala Leu Tyr Pro Ser Ile
                405                 410                 415

Ile Ile Thr His Asn Val Ser Pro Asp Thr Leu Asn Leu Glu Gly Cys
            420                 425                 430

Lys Asn Tyr Asp Ile Ala Pro Gln Val Gly His Lys Phe Cys Lys Asp
        435                 440                 445

Ile Pro Gly Phe Ile Pro Ser Leu Leu Gly His Leu Leu Glu Glu Arg
    450                 455                 460

Gln Lys Ile Lys Thr Lys Met Lys Glu Thr Gln Asp Pro Ile Glu Lys
465                 470                 475                 480

Ile Leu Leu Asp Tyr Arg Gln Lys Ala Ile Lys Leu Leu Ala Asn Ser
                485                 490                 495

Phe Tyr Gly Tyr Tyr Gly Tyr Ala Lys Ala Arg Trp Tyr Cys Lys Glu
            500                 505                 510

Cys Ala Glu Ser Val Thr Ala Trp Gly Arg Lys Tyr Ile Glu Leu Val
        515                 520                 525

Trp Lys Glu Leu Glu Glu Lys Phe Gly Phe Lys Val Leu Tyr Ile Asp
    530                 535                 540

Thr Asp Gly Leu Tyr Ala Thr Ile Pro Gly Gly Glu Ser Glu Glu Ile
```

```
545                 550                 555                 560

Lys Lys Lys Ala Leu Glu Phe Val Lys Tyr Ile Asn Ser Lys Leu Pro
                565                 570                 575

Gly Leu Leu Glu Leu Glu Tyr Glu Gly Phe Tyr Lys Arg Gly Phe Phe
            580                 585                 590

Val Thr Lys Lys Arg Tyr Ala Val Ile Asp Glu Glu Gly Lys Val Ile
        595                 600                 605

Thr Arg Gly Leu Glu Ile Val Arg Arg Asp Trp Ser Glu Ile Ala Lys
    610                 615                 620

Glu Thr Gln Ala Arg Val Leu Glu Thr Ile Leu Lys His Gly Asp Val
625                 630                 635                 640

Glu Glu Ala Val Arg Ile Val Lys Glu Val Ile Gln Lys Leu Ala Asn
                645                 650                 655

Tyr Glu Ile Pro Pro Glu Lys Leu Ala Ile Tyr Glu Gln Ile Thr Arg
            660                 665                 670

Pro Leu His Glu Tyr Lys Ala Ile Gly Pro His Val Ala Val Ala Lys
        675                 680                 685

Lys Leu Ala Ala Lys Gly Val Lys Ile Lys Pro Gly Met Val Ile Gly
    690                 695                 700

Tyr Ile Val Leu Arg Gly Asp Gly Pro Ile Ser Asn Arg Ala Ile Leu
705                 710                 715                 720

Ala Glu Glu Tyr Asp Pro Lys Lys His Lys Tyr Asp Ala Glu Tyr Tyr
                725                 730                 735

Ile Glu Asn Gln Val Leu Pro Ala Val Leu Arg Ile Leu Glu Gly Phe
            740                 745                 750

Gly Tyr Arg Lys Glu Asp Leu Arg Tyr Gln Lys Thr Arg Gln Val Gly
        755                 760                 765

Leu Thr Ser Trp Leu Asn Ile Lys Lys Ser
    770                 775


<210> SEQ ID NO 11
<211> LENGTH: 774
<212> TYPE: PRT
<213> ORGANISM: Thermococcus sp.

<400> SEQUENCE: 11

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140
```

-continued

```
Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
```

```
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770


<210> SEQ ID NO 12
<211> LENGTH: 777
<212> TYPE: PRT
<213> ORGANISM: Artificial Sequence
<220> FEATURE:
<223> OTHER INFORMATION: KOD amino acid sequence, extra 3 aa in 5' area.

<400> SEQUENCE: 12

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
```

-continued

```
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Glu Leu Ala Arg Arg Arg
    370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
        435                 440                 445

Pro Gly Phe Ile Pro Ser Leu Leu Gly Asp Leu Leu Glu Glu Arg Gln
    450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
        515                 520                 525

Lys Glu Ile Glu Glu Lys Tyr Gly Phe Lys Val Ile Tyr Ser Asp Thr
    530                 535                 540

Asp Gly Phe Phe Ala Thr Ile Pro Gly Ala Asp Ala Glu Thr Val Lys
545                 550                 555                 560

Lys Lys Ala Met Glu Phe Leu Lys Tyr Ile Asn Ala Lys Leu Pro Gly
                565                 570                 575
```

```
Ala Leu Glu Leu Glu Tyr Glu Gly Phe Tyr Lys Arg Gly Phe Phe Val
            580                 585                 590

Thr Lys Lys Lys Tyr Ala Val Ile Asp Glu Glu Gly Lys Ile Thr Thr
        595                 600                 605

Arg Gly Leu Glu Ile Val Arg Arg Asp Trp Ser Glu Ile Ala Lys Glu
    610                 615                 620

Thr Gln Ala Arg Val Leu Glu Ala Leu Leu Lys Asp Gly Asp Val Glu
625                 630                 635                 640

Lys Ala Val Arg Ile Val Lys Glu Val Thr Glu Lys Leu Ser Lys Tyr
                645                 650                 655

Glu Val Pro Pro Glu Lys Leu Val Ile His Glu Gln Ile Thr Arg Asp
            660                 665                 670

Leu Lys Asp Tyr Lys Ala Thr Gly Pro His Val Ala Val Ala Lys Arg
        675                 680                 685

Leu Ala Ala Arg Gly Val Lys Ile Arg Pro Gly Thr Val Ile Ser Tyr
    690                 695                 700

Ile Val Leu Lys Gly Ser Gly Arg Ile Gly Asp Arg Ala Ile Pro Phe
705                 710                 715                 720

Asp Glu Phe Asp Pro Thr Lys His Lys Tyr Asp Ala Glu Tyr Tyr Ile
                725                 730                 735

Glu Asn Gln Val Leu Pro Ala Val Glu Arg Ile Leu Arg Ala Phe Gly
            740                 745                 750

Tyr Arg Lys Glu Asp Leu Arg Tyr Gln Lys Thr Arg Gln Val Gly Leu
        755                 760                 765

Ser Ala Trp Leu Lys Pro Lys Gly Thr
    770                 775
```

<210> SEQ ID NO 13
<211> LENGTH: 2334
<212> TYPE: DNA
<213> ORGANISM: Artificial Sequence
<220> FEATURE:
<223> OTHER INFORMATION: Pod codon optimized nucleotide sequence

<400> SEQUENCE: 13

```
atggctagcg ccattctgga tgtggactat atcaccgaag agggcaaacc ggttatacgt      60

ttatttaaga aagagaatgg taaattcaag atcgagcatg accgcacgtt ccgtccatac     120

atttacgcgt tgcttcggga tgatagcaaa attgaggaag tcaaaaagat caccggggaa     180

cgtcatggaa aaatagtaag aattgtggac gttgaaaaag tcgaaaagaa atttctgggc     240

aaaccgatca ctgtatggaa gctctatctg gaacatcctc aggatgtgcc cacaattcga     300

gaaaaagttc gtgagcaccc agccgtcgtg gatatatttg aatatgacat ccccttttgca     360

aaacgctact taattgataa aggcctgatc ccgatggagg gggaagaaga acttaaaatt     420

ctggcttttg acatagaaac gctctatcat gagggagaag aatttggcaa aggtcccatc     480

attatgattt cttacgcgga tgagaacgaa gccaaggtaa tcacttggaa aaatattgac     540

ctgccgtacg ttgaagtggt cagttcagag cgggaaatga ttaaacgttt tttacgcatc     600

attagagaga aagatccaga tataatcgtt acatataacg gcgactcctt cgattttcct     660

tacctggcaa aacgagctga aaaattgggt attaaactta ccatcgggcg tgacggatcg     720

gaaccgaaaa tgcaacgcat tggcgatatg acggcggtag aggtgaaagg tcggatacac     780

tttgatctgt atcatgtcat cacccgtact attaatctcc ccacatacac gttagaagcc     840

gtttatgagg caatattcgg caagccgaaa gaaaaagtgt acgctgacga aatcgcgaag     900
```

```
gcatgggaga gcggcgaaaa cctggagcgc gtagcaaaat attctatgga agatgctaaa    960
gcgacctacg aattggggaa agaatttctt ccaatggaaa ttcagctgtc gagattaata   1020
gggcagagcc tgtgggacgt gtctcgaagt tcaacgggaa acctcgtcga atggtttctg   1080
ttgcggaaag catacgagcg taatgaactt gcccctaaca aaccggatga aaaggagctg   1140
gcacgccgtc gccaatccta tgaaggcggt tacgttaaag aaccagagcg gggttatgg    1200
gaaaatatcg tgtatctgga tttccgttcg ctctacccga gcattatcat tacccacaac   1260
gtatctcccg acactttgaa tcgcgagggc tgtaaagaat atgatgtcgc gccgcaggtt   1320
ggtcatagat tttgcaagga cttcccggga tttataccaa gtctgcttgg cgatttactg   1380
gaagagcgac aaaaaatcaa aaagaaaatg aaagctacaa tcgatccgat agaacgtaag   1440
ctgctcgact accgccagcg ggccatcaaa attttggcaa actcatatta tggttactat   1500
gggtacgcgc gtgctcgctg gtattgtaaa gagtgcgccg aatccgtgac ggcatggggc   1560
cgtgaataca tcaccatgac tattaaggag atagaagaga aatatggttt caaagtaatc   1620
tactcggata cagacggatt ctttgcgacg attcccggtg ccgatgcaga aaccgtcaag   1680
aaaaaagcga tggaattcgt taagtacatt aatagtaaat taccgggact gcttgaactg   1740
gagtatgaag gcttctacaa aagaggtttt ttcgttacta agaaacgata tgccgtaata   1800
gatgaagagg ggaaagtcat cacacgtggc ctcgagattg ttcgccggga ctggtcagag   1860
atagcaaagg aaacgcaggc gcgcgtgctc gaaaccatct tgaaacatgg tgatgtagag   1920
gaagccgtcc gcattgttaa agaggtgatc cagaagttag caaactatga aattccaccg   1980
gaaaaactgg cgatatacga gcaaatcact cgtccccttc acgaatataa agctattgga   2040
cctcatgtag ccgtcgcgaa gaaactggct gcaaaaggcg ttaagataaa accaggtatg   2100
gtgatcgggt acattgtact ccgcggcgac ggtccgattt ccaatagagc catcttggcg   2160
gaggaatatg atcctaaaaa gcataaatac gacgctgaat attacattga gaaccaggtc   2220
ttgccggcag ttctgcggat acttgaagga tttggctatc gtaaagaaga tctgcgctat   2280
caaaagacgc gacaggtggg tctgactagc tggttgaata tcaaaaaatc gtaa         2334
```

<210> SEQ ID NO 14
<211> LENGTH: 2337
<212> TYPE: DNA
<213> ORGANISM: Artificial Sequence
<220> FEATURE:
<223> OTHER INFORMATION: Kofu codon optimized nucleotide sequence

<400> SEQUENCE: 14

```
atggctagcg ccattctgga taccgactat atcacggaag atggcaaacc ggtgatacgt     60
atttttaaga aagagaatgg tgagttcaaa atcgagtacg accgcacttt tgagccatat    120
ttctacgcgt tactgaagga cgatagcgcc attgaagaag ttaaaaaaat caccgcagag    180
cggcatggga cagtggtaac cgtgaagaga gttgaaaaag tccagaaaaa atttttggga    240
cgacctgtag aagtgtggaa actttatttc actcaccccc aagatgttcc ggctatacgt    300
gataaaattc gcgaacatcc agcggtcatt gatatttacg aatatgatat accttttgcc    360
aagcgttacc tcatcgacaa aggcctggtg ccgatggaag gtgatgaaga attaaaaatg    420
ttggcattcg acattgaaac actttatcac gagggggaag agtttgctga gggtcccatc    480
ctgatgattt cttatgcgga tgaagagggt gcccgcgtaa taacctggaa gaacgttgat    540
ctcccgtacg tggacgtcgt tagtacggaa cgggaaatga tcaaacgttt cctgcgcgta    600
```

-continued

```
gtgaaagaga aagatccaga cgtcttaatt acctataatg gtgataactt tgattttgca    660

tacctgaaaa aaagatgcga aaagttgggc ataaatttcg ctcttggtcg agacgggtca    720

gagcctaaaa tccagcgtat gggagatcgc tttgcggttg aagtgaaagg ccggattcat    780

ttcgacctgt atccggtaat tcgtcgcact atcaacctcc ccacatacac gttagaagcc    840

gtctatgagg cagtttttgg tcaaccgaag gaaaaagttt acgctgagga aattaccact    900

gcgtgggaaa caggcgagaa tctggaacgt gtagcccgct attctatgga ggatgcaaaa    960

gttacctatg aattgggtaa ggaatttctt ccaatggagg cgcagctgag tcgtttagtc   1020

ggacaacctc tgtgggacgt ttcacgctcc tcgactggca atctcgtgga gtggttcctg   1080

ttgagaaaag cctatgaacg aaacgaagta gcaccgaata aaccaagcga ggaagaatat   1140

cagcgtcgcc ttcgcgagtc ttacacaggt gggtttgtta aggaaccgga gaaaggtctt   1200

tgggaaaaca tcgtgtattt agatttccgt gcgctgtacc ccagtattat aatcacccac   1260

aatgtctcac ctgacacgct caacttggaa ggttgcaaaa attatgatat tgctccgcaa   1320

gttggacata agttttgtaa agatattccg ggcttcatcc cgtccctgct tggtcactta   1380

ctggaagagc gccaaaaaat taagaccaaa atgaaagaga ctcaggatcc cattgaaaag   1440

atcctgctcg attaccggca aaaagccatt aaattgcttg caaactcgtt ttatgggtac   1500

tatggctatg cgaaggctcg ttggtactgc aaagaatgtg ccgagagcgt gacagcatgg   1560

ggtcgcaaat atatagaatt agtatggaag gagctggaag aaaaattcgg attcaaagtc   1620

ctgtacatcg atacggatgg cctctatgcg accattcctg gtggggagtc tgaagaaatc   1680

aagaaaaaag ccttggaatt ccttaagtat ataaatgcta aattacctgg tgccctggag   1740

ctggaatacg aagggtttta caaacgcgga ttctttgtta ctaagaaaaa atatgcggtg   1800

atcgacgagg aaggcaagat tacgaccaga ggcctcgaga ttgtacggcg tgattggagc   1860

gaaatcgcta aagaaacaca ggcacgtgtc ttggaggcat tactgaaaga tggggacgtt   1920

gaaaaggcgg tgcgaattgt aaaagaagtc accgaaaaac tttctaagta cgaagttccg   1980

ccagagaaac tggtgataca cgaacaaatc actcgtgatc tgaaagacta taaggctaca   2040

ggcccgcatg tagcagtcgc caaacgcctc gcggctcggg gtgttaaaat tcgtcccgga   2100

acggtgatca gttacattgt attgaagggc tcaggtcgca taggggatag agcaatccct   2160

ttcgacgagt ttgatccaac caaacacaaa tatgatgccg aatactatat tgaaaaccag   2220

gtcttgccgg cggttgagcg tatactgcgc gctttcggct atcgaaagga agatcttcgt   2280

taccaaaaaa ctagacaggt gggtctgtcc gcatggctca aacctaaggg aacgtaa      2337
```

<210> SEQ ID NO 15
<211> LENGTH: 777
<212> TYPE: PRT
<213> ORGANISM: Artificial Sequence
<220> FEATURE:
<223> OTHER INFORMATION: Pod amino acid sequence

<400> SEQUENCE: 15

```
Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60
```

-continued

```
Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270

Leu Pro Thr Tyr Thr Leu Glu Ala Val Tyr Glu Ala Ile Phe Gly Lys
        275                 280                 285

Pro Lys Glu Lys Val Tyr Ala Asp Glu Ile Ala Lys Ala Trp Glu Ser
    290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Glu Leu Ala Arg Arg Arg
    370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
        435                 440                 445

Pro Gly Phe Ile Pro Ser Leu Leu Gly Asp Leu Leu Glu Glu Arg Gln
    450                 455                 460

Lys Ile Lys Lys Lys Met Lys Ala Thr Ile Asp Pro Ile Glu Arg Lys
465                 470                 475                 480
```

-continued

```
Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
        515                 520                 525

Lys Glu Ile Glu Glu Lys Tyr Gly Phe Lys Val Ile Tyr Ser Asp Thr
    530                 535                 540

Asp Gly Phe Phe Ala Thr Ile Pro Gly Ala Asp Ala Glu Thr Val Lys
545                 550                 555                 560

Lys Lys Ala Met Glu Phe Val Lys Tyr Ile Asn Ser Lys Leu Pro Gly
                565                 570                 575

Leu Leu Glu Leu Glu Tyr Glu Gly Phe Tyr Lys Arg Gly Phe Phe Val
            580                 585                 590

Thr Lys Lys Arg Tyr Ala Val Ile Asp Glu Glu Gly Lys Val Ile Thr
        595                 600                 605

Arg Gly Leu Glu Ile Val Arg Arg Asp Trp Ser Glu Ile Ala Lys Glu
    610                 615                 620

Thr Gln Ala Arg Val Leu Glu Thr Ile Leu Lys His Gly Asp Val Glu
625                 630                 635                 640

Glu Ala Val Arg Ile Val Lys Glu Val Ile Gln Lys Leu Ala Asn Tyr
                645                 650                 655

Glu Ile Pro Pro Glu Lys Leu Ala Ile Tyr Glu Gln Ile Thr Arg Pro
            660                 665                 670

Leu His Glu Tyr Lys Ala Ile Gly Pro His Val Ala Val Ala Lys Lys
        675                 680                 685

Leu Ala Ala Lys Gly Val Lys Ile Lys Pro Gly Met Val Ile Gly Tyr
    690                 695                 700

Ile Val Leu Arg Gly Asp Gly Pro Ile Ser Asn Arg Ala Ile Leu Ala
705                 710                 715                 720

Glu Glu Tyr Asp Pro Lys Lys His Lys Tyr Asp Ala Glu Tyr Tyr Ile
                725                 730                 735

Glu Asn Gln Val Leu Pro Ala Val Leu Arg Ile Leu Glu Gly Phe Gly
            740                 745                 750

Tyr Arg Lys Glu Asp Leu Arg Tyr Gln Lys Thr Arg Gln Val Gly Leu
        755                 760                 765

Thr Ser Trp Leu Asn Ile Lys Lys Ser
    770                 775


<210> SEQ ID NO 16
<211> LENGTH: 778
<212> TYPE: PRT
<213> ORGANISM: Artificial Sequence
<220> FEATURE:
<223> OTHER INFORMATION: Kofu amino acid sequence

<400> SEQUENCE: 16

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60
```

-continued

```
Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Val Gly Gln Pro Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Val Ala Pro Asn Lys Pro Ser Glu Glu Glu Tyr Gln Arg Arg Leu
    370                 375                 380

Arg Glu Ser Tyr Thr Gly Gly Phe Val Lys Glu Pro Glu Lys Gly Leu
385                 390                 395                 400

Trp Glu Asn Ile Val Tyr Leu Asp Phe Arg Ala Leu Tyr Pro Ser Ile
                405                 410                 415

Ile Ile Thr His Asn Val Ser Pro Asp Thr Leu Asn Leu Glu Gly Cys
            420                 425                 430

Lys Asn Tyr Asp Ile Ala Pro Gln Val Gly His Lys Phe Cys Lys Asp
        435                 440                 445

Ile Pro Gly Phe Ile Pro Ser Leu Leu Gly His Leu Leu Glu Glu Arg
    450                 455                 460

Gln Lys Ile Lys Thr Lys Met Lys Glu Thr Gln Asp Pro Ile Glu Lys
465                 470                 475                 480

Ile Leu Leu Asp Tyr Arg Gln Lys Ala Ile Lys Leu Leu Ala Asn Ser
```

```
                485                 490                 495

Phe Tyr Gly Tyr Tyr Gly Tyr Ala Lys Ala Arg Trp Tyr Cys Lys Glu
            500                 505                 510

Cys Ala Glu Ser Val Thr Ala Trp Gly Arg Lys Tyr Ile Glu Leu Val
        515                 520                 525

Trp Lys Glu Leu Glu Glu Lys Phe Gly Phe Lys Val Leu Tyr Ile Asp
    530                 535                 540

Thr Asp Gly Leu Tyr Ala Thr Ile Pro Gly Gly Glu Ser Glu Glu Ile
545                 550                 555                 560

Lys Lys Lys Ala Leu Glu Phe Leu Lys Tyr Ile Asn Ala Lys Leu Pro
                565                 570                 575

Gly Ala Leu Glu Leu Glu Tyr Glu Gly Phe Tyr Lys Arg Gly Phe Phe
            580                 585                 590

Val Thr Lys Lys Lys Tyr Ala Val Ile Asp Glu Glu Gly Lys Ile Thr
        595                 600                 605

Thr Arg Gly Leu Glu Ile Val Arg Arg Asp Trp Ser Glu Ile Ala Lys
    610                 615                 620

Glu Thr Gln Ala Arg Val Leu Glu Ala Leu Leu Lys Asp Gly Asp Val
625                 630                 635                 640

Glu Lys Ala Val Arg Ile Val Lys Glu Val Thr Glu Lys Leu Ser Lys
                645                 650                 655

Tyr Glu Val Pro Pro Glu Lys Leu Val Ile His Glu Gln Ile Thr Arg
            660                 665                 670

Asp Leu Lys Asp Tyr Lys Ala Thr Gly Pro His Val Ala Val Ala Lys
        675                 680                 685

Arg Leu Ala Ala Arg Gly Val Lys Ile Arg Pro Gly Thr Val Ile Ser
    690                 695                 700

Tyr Ile Val Leu Lys Gly Ser Gly Arg Ile Gly Asp Arg Ala Ile Pro
705                 710                 715                 720

Phe Asp Glu Phe Asp Pro Thr Lys His Lys Tyr Asp Ala Glu Tyr Tyr
                725                 730                 735

Ile Glu Asn Gln Val Leu Pro Ala Val Glu Arg Ile Leu Arg Ala Phe
            740                 745                 750

Gly Tyr Arg Lys Glu Asp Leu Arg Tyr Gln Lys Thr Arg Gln Val Gly
        755                 760                 765

Leu Ser Ala Trp Leu Lys Pro Lys Gly Thr
    770                 775
```

<210> SEQ ID NO 17
<211> LENGTH: 3778
<212> TYPE: DNA
<213> ORGANISM: Artificial Sequence
<220> FEATURE:
<223> OTHER INFORMATION: Plasmid "pLACIQZa" sequence

<400> SEQUENCE: 17

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acccggggat    420
```

```
cctctagagc cgtaatcatg gtcatagctg tttcctgtgt gaaattgtta tccgctcaca    480
attccacaca acatacgagc cggaagcata aagtgtaaag cctggggtgc ctaatgagtg    540
agctaactca cattaattgc gttgcgctca ctgcccgctt tccagtcggg aaacctgtcg    600
tgccagctgc attaatgaat cggccaacgc gcggggagag gcggtttgcg tattgggcgc    660
cagggtggtt tttcttttca ccagtgagac gggcaacagc tgattgccct tcaccgcctg    720
gccctgagag agttgcagca agcggtccac gctggtttgc cccagcaggc gaaaatcctg    780
tttgatggtg gttgacggcg ggatataaca tgagctgtct tcggtatcgt cgtatcccac    840
taccgagata tccgcaccaa cgcgcagccc ggactcggta atggcgcgca ttgcgcccag    900
cgccatctga tcgttggcaa ccagcatcgc agtgggaacg atgccctcat tcagcatttg    960
catggtttgt tgaaaaccgg acatggcact ccagtcgcct tcccgttccg ctatcggctg   1020
aatttgattg cgagtgagat atttatgcca gccagccaga cgcagacgcg ccgagacaga   1080
acttaatggg cccgctaaca gcgcgatttg ctggtgaccc aatgcgacca gatgctccac   1140
gcccagtcgc gtaccgtctt catgggagaa aataatactg ttgatgggtg tctggtcaga   1200
gacatcaaga aataacgccg gaacattagt gcaggcagct tccacagcaa tggcatcctg   1260
gtcatccagc ggatagttaa tgatcagccc actgacgcgt tgcgcgagaa gattgtgcac   1320
cgccgcttta caggcttcga cgccgcttcg ttctaccatc gacaccacca cgctggcacc   1380
cagttgatcg gcgcgagatt taatcgccgc gacaatttgc gacggcgcgt gcagggccag   1440
actggaggtg gcaacgccaa tcagcaacga ctgtttgccc gccagttgtt gtgccacgcg   1500
gttgggaatg taattcagct ccgccatcgc cgcttccact ttttcccgcg ttttcgcaga   1560
aacgtggctg gcctggttca ccacgcggga aacggtctga taagagacac cggcatactc   1620
tgcgacatcg tataacgtta ctggtttcac attcaccacc ctgaattgac tctcttccgg   1680
gcgctatcat gccataccgc gaaaggtttt gcgccattcg atggtgtcaa cgtaaatgca   1740
tgccgcttcg ccttccggcc accagaatag cctgcgccat gggcttcctc gctcactgac   1800
tcgctgcgct cggtcgttcg gctgcggcga gcggtatcag ctcactcaaa ggcggtaata   1860
cggttatcca cagaatcagg ggataacgca ggaaagaaca tgtgagcaaa aggccagcaa   1920
aaggccagga accgtaaaaa ggccgcgttg ctggcgtttt tccataggct ccgcccccct   1980
gacgagcatc acaaaaatcg acgctcaagt cagaggtggc gaaacccgac aggactataa   2040
agataccagg cgtttccccc tggaagctcc ctcgtgcgct ctcctgttcc gaccctgccg   2100
cttaccggat acctgtccgc ctttctccct tcgggaagcg tggcgctttc tcatagctca   2160
cgctgtaggt atctcagttc ggtgtaggtc gttcgctcca agctgggctg tgtgcacgaa   2220
ccccccgttc agcccgaccg ctgcgcctta tccggtaact atcgtcttga gtccaacccg   2280
gtaagacacg acttatcgcc actggcagca gccactggta acaggattag cagagcgagg   2340
tatgtaggcg gtgctacaga gttcttgaag tggtggccta actacggcta cactagaaga   2400
acagtatttg gtatctgcgc tctgctgaag ccagttacct tcggaaaaag agttggtagc   2460
tcttgatccg gcaaacaaac caccgctggt agcggtggtt tttttgtttg caagcagcag   2520
attacgcgca gaaaaaaagg atctcaagaa gatcctttga tcttttctac ggggtctgac   2580
gctcagtgga acgaaaactc acgttaaggg attttggtca tgagattatc aaaaaggatc   2640
ttcacctaga tccttttaaa ttaaaaatga agttttaaat caatctaaag tatatatgag   2700
taaacttggt ctgacagtta ccaatgctta atcagtgagg cacctatctc agcgatctgt   2760
```

```
ctatttcgtt catccatagt tgcctgactc cccgtcgtgt agataactac gatacgggag   2820

ggcttaccat ctggccccag tgctgcaatg ataccgcgag acccacgctc accggctcca   2880

gatttatcag caataaacca gccagccgga agggccgagc gcagaagtgg tcctgcaact   2940

ttatccgcct ccatccagtc tattaattgt tgccgggaag ctagagtaag tagttcgcca   3000

gttaatagtt tgcgcaacgt tgttgccatt gctacaggca tcgtggtgtc acgctcgtcg   3060

tttggtatgg cttcattcag ctccggttcc caacgatcaa ggcgagttac atgatccccc   3120

atgttgtgca aaaaagcggt tagctccttc ggtcctccga tcgttgtcag aagtaagttg   3180

gccgcagtgt tatcactcat ggttatggca gcactgcata attctcttac tgtcatgcca   3240

tccgtaagat gcttttctgt gactggtgag tactcaacca agtcattctg agaatagtgt   3300

atgcggcgac cgagttgctc ttgcccggcg tcaatacggg ataataccgc gccacatagc   3360

agaactttaa aagtgctcat cattggaaaa cgttcttcgg ggcgaaaact ctcaaggatc   3420

ttaccgctgt tgagatccag ttcgatgtaa cccactcgtg cacccaactg atcttcagca   3480

tcttttactt tcaccagcgt ttctgggtga gcaaaaacag gaaggcaaaa tgccgcaaaa   3540

aagggaataa gggcgacacg gaaatgttga atactcatac tcttcctttt tcaatattat   3600

tgaagcattt atcagggtta ttgtctcatg agcggataca tatttgaatg tatttagaaa   3660

aataaacaaa taggggttcc gcgcacattt ccccgaaaag tgccacctga cgtctaagaa   3720

accattatta tcatgacatt aacctataaa aataggcgta tcacgaggcc ctttcgtc     3778
```

```
<210> SEQ ID NO 18
<211> LENGTH: 775
<212> TYPE: PRT
<213> ORGANISM: Thermococcus sp.

<400> SEQUENCE: 18

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
```

-continued

```
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620
```

-continued

```
Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775


<210> SEQ ID NO 19
<211> LENGTH: 774
<212> TYPE: PRT
<213> ORGANISM: Thermococcus litoralis

<400> SEQUENCE: 19

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
```

```
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640
```

Lys Ala Val Glu Val Val Arg Asp Val Val Glu Lys Ile Ala Lys Tyr
645 650 655

Arg Val Pro Leu Glu Lys Leu Val Ile His Glu Gln Ile Thr Arg Asp
660 665 670

Leu Lys Asp Tyr Lys Ala Ile Gly Pro His Val Ala Ile Ala Lys Arg
675 680 685

Leu Ala Ala Arg Gly Ile Lys Val Lys Pro Gly Thr Ile Ile Ser Tyr
690 695 700

Ile Val Leu Lys Gly Ser Gly Lys Ile Ser Asp Arg Val Ile Leu Leu
705 710 715 720

Thr Glu Tyr Asp Pro Arg Lys His Lys Tyr Asp Pro Asp Tyr Tyr Ile
725 730 735

Glu Asn Gln Val Leu Pro Ala Val Leu Arg Ile Leu Glu Ala Phe Gly
740 745 750

Tyr Arg Lys Glu Asp Leu Arg Tyr Gln Ser Ser Lys Gln Thr Gly Leu
755 760 765

Asp Ala Trp Leu Lys Arg
770

<210> SEQ ID NO 20
<211> LENGTH: 776
<212> TYPE: PRT
<213> ORGANISM: Artificial Sequence
<220> FEATURE:
<223> OTHER INFORMATION: Chimeric DNA polymerase 9Nli

<400> SEQUENCE: 20

Met Ile Leu Asp Thr Asp Tyr Ile Thr Glu Asn Gly Lys Pro Val Ile
1 5 10 15

Arg Val Phe Lys Lys Glu Asn Gly Glu Phe Lys Ile Glu Tyr Asp Arg
20 25 30

Thr Phe Glu Pro Tyr Phe Tyr Ala Leu Leu Lys Asp Asp Ser Ala Ile
35 40 45

Glu Asp Val Lys Lys Val Thr Ala Lys Arg His Gly Thr Val Val Lys
50 55 60

Val Lys Arg Ala Glu Lys Val Gln Lys Lys Phe Leu Gly Arg Pro Ile
65 70 75 80

Glu Val Trp Lys Leu Tyr Phe Asn His Pro Gln Asp Val Pro Ala Ile
85 90 95

Arg Asp Arg Ile Arg Ala His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Thr Met Leu Ala Phe Asp Ile Glu Thr
130 135 140

Leu Tyr His Glu Gly Glu Glu Phe Gly Thr Gly Pro Ile Leu Met Ile
145 150 155 160

Ser Tyr Ala Asp Gly Ser Glu Ala Arg Val Ile Thr Trp Lys Lys Ile
165 170 175

Asp Leu Pro Tyr Val Asp Val Val Ser Thr Glu Lys Glu Met Ile Lys
180 185 190

Arg Phe Leu Arg Val Val Arg Glu Lys Asp Pro Asp Val Leu Ile Thr
195 200 205

Tyr Asn Gly Asp Asn Phe Asp Phe Ala Tyr Leu Lys Lys Arg Cys Glu
210 215 220

-continued

```
Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Tyr Leu Leu Arg Val Ala Tyr Ala Arg Asn Glu Leu Ala
        355                 360                 365

Pro Asn Lys Pro Asp Glu Glu Glu Tyr Lys Arg Arg Leu Arg Thr Thr
    370                 375                 380

Tyr Leu Gly Gly Tyr Val Lys Glu Pro Glu Lys Gly Leu Trp Glu Asn
385                 390                 395                 400

Ile Ile Tyr Leu Asp Phe Arg Ser Leu Tyr Pro Ser Ile Ile Val Thr
                405                 410                 415

His Asn Val Ser Pro Asp Thr Leu Glu Lys Glu Gly Cys Lys Asn Tyr
            420                 425                 430

Asp Val Ala Pro Ile Val Gly Tyr Arg Phe Cys Lys Asp Phe Pro Gly
        435                 440                 445

Phe Ile Pro Ser Ile Leu Gly Asp Leu Ile Ala Met Arg Gln Asp Ile
    450                 455                 460

Lys Lys Lys Met Lys Ser Thr Ile Asp Pro Ile Glu Lys Lys Met Leu
465                 470                 475                 480

Asp Tyr Arg Gln Arg Ala Ile Lys Leu Leu Ala Asn Ser Tyr Tyr Gly
                485                 490                 495

Tyr Met Gly Tyr Pro Lys Ala Arg Trp Tyr Ser Lys Glu Cys Ala Glu
            500                 505                 510

Ser Val Thr Ala Trp Gly Arg His Tyr Ile Glu Met Thr Ile Arg Glu
        515                 520                 525

Ile Glu Glu Lys Phe Gly Phe Lys Val Leu Tyr Ala Asp Thr Asp Gly
    530                 535                 540

Phe Tyr Ala Thr Ile Pro Gly Glu Lys Pro Glu Leu Ile Lys Lys Lys
545                 550                 555                 560

Ala Lys Glu Phe Leu Asn Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Val Ile Asp Glu Glu Gly Lys Ile Thr Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asp Val Glu Glu Ala
625                 630                 635                 640
```

```
Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Arg
            660                 665                 670

Asp Tyr Lys Ala Thr Gly Pro His Val Ala Val Ala Lys Arg Leu Ala
        675                 680                 685

Ala Arg Gly Val Lys Ile Arg Pro Gly Thr Val Ile Ser Tyr Ile Val
    690                 695                 700

Leu Lys Gly Ser Gly Arg Ile Gly Asp Arg Ala Ile Pro Ala Asp Glu
705                 710                 715                 720

Phe Asp Pro Thr Lys His Arg Tyr Asp Ala Glu Tyr Tyr Ile Glu Asn
                725                 730                 735

Gln Val Leu Pro Ala Val Glu Arg Ile Leu Lys Ala Phe Gly Tyr Arg
            740                 745                 750

Lys Glu Asp Leu Arg Tyr Gln Lys Thr Lys Gln Val Gly Leu Gly Ala
        755                 760                 765

Trp Leu Lys Val Lys Gly Lys Lys
    770                 775


<210> SEQ ID NO 21
<211> LENGTH: 773
<212> TYPE: PRT
<213> ORGANISM: Artificial Sequence
<220> FEATURE:
<223> OTHER INFORMATION: Chimeric DNA polymerase Li9N

<400> SEQUENCE: 21

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220
```

-continued

Lys Leu Gly Val Arg Leu Val Leu Gly Arg Asp Lys Glu His Pro Glu
225 230 235 240

Pro Lys Ile Gln Arg Met Gly Asp Ser Phe Ala Val Glu Ile Lys Gly
245 250 255

Arg Ile His Phe Asp Leu Phe Pro Val Val Arg Arg Thr Ile Asn Leu
260 265 270

Pro Thr Tyr Thr Leu Glu Ala Val Tyr Glu Ala Val Leu Gly Lys Thr
275 280 285

Lys Ser Lys Leu Gly Ala Glu Glu Ile Ala Ala Ile Trp Glu Thr Glu
290 295 300

Glu Ser Met Lys Lys Leu Ala Gln Tyr Ser Met Glu Asp Ala Arg Ala
305 310 315 320

Thr Tyr Glu Leu Gly Lys Glu Phe Phe Pro Met Glu Ala Glu Leu Ala
325 330 335

Lys Leu Ile Gly Gln Ser Val Trp Asp Val Ser Arg Ser Ser Thr Gly
340 345 350

Asn Leu Val Glu Trp Phe Leu Leu Arg Lys Ala Tyr Lys Arg Asn Glu
355 360 365

Leu Ala Pro Asn Lys Pro Asp Glu Arg Glu Leu Ala Arg Arg Arg Gly
370 375 380

Gly Tyr Ala Gly Gly Tyr Val Lys Glu Pro Glu Arg Gly Leu Trp Asp
385 390 395 400

Asn Ile Val Tyr Leu Asp Phe Arg Ser Leu Tyr Pro Ser Ile Ile Ile
405 410 415

Thr His Asn Val Ser Pro Asp Thr Leu Asn Arg Glu Gly Cys Lys Glu
420 425 430

Tyr Asp Val Ala Pro Glu Val Gly His Lys Phe Cys Lys Asp Phe Pro
435 440 445

Gly Phe Ile Pro Ser Leu Leu Gly Asp Leu Leu Glu Glu Arg Gln Lys
450 455 460

Ile Lys Arg Lys Met Lys Ala Thr Val Asp Pro Leu Glu Lys Lys Leu
465 470 475 480

Leu Asp Tyr Arg Gln Arg Ala Ile Lys Ile Leu Ala Asn Ser Phe Tyr
485 490 495

Gly Tyr Tyr Gly Tyr Ala Lys Ala Arg Trp Tyr Cys Lys Glu Cys Ala
500 505 510

Glu Ser Val Thr Ala Trp Gly Arg Glu Tyr Ile Glu Met Val Ile Arg
515 520 525

Glu Leu Glu Glu Lys Phe Gly Phe Lys Val Leu Tyr Ala Asp Thr Asp
530 535 540

Gly Leu His Ala Thr Ile Pro Gly Ala Asp Ala Glu Thr Val Lys Lys
545 550 555 560

Lys Ala Lys Glu Phe Leu Lys Tyr Ile Asn Pro Lys Leu Pro Gly Leu
565 570 575

Leu Glu Leu Glu Tyr Glu Gly Phe Tyr Leu Arg Gly Phe Phe Val Thr
580 585 590

Lys Lys Arg Tyr Ala Val Ile Asp Glu Glu Gly Arg Ile Thr Thr Arg
595 600 605

Gly Leu Glu Val Val Arg Arg Asp Trp Ser Glu Ile Ala Lys Glu Thr
610 615 620

Gln Ala Lys Val Leu Glu Ala Ile Leu Lys Glu Gly Ser Val Glu Lys
625 630 635 640

Ala Val Glu Val Val Arg Asp Val Val Glu Lys Ile Ala Lys Tyr Arg

```
                645                 650                 655

Val Pro Leu Glu Lys Leu Val Ile His Glu Gln Ile Thr Arg Asp Leu
            660                 665                 670

Lys Asp Tyr Lys Ala Ile Gly Pro His Val Ala Ile Ala Lys Arg Leu
        675                 680                 685

Ala Ala Arg Gly Ile Lys Val Lys Pro Gly Thr Ile Ile Ser Tyr Ile
    690                 695                 700

Val Leu Lys Gly Ser Gly Lys Ile Ser Asp Arg Val Ile Leu Leu Thr
705                 710                 715                 720

Glu Tyr Asp Pro Arg Lys His Lys Tyr Asp Pro Asp Tyr Tyr Ile Glu
                725                 730                 735

Asn Gln Val Leu Pro Ala Val Leu Arg Ile Leu Glu Ala Phe Gly Tyr
            740                 745                 750

Arg Lys Glu Asp Leu Arg Tyr Gln Ser Ser Lys Gln Thr Gly Leu Asp
        755                 760                 765

Ala Trp Leu Lys Arg
    770


<210> SEQ ID NO 22
<211> LENGTH: 773
<212> TYPE: PRT
<213> ORGANISM: Thermococcus sp.

<400> SEQUENCE: 22

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240
```

-continued

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Ile Phe Gly Gln Pro Lys Glu
275 280 285

Lys Val Tyr Ala Glu Glu Ile Ala Gln Ala Trp Glu Thr Gly Glu Gly
290 295 300

Leu Glu Arg Val Ala Arg Tyr Ser Met Glu Asp Ala Lys Val Thr Tyr
305 310 315 320

Glu Leu Gly Lys Glu Phe Phe Pro Met Glu Ala Gln Leu Ser Arg Leu
325 330 335

Val Gly Gln Ser Leu Trp Asp Val Ser Arg Ser Ser Thr Gly Asn Leu
340 345 350

Val Glu Trp Phe Leu Leu Arg Lys Ala Tyr Glu Arg Asn Glu Leu Ala
355 360 365

Pro Asn Lys Pro Asp Glu Arg Glu Leu Ala Arg Arg Arg Glu Ser Tyr
370 375 380

Ala Gly Gly Tyr Val Lys Glu Pro Glu Arg Gly Leu Trp Glu Asn Ile
385 390 395 400

Val Tyr Leu Asp Phe Arg Ser Leu Tyr Pro Ser Ile Ile Ile Thr His
405 410 415

Asn Val Ser Pro Asp Thr Leu Asn Arg Glu Gly Cys Glu Glu Tyr Asp
420 425 430

Val Ala Pro Gln Val Gly His Lys Phe Cys Lys Asp Phe Pro Gly Phe
435 440 445

Ile Pro Ser Leu Leu Gly Asp Leu Leu Glu Glu Arg Gln Lys Val Lys
450 455 460

Lys Lys Met Lys Ala Thr Ile Asp Pro Ile Glu Lys Lys Leu Leu Asp
465 470 475 480

Tyr Arg Gln Arg Ala Ile Lys Ile Leu Ala Asn Ser Phe Tyr Gly Tyr
485 490 495

Tyr Gly Tyr Ala Lys Ala Arg Trp Tyr Cys Lys Glu Cys Ala Glu Ser
500 505 510

Val Thr Ala Trp Gly Arg Gln Tyr Ile Glu Thr Thr Ile Arg Glu Ile
515 520 525

Glu Glu Lys Phe Gly Phe Lys Val Leu Tyr Ala Asp Thr Asp Gly Phe
530 535 540

Phe Ala Thr Ile Pro Gly Ala Asp Ala Glu Thr Val Lys Lys Lys Ala
545 550 555 560

Lys Glu Phe Leu Asp Tyr Ile Asn Ala Lys Leu Pro Gly Leu Leu Glu
565 570 575

Leu Glu Tyr Glu Gly Phe Tyr Lys Arg Gly Phe Phe Val Thr Lys Lys
580 585 590

Lys Tyr Ala Val Ile Asp Glu Glu Asp Lys Ile Thr Thr Arg Gly Leu
595 600 605

Glu Ile Val Arg Arg Asp Trp Ser Glu Ile Ala Lys Glu Thr Gln Ala
610 615 620

Arg Val Leu Glu Ala Ile Leu Lys His Gly Asp Val Glu Glu Ala Val
625 630 635 640

Arg Ile Val Lys Glu Val Thr Glu Lys Leu Ser Lys Tyr Glu Val Pro
645 650 655

Pro Glu Lys Leu Val Ile Tyr Glu Gln Ile Thr Arg Asp Leu Lys Asp

```
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 23
<211> LENGTH: 773
<212> TYPE: PRT
<213> ORGANISM: Thermococcus sp.

<400> SEQUENCE: 23

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255
```

-continued

```
His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Arg Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asp Leu Arg Asp
            660                 665                 670

Tyr Arg Ala Thr Gly Pro His Val Ala Val Ala Lys Arg Leu Ala Ala
```

```
        675                 680                 685

Arg Gly Ile Lys Ile Arg Pro Gly Thr Val Ile Ser Tyr Ile Val Leu
    690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr
    770


<210> SEQ ID NO 24
<211> LENGTH: 773
<212> TYPE: PRT
<213> ORGANISM: Artificial Sequence
<220> FEATURE:
<223> OTHER INFORMATION: Chimeric DNA polymerase GoZi

<400> SEQUENCE: 24

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
```

-continued

```
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685
```

```
Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 25
<211> LENGTH: 773
<212> TYPE: PRT
<213> ORGANISM: Artificial Sequence
<220> FEATURE:
<223> OTHER INFORMATION: Chimeric DNA polymerase ZiGo

<400> SEQUENCE: 25

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270
```

-continued

```
Tyr Thr Leu Glu Thr Val Tyr Glu Ala Ile Phe Gly Gln Pro Lys Glu
        275                 280                 285

Lys Val Tyr Ala Glu Glu Ile Ala Arg Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asp Leu Arg Asp
            660                 665                 670

Tyr Arg Ala Thr Gly Pro His Val Ala Val Ala Lys Arg Leu Ala Ala
        675                 680                 685
```

```
Arg Gly Ile Lys Ile Arg Pro Gly Thr Val Ile Ser Tyr Ile Val Leu
    690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr
    770


<210> SEQ ID NO 26
<211> LENGTH: 778
<212> TYPE: PRT
<213> ORGANISM: Artificial Sequence
<220> FEATURE:
<223> OTHER INFORMATION: Chimeric DNA polymerase Kofu-II

<400> SEQUENCE: 26

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270
```

-continued

```
Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Val Gly Gln Pro Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Val Ala Pro Asn Lys Pro Ser Glu Glu Glu Tyr Gln Arg Arg Leu
    370                 375                 380

Arg Glu Ser Tyr Thr Gly Gly Phe Val Lys Glu Pro Glu Lys Gly Leu
385                 390                 395                 400

Trp Glu Asn Ile Val Tyr Leu Asp Phe Arg Ala Leu Tyr Pro Ser Ile
                405                 410                 415

Ile Ile Thr His Asn Val Ser Pro Asp Thr Leu Asn Leu Glu Gly Cys
            420                 425                 430

Lys Asn Tyr Asp Ile Ala Pro Gln Val Gly His Lys Phe Cys Lys Asp
        435                 440                 445

Ile Pro Gly Phe Ile Pro Ser Leu Leu Gly His Leu Leu Glu Glu Arg
    450                 455                 460

Gln Lys Ile Lys Thr Lys Met Lys Glu Thr Gln Asp Pro Ile Glu Lys
465                 470                 475                 480

Ile Leu Leu Asp Tyr Arg Gln Lys Ala Ile Lys Leu Leu Ala Asn Ser
                485                 490                 495

Phe Tyr Gly Tyr Tyr Gly Tyr Ala Lys Ala Arg Trp Tyr Cys Lys Glu
            500                 505                 510

Cys Ala Glu Ser Val Thr Ala Trp Gly Arg Lys Tyr Ile Glu Leu Val
        515                 520                 525

Trp Lys Glu Leu Glu Glu Lys Phe Gly Phe Lys Val Leu Tyr Ile Asp
    530                 535                 540

Thr Asp Gly Leu Tyr Ala Thr Ile Pro Gly Gly Glu Ser Glu Glu Ile
545                 550                 555                 560

Lys Lys Lys Ala Leu Glu Phe Val Lys Tyr Ile Asn Ser Lys Leu Pro
                565                 570                 575

Gly Leu Leu Glu Leu Glu Tyr Glu Gly Phe Tyr Lys Arg Gly Phe Phe
            580                 585                 590

Val Thr Lys Lys Arg Tyr Ala Val Ile Asp Glu Glu Gly Lys Val Ile
        595                 600                 605

Thr Arg Gly Leu Glu Ile Val Arg Arg Asp Trp Ser Glu Ile Ala Lys
    610                 615                 620

Glu Thr Gln Ala Arg Val Leu Glu Ala Leu Leu Lys Asp Gly Asp Val
625                 630                 635                 640

Glu Lys Ala Val Arg Ile Val Lys Glu Val Thr Glu Lys Leu Ser Lys
                645                 650                 655

Tyr Glu Val Pro Pro Glu Lys Leu Val Ile His Glu Gln Ile Thr Arg
            660                 665                 670

Asp Leu Lys Asp Tyr Lys Ala Thr Gly Pro His Val Ala Val Ala Lys
        675                 680                 685

Arg Leu Ala Ala Arg Gly Val Lys Ile Arg Pro Gly Thr Val Ile Ser
```

-continued

```
    690                 695                 700

Tyr Ile Val Leu Lys Gly Ser Gly Arg Ile Gly Asp Arg Ala Ile Pro
705                 710                 715                 720

Phe Asp Glu Phe Asp Pro Thr Lys His Lys Tyr Asp Ala Glu Tyr Tyr
                725                 730                 735

Ile Glu Asn Gln Val Leu Pro Ala Val Glu Arg Ile Leu Arg Ala Phe
            740                 745                 750

Gly Tyr Arg Lys Glu Asp Leu Arg Tyr Gln Lys Thr Arg Gln Val Gly
        755                 760                 765

Leu Ser Ala Trp Leu Lys Pro Lys Gly Thr
    770                 775


<210> SEQ ID NO 27
<211> LENGTH: 777
<212> TYPE: PRT
<213> ORGANISM: Artificial Sequence
<220> FEATURE:
<223> OTHER INFORMATION: Chimeric DNA polymerase Pod-II

<400> SEQUENCE: 27

Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270

Leu Pro Thr Tyr Thr Leu Glu Ala Val Tyr Glu Ala Ile Phe Gly Lys
```

-continued

```
        275                 280                 285

Pro Lys Glu Lys Val Tyr Ala Asp Glu Ile Ala Lys Ala Trp Glu Ser
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Glu Leu Ala Arg Arg Arg
    370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
        435                 440                 445

Pro Gly Phe Ile Pro Ser Leu Leu Gly Asp Leu Leu Glu Glu Arg Gln
    450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
        515                 520                 525

Lys Glu Ile Glu Glu Lys Tyr Gly Phe Lys Val Ile Tyr Ser Asp Thr
    530                 535                 540

Asp Gly Phe Phe Ala Thr Ile Pro Gly Ala Asp Ala Glu Thr Val Lys
545                 550                 555                 560

Lys Lys Ala Met Glu Phe Leu Lys Tyr Ile Asn Ala Lys Leu Pro Gly
                565                 570                 575

Ala Leu Glu Leu Glu Tyr Glu Gly Phe Tyr Lys Arg Gly Phe Phe Val
            580                 585                 590

Thr Lys Lys Lys Tyr Ala Val Ile Asp Glu Glu Gly Lys Ile Thr Thr
        595                 600                 605

Arg Gly Leu Glu Ile Val Arg Arg Asp Trp Ser Glu Ile Ala Lys Glu
    610                 615                 620

Thr Gln Ala Arg Val Leu Glu Thr Ile Leu Lys His Gly Asp Val Glu
625                 630                 635                 640

Glu Ala Val Arg Ile Val Lys Glu Val Ile Gln Lys Leu Ala Asn Tyr
                645                 650                 655

Glu Ile Pro Pro Glu Lys Leu Ala Ile Tyr Glu Gln Ile Thr Arg Pro
            660                 665                 670

Leu His Glu Tyr Lys Ala Ile Gly Pro His Val Ala Val Ala Lys Lys
        675                 680                 685

Leu Ala Ala Lys Gly Val Lys Ile Lys Pro Gly Met Val Ile Gly Tyr
    690                 695                 700
```

```
Ile Val Leu Arg Gly Asp Gly Pro Ile Ser Asn Arg Ala Ile Leu Ala
705                 710                 715                 720

Glu Glu Tyr Asp Pro Lys Lys His Lys Tyr Asp Ala Glu Tyr Tyr Ile
                725                 730                 735

Glu Asn Gln Val Leu Pro Ala Val Leu Arg Ile Leu Glu Gly Phe Gly
            740                 745                 750

Tyr Arg Lys Glu Asp Leu Arg Tyr Gln Lys Thr Arg Gln Val Gly Leu
        755                 760                 765

Thr Ser Trp Leu Asn Ile Lys Lys Ser
    770                 775
```

<210> SEQ ID NO 28
<211> LENGTH: 777
<212> TYPE: PRT
<213> ORGANISM: Artificial Sequence
<220> FEATURE:
<223> OTHER INFORMATION: Chimeric DNA polymerase Kofu-III

<400> SEQUENCE: 28

```
Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285
```

-continued

```
Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Glu Leu Ala Arg Arg Arg
    370                 375                 380

Gln Ser Tyr Glu Gly Gly Tyr Val Lys Glu Pro Glu Lys Gly Leu Trp
385                 390                 395                 400

Glu Asn Ile Val Tyr Leu Asp Phe Arg Ala Leu Tyr Pro Ser Ile Ile
                405                 410                 415

Ile Thr His Asn Val Ser Pro Asp Thr Leu Asn Leu Glu Gly Cys Lys
            420                 425                 430

Asn Tyr Asp Ile Ala Pro Gln Val Gly His Lys Phe Cys Lys Asp Ile
        435                 440                 445

Pro Gly Phe Ile Pro Ser Leu Leu Gly His Leu Leu Glu Glu Arg Gln
    450                 455                 460

Lys Ile Lys Thr Lys Met Lys Glu Thr Gln Asp Pro Ile Glu Lys Ile
465                 470                 475                 480

Leu Leu Asp Tyr Arg Gln Lys Ala Ile Lys Leu Leu Ala Asn Ser Phe
                485                 490                 495

Tyr Gly Tyr Tyr Gly Tyr Ala Lys Ala Arg Trp Tyr Cys Lys Glu Cys
            500                 505                 510

Ala Glu Ser Val Thr Ala Trp Gly Arg Lys Tyr Ile Glu Leu Val Trp
        515                 520                 525

Lys Glu Leu Glu Glu Lys Phe Gly Phe Lys Val Leu Tyr Ile Asp Thr
    530                 535                 540

Asp Gly Leu Tyr Ala Thr Ile Pro Gly Gly Glu Ser Glu Glu Ile Lys
545                 550                 555                 560

Lys Lys Ala Leu Glu Phe Leu Lys Tyr Ile Asn Ala Lys Leu Pro Gly
                565                 570                 575

Ala Leu Glu Leu Glu Tyr Glu Gly Phe Tyr Lys Arg Gly Phe Phe Val
            580                 585                 590

Thr Lys Lys Lys Tyr Ala Val Ile Asp Glu Glu Gly Lys Ile Thr Thr
        595                 600                 605

Arg Gly Leu Glu Ile Val Arg Arg Asp Trp Ser Glu Ile Ala Lys Glu
    610                 615                 620

Thr Gln Ala Arg Val Leu Glu Ala Leu Leu Lys Asp Gly Asp Val Glu
625                 630                 635                 640

Lys Ala Val Arg Ile Val Lys Glu Val Thr Glu Lys Leu Ser Lys Tyr
                645                 650                 655

Glu Val Pro Pro Glu Lys Leu Val Ile His Glu Gln Ile Thr Arg Asp
            660                 665                 670

Leu Lys Asp Tyr Lys Ala Thr Gly Pro His Val Ala Val Ala Lys Arg
        675                 680                 685

Leu Ala Ala Arg Gly Val Lys Ile Arg Pro Gly Thr Val Ile Ser Tyr
    690                 695                 700
```

```
Ile Val Leu Lys Gly Ser Gly Arg Ile Gly Asp Arg Ala Ile Pro Phe
705                 710                 715                 720

Asp Glu Phe Asp Pro Thr Lys His Lys Tyr Asp Ala Glu Tyr Tyr Ile
                725                 730                 735

Glu Asn Gln Val Leu Pro Ala Val Glu Arg Ile Leu Arg Ala Phe Gly
            740                 745                 750

Tyr Arg Lys Glu Asp Leu Arg Tyr Gln Lys Thr Arg Gln Val Gly Leu
        755                 760                 765

Ser Ala Trp Leu Lys Pro Lys Gly Thr
    770                 775


<210> SEQ ID NO 29
<211> LENGTH: 778
<212> TYPE: PRT
<213> ORGANISM: Artificial Sequence
<220> FEATURE:
<223> OTHER INFORMATION: Chimeric DNA polymerase Pod-III

<400> SEQUENCE: 29

Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270

Leu Pro Thr Tyr Thr Leu Glu Ala Val Tyr Glu Ala Ile Phe Gly Lys
        275                 280                 285
```

```
Pro Lys Glu Lys Val Tyr Ala Asp Glu Ile Ala Lys Ala Trp Glu Ser
    290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Val Gly Gln Pro Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Val Ala Pro Asn Lys Pro Ser Glu Glu Glu Tyr Gln Arg Arg Leu
    370                 375                 380

Arg Glu Ser Tyr Thr Gly Gly Phe Val Lys Glu Pro Glu Arg Gly Leu
385                 390                 395                 400

Trp Glu Asn Ile Val Tyr Leu Asp Phe Arg Ser Leu Tyr Pro Ser Ile
                405                 410                 415

Ile Ile Thr His Asn Val Ser Pro Asp Thr Leu Asn Arg Glu Gly Cys
            420                 425                 430

Lys Glu Tyr Asp Val Ala Pro Gln Val Gly His Arg Phe Cys Lys Asp
        435                 440                 445

Phe Pro Gly Phe Ile Pro Ser Leu Leu Gly Asp Leu Leu Glu Glu Arg
    450                 455                 460

Gln Lys Ile Lys Lys Lys Met Lys Ala Thr Ile Asp Pro Ile Glu Arg
465                 470                 475                 480

Lys Leu Leu Asp Tyr Arg Gln Arg Ala Ile Lys Ile Leu Ala Asn Ser
                485                 490                 495

Tyr Tyr Gly Tyr Tyr Gly Tyr Ala Arg Ala Arg Trp Tyr Cys Lys Glu
            500                 505                 510

Cys Ala Glu Ser Val Thr Ala Trp Gly Arg Glu Tyr Ile Thr Met Thr
        515                 520                 525

Ile Lys Glu Ile Glu Glu Lys Tyr Gly Phe Lys Val Ile Tyr Ser Asp
    530                 535                 540

Thr Asp Gly Phe Phe Ala Thr Ile Pro Gly Ala Asp Ala Glu Thr Val
545                 550                 555                 560

Lys Lys Lys Ala Met Glu Phe Val Lys Tyr Ile Asn Ser Lys Leu Pro
                565                 570                 575

Gly Leu Leu Glu Leu Glu Tyr Glu Gly Phe Tyr Lys Arg Gly Phe Phe
            580                 585                 590

Val Thr Lys Lys Arg Tyr Ala Val Ile Asp Glu Glu Gly Lys Val Ile
        595                 600                 605

Thr Arg Gly Leu Glu Ile Val Arg Arg Asp Trp Ser Glu Ile Ala Lys
    610                 615                 620

Glu Thr Gln Ala Arg Val Leu Glu Thr Ile Leu Lys His Gly Asp Val
625                 630                 635                 640

Glu Glu Ala Val Arg Ile Val Lys Glu Val Ile Gln Lys Leu Ala Asn
                645                 650                 655

Tyr Glu Ile Pro Pro Glu Lys Leu Ala Ile Tyr Glu Gln Ile Thr Arg
            660                 665                 670

Pro Leu His Glu Tyr Lys Ala Ile Gly Pro His Val Ala Val Ala Lys
        675                 680                 685

Lys Leu Ala Ala Lys Gly Val Lys Ile Lys Pro Gly Met Val Ile Gly
    690                 695                 700

Tyr Ile Val Leu Arg Gly Asp Gly Pro Ile Ser Asn Arg Ala Ile Leu
```

```
705                 710                 715                 720

Ala Glu Glu Tyr Asp Pro Lys Lys His Lys Tyr Asp Ala Glu Tyr Tyr
                725                 730                 735

Ile Glu Asn Gln Val Leu Pro Ala Val Leu Arg Ile Leu Glu Gly Phe
            740                 745                 750

Gly Tyr Arg Lys Glu Asp Leu Arg Tyr Gln Lys Thr Arg Gln Val Gly
        755                 760                 765

Leu Thr Ser Trp Leu Asn Ile Lys Lys Ser
    770                 775
```

```
<210> SEQ ID NO 30
<211> LENGTH: 150
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(2)
<223> OTHER INFORMATION: Xaa is any amino acid or absent
<220> FEATURE:
<221> NAME/KEY: Xaa
<222> LOCATION: (4)..(10)
<223> OTHER INFORMATION: Xaa is any amino acid or absent
<220> FEATURE:
<221> NAME/KEY: Xaa
<222> LOCATION: (13)..(13)
<223> OTHER INFORMATION: Xaa is any amino acid or absent
<220> FEATURE:
<221> NAME/KEY: Xaa
<222> LOCATION: (15)..(20)
<223> OTHER INFORMATION: Xaa is any amino acid or absent
<220> FEATURE:
<221> NAME/KEY: Xaa
<222> LOCATION: (22)..(26)
<223> OTHER INFORMATION: Xaa is any amino acid or absent
<220> FEATURE:
<221> NAME/KEY: Xaa
<222> LOCATION: (28)..(30)
<223> OTHER INFORMATION: Xaa is any amino acid or absent
<220> FEATURE:
<221> NAME/KEY: Xaa
<222> LOCATION: (32)..(41)
<223> OTHER INFORMATION: Xaa is any amino acid or absent
<220> FEATURE:
<221> NAME/KEY: Xaa
<222> LOCATION: (45)..(49)
<223> OTHER INFORMATION: Xaa is any amino acid or absent
<220> FEATURE:
<221> NAME/KEY: Xaa
<222> LOCATION: (53)..(57)
<223> OTHER INFORMATION: Xaa is any amino acid or absent
<220> FEATURE:
<221> NAME/KEY: Xaa
<222> LOCATION: (59)..(61)
<223> OTHER INFORMATION: Xaa is any amino acid or absent
<220> FEATURE:
<221> NAME/KEY: Xaa
<222> LOCATION: (63)..(64)
<223> OTHER INFORMATION: Xaa is any amino acid or absent
<220> FEATURE:
<221> NAME/KEY: Xaa
<222> LOCATION: (66)..(67)
<223> OTHER INFORMATION: Xaa is any amino acid or absent
<220> FEATURE:
<221> NAME/KEY: Xaa
<222> LOCATION: (69)..(73)
<223> OTHER INFORMATION: Xaa is any amino acid or absent
<220> FEATURE:
<221> NAME/KEY: Xaa
<222> LOCATION: (78)..(89)
<223> OTHER INFORMATION: Xaa is any amino acid or absent
<220> FEATURE:
<221> NAME/KEY: Xaa
```

<222> LOCATION: (91)..(92)
<223> OTHER INFORMATION: Xaa is any amino acid or absent
<220> FEATURE:
<221> NAME/KEY: Xaa
<222> LOCATION: (94)..(95)
<223> OTHER INFORMATION: Xaa is any amino acid or absent
<220> FEATURE:
<221> NAME/KEY: Xaa
<222> LOCATION: (98)..(110)
<223> OTHER INFORMATION: Xaa is any amino acid or absent
<220> FEATURE:
<221> NAME/KEY: Xaa
<222> LOCATION: (112)..(113)
<223> OTHER INFORMATION: Xaa is any amino acid or absent
<220> FEATURE:
<221> NAME/KEY: Xaa
<222> LOCATION: (115)..(130)
<223> OTHER INFORMATION: Xaa is any amino acid or absent
<220> FEATURE:
<221> NAME/KEY: Xaa
<222> LOCATION: (132)..(133)
<223> OTHER INFORMATION: Xaa is any amino acid or absent
<220> FEATURE:
<221> NAME/KEY: Xaa
<222> LOCATION: (135)..(141)
<223> OTHER INFORMATION: Xaa is any amino acid or absent
<220> FEATURE:
<221> NAME/KEY: Xaa
<222> LOCATION: (143)..(144)
<223> OTHER INFORMATION: Xaa is any amino acid or absent
<220> FEATURE:
<221> NAME/KEY: Xaa
<222> LOCATION: (147)..(149)
<223> OTHER INFORMATION: Xaa is any amino acid or absent

<400> SEQUENCE: 30

```
Xaa Xaa Leu Xaa Xaa Xaa Xaa Xaa Xaa Xaa Glu Gly Xaa Arg Xaa Xaa
1               5                   10                  15

Xaa Xaa Xaa Xaa Val Xaa Xaa Xaa Xaa Xaa Asp Xaa Xaa Xaa Thr Xaa
            20                  25                  30

Xaa Xaa Xaa Xaa Xaa Xaa Xaa Xaa Xaa Val Val Lys Xaa Xaa Xaa Xaa
        35                  40                  45

Xaa Val Leu Ile Xaa Xaa Xaa Xaa Xaa Asn Xaa Xaa Xaa Ala Xaa Xaa
    50                  55                  60

Lys Xaa Xaa Cys Xaa Xaa Xaa Xaa Xaa Asn Phe Ala Leu Xaa Xaa Xaa
65                  70                  75                  80

Xaa Xaa Xaa Xaa Xaa Xaa Xaa Xaa Xaa Ile Xaa Xaa Met Xaa Xaa Arg
                85                  90                  95

Phe Xaa Xaa Xaa Xaa Xaa Xaa Xaa Xaa Xaa Xaa Xaa Xaa Xaa Pro Xaa
            100                 105                 110

Xaa Arg Xaa Xaa Xaa Xaa Xaa Xaa Xaa Xaa Xaa Xaa Xaa Xaa Xaa Xaa
        115                 120                 125

Xaa Xaa Val Xaa Xaa Gln Xaa Xaa Xaa Xaa Xaa Xaa Xaa Glu Xaa Xaa
    130                 135                 140

Thr Thr Xaa Xaa Xaa Thr
145                 150
```

<210> SEQ ID NO 31
<211> LENGTH: 83
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(2)
<223> OTHER INFORMATION: Xaa is any amino acid or absent
<220> FEATURE:

<221> NAME/KEY: Xaa
<222> LOCATION: (4)..(7)
<223> OTHER INFORMATION: Xaa is any amino acid or absent
<220> FEATURE:
<221> NAME/KEY: Xaa
<222> LOCATION: (9)..(12)
<223> OTHER INFORMATION: Xaa is any amino acid or absent
<220> FEATURE:
<221> NAME/KEY: Xaa
<222> LOCATION: (14)..(15)
<223> OTHER INFORMATION: Xaa is any amino acid or absent
<220> FEATURE:
<221> NAME/KEY: Xaa
<222> LOCATION: (17)..(20)
<223> OTHER INFORMATION: Xaa is any amino acid or absent
<220> FEATURE:
<221> NAME/KEY: Xaa
<222> LOCATION: (22)..(24)
<223> OTHER INFORMATION: Xaa is any amino acid or absent
<220> FEATURE:
<221> NAME/KEY: Xaa
<222> LOCATION: (26)..(33)
<223> OTHER INFORMATION: Xaa is any amino acid or absent
<220> FEATURE:
<221> NAME/KEY: Xaa
<222> LOCATION: (35)..(38)
<223> OTHER INFORMATION: Xaa is any amino acid or absent
<220> FEATURE:
<221> NAME/KEY: Xaa
<222> LOCATION: (41)..(41)
<223> OTHER INFORMATION: Xaa is any amino acid or absent
<220> FEATURE:
<221> NAME/KEY: Xaa
<222> LOCATION: (46)..(49)
<223> OTHER INFORMATION: Xaa is any amino acid or absent
<220> FEATURE:
<221> NAME/KEY: Xaa
<222> LOCATION: (51)..(55)
<223> OTHER INFORMATION: Xaa is any amino acid or absent
<220> FEATURE:
<221> NAME/KEY: Xaa
<222> LOCATION: (57)..(57)
<223> OTHER INFORMATION: Xaa is any amino acid or absent
<220> FEATURE:
<221> NAME/KEY: Xaa
<222> LOCATION: (60)..(64)
<223> OTHER INFORMATION: Xaa is any amino acid or absent
<220> FEATURE:
<221> NAME/KEY: Xaa
<222> LOCATION: (67)..(72)
<223> OTHER INFORMATION: Xaa is any amino acid or absent
<220> FEATURE:
<221> NAME/KEY: Xaa
<222> LOCATION: (74)..(75)
<223> OTHER INFORMATION: Xaa is any amino acid or absent
<220> FEATURE:
<221> NAME/KEY: Xaa
<222> LOCATION: (77)..(77)
<223> OTHER INFORMATION: Xaa is any amino acid or absent
<220> FEATURE:
<221> NAME/KEY: Xaa
<222> LOCATION: (79)..(83)
<223> OTHER INFORMATION: Xaa is any amino acid or absent

<400> SEQUENCE: 31

```
Xaa Xaa Glu Xaa Xaa Xaa Xaa Tyr Xaa Xaa Xaa Xaa Glu Xaa Xaa Phe
1               5                   10                  15

Xaa Xaa Xaa Xaa Lys Xaa Xaa Xaa Ala Xaa Xaa Xaa Xaa Xaa Xaa Xaa
            20                  25                  30

Xaa Ala Xaa Xaa Xaa Xaa Thr Val Xaa Thr Val Lys Arg Xaa Xaa Xaa
        35                  40                  45

Xaa Gln Xaa Xaa Xaa Xaa Xaa Arg Xaa Val Glu Xaa Xaa Xaa Xaa Xaa
    50                  55                  60

Phe Thr Xaa Xaa Xaa Xaa Xaa Xaa Ala Xaa Xaa Asp Xaa Ile Xaa Xaa
```

-continued 65 70 75 80

Xaa Xaa Xaa

<210> SEQ ID NO 32
<211> LENGTH: 137
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(16)
<223> OTHER INFORMATION: Xaa is any amino acid or absent
<220> FEATURE:
<221> NAME/KEY: Xaa
<222> LOCATION: (19)..(20)
<223> OTHER INFORMATION: Xaa is any amino acid or absent
<220> FEATURE:
<221> NAME/KEY: Xaa
<222> LOCATION: (22)..(25)
<223> OTHER INFORMATION: Xaa is any amino acid or absent
<220> FEATURE:
<221> NAME/KEY: Xaa
<222> LOCATION: (27)..(34)
<223> OTHER INFORMATION: Xaa is any amino acid or absent
<220> FEATURE:
<221> NAME/KEY: Xaa
<222> LOCATION: (37)..(38)
<223> OTHER INFORMATION: Xaa is any amino acid or absent
<220> FEATURE:
<221> NAME/KEY: Xaa
<222> LOCATION: (41)..(42)
<223> OTHER INFORMATION: Xaa is any amino acid or absent
<220> FEATURE:
<221> NAME/KEY: Xaa
<222> LOCATION: (44)..(48)
<223> OTHER INFORMATION: Xaa is any amino acid or absent
<220> FEATURE:
<221> NAME/KEY: Xaa
<222> LOCATION: (50)..(50)
<223> OTHER INFORMATION: Xaa is any amino acid or absent
<220> FEATURE:
<221> NAME/KEY: Xaa
<222> LOCATION: (52)..(56)
<223> OTHER INFORMATION: Xaa is any amino acid or absent
<220> FEATURE:
<221> NAME/KEY: Xaa
<222> LOCATION: (58)..(58)
<223> OTHER INFORMATION: Xaa is any amino acid or absent
<220> FEATURE:
<221> NAME/KEY: Xaa
<222> LOCATION: (61)..(63)
<223> OTHER INFORMATION: Xaa is any amino acid or absent
<220> FEATURE:
<221> NAME/KEY: Xaa
<222> LOCATION: (65)..(72)
<223> OTHER INFORMATION: Xaa is any amino acid or absent
<220> FEATURE:
<221> NAME/KEY: Xaa
<222> LOCATION: (74)..(76)
<223> OTHER INFORMATION: Xaa is any amino acid or absent
<220> FEATURE:
<221> NAME/KEY: Xaa
<222> LOCATION: (78)..(81)
<223> OTHER INFORMATION: Xaa is any amino acid or absent
<220> FEATURE:
<221> NAME/KEY: Xaa
<222> LOCATION: (83)..(84)
<223> OTHER INFORMATION: Xaa is any amino acid or absent
<220> FEATURE:
<221> NAME/KEY: Xaa
<222> LOCATION: (86)..(87)
<223> OTHER INFORMATION: Xaa is any amino acid or absent
<220> FEATURE:
<221> NAME/KEY: Xaa
<222> LOCATION: (88)..(92)
<223> OTHER INFORMATION: Xaa is any amino acid or absent

```
<220> FEATURE:
<221> NAME/KEY: Xaa
<222> LOCATION: (94)..(94)
<223> OTHER INFORMATION: Xaa is any amino acid or absent
<220> FEATURE:
<221> NAME/KEY: Xaa
<222> LOCATION: (96)..(96)
<223> OTHER INFORMATION: Xaa is any amino acid or absent
<220> FEATURE:
<221> NAME/KEY: Xaa
<222> LOCATION: (98)..(98)
<223> OTHER INFORMATION: Xaa is any amino acid or absent
<220> FEATURE:
<221> NAME/KEY: Xaa
<222> LOCATION: (101)..(103)
<223> OTHER INFORMATION: Xaa is any amino acid or absent
<220> FEATURE:
<221> NAME/KEY: Xaa
<222> LOCATION: (107)..(107)
<223> OTHER INFORMATION: Xaa is any amino acid or absent
<220> FEATURE:
<221> NAME/KEY: Xaa
<222> LOCATION: (109)..(110)
<223> OTHER INFORMATION: Xaa is any amino acid or absent
<220> FEATURE:
<221> NAME/KEY: Xaa
<222> LOCATION: (112)..(129)
<223> OTHER INFORMATION: Xaa is any amino acid or absent
<220> FEATURE:
<221> NAME/KEY: Xaa
<222> LOCATION: (131)..(133)
<223> OTHER INFORMATION: Xaa is any amino acid or absent
<220> FEATURE:
<221> NAME/KEY: Xaa
<222> LOCATION: (136)..(137)
<223> OTHER INFORMATION: Xaa is any amino acid or absent

<400> SEQUENCE: 32

Xaa Xaa Xaa Xaa Xaa Xaa Xaa Xaa Xaa Xaa Xaa Xaa Xaa Xaa Xaa Xaa
1               5                   10                  15

Ala Leu Xaa Xaa Asp Xaa Xaa Xaa Xaa Lys Xaa Xaa Xaa Xaa Xaa Xaa
            20                  25                  30

Xaa Xaa Thr Glu Xaa Xaa Ser Lys Xaa Xaa Val Xaa Xaa Xaa Xaa Xaa
        35                  40                  45

Val Xaa His Xaa Xaa Xaa Xaa Xaa Asp Xaa Lys Asp Xaa Xaa Xaa Thr
    50                  55                  60

Xaa Xaa Xaa Xaa Xaa Xaa Xaa Xaa Arg Xaa Xaa Xaa Arg Xaa Xaa Xaa
65                  70                  75                  80

Xaa Arg Xaa Xaa Thr Xaa Xaa Ser Xaa Xaa Xaa Xaa Lys Xaa Ser Xaa
                85                  90                  95

Arg Xaa Gly Asp Xaa Xaa Xaa Pro Phe Asp Xaa Phe Xaa Xaa Thr Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Glu Xaa Xaa Xaa Arg Ala Xaa Xaa
    130                 135


<210> SEQ ID NO 33
<211> LENGTH: 83
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (3)..(3)
<223> OTHER INFORMATION: Xaa is any amino acid or absent, but not K
<220> FEATURE:
<221> NAME/KEY: Xaa
```

<222> LOCATION: (8)..(8)
<223> OTHER INFORMATION: Xaa is any amino acid or absent, but not H
<220> FEATURE:
<221> NAME/KEY: Xaa
<222> LOCATION: (13)..(13)
<223> OTHER INFORMATION: Xaa is any amino acid or absent, but not R
<220> FEATURE:
<221> NAME/KEY: Xaa
<222> LOCATION: (16)..(16)
<223> OTHER INFORMATION: Xaa is any amino acid or absent, but not I
<220> FEATURE:
<221> NAME/KEY: Xaa
<222> LOCATION: (21)..(21)
<223> OTHER INFORMATION: Xaa is any amino acid or absent, but not R
<220> FEATURE:
<221> NAME/KEY: Xaa
<222> LOCATION: (25)..(25)
<223> OTHER INFORMATION: Xaa is any amino acid or absent, but not K
<220> FEATURE:
<221> NAME/KEY: Xaa
<222> LOCATION: (34)..(34)
<223> OTHER INFORMATION: Xaa is any amino acid or absent, but not G
<220> FEATURE:
<221> NAME/KEY: Xaa
<222> LOCATION: (39)..(39)
<223> OTHER INFORMATION: Xaa is any amino acid or absent, but not K
<220> FEATURE:
<221> NAME/KEY: Xaa
<222> LOCATION: (40)..(40)
<223> OTHER INFORMATION: Xaa is any amino acid or absent, but not I
<220> FEATURE:
<221> NAME/KEY: Xaa
<222> LOCATION: (42)..(42)
<223> OTHER INFORMATION: Xaa is any amino acid or absent, but not R
<220> FEATURE:
<221> NAME/KEY: Xaa
<222> LOCATION: (43)..(43)
<223> OTHER INFORMATION: Xaa is any amino acid or absent, but not I
<220> FEATURE:
<221> NAME/KEY: Xaa
<222> LOCATION: (44)..(44)
<223> OTHER INFORMATION: Xaa is any amino acid or absent, but not V
<220> FEATURE:
<221> NAME/KEY: Xaa
<222> LOCATION: (45)..(45)
<223> OTHER INFORMATION: Xaa is any amino acid or absent, but not D
<220> FEATURE:
<221> NAME/KEY: Xaa
<222> LOCATION: (50)..(50)
<223> OTHER INFORMATION: Xaa is any amino acid or absent, but not E
<220> FEATURE:
<221> NAME/KEY: Xaa
<222> LOCATION: (56)..(56)
<223> OTHER INFORMATION: Xaa is any amino acid or absent, but not K
<220> FEATURE:
<221> NAME/KEY: Xaa
<222> LOCATION: (58)..(58)
<223> OTHER INFORMATION: Xaa is any amino acid or absent, but not I
<220> FEATURE:
<221> NAME/KEY: Xaa
<222> LOCATION: (59)..(59)
<223> OTHER INFORMATION: Xaa is any amino acid or absent, but not T
<220> FEATURE:
<221> NAME/KEY: Xaa
<222> LOCATION: (65)..(65)
<223> OTHER INFORMATION: Xaa is any amino acid or absent, but not L
<220> FEATURE:
<221> NAME/KEY: Xaa
<222> LOCATION: (66)..(66)
<223> OTHER INFORMATION: Xaa is any amino acid or absent, but not E
<220> FEATURE:
<221> NAME/KEY: Xaa
<222> LOCATION: (73)..(73)
<223> OTHER INFORMATION: Xaa is any amino acid or absent, but not T
<220> FEATURE:
<221> NAME/KEY: Xaa
<222> LOCATION: (76)..(76)
<223> OTHER INFORMATION: Xaa is any amino acid or absent, but not E
<220> FEATURE:

<221> NAME/KEY: Xaa
<222> LOCATION: (78)..(78)
<223> OTHER INFORMATION: Xaa is any amino acid or absent, but not V

<400> SEQUENCE: 33

```
Asn Gly Xaa Phe Lys Ile Glu Xaa Asp Arg Thr Phe Xaa Pro Tyr Xaa
1               5                   10                  15

Tyr Ala Leu Leu Xaa Asp Asp Ser Xaa Ile Glu Glu Val Lys Lys Ile
            20                  25                  30

Thr Xaa Glu Arg His Gly Xaa Xaa Val Xaa Xaa Xaa Xaa Val Glu Lys
        35                  40                  45

Val Xaa Lys Lys Phe Leu Gly Xaa Pro Xaa Xaa Val Trp Lys Leu Tyr
    50                  55                  60

Xaa Xaa His Pro Gln Asp Val Pro Xaa Ile Arg Xaa Lys Xaa Arg Glu
65                  70                  75                  80

His Pro Ala
```

<210> SEQ ID NO 34
<211> LENGTH: 146
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (3)..(3)
<223> OTHER INFORMATION: Xaa is any amino acid or absent, but not I
<220> FEATURE:
<221> NAME/KEY: Xaa
<222> LOCATION: (11)..(11)
<223> OTHER INFORMATION: Xaa is any amino acid or absent, but not N
<220> FEATURE:
<221> NAME/KEY: Xaa
<222> LOCATION: (12)..(12)
<223> OTHER INFORMATION: Xaa is any amino acid or absent, but not E
<220> FEATURE:
<221> NAME/KEY: Xaa
<222> LOCATION: (14)..(14)
<223> OTHER INFORMATION: Xaa is any amino acid or absent, but not K
<220> FEATURE:
<221> NAME/KEY: Xaa
<222> LOCATION: (21)..(21)
<223> OTHER INFORMATION: Xaa is any amino acid or absent, but not I
<220> FEATURE:
<221> NAME/KEY: Xaa
<222> LOCATION: (27)..(27)
<223> OTHER INFORMATION: Xaa is any amino acid or absent, but not E
<220> FEATURE:
<221> NAME/KEY: Xaa
<222> LOCATION: (31)..(31)
<223> OTHER INFORMATION: Xaa is any amino acid or absent, but not S
<220> FEATURE:
<221> NAME/KEY: Xaa
<222> LOCATION: (42)..(42)
<223> OTHER INFORMATION: Xaa is any amino acid or absent, but not I
<220> FEATURE:
<221> NAME/KEY: Xaa
<222> LOCATION: (43)..(43)
<223> OTHER INFORMATION: Xaa is any amino acid or absent, but not I
<220> FEATURE:
<221> NAME/KEY: Xaa
<222> LOCATION: (44)..(44)
<223> OTHER INFORMATION: Xaa is any amino acid or absent, but not R
<220> FEATURE:
<221> NAME/KEY: Xaa
<222> LOCATION: (50)..(50)
<223> OTHER INFORMATION: Xaa is any amino acid or absent, but not I
<220> FEATURE:
<221> NAME/KEY: Xaa
<222> LOCATION: (51)..(51)
<223> OTHER INFORMATION: Xaa is any amino acid or absent, but not I
<220> FEATURE:

<221> NAME/KEY: Xaa
<222> LOCATION: (52)..(52)
<223> OTHER INFORMATION: Xaa is any amino acid or absent, but not V
<220> FEATURE:
<221> NAME/KEY: Xaa
<222> LOCATION: (58)..(58)
<223> OTHER INFORMATION: Xaa is any amino acid or absent, but not S
<220> FEATURE:
<221> NAME/KEY: Xaa
<222> LOCATION: (62)..(62)
<223> OTHER INFORMATION: Xaa is any amino acid or absent, but not P
<220> FEATURE:
<221> NAME/KEY: Xaa
<222> LOCATION: (65)..(65)
<223> OTHER INFORMATION: Xaa is any amino acid or absent, but not A
<220> FEATURE:
<221> NAME/KEY: Xaa
<222> LOCATION: (68)..(68)
<223> OTHER INFORMATION: Xaa is any amino acid or absent, but not A
<220> FEATURE:
<221> NAME/KEY: Xaa
<222> LOCATION: (74)..(74)
<223> OTHER INFORMATION: Xaa is any amino acid or absent, but not K
<220> FEATURE:
<221> NAME/KEY: Xaa
<222> LOCATION: (75)..(75)
<223> OTHER INFORMATION: Xaa is any amino acid or absent, but not L
<220> FEATURE:
<221> NAME/KEY: Xaa
<222> LOCATION: (76)..(76)
<223> OTHER INFORMATION: Xaa is any amino acid or absent, but not T
<220> FEATURE:
<221> NAME/KEY: Xaa
<222> LOCATION: (77)..(77)
<223> OTHER INFORMATION: Xaa is any amino acid or absent, but not I
<220> FEATURE:
<221> NAME/KEY: Xaa
<222> LOCATION: (86)..(86)
<223> OTHER INFORMATION: Xaa is any amino acid or absent, but not M
<220> FEATURE:
<221> NAME/KEY: Xaa
<222> LOCATION: (89)..(89)
<223> OTHER INFORMATION: Xaa is any amino acid or absent, but not I
<220> FEATURE:
<221> NAME/KEY: Xaa
<222> LOCATION: (92)..(92)
<223> OTHER INFORMATION: Xaa is any amino acid or absent, but not M
<220> FEATURE:
<221> NAME/KEY: Xaa
<222> LOCATION: (93)..(93)
<223> OTHER INFORMATION: Xaa is any amino acid or absent, but not T
<220> FEATURE:
<221> NAME/KEY: Xaa
<222> LOCATION: (107)..(107)
<223> OTHER INFORMATION: Xaa is any amino acid or absent, but not H
<220> FEATURE:
<221> NAME/KEY: Xaa
<222> LOCATION: (110)..(110)
<223> OTHER INFORMATION: Xaa is any amino acid or absent, but not T
<220> FEATURE:
<221> NAME/KEY: Xaa
<222> LOCATION: (127)..(127)
<223> OTHER INFORMATION: Xaa is any amino acid or absent, but not I
<220> FEATURE:
<221> NAME/KEY: Xaa
<222> LOCATION: (130)..(130)
<223> OTHER INFORMATION: Xaa is any amino acid or absent, but not K
<220> FEATURE:
<221> NAME/KEY: Xaa
<222> LOCATION: (138)..(138)
<223> OTHER INFORMATION: Xaa is any amino acid or absent, but not D
<220> FEATURE:
<221> NAME/KEY: Xaa
<222> LOCATION: (141)..(141)
<223> OTHER INFORMATION: Xaa is any amino acid or absent, but not A
<220> FEATURE:
<221> NAME/KEY: Xaa
<222> LOCATION: (142)..(142)
<223> OTHER INFORMATION: Xaa is any amino acid or absent, but not K
<220> FEATURE:
<221> NAME/KEY: Xaa
<222> LOCATION: (146)..(146)
<223> OTHER INFORMATION: Xaa is any amino acid or absent, but not S

<400> SEQUENCE: 34

```
Pro Ile Xaa Met Ile Ser Tyr Ala Asp Glu Xaa Xaa Ala Xaa Val Ile
1               5                   10                  15

Thr Trp Lys Asn Xaa Asp Leu Pro Tyr Val Xaa Val Val Ser Xaa Glu
            20                  25                  30

Arg Glu Met Ile Lys Arg Phe Leu Arg Xaa Xaa Xaa Glu Lys Asp Pro
        35                  40                  45

Asp Xaa Xaa Xaa Thr Tyr Asn Gly Asp Xaa Phe Asp Phe Xaa Tyr Leu
    50                  55                  60

Xaa Lys Arg Xaa Glu Lys Leu Gly Ile Xaa Xaa Xaa Xaa Gly Arg Asp
65                  70                  75                  80

Gly Ser Glu Pro Lys Xaa Gln Arg Xaa Gly Asp Xaa Xaa Ala Val Glu
                85                  90                  95

Val Lys Gly Arg Ile His Phe Asp Leu Tyr Xaa Val Ile Xaa Arg Thr
            100                 105                 110

Ile Asn Leu Pro Thr Tyr Thr Leu Glu Ala Val Tyr Glu Ala Xaa Phe
        115                 120                 125

Gly Xaa Pro Lys Glu Lys Val Tyr Ala Xaa Glu Ile Xaa Xaa Ala Trp
    130                 135                 140

Glu Xaa
145
```

<210> SEQ ID NO 35
<211> LENGTH: 137
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (17)..(17)
<223> OTHER INFORMATION: Xaa is any amino acid or absent, but not T
<220> FEATURE:
<221> NAME/KEY: Xaa
<222> LOCATION: (18)..(18)
<223> OTHER INFORMATION: Xaa is any amino acid or absent, but not I
<220> FEATURE:
<221> NAME/KEY: Xaa
<222> LOCATION: (21)..(21)
<223> OTHER INFORMATION: Xaa is any amino acid or absent, but not H
<220> FEATURE:
<221> NAME/KEY: Xaa
<222> LOCATION: (26)..(26)
<223> OTHER INFORMATION: Xaa is any amino acid or absent, but not E
<220> FEATURE:
<221> NAME/KEY: Xaa
<222> LOCATION: (35)..(35)
<223> OTHER INFORMATION: Xaa is any amino acid or absent, but not I
<220> FEATURE:
<221> NAME/KEY: Xaa
<222> LOCATION: (36)..(36)
<223> OTHER INFORMATION: Xaa is any amino acid or absent, but not Q
<220> FEATURE:
<221> NAME/KEY: Xaa
<222> LOCATION: (39)..(39)
<223> OTHER INFORMATION: Xaa is any amino acid or absent, but not A
<220> FEATURE:
<221> NAME/KEY: Xaa
<222> LOCATION: (40)..(40)
<223> OTHER INFORMATION: Xaa is any amino acid or absent, but not N
<220> FEATURE:
<221> NAME/KEY: Xaa
<222> LOCATION: (43)..(43)

<223> OTHER INFORMATION: Xaa is any amino acid or absent, but not I
<220> FEATURE:
<221> NAME/KEY: Xaa
<222> LOCATION: (49)..(49)
<223> OTHER INFORMATION: Xaa is any amino acid or absent, but not A
<220> FEATURE:
<221> NAME/KEY: Xaa
<222> LOCATION: (51)..(51)
<223> OTHER INFORMATION: Xaa is any amino acid or absent, but not Y
<220> FEATURE:
<221> NAME/KEY: Xaa
<222> LOCATION: (57)..(57)
<223> OTHER INFORMATION: Xaa is any amino acid or absent, but not P
<220> FEATURE:
<221> NAME/KEY: Xaa
<222> LOCATION: (59)..(59)
<223> OTHER INFORMATION: Xaa is any amino acid or absent, but not H
<220> FEATURE:
<221> NAME/KEY: Xaa
<222> LOCATION: (60)..(60)
<223> OTHER INFORMATION: Xaa is any amino acid or absent, but not E
<220> FEATURE:
<221> NAME/KEY: Xaa
<222> LOCATION: (64)..(64)
<223> OTHER INFORMATION: Xaa is any amino acid or absent, but not I
<220> FEATURE:
<221> NAME/KEY: Xaa
<222> LOCATION: (73)..(73)
<223> OTHER INFORMATION: Xaa is any amino acid or absent, but not K
<220> FEATURE:
<221> NAME/KEY: Xaa
<222> LOCATION: (77)..(77)
<223> OTHER INFORMATION: Xaa is any amino acid or absent, but not K
<220> FEATURE:
<221> NAME/KEY: Xaa
<222> LOCATION: (82)..(82)
<223> OTHER INFORMATION: Xaa is any amino acid or absent, but not K
<220> FEATURE:
<221> NAME/KEY: Xaa
<222> LOCATION: (85)..(85)
<223> OTHER INFORMATION: Xaa is any amino acid or absent, but not M
<220> FEATURE:
<221> NAME/KEY: Xaa
<222> LOCATION: (88)..(88)
<223> OTHER INFORMATION: Xaa is any amino acid or absent, but not G
<220> FEATURE:
<221> NAME/KEY: Xaa
<222> LOCATION: (93)..(93)
<223> OTHER INFORMATION: Xaa is any amino acid or absent, but not R
<220> FEATURE:
<221> NAME/KEY: Xaa
<222> LOCATION: (95)..(95)
<223> OTHER INFORMATION: Xaa is any amino acid or absent, but not D
<220> FEATURE:
<221> NAME/KEY: Xaa
<222> LOCATION: (97)..(97)
<223> OTHER INFORMATION: Xaa is any amino acid or absent, but not P
<220> FEATURE:
<221> NAME/KEY: Xaa
<222> LOCATION: (99)..(99)
<223> OTHER INFORMATION: Xaa is any amino acid or absent, but not S
<220> FEATURE:
<221> NAME/KEY: Xaa
<222> LOCATION: (100)..(100)
<223> OTHER INFORMATION: Xaa is any amino acid or absent, but not N
<220> FEATURE:
<221> NAME/KEY: Xaa
<222> LOCATION: (104)..(104)
<223> OTHER INFORMATION: Xaa is any amino acid or absent, but not L
<220> FEATURE:
<221> NAME/KEY: Xaa
<222> LOCATION: (105)..(105)
<223> OTHER INFORMATION: Xaa is any amino acid or absent, but not A
<220> FEATURE:
<221> NAME/KEY: Xaa
<222> LOCATION: (106)..(106)
<223> OTHER INFORMATION: Xaa is any amino acid or absent, but not E
<220> FEATURE:
<221> NAME/KEY: Xaa
<222> LOCATION: (108)..(108)
<223> OTHER INFORMATION: Xaa is any amino acid or absentd, but not Y
<220> FEATURE:
<221> NAME/KEY: Xaa
<222> LOCATION: (111)..(111)
<223> OTHER INFORMATION: Xaa is any amino acid or absent, but not K
<220> FEATURE:
<221> NAME/KEY: Xaa
<222> LOCATION: (130)..(130)
<223> OTHER INFORMATION: Xaa is any amino acid or absent, but not L
<220> FEATURE:
<221> NAME/KEY: Xaa
<222> LOCATION: (134)..(134)
<223> OTHER INFORMATION: Xaa is any amino acid or absent, but not E
<220> FEATURE:
<221> NAME/KEY: Xaa
<222> LOCATION: (135)..(135)
<223> OTHER INFORMATION: Xaa is any amino acid or absent, but not G

<400> SEQUENCE: 35

```
Arg Asp Trp Ser Glu Ile Ala Lys Glu Thr Gln Ala Arg Val Leu Glu
1               5                   10                  15

Xaa Xaa Leu Lys Xaa Gly Asp Val Glu Xaa Ala Val Arg Ile Val Lys
            20                  25                  30

Glu Val Xaa Xaa Lys Leu Xaa Xaa Tyr Glu Xaa Pro Pro Glu Lys Leu
        35                  40                  45

Xaa Ile Xaa Glu Gln Ile Thr Arg Xaa Leu Xaa Xaa Tyr Lys Ala Xaa
    50                  55                  60

Gly Pro His Val Ala Val Ala Lys Xaa Leu Ala Ala Xaa Gly Val Lys
65                  70                  75                  80

Ile Xaa Pro Gly Xaa Val Ile Xaa Tyr Ile Val Leu Xaa Gly Xaa Gly
                85                  90                  95

Xaa Ile Xaa Xaa Arg Ala Ile Xaa Xaa Xaa Glu Xaa Asp Pro Xaa Lys
            100                 105                 110

His Lys Tyr Asp Ala Glu Tyr Tyr Ile Glu Asn Gln Val Leu Pro Ala
        115                 120                 125

Val Xaa Arg Ile Leu Xaa Xaa Phe Gly
    130                 135
```

<210> SEQ ID NO 36
<211> LENGTH: 170
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(1)
<223> OTHER INFORMATION: Xaa is any amino acid or absent
<220> FEATURE:
<221> NAME/KEY: Xaa
<222> LOCATION: (3)..(14)
<223> OTHER INFORMATION: Xaa is any amino acid or absent
<220> FEATURE:
<221> NAME/KEY: Xaa
<222> LOCATION: (16)..(32)
<223> OTHER INFORMATION: Xaa is any amino acid or absent
<220> FEATURE:
<221> NAME/KEY: Xaa
<222> LOCATION: (34)..(37)
<223> OTHER INFORMATION: Xaa is any amino acid or absent
<220> FEATURE:
<221> NAME/KEY: Xaa
<222> LOCATION: (39)..(40)
<223> OTHER INFORMATION: Xaa is any amino acid or absent
<220> FEATURE:
<221> NAME/KEY: Xaa
<222> LOCATION: (42)..(47)
<223> OTHER INFORMATION: Xaa is any amino acid or absent -continued
<220> FEATURE:
<221> NAME/KEY: Xaa
<222> LOCATION: (49)..(52)
<223> OTHER INFORMATION: Xaa is any amino acid or absent
<220> FEATURE:
<221> NAME/KEY: Xaa
<222> LOCATION: (54)..(62)
<223> OTHER INFORMATION: Xaa is any amino acid or absent
<220> FEATURE:
<221> NAME/KEY: Xaa
<222> LOCATION: (64)..(72)
<223> OTHER INFORMATION: Xaa is any amino acid or absent
<220> FEATURE:
<221> NAME/KEY: Xaa
<222> LOCATION: (74)..(76)
<223> OTHER INFORMATION: Xaa is any amino acid or absent
<220> FEATURE:
<221> NAME/KEY: Xaa
<222> LOCATION: (78)..(78)
<223> OTHER INFORMATION: Xaa is any amino acid or absent
<220> FEATURE:
<221> NAME/KEY: Xaa
<222> LOCATION: (80)..(83)
<223> OTHER INFORMATION: Xaa is any amino acid or absent
<220> FEATURE:
<221> NAME/KEY: Xaa
<222> LOCATION: (86)..(91)
<223> OTHER INFORMATION: Xaa is any amino acid or absent
<220> FEATURE:
<221> NAME/KEY: Xaa
<222> LOCATION: (93)..(95)
<223> OTHER INFORMATION: Xaa is any amino acid or absent
<220> FEATURE:
<221> NAME/KEY: Xaa
<222> LOCATION: (97)..(100)
<223> OTHER INFORMATION: Xaa is any amino acid or absent
<220> FEATURE:
<221> NAME/KEY: Xaa
<222> LOCATION: (102)..(108)
<223> OTHER INFORMATION: Xaa is any amino acid or absent
<220> FEATURE:
<221> NAME/KEY: Xaa
<222> LOCATION: (110)..(126)
<223> OTHER INFORMATION: Xaa is any amino acid or absent
<220> FEATURE:
<221> NAME/KEY: Xaa
<222> LOCATION: (128)..(129)
<223> OTHER INFORMATION: Xaa is any amino acid or absent
<220> FEATURE:
<221> NAME/KEY: Xaa
<222> LOCATION: (134)..(135)
<223> OTHER INFORMATION: Xaa is any amino acid or absent
<220> FEATURE:
<221> NAME/KEY: Xaa
<222> LOCATION: (137)..(139)
<223> OTHER INFORMATION: Xaa is any amino acid or absent
<220> FEATURE:
<221> NAME/KEY: Xaa
<222> LOCATION: (141)..(144)
<223> OTHER INFORMATION: Xaa is any amino acid or absent
<220> FEATURE:
<221> NAME/KEY: Xaa
<222> LOCATION: (146)..(146)
<223> OTHER INFORMATION: Xaa is any amino acid or absent
<220> FEATURE:
<221> NAME/KEY: Xaa
<222> LOCATION: (148)..(151)
<223> OTHER INFORMATION: Xaa is any amino acid or absent
<220> FEATURE:
<221> NAME/KEY: Xaa
<222> LOCATION: (154)..(158)
<223> OTHER INFORMATION: Xaa is any amino acid or absent
<220> FEATURE:
<221> NAME/KEY: Xaa
<222> LOCATION: (162)..(162)
<223> OTHER INFORMATION: Xaa is any amino acid or absent
<220> FEATURE:
<221> NAME/KEY: Xaa
<222> LOCATION: (165)..(168)

<223> OTHER INFORMATION: Xaa is any amino acid or absent
<220> FEATURE:
<221> NAME/KEY: Xaa
<222> LOCATION: (170)..(170)
<223> OTHER INFORMATION: Xaa is any amino acid or absent

<400> SEQUENCE: 36

```
Xaa Lys Xaa Xaa Xaa Xaa Xaa Xaa Xaa Xaa Xaa Xaa Xaa Xaa Ala Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Leu Xaa Xaa Xaa Xaa Asn Xaa Xaa Ile Xaa Xaa Xaa Xaa Xaa Xaa Lys
        35                  40                  45

Xaa Xaa Xaa Xaa Ile Xaa Xaa Xaa Xaa Xaa Xaa Xaa Xaa Xaa His Xaa
    50                  55                  60

Xaa Xaa Xaa Xaa Xaa Xaa Xaa Xaa Thr Xaa Xaa Xaa Glu Xaa Gln Xaa
65                  70                  75                  80

Xaa Xaa Xaa Lys Ile Xaa Xaa Xaa Xaa Xaa Xaa Lys Xaa Xaa Xaa Leu
                85                  90                  95

Xaa Xaa Xaa Xaa Phe Xaa Xaa Xaa Xaa Xaa Xaa Xaa Lys Xaa Xaa Xaa
            100                 105                 110

Xaa Xaa Xaa Xaa Xaa Xaa Xaa Xaa Xaa Xaa Xaa Xaa Xaa Xaa Lys Xaa
        115                 120                 125

Xaa Glu Leu Val Trp Xaa Xaa Leu Xaa Xaa Xaa Phe Xaa Xaa Xaa Xaa
    130                 135                 140

Leu Xaa Ile Xaa Xaa Xaa Xaa Leu Tyr Xaa Xaa Xaa Xaa Xaa Gly Glu
145                 150                 155                 160

Ser Xaa Glu Ile Xaa Xaa Xaa Xaa Leu Xaa
                165                 170
```

<210> SEQ ID NO 37
<211> LENGTH: 170
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (2)..(2)
<223> OTHER INFORMATION: Xaa is any amino acid or absent, but not R
<220> FEATURE:
<221> NAME/KEY: Xaa
<222> LOCATION: (15)..(15)
<223> OTHER INFORMATION: Xaa is any amino acid or absent, but not S
<220> FEATURE:
<221> NAME/KEY: Xaa
<222> LOCATION: (33)..(33)
<223> OTHER INFORMATION: Xaa is any amino acid or absent, but not R
<220> FEATURE:
<221> NAME/KEY: Xaa
<222> LOCATION: (38)..(38)
<223> OTHER INFORMATION: Xaa is any amino acid or absent, but not E
<220> FEATURE:
<221> NAME/KEY: Xaa
<222> LOCATION: (41)..(41)
<223> OTHER INFORMATION: Xaa is any amino acid or absent, but not V
<220> FEATURE:
<221> NAME/KEY: Xaa
<222> LOCATION: (48)..(48)
<223> OTHER INFORMATION: Xaa is any amino acid or absent, but not R
<220> FEATURE:
<221> NAME/KEY: Xaa
<222> LOCATION: (53)..(53)
<223> OTHER INFORMATION: Xaa is any amino acid or absent, but not F
<220> FEATURE:
<221> NAME/KEY: Xaa
<222> LOCATION: (63)..(63)

<223> OTHER INFORMATION: Xaa is any amino acid or absent, but not D
<220> FEATURE:
<221> NAME/KEY: Xaa
<222> LOCATION: (73)..(73)
<223> OTHER INFORMATION: Xaa is any amino acid or absent, but not K
<220> FEATURE:
<221> NAME/KEY: Xaa
<222> LOCATION: (77)..(77)
<223> OTHER INFORMATION: Xaa is any amino acid or absent, but not A
<220> FEATURE:
<221> NAME/KEY: Xaa
<222> LOCATION: (79)..(79)
<223> OTHER INFORMATION: Xaa is any amino acid or absent, but not I
<220> FEATURE:
<221> NAME/KEY: Xaa
<222> LOCATION: (84)..(84)
<223> OTHER INFORMATION: Xaa is any amino acid or absent, but not R
<220> FEATURE:
<221> NAME/KEY: Xaa
<222> LOCATION: (85)..(85)
<223> OTHER INFORMATION: Xaa is any amino acid or absent, but not K
<220> FEATURE:
<221> NAME/KEY: Xaa
<222> LOCATION: (92)..(92)
<223> OTHER INFORMATION: Xaa is any amino acid or absent, but not R
<220> FEATURE:
<221> NAME/KEY: Xaa
<222> LOCATION: (96)..(96)
<223> OTHER INFORMATION: Xaa is any amino acid or absent, but not I
<220> FEATURE:
<221> NAME/KEY: Xaa
<222> LOCATION: (101)..(101)
<223> OTHER INFORMATION: Xaa is any amino acid or absent, but not Y
<220> FEATURE:
<221> NAME/KEY: Xaa
<222> LOCATION: (109)..(109)
<223> OTHER INFORMATION: Xaa is any amino acid or absent, but not R
<220> FEATURE:
<221> NAME/KEY: Xaa
<222> LOCATION: (127)..(127)
<223> OTHER INFORMATION: Xaa is any amino acid or absent, but not E
<220> FEATURE:
<221> NAME/KEY: Xaa
<222> LOCATION: (130)..(130)
<223> OTHER INFORMATION: Xaa is any amino acid or absent, but not T
<220> FEATURE:
<221> NAME/KEY: Xaa
<222> LOCATION: (131)..(131)
<223> OTHER INFORMATION: Xaa is any amino acid or absent, but not M
<220> FEATURE:
<221> NAME/KEY: Xaa
<222> LOCATION: (132)..(132)
<223> OTHER INFORMATION: Xaa is any amino acid or absent, but not T
<220> FEATURE:
<221> NAME/KEY: Xaa
<222> LOCATION: (133)..(133)
<223> OTHER INFORMATION: Xaa is any amino acid or absent, but not I
<220> FEATURE:
<221> NAME/KEY: Xaa
<222> LOCATION: (136)..(136)
<223> OTHER INFORMATION: Xaa is any amino acid or absent, but not I
<220> FEATURE:
<221> NAME/KEY: Xaa
<222> LOCATION: (140)..(140)
<223> OTHER INFORMATION: Xaa is any amino acid or absent, but not Y
<220> FEATURE:
<221> NAME/KEY: Xaa
<222> LOCATION: (145)..(145)
<223> OTHER INFORMATION: Xaa is any amino acid or absent, but not I
<220> FEATURE:
<221> NAME/KEY: Xaa
<222> LOCATION: (147)..(147)
<223> OTHER INFORMATION: Xaa is any amino acid or absent, but not S
<220> FEATURE:
<221> NAME/KEY: Xaa
<222> LOCATION: (152)..(152)
<223> OTHER INFORMATION: Xaa is any amino acid or absent, but not F
<220> FEATURE:
<221> NAME/KEY: Xaa
<222> LOCATION: (153)..(153)
<223> OTHER INFORMATION: Xaa is any amino acid or absent, but not F
<220> FEATURE:
<221> NAME/KEY: Xaa
<222> LOCATION: (159)..(159)
<223> OTHER INFORMATION: Xaa is any amino acid or absent, but not A
<220> FEATURE:
<221> NAME/KEY: Xaa
<222> LOCATION: (160)..(160)
<223> OTHER INFORMATION: Xaa is any amino acid or absent, but not D
<220> FEATURE:
<221> NAME/KEY: Xaa
<222> LOCATION: (161)..(161)
<223> OTHER INFORMATION: Xaa is any amino acid or absent, but not A
<220> FEATURE:
<221> NAME/KEY: Xaa
<222> LOCATION: (163)..(163)
<223> OTHER INFORMATION: Xaa is any amino acid or absent, but not T
<220> FEATURE:
<221> NAME/KEY: Xaa
<222> LOCATION: (164)..(164)
<223> OTHER INFORMATION: Xaa is any amino acid or absent, but not V
<220> FEATURE:
<221> NAME/KEY: Xaa
<222> LOCATION: (169)..(169)
<223> OTHER INFORMATION: Xaa is any amino acid or absent, but not M

<400> SEQUENCE: 37

```
Glu Xaa Gly Leu Trp Glu Asn Ile Val Tyr Leu Asp Phe Arg Xaa Leu
1               5                   10                  15

Tyr Pro Ser Ile Ile Ile Thr His Asn Val Ser Pro Asp Thr Leu Asn
            20                  25                  30

Xaa Glu Gly Cys Lys Xaa Tyr Asp Xaa Ala Pro Gln Val Gly His Xaa
        35                  40                  45

Phe Cys Lys Asp Xaa Pro Gly Phe Ile Pro Ser Leu Leu Gly Xaa Leu
    50                  55                  60

Leu Glu Glu Arg Gln Lys Ile Lys Xaa Lys Met Lys Xaa Thr Xaa Asp
65                  70                  75                  80

Pro Ile Glu Xaa Xaa Leu Leu Asp Tyr Arg Gln Xaa Ala Ile Lys Xaa
                85                  90                  95

Leu Ala Asn Ser Xaa Tyr Gly Tyr Tyr Gly Tyr Ala Xaa Ala Arg Trp
            100                 105                 110

Tyr Cys Lys Glu Cys Ala Glu Ser Val Thr Ala Trp Gly Arg Xaa Tyr
        115                 120                 125

Ile Xaa Xaa Xaa Xaa Lys Glu Xaa Glu Glu Lys Xaa Gly Phe Lys Val
    130                 135                 140

Xaa Tyr Xaa Asp Thr Asp Gly Xaa Xaa Ala Thr Ile Pro Gly Xaa Xaa
145                 150                 155                 160

Xaa Glu Xaa Xaa Lys Lys Lys Ala Xaa Glu
                165                 170
```

<210> SEQ ID NO 38
<211> LENGTH: 777
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(4)
<223> OTHER INFORMATION: Xaa is any amino acid or absent
<220> FEATURE:
<221> NAME/KEY: Xaa
<222> LOCATION: (6)..(10)
<223> OTHER INFORMATION: Xaa is any amino acid or absent
<220> FEATURE:
<221> NAME/KEY: Xaa
<222> LOCATION: (12)..(17)
<223> OTHER INFORMATION: Xaa is any amino acid or absent
<220> FEATURE:
<221> NAME/KEY: Xaa
<222> LOCATION: (19)..(24)
<223> OTHER INFORMATION: Xaa is any amino acid or absent
<220> FEATURE:
<221> NAME/KEY: Xaa
<222> LOCATION: (26)..(29)
<223> OTHER INFORMATION: Xaa is any amino acid or absent
<220> FEATURE:
<221> NAME/KEY: Xaa
<222> LOCATION: (31)..(34)
<223> OTHER INFORMATION: Xaa is any amino acid or absent
<220> FEATURE:
<221> NAME/KEY: Xaa
<222> LOCATION: (36)..(37)
<223> OTHER INFORMATION: Xaa is any amino acid or absent
<220> FEATURE:
<221> NAME/KEY: Xaa
<222> LOCATION: (39)..(42)
<223> OTHER INFORMATION: Xaa is any amino acid or absent
<220> FEATURE:
<221> NAME/KEY: Xaa
<222> LOCATION: (44)..(46)
<223> OTHER INFORMATION: Xaa is any amino acid or absent
<220> FEATURE:
<221> NAME/KEY: Xaa
<222> LOCATION: (48)..(55)
<223> OTHER INFORMATION: Xaa is any amino acid or absent
<220> FEATURE:
<221> NAME/KEY: Xaa
<222> LOCATION: (57)..(60)
<223> OTHER INFORMATION: Xaa is any amino acid or absent
<220> FEATURE:
<221> NAME/KEY: Xaa
<222> LOCATION: (63)..(63)
<223> OTHER INFORMATION: Xaa is any amino acid or absent
<220> FEATURE:
<221> NAME/KEY: Xaa
<222> LOCATION: (68)..(71)
<223> OTHER INFORMATION: Xaa is any amino acid or absent
<220> FEATURE:
<221> NAME/KEY: Xaa
<222> LOCATION: (73)..(77)
<223> OTHER INFORMATION: Xaa is any amino acid or absent
<220> FEATURE:
<221> NAME/KEY: Xaa
<222> LOCATION: (79)..(79)
<223> OTHER INFORMATION: Xaa is any amino acid or absent
<220> FEATURE:
<221> NAME/KEY: Xaa
<222> LOCATION: (82)..(86)
<223> OTHER INFORMATION: Xaa is any amino acid or absent
<220> FEATURE:
<221> NAME/KEY: Xaa
<222> LOCATION: (89)..(94)
<223> OTHER INFORMATION: Xaa is any amino acid or absent
<220> FEATURE:
<221> NAME/KEY: Xaa
<222> LOCATION: (96)..(97)
<223> OTHER INFORMATION: Xaa is any amino acid or absent
<220> FEATURE:
<221> NAME/KEY: Xaa
<222> LOCATION: (99)..(99)
<223> OTHER INFORMATION: Xaa is any amino acid or absent
<220> FEATURE:
<221> NAME/KEY: Xaa
<222> LOCATION: (101)..(106)
<223> OTHER INFORMATION: Xaa is any amino acid or absent
<220> FEATURE:
<221> NAME/KEY: Xaa
<222> LOCATION: (108)..(109)
<223> OTHER INFORMATION: Xaa is any amino acid or absent
<220> FEATURE:
<221> NAME/KEY: Xaa
<222> LOCATION: (111)..(126)
<223> OTHER INFORMATION: Xaa is any amino acid or absent
<220> FEATURE:

<221> NAME/KEY: Xaa
<222> LOCATION: (128)..(131)
<223> OTHER INFORMATION: Xaa is any amino acid or absent
<220> FEATURE:
<221> NAME/KEY: Xaa
<222> LOCATION: (133)..(136)
<223> OTHER INFORMATION: Xaa is any amino acid or absent
<220> FEATURE:
<221> NAME/KEY: Xaa
<222> LOCATION: (138)..(152)
<223> OTHER INFORMATION: Xaa is any amino acid or absent
<220> FEATURE:
<221> NAME/KEY: Xaa
<222> LOCATION: (155)..(157)
<223> OTHER INFORMATION: Xaa is any amino acid or absent
<220> FEATURE:
<221> NAME/KEY: Xaa
<222> LOCATION: (159)..(165)
<223> OTHER INFORMATION: Xaa is any amino acid or absent
<220> FEATURE:
<221> NAME/KEY: Xaa
<222> LOCATION: (168)..(168)
<223> OTHER INFORMATION: Xaa is any amino acid or absent
<220> FEATURE:
<221> NAME/KEY: Xaa
<222> LOCATION: (170)..(175)
<223> OTHER INFORMATION: Xaa is any amino acid or absent
<220> FEATURE:
<221> NAME/KEY: Xaa
<222> LOCATION: (177)..(181)
<223> OTHER INFORMATION: Xaa is any amino acid or absent
<220> FEATURE:
<221> NAME/KEY: Xaa
<222> LOCATION: (183)..(185)
<223> OTHER INFORMATION: Xaa is any amino acid or absent
<220> FEATURE:
<221> NAME/KEY: Xaa
<222> LOCATION: (187)..(196)
<223> OTHER INFORMATION: Xaa is any amino acid or absent
<220> FEATURE:
<221> NAME/KEY: Xaa
<222> LOCATION: (200)..(204)
<223> OTHER INFORMATION: Xaa is any amino acid or absent
<220> FEATURE:
<221> NAME/KEY: Xaa
<222> LOCATION: (208)..(212)
<223> OTHER INFORMATION: Xaa is any amino acid or absent
<220> FEATURE:
<221> NAME/KEY: Xaa
<222> LOCATION: (214)..(216)
<223> OTHER INFORMATION: Xaa is any amino acid or absent
<220> FEATURE:
<221> NAME/KEY: Xaa
<222> LOCATION: (218)..(219)
<223> OTHER INFORMATION: Xaa is any amino acid or absent
<220> FEATURE:
<221> NAME/KEY: Xaa
<222> LOCATION: (221)..(222)
<223> OTHER INFORMATION: Xaa is any amino acid or absent
<220> FEATURE:
<221> NAME/KEY: Xaa
<222> LOCATION: (224)..(228)
<223> OTHER INFORMATION: Xaa is any amino acid or absent
<220> FEATURE:
<221> NAME/KEY: Xaa
<222> LOCATION: (233)..(242)
<223> OTHER INFORMATION: Xaa is any amino acid or absent
<220> FEATURE:
<221> NAME/KEY: Xaa
<222> LOCATION: (244)..(245)
<223> OTHER INFORMATION: Xaa is any amino acid or absent
<220> FEATURE:
<221> NAME/KEY: Xaa
<222> LOCATION: (247)..(248)
<223> OTHER INFORMATION: Xaa is any amino acid or absent
<220> FEATURE:
<221> NAME/KEY: Xaa
<222> LOCATION: (251)..(263)
<223> OTHER INFORMATION: Xaa is any amino acid or absent
<220> FEATURE:
<221> NAME/KEY: Xaa
<222> LOCATION: (265)..(266)
<223> OTHER INFORMATION: Xaa is any amino acid or absent
<220> FEATURE:
<221> NAME/KEY: Xaa
<222> LOCATION: (268)..(283)
<223> OTHER INFORMATION: Xaa is any amino acid or absent
<220> FEATURE:
<221> NAME/KEY: Xaa
<222> LOCATION: (285)..(286)
<223> OTHER INFORMATION: Xaa is any amino acid or absent
<220> FEATURE:
<221> NAME/KEY: Xaa
<222> LOCATION: (288)..(294)
<223> OTHER INFORMATION: Xaa is any amino acid or absent
<220> FEATURE:
<221> NAME/KEY: Xaa
<222> LOCATION: (296)..(297)
<223> OTHER INFORMATION: Xaa is any amino acid or absent
<220> FEATURE:
<221> NAME/KEY: Xaa
<222> LOCATION: (300)..(302)
<223> OTHER INFORMATION: Xaa is any amino acid or absent
<220> FEATURE:
<221> NAME/KEY: Xaa
<222> LOCATION: (304)..(311)
<223> OTHER INFORMATION: Xaa is any amino acid or absent
<220> FEATURE:
<221> NAME/KEY: Xaa
<222> LOCATION: (313)..(319)
<223> OTHER INFORMATION: Xaa is any amino acid or absent
<220> FEATURE:
<221> NAME/KEY: Xaa
<222> LOCATION: (321)..(332)
<223> OTHER INFORMATION: Xaa is any amino acid or absent
<220> FEATURE:
<221> NAME/KEY: Xaa
<222> LOCATION: (334)..(338)
<223> OTHER INFORMATION: Xaa is any amino acid or absent
<220> FEATURE:
<221> NAME/KEY: Xaa
<222> LOCATION: (340)..(341)
<223> OTHER INFORMATION: Xaa is any amino acid or absent
<220> FEATURE:
<221> NAME/KEY: Xaa
<222> LOCATION: (343)..(368)
<223> OTHER INFORMATION: Xaa is any amino acid or absent
<220> FEATURE:
<221> NAME/KEY: Xaa
<222> LOCATION: (370)..(374)
<223> OTHER INFORMATION: Xaa is any amino acid or absent
<220> FEATURE:
<221> NAME/KEY: Xaa
<222> LOCATION: (376)..(376)
<223> OTHER INFORMATION: Xaa is any amino acid or absent
<220> FEATURE:
<221> NAME/KEY: Xaa
<222> LOCATION: (378)..(378)
<223> OTHER INFORMATION: Xaa is any amino acid or absent
<220> FEATURE:
<221> NAME/KEY: Xaa
<222> LOCATION: (381)..(384)
<223> OTHER INFORMATION: Xaa is any amino acid or absent
<220> FEATURE:
<221> NAME/KEY: Xaa
<222> LOCATION: (386)..(387)
<223> OTHER INFORMATION: Xaa is any amino acid or absent
<220> FEATURE:
<221> NAME/KEY: Xaa
<222> LOCATION: (389)..(390)
<223> OTHER INFORMATION: Xaa is any amino acid or absent
<220> FEATURE:
<221> NAME/KEY: Xaa
<222> LOCATION: (392)..(396)
<223> OTHER INFORMATION: Xaa is any amino acid or absent
<220> FEATURE:
<221> NAME/KEY: Xaa
<222> LOCATION: (398)..(409)

-continued

<223> OTHER INFORMATION: Xaa is any amino acid or absent
<220> FEATURE:
<221> NAME/KEY: Xaa
<222> LOCATION: (411)..(427)
<223> OTHER INFORMATION: Xaa is any amino acid or absent
<220> FEATURE:
<221> NAME/KEY: Xaa
<222> LOCATION: (429)..(432)
<223> OTHER INFORMATION: Xaa is any amino acid or absent
<220> FEATURE:
<221> NAME/KEY: Xaa
<222> LOCATION: (434)..(435)
<223> OTHER INFORMATION: Xaa is any amino acid or absent
<220> FEATURE:
<221> NAME/KEY: Xaa
<222> LOCATION: (437)..(442)
<223> OTHER INFORMATION: Xaa is any amino acid or absent
<220> FEATURE:
<221> NAME/KEY: Xaa
<222> LOCATION: (444)..(447)
<223> OTHER INFORMATION: Xaa is any amino acid or absent
<220> FEATURE:
<221> NAME/KEY: Xaa
<222> LOCATION: (449)..(457)
<223> OTHER INFORMATION: Xaa is any amino acid or absent
<220> FEATURE:
<221> NAME/KEY: Xaa
<222> LOCATION: (459)..(467)
<223> OTHER INFORMATION: Xaa is any amino acid or absent
<220> FEATURE:
<221> NAME/KEY: Xaa
<222> LOCATION: (469)..(471)
<223> OTHER INFORMATION: Xaa is any amino acid or absent
<220> FEATURE:
<221> NAME/KEY: Xaa
<222> LOCATION: (473)..(473)
<223> OTHER INFORMATION: Xaa is any amino acid or absent
<220> FEATURE:
<221> NAME/KEY: Xaa
<222> LOCATION: (475)..(478)
<223> OTHER INFORMATION: Xaa is any amino acid or absent
<220> FEATURE:
<221> NAME/KEY: Xaa
<222> LOCATION: (481)..(486)
<223> OTHER INFORMATION: Xaa is any amino acid or absent
<220> FEATURE:
<221> NAME/KEY: Xaa
<222> LOCATION: (488)..(490)
<223> OTHER INFORMATION: Xaa is any amino acid or absent
<220> FEATURE:
<221> NAME/KEY: Xaa
<222> LOCATION: (492)..(495)
<223> OTHER INFORMATION: Xaa is any amino acid or absent
<220> FEATURE:
<221> NAME/KEY: Xaa
<222> LOCATION: (497)..(503)
<223> OTHER INFORMATION: Xaa is any amino acid or absent
<220> FEATURE:
<221> NAME/KEY: Xaa
<222> LOCATION: (505)..(521)
<223> OTHER INFORMATION: Xaa is any amino acid or absent
<220> FEATURE:
<221> NAME/KEY: Xaa
<222> LOCATION: (523)..(524)
<223> OTHER INFORMATION: Xaa is any amino acid or absent
<220> FEATURE:
<221> NAME/KEY: Xaa
<222> LOCATION: (529)..(530)
<223> OTHER INFORMATION: Xaa is any amino acid or absent
<220> FEATURE:
<221> NAME/KEY: Xaa
<222> LOCATION: (532)..(534)
<223> OTHER INFORMATION: Xaa is any amino acid or absent
<220> FEATURE:
<221> NAME/KEY: Xaa
<222> LOCATION: (536)..(539)
<223> OTHER INFORMATION: Xaa is any amino acid or absent
<220> FEATURE:
<221> NAME/KEY: Xaa
<222> LOCATION: (541)..(541)
<223> OTHER INFORMATION: Xaa is any amino acid or absent
<220> FEATURE:
<221> NAME/KEY: Xaa
<222> LOCATION: (543)..(546)
<223> OTHER INFORMATION: Xaa is any amino acid or absent
<220> FEATURE:
<221> NAME/KEY: Xaa
<222> LOCATION: (549)..(553)
<223> OTHER INFORMATION: Xaa is any amino acid or absent
<220> FEATURE:
<221> NAME/KEY: Xaa
<222> LOCATION: (557)..(557)
<223> OTHER INFORMATION: Xaa is any amino acid or absent
<220> FEATURE:
<221> NAME/KEY: Xaa
<222> LOCATION: (560)..(563)
<223> OTHER INFORMATION: Xaa is any amino acid or absent
<220> FEATURE:
<221> NAME/KEY: Xaa
<222> LOCATION: (565)..(566)
<223> OTHER INFORMATION: Xaa is any amino acid or absent
<220> FEATURE:
<221> NAME/KEY: Xaa
<222> LOCATION: (568)..(571)
<223> OTHER INFORMATION: Xaa is any amino acid or absent
<220> FEATURE:
<221> NAME/KEY: Xaa
<222> LOCATION: (573)..(576)
<223> OTHER INFORMATION: Xaa is any amino acid or absent
<220> FEATURE:
<221> NAME/KEY: Xaa
<222> LOCATION: (578)..(595)
<223> OTHER INFORMATION: Xaa is any amino acid or absent
<220> FEATURE:
<221> NAME/KEY: Xaa
<222> LOCATION: (597)..(605)
<223> OTHER INFORMATION: Xaa is any amino acid or absent
<220> FEATURE:
<221> NAME/KEY: Xaa
<222> LOCATION: (608)..(631)
<223> OTHER INFORMATION: Xaa is any amino acid or absent
<220> FEATURE:
<221> NAME/KEY: Xaa
<222> LOCATION: (634)..(635)
<223> OTHER INFORMATION: Xaa is any amino acid or absent
<220> FEATURE:
<221> NAME/KEY: Xaa
<222> LOCATION: (637)..(640)
<223> OTHER INFORMATION: Xaa is any amino acid or absent
<220> FEATURE:
<221> NAME/KEY: Xaa
<222> LOCATION: (642)..(649)
<223> OTHER INFORMATION: Xaa is any amino acid or absent
<220> FEATURE:
<221> NAME/KEY: Xaa
<222> LOCATION: (652)..(653)
<223> OTHER INFORMATION: Xaa is any amino acid or absent
<220> FEATURE:
<221> NAME/KEY: Xaa
<222> LOCATION: (656)..(657)
<223> OTHER INFORMATION: Xaa is any amino acid or absent
<220> FEATURE:
<221> NAME/KEY: Xaa
<222> LOCATION: (659)..(663)
<223> OTHER INFORMATION: Xaa is any amino acid or absent
<220> FEATURE:
<221> NAME/KEY: Xaa
<222> LOCATION: (665)..(665)
<223> OTHER INFORMATION: Xaa is any amino acid or absent
<220> FEATURE:
<221> NAME/KEY: Xaa
<222> LOCATION: (667)..(671)
<223> OTHER INFORMATION: Xaa is any amino acid or absent
<220> FEATURE:
<221> NAME/KEY: Xaa
<222> LOCATION: (673)..(673)
<223> OTHER INFORMATION: Xaa is any amino acid or absent
<220> FEATURE:

<221> NAME/KEY: Xaa
<222> LOCATION: (676)..(678)
<223> OTHER INFORMATION: Xaa is any amino acid or absent
<220> FEATURE:
<221> NAME/KEY: Xaa
<222> LOCATION: (680)..(687)
<223> OTHER INFORMATION: Xaa is any amino acid or absent
<220> FEATURE:
<221> NAME/KEY: Xaa
<222> LOCATION: (689)..(691)
<223> OTHER INFORMATION: Xaa is any amino acid or absent
<220> FEATURE:
<221> NAME/KEY: Xaa
<222> LOCATION: (693)..(696)
<223> OTHER INFORMATION: Xaa is any amino acid or absent
<220> FEATURE:
<221> NAME/KEY: Xaa
<222> LOCATION: (698)..(699)
<223> OTHER INFORMATION: Xaa is any amino acid or absent
<220> FEATURE:
<221> NAME/KEY: Xaa
<222> LOCATION: (701)..(702)
<223> OTHER INFORMATION: Xaa is any amino acid or absent
<220> FEATURE:
<221> NAME/KEY: Xaa
<222> LOCATION: (704)..(707)
<223> OTHER INFORMATION: Xaa is any amino acid or absent
<220> FEATURE:
<221> NAME/KEY: Xaa
<222> LOCATION: (709)..(709)
<223> OTHER INFORMATION: Xaa is any amino acid or absent
<220> FEATURE:
<221> NAME/KEY: Xaa
<222> LOCATION: (711)..(711)
<223> OTHER INFORMATION: Xaa is any amino acid or absent
<220> FEATURE:
<221> NAME/KEY: Xaa
<222> LOCATION: (713)..(713)
<223> OTHER INFORMATION: Xaa is any amino acid or absent
<220> FEATURE:
<221> NAME/KEY: Xaa
<222> LOCATION: (716)..(718)
<223> OTHER INFORMATION: Xaa is any amino acid or absent
<220> FEATURE:
<221> NAME/KEY: Xaa
<222> LOCATION: (722)..(722)
<223> OTHER INFORMATION: Xaa is any amino acid or absent
<220> FEATURE:
<221> NAME/KEY: Xaa
<222> LOCATION: (724)..(725)
<223> OTHER INFORMATION: Xaa is any amino acid or absent
<220> FEATURE:
<221> NAME/KEY: Xaa
<222> LOCATION: (727)..(744)
<223> OTHER INFORMATION: Xaa is any amino acid or absent
<220> FEATURE:
<221> NAME/KEY: Xaa
<222> LOCATION: (746)..(748)
<223> OTHER INFORMATION: Xaa is any amino acid or absent
<220> FEATURE:
<221> NAME/KEY: Xaa
<222> LOCATION: (751)..(768)
<223> OTHER INFORMATION: Xaa is any amino acid or absent
<220> FEATURE:
<221> NAME/KEY: Xaa
<222> LOCATION: (771)..(772)
<223> OTHER INFORMATION: Xaa is any amino acid or absent
<220> FEATURE:
<221> NAME/KEY: Xaa
<222> LOCATION: (775)..(775)
<223> OTHER INFORMATION: Xaa is any amino acid or absent

<400> SEQUENCE: 38

```
Xaa Xaa Xaa Xaa Thr Xaa Xaa Xaa Xaa Xaa Asp Xaa Xaa Xaa Xaa Xaa
1               5                   10                  15

Xaa Ile Xaa Xaa Xaa Xaa Xaa Xaa Glu Xaa Xaa Xaa Xaa Tyr Xaa Xaa
            20                  25                  30
```

-continued

```
Xaa Xaa Glu Xaa Xaa Phe Xaa Xaa Xaa Xaa Lys Xaa Xaa Xaa Ala Xaa
        35                  40                  45

Xaa Xaa Xaa Xaa Xaa Xaa Xaa Ala Xaa Xaa Xaa Xaa Thr Val Xaa Thr
    50                  55                  60

Val Lys Arg Xaa Xaa Xaa Xaa Gln Xaa Xaa Xaa Xaa Xaa Arg Xaa Val
65                  70                  75                  80

Glu Xaa Xaa Xaa Xaa Xaa Phe Thr Xaa Xaa Xaa Xaa Xaa Xaa Ala Xaa
                85                  90                  95

Xaa Asp Xaa Ile Xaa Xaa Xaa Xaa Xaa Xaa Ile Xaa Xaa Tyr Xaa Xaa
            100                 105                 110

Xaa Xaa Xaa Xaa Xaa Xaa Xaa Xaa Xaa Xaa Xaa Xaa Xaa Xaa Val Xaa
        115                 120                 125

Xaa Xaa Xaa Asp Xaa Xaa Xaa Xaa Met Xaa Xaa Xaa Xaa Xaa Xaa Xaa
    130                 135                 140

Xaa Xaa Xaa Xaa Xaa Xaa Xaa Xaa Ala Glu Xaa Xaa Xaa Leu Xaa Xaa
145                 150                 155                 160

Xaa Xaa Xaa Xaa Xaa Glu Gly Xaa Arg Xaa Xaa Xaa Xaa Xaa Xaa Val
                165                 170                 175

Xaa Xaa Xaa Xaa Xaa Asp Xaa Xaa Xaa Thr Xaa Xaa Xaa Xaa Xaa Xaa
            180                 185                 190

Xaa Xaa Xaa Xaa Val Val Lys Xaa Xaa Xaa Xaa Xaa Val Leu Ile Xaa
        195                 200                 205

Xaa Xaa Xaa Xaa Asn Xaa Xaa Xaa Ala Xaa Xaa Lys Xaa Xaa Cys Xaa
    210                 215                 220

Xaa Xaa Xaa Xaa Asn Phe Ala Leu Xaa Xaa Xaa Xaa Xaa Xaa Xaa Xaa
225                 230                 235                 240

Xaa Xaa Ile Xaa Xaa Met Xaa Xaa Arg Phe Xaa Xaa Xaa Xaa Xaa Xaa
                245                 250                 255

Xaa Xaa Xaa Xaa Xaa Xaa Xaa Pro Xaa Xaa Arg Xaa Xaa Xaa Xaa Xaa
            260                 265                 270

Xaa Xaa Xaa Xaa Xaa Xaa Xaa Xaa Xaa Xaa Xaa Val Xaa Xaa Gln Xaa
        275                 280                 285

Xaa Xaa Xaa Xaa Xaa Xaa Glu Xaa Xaa Thr Thr Xaa Xaa Xaa Thr Xaa
    290                 295                 300

Xaa Xaa Xaa Xaa Xaa Xaa Xaa Arg Xaa Xaa Xaa Xaa Xaa Xaa Xaa Val
305                 310                 315                 320

Xaa Xaa Xaa Xaa Xaa Xaa Xaa Xaa Xaa Xaa Xaa Xaa Ala Xaa Xaa Xaa
                325                 330                 335

Xaa Xaa Val Xaa Xaa Pro Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Val Xaa Xaa Xaa Xaa Xaa Ser Xaa Glu Xaa Tyr Gln Xaa Xaa Xaa Xaa
    370                 375                 380

Glu Xaa Xaa Thr Xaa Xaa Phe Xaa Xaa Xaa Xaa Xaa Lys Xaa Xaa Xaa
385                 390                 395                 400

Xaa Xaa Xaa Xaa Xaa Xaa Xaa Xaa Xaa Ala Xaa Xaa Xaa Xaa Xaa Xaa
                405                 410                 415

Xaa Xaa Xaa Xaa Xaa Xaa Xaa Xaa Xaa Xaa Xaa Leu Xaa Xaa Xaa Xaa
            420                 425                 430

Asn Xaa Xaa Ile Xaa Xaa Xaa Xaa Xaa Xaa Lys Xaa Xaa Xaa Xaa Ile
        435                 440                 445
```

```
Xaa Xaa Xaa Xaa Xaa Xaa Xaa Xaa Xaa His Xaa Xaa Xaa Xaa Xaa Xaa
    450                 455                 460

Xaa Xaa Xaa Thr Xaa Xaa Xaa Glu Xaa Gln Xaa Xaa Xaa Xaa Lys Ile
465                 470                 475                 480

Xaa Xaa Xaa Xaa Xaa Xaa Lys Xaa Xaa Xaa Leu Xaa Xaa Xaa Xaa Phe
                485                 490                 495

Xaa Xaa Xaa Xaa Xaa Xaa Xaa Lys Xaa Xaa Xaa Xaa Xaa Xaa Xaa Xaa
            500                 505                 510

Xaa Xaa Xaa Xaa Xaa Xaa Xaa Xaa Xaa Lys Xaa Xaa Glu Leu Val Trp
        515                 520                 525

Xaa Xaa Leu Xaa Xaa Xaa Phe Xaa Xaa Xaa Xaa Leu Xaa Ile Xaa Xaa
    530                 535                 540

Xaa Xaa Leu Tyr Xaa Xaa Xaa Xaa Xaa Gly Glu Ser Xaa Glu Ile Xaa
545                 550                 555                 560

Xaa Xaa Xaa Leu Xaa Xaa Leu Xaa Xaa Xaa Xaa Ala Xaa Xaa Xaa Xaa
                565                 570                 575

Ala Xaa Xaa Xaa Xaa Xaa Xaa Xaa Xaa Xaa Xaa Xaa Xaa Xaa Xaa Xaa
            580                 585                 590

Xaa Xaa Xaa Lys Xaa Xaa Xaa Xaa Xaa Xaa Xaa Xaa Xaa Ile Thr Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Ala Leu Xaa Xaa Asp Xaa Xaa Xaa Xaa
625                 630                 635                 640

Lys Xaa Xaa Xaa Xaa Xaa Xaa Xaa Xaa Thr Glu Xaa Xaa Ser Lys Xaa
                645                 650                 655

Xaa Val Xaa Xaa Xaa Xaa Val Xaa His Xaa Xaa Xaa Xaa Xaa Asp
            660                 665                 670

Xaa Lys Asp Xaa Xaa Xaa Thr Xaa Xaa Xaa Xaa Xaa Xaa Xaa Xaa Arg
        675                 680                 685

Xaa Xaa Xaa Arg Xaa Xaa Xaa Xaa Arg Xaa Xaa Thr Xaa Xaa Ser Xaa
    690                 695                 700

Xaa Xaa Xaa Lys Xaa Ser Xaa Arg Xaa Gly Asp Xaa Xaa Xaa Pro Phe
705                 710                 715                 720

Asp Xaa Phe Xaa Xaa Thr Xaa Xaa Xaa Xaa Xaa Xaa Xaa Xaa Xaa Xaa
                725                 730                 735

Xaa Xaa Xaa Xaa Xaa Xaa Xaa Xaa Glu Xaa Xaa Xaa Arg Ala Xaa Xaa
            740                 745                 750

Xaa Xaa Xaa Xaa Xaa Xaa Xaa Xaa Xaa Xaa Xaa Xaa Xaa Xaa Xaa Xaa
        755                 760                 765

Ser Ala Xaa Xaa Lys Pro Xaa Gly Thr
    770                 775
```

<210> SEQ ID NO 39
<211> LENGTH: 777
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(1)
<223> OTHER INFORMATION: Xaa is any amino acid or absent
<220> FEATURE:
<221> NAME/KEY: Xaa
<222> LOCATION: (3)..(3)
<223> OTHER INFORMATION: Xaa is any amino acid or absent
<220> FEATURE:

```
<221> NAME/KEY: Xaa
<222> LOCATION: (8)..(8)
<223> OTHER INFORMATION: Xaa is any amino acid or absent
<220> FEATURE:
<221> NAME/KEY: Xaa
<222> LOCATION: (10)..(10)
<223> OTHER INFORMATION: Xaa is any amino acid or absent
<220> FEATURE:
<221> NAME/KEY: Xaa
<222> LOCATION: (13)..(13)
<223> OTHER INFORMATION: Xaa is any amino acid or absent
<220> FEATURE:
<221> NAME/KEY: Xaa
<222> LOCATION: (15)..(16)
<223> OTHER INFORMATION: Xaa is any amino acid or absent
<220> FEATURE:
<221> NAME/KEY: Xaa
<222> LOCATION: (20)..(20)
<223> OTHER INFORMATION: Xaa is any amino acid or absent
<220> FEATURE:
<221> NAME/KEY: Xaa
<222> LOCATION: (22)..(23)
<223> OTHER INFORMATION: Xaa is any amino acid or absent
<220> FEATURE:
<221> NAME/KEY: Xaa
<222> LOCATION: (27)..(29)
<223> OTHER INFORMATION: Xaa is any amino acid or absent
<220> FEATURE:
<221> NAME/KEY: Xaa
<222> LOCATION: (32)..(33)
<223> OTHER INFORMATION: Xaa is any amino acid or absent
<220> FEATURE:
<221> NAME/KEY: Xaa
<222> LOCATION: (49)..(55)
<223> OTHER INFORMATION: Xaa is any amino acid or absent
<220> FEATURE:
<221> NAME/KEY: Xaa
<222> LOCATION: (57)..(57)
<223> OTHER INFORMATION: Xaa is any amino acid or absent
<220> FEATURE:
<221> NAME/KEY: Xaa
<222> LOCATION: (63)..(63)
<223> OTHER INFORMATION: Xaa is any amino acid or absent
<220> FEATURE:
<221> NAME/KEY: Xaa
<222> LOCATION: (68)..(71)
<223> OTHER INFORMATION: Xaa is any amino acid or absent
<220> FEATURE:
<221> NAME/KEY: Xaa
<222> LOCATION: (73)..(73)
<223> OTHER INFORMATION: Xaa is any amino acid or absent
<220> FEATURE:
<221> NAME/KEY: Xaa
<222> LOCATION: (77)..(77)
<223> OTHER INFORMATION: Xaa is any amino acid or absent
<220> FEATURE:
<221> NAME/KEY: Xaa
<222> LOCATION: (79)..(79)
<223> OTHER INFORMATION: Xaa is any amino acid or absent
<220> FEATURE:
<221> NAME/KEY: Xaa
<222> LOCATION: (84)..(84)
<223> OTHER INFORMATION: Xaa is any amino acid or absent
<220> FEATURE:
<221> NAME/KEY: Xaa
<222> LOCATION: (86)..(86)
<223> OTHER INFORMATION: Xaa is any amino acid or absent
<220> FEATURE:
<221> NAME/KEY: Xaa
<222> LOCATION: (96)..(97)
<223> OTHER INFORMATION: Xaa is any amino acid or absent
<220> FEATURE:
<221> NAME/KEY: Xaa
<222> LOCATION: (99)..(99)
<223> OTHER INFORMATION: Xaa is any amino acid or absent
<220> FEATURE:
<221> NAME/KEY: Xaa
<222> LOCATION: (101)..(102)
<223> OTHER INFORMATION: Xaa is any amino acid or absent
```

-continued

<220> FEATURE:
<221> NAME/KEY: Xaa
<222> LOCATION: (104)..(105)
<223> OTHER INFORMATION: Xaa is any amino acid or absent
<220> FEATURE:
<221> NAME/KEY: Xaa
<222> LOCATION: (124)..(124)
<223> OTHER INFORMATION: Xaa is any amino acid or absent
<220> FEATURE:
<221> NAME/KEY: Xaa
<222> LOCATION: (134)..(134)
<223> OTHER INFORMATION: Xaa is any amino acid or absent
<220> FEATURE:
<221> NAME/KEY: Xaa
<222> LOCATION: (136)..(136)
<223> OTHER INFORMATION: Xaa is any amino acid or absent
<220> FEATURE:
<221> NAME/KEY: Xaa
<222> LOCATION: (138)..(140)
<223> OTHER INFORMATION: Xaa is any amino acid or absent
<220> FEATURE:
<221> NAME/KEY: Xaa
<222> LOCATION: (145)..(145)
<223> OTHER INFORMATION: Xaa is any amino acid or absent
<220> FEATURE:
<221> NAME/KEY: Xaa
<222> LOCATION: (150)..(150)
<223> OTHER INFORMATION: Xaa is any amino acid or absent
<220> FEATURE:
<221> NAME/KEY: Xaa
<222> LOCATION: (156)..(157)
<223> OTHER INFORMATION: Xaa is any amino acid or absent
<220> FEATURE:
<221> NAME/KEY: Xaa
<222> LOCATION: (165)..(165)
<223> OTHER INFORMATION: Xaa is any amino acid or absent
<220> FEATURE:
<221> NAME/KEY: Xaa
<222> LOCATION: (175)..(175)
<223> OTHER INFORMATION: Xaa is any amino acid or absent
<220> FEATURE:
<221> NAME/KEY: Xaa
<222> LOCATION: (188)..(188)
<223> OTHER INFORMATION: Xaa is any amino acid or absent
<220> FEATURE:
<221> NAME/KEY: Xaa
<222> LOCATION: (194)..(196)
<223> OTHER INFORMATION: Xaa is any amino acid or absent
<220> FEATURE:
<221> NAME/KEY: Xaa
<222> LOCATION: (208)..(208)
<223> OTHER INFORMATION: Xaa is any amino acid or absent
<220> FEATURE:
<221> NAME/KEY: Xaa
<222> LOCATION: (210)..(210)
<223> OTHER INFORMATION: Xaa is any amino acid or absent
<220> FEATURE:
<221> NAME/KEY: Xaa
<222> LOCATION: (216)..(216)
<223> OTHER INFORMATION: Xaa is any amino acid or absent
<220> FEATURE:
<221> NAME/KEY: Xaa
<222> LOCATION: (221)..(221)
<223> OTHER INFORMATION: Xaa is any amino acid or absent
<220> FEATURE:
<221> NAME/KEY: Xaa
<222> LOCATION: (225)..(225)
<223> OTHER INFORMATION: Xaa is any amino acid or absent
<220> FEATURE:
<221> NAME/KEY: Xaa
<222> LOCATION: (228)..(228)
<223> OTHER INFORMATION: Xaa is any amino acid or absent
<220> FEATURE:
<221> NAME/KEY: Xaa
<222> LOCATION: (233)..(233)
<223> OTHER INFORMATION: Xaa is any amino acid or absent
<220> FEATURE:
<221> NAME/KEY: Xaa
<222> LOCATION: (235)..(239)

<223> OTHER INFORMATION: Xaa is any amino acid or absent
<220> FEATURE:
<221> NAME/KEY: Xaa
<222> LOCATION: (244)..(245)
<223> OTHER INFORMATION: Xaa is any amino acid or absent
<220> FEATURE:
<221> NAME/KEY: Xaa
<222> LOCATION: (248)..(248)
<223> OTHER INFORMATION: Xaa is any amino acid or absent
<220> FEATURE:
<221> NAME/KEY: Xaa
<222> LOCATION: (254)..(254)
<223> OTHER INFORMATION: Xaa is any amino acid or absent
<220> FEATURE:
<221> NAME/KEY: Xaa
<222> LOCATION: (258)..(258)
<223> OTHER INFORMATION: Xaa is any amino acid or absent
<220> FEATURE:
<221> NAME/KEY: Xaa
<222> LOCATION: (263)..(263)
<223> OTHER INFORMATION: Xaa is any amino acid or absent
<220> FEATURE:
<221> NAME/KEY: Xaa
<222> LOCATION: (265)..(266)
<223> OTHER INFORMATION: Xaa is any amino acid or absent
<220> FEATURE:
<221> NAME/KEY: Xaa
<222> LOCATION: (268)..(268)
<223> OTHER INFORMATION: Xaa is any amino acid or absent
<220> FEATURE:
<221> NAME/KEY: Xaa
<222> LOCATION: (270)..(270)
<223> OTHER INFORMATION: Xaa is any amino acid or absent
<220> FEATURE:
<221> NAME/KEY: Xaa
<222> LOCATION: (276)..(276)
<223> OTHER INFORMATION: Xaa is any amino acid or absent
<220> FEATURE:
<221> NAME/KEY: Xaa
<222> LOCATION: (278)..(279)
<223> OTHER INFORMATION: Xaa is any amino acid or absent
<220> FEATURE:
<221> NAME/KEY: Xaa
<222> LOCATION: (283)..(283)
<223> OTHER INFORMATION: Xaa is any amino acid or absent
<220> FEATURE:
<221> NAME/KEY: Xaa
<222> LOCATION: (285)..(285)
<223> OTHER INFORMATION: Xaa is any amino acid or absent
<220> FEATURE:
<221> NAME/KEY: Xaa
<222> LOCATION: (288)..(288)
<223> OTHER INFORMATION: Xaa is any amino acid or absent
<220> FEATURE:
<221> NAME/KEY: Xaa
<222> LOCATION: (290)..(290)
<223> OTHER INFORMATION: Xaa is any amino acid or absent
<220> FEATURE:
<221> NAME/KEY: Xaa
<222> LOCATION: (292)..(294)
<223> OTHER INFORMATION: Xaa is any amino acid or absent
<220> FEATURE:
<221> NAME/KEY: Xaa
<222> LOCATION: (300)..(300)
<223> OTHER INFORMATION: Xaa is any amino acid or absent
<220> FEATURE:
<221> NAME/KEY: Xaa
<222> LOCATION: (304)..(310)
<223> OTHER INFORMATION: Xaa is any amino acid or absent
<220> FEATURE:
<221> NAME/KEY: Xaa
<222> LOCATION: (319)..(319)
<223> OTHER INFORMATION: Xaa is any amino acid or absent
<220> FEATURE:
<221> NAME/KEY: Xaa
<222> LOCATION: (322)..(322)
<223> OTHER INFORMATION: Xaa is any amino acid or absent
<220> FEATURE:
<221> NAME/KEY: Xaa
<222> LOCATION: (326)..(326)
<223> OTHER INFORMATION: Xaa is any amino acid or absent
<220> FEATURE:
<221> NAME/KEY: Xaa
<222> LOCATION: (329)..(329)
<223> OTHER INFORMATION: Xaa is any amino acid or absent
<220> FEATURE:
<221> NAME/KEY: Xaa
<222> LOCATION: (334)..(334)
<223> OTHER INFORMATION: Xaa is any amino acid or absent
<220> FEATURE:
<221> NAME/KEY: Xaa
<222> LOCATION: (336)..(337)
<223> OTHER INFORMATION: Xaa is any amino acid or absent
<220> FEATURE:
<221> NAME/KEY: Xaa
<222> LOCATION: (341)..(341)
<223> OTHER INFORMATION: Xaa is any amino acid or absent
<220> FEATURE:
<221> NAME/KEY: Xaa
<222> LOCATION: (343)..(343)
<223> OTHER INFORMATION: Xaa is any amino acid or absent
<220> FEATURE:
<221> NAME/KEY: Xaa
<222> LOCATION: (347)..(347)
<223> OTHER INFORMATION: Xaa is any amino acid or absent
<220> FEATURE:
<221> NAME/KEY: Xaa
<222> LOCATION: (358)..(358)
<223> OTHER INFORMATION: Xaa is any amino acid or absent
<220> FEATURE:
<221> NAME/KEY: Xaa
<222> LOCATION: (361)..(362)
<223> OTHER INFORMATION: Xaa is any amino acid or absent
<220> FEATURE:
<221> NAME/KEY: Xaa
<222> LOCATION: (365)..(365)
<223> OTHER INFORMATION: Xaa is any amino acid or absent
<220> FEATURE:
<221> NAME/KEY: Xaa
<222> LOCATION: (376)..(376)
<223> OTHER INFORMATION: Xaa is any amino acid or absent
<220> FEATURE:
<221> NAME/KEY: Xaa
<222> LOCATION: (381)..(381)
<223> OTHER INFORMATION: Xaa is any amino acid or absent
<220> FEATURE:
<221> NAME/KEY: Xaa
<222> LOCATION: (383)..(384)
<223> OTHER INFORMATION: Xaa is any amino acid or absent
<220> FEATURE:
<221> NAME/KEY: Xaa
<222> LOCATION: (386)..(386)
<223> OTHER INFORMATION: Xaa is any amino acid or absent
<220> FEATURE:
<221> NAME/KEY: Xaa
<222> LOCATION: (390)..(390)
<223> OTHER INFORMATION: Xaa is any amino acid or absent
<220> FEATURE:
<221> NAME/KEY: Xaa
<222> LOCATION: (393)..(393)
<223> OTHER INFORMATION: Xaa is any amino acid or absent
<220> FEATURE:
<221> NAME/KEY: Xaa
<222> LOCATION: (401)..(405)
<223> OTHER INFORMATION: Xaa is any amino acid or absent
<220> FEATURE:
<221> NAME/KEY: Xaa
<222> LOCATION: (408)..(409)
<223> OTHER INFORMATION: Xaa is any amino acid or absent
<220> FEATURE:
<221> NAME/KEY: Xaa
<222> LOCATION: (417)..(418)
<223> OTHER INFORMATION: Xaa is any amino acid or absent
<220> FEATURE:
<221> NAME/KEY: Xaa
<222> LOCATION: (427)..(427)
<223> OTHER INFORMATION: Xaa is any amino acid or absent
<220> FEATURE:

<221> NAME/KEY: Xaa
<222> LOCATION: (430)..(430)
<223> OTHER INFORMATION: Xaa is any amino acid or absent
<220> FEATURE:
<221> NAME/KEY: Xaa
<222> LOCATION: (432)..(432)
<223> OTHER INFORMATION: Xaa is any amino acid or absent
<220> FEATURE:
<221> NAME/KEY: Xaa
<222> LOCATION: (439)..(439)
<223> OTHER INFORMATION: Xaa is any amino acid or absent
<220> FEATURE:
<221> NAME/KEY: Xaa
<222> LOCATION: (442)..(442)
<223> OTHER INFORMATION: Xaa is any amino acid or absent
<220> FEATURE:
<221> NAME/KEY: Xaa
<222> LOCATION: (455)..(455)
<223> OTHER INFORMATION: Xaa is any amino acid or absent
<220> FEATURE:
<221> NAME/KEY: Xaa
<222> LOCATION: (457)..(457)
<223> OTHER INFORMATION: Xaa is any amino acid or absent
<220> FEATURE:
<221> NAME/KEY: Xaa
<222> LOCATION: (460)..(462)
<223> OTHER INFORMATION: Xaa is any amino acid or absent
<220> FEATURE:
<221> NAME/KEY: Xaa
<222> LOCATION: (465)..(466)
<223> OTHER INFORMATION: Xaa is any amino acid or absent
<220> FEATURE:
<221> NAME/KEY: Xaa
<222> LOCATION: (469)..(469)
<223> OTHER INFORMATION: Xaa is any amino acid or absent
<220> FEATURE:
<221> NAME/KEY: Xaa
<222> LOCATION: (471)..(471)
<223> OTHER INFORMATION: Xaa is any amino acid or absent
<220> FEATURE:
<221> NAME/KEY: Xaa
<222> LOCATION: (473)..(473)
<223> OTHER INFORMATION: Xaa is any amino acid or absent
<220> FEATURE:
<221> NAME/KEY: Xaa
<222> LOCATION: (477)..(477)
<223> OTHER INFORMATION: Xaa is any amino acid or absent
<220> FEATURE:
<221> NAME/KEY: Xaa
<222> LOCATION: (481)..(481)
<223> OTHER INFORMATION: Xaa is any amino acid or absent
<220> FEATURE:
<221> NAME/KEY: Xaa
<222> LOCATION: (489)..(489)
<223> OTHER INFORMATION: Xaa is any amino acid or absent
<220> FEATURE:
<221> NAME/KEY: Xaa
<222> LOCATION: (493)..(493)
<223> OTHER INFORMATION: Xaa is any amino acid or absent
<220> FEATURE:
<221> NAME/KEY: Xaa
<222> LOCATION: (500)..(500)
<223> OTHER INFORMATION: Xaa is any amino acid or absent
<220> FEATURE:
<221> NAME/KEY: Xaa
<222> LOCATION: (503)..(503)
<223> OTHER INFORMATION: Xaa is any amino acid or absent
<220> FEATURE:
<221> NAME/KEY: Xaa
<222> LOCATION: (509)..(510)
<223> OTHER INFORMATION: Xaa is any amino acid or absent
<220> FEATURE:
<221> NAME/KEY: Xaa
<222> LOCATION: (518)..(518)
<223> OTHER INFORMATION: Xaa is any amino acid or absent
<220> FEATURE:
<221> NAME/KEY: Xaa
<222> LOCATION: (529)..(529)
<223> OTHER INFORMATION: Xaa is any amino acid or absent
<220> FEATURE:
<221> NAME/KEY: Xaa
<222> LOCATION: (533)..(534)
<223> OTHER INFORMATION: Xaa is any amino acid or absent
<220> FEATURE:
<221> NAME/KEY: Xaa
<222> LOCATION: (539)..(539)
<223> OTHER INFORMATION: Xaa is any amino acid or absent
<220> FEATURE:
<221> NAME/KEY: Xaa
<222> LOCATION: (557)..(557)
<223> OTHER INFORMATION: Xaa is any amino acid or absent
<220> FEATURE:
<221> NAME/KEY: Xaa
<222> LOCATION: (561)..(563)
<223> OTHER INFORMATION: Xaa is any amino acid or absent
<220> FEATURE:
<221> NAME/KEY: Xaa
<222> LOCATION: (565)..(565)
<223> OTHER INFORMATION: Xaa is any amino acid or absent
<220> FEATURE:
<221> NAME/KEY: Xaa
<222> LOCATION: (568)..(568)
<223> OTHER INFORMATION: Xaa is any amino acid or absent
<220> FEATURE:
<221> NAME/KEY: Xaa
<222> LOCATION: (573)..(573)
<223> OTHER INFORMATION: Xaa is any amino acid or absent
<220> FEATURE:
<221> NAME/KEY: Xaa
<222> LOCATION: (584)..(584)
<223> OTHER INFORMATION: Xaa is any amino acid or absent
<220> FEATURE:
<221> NAME/KEY: Xaa
<222> LOCATION: (587)..(587)
<223> OTHER INFORMATION: Xaa is any amino acid or absent
<220> FEATURE:
<221> NAME/KEY: Xaa
<222> LOCATION: (593)..(593)
<223> OTHER INFORMATION: Xaa is any amino acid or absent
<220> FEATURE:
<221> NAME/KEY: Xaa
<222> LOCATION: (599)..(599)
<223> OTHER INFORMATION: Xaa is any amino acid or absent
<220> FEATURE:
<221> NAME/KEY: Xaa
<222> LOCATION: (604)..(605)
<223> OTHER INFORMATION: Xaa is any amino acid or absent
<220> FEATURE:
<221> NAME/KEY: Xaa
<222> LOCATION: (613)..(613)
<223> OTHER INFORMATION: Xaa is any amino acid or absent
<220> FEATURE:
<221> NAME/KEY: Xaa
<222> LOCATION: (620)..(621)
<223> OTHER INFORMATION: Xaa is any amino acid or absent
<220> FEATURE:
<221> NAME/KEY: Xaa
<222> LOCATION: (626)..(626)
<223> OTHER INFORMATION: Xaa is any amino acid or absent
<220> FEATURE:
<221> NAME/KEY: Xaa
<222> LOCATION: (628)..(628)
<223> OTHER INFORMATION: Xaa is any amino acid or absent
<220> FEATURE:
<221> NAME/KEY: Xaa
<222> LOCATION: (635)..(635)
<223> OTHER INFORMATION: Xaa is any amino acid or absent
<220> FEATURE:
<221> NAME/KEY: Xaa
<222> LOCATION: (637)..(638)
<223> OTHER INFORMATION: Xaa is any amino acid or absent
<220> FEATURE:
<221> NAME/KEY: Xaa
<222> LOCATION: (640)..(640)
<223> OTHER INFORMATION: Xaa is any amino acid or absent
<220> FEATURE:
<221> NAME/KEY: Xaa
<222> LOCATION: (644)..(645)

<223> OTHER INFORMATION: Xaa is any amino acid or absent
<220> FEATURE:
<221> NAME/KEY: Xaa
<222> LOCATION: (647)..(649)
<223> OTHER INFORMATION: Xaa is any amino acid or absent
<220> FEATURE:
<221> NAME/KEY: Xaa
<222> LOCATION: (652)..(653)
<223> OTHER INFORMATION: Xaa is any amino acid or absent
<220> FEATURE:
<221> NAME/KEY: Xaa
<222> LOCATION: (657)..(657)
<223> OTHER INFORMATION: Xaa is any amino acid or absent
<220> FEATURE:
<221> NAME/KEY: Xaa
<222> LOCATION: (660)..(660)
<223> OTHER INFORMATION: Xaa is any amino acid or absent
<220> FEATURE:
<221> NAME/KEY: Xaa
<222> LOCATION: (673)..(673)
<223> OTHER INFORMATION: Xaa is any amino acid or absent
<220> FEATURE:
<221> NAME/KEY: Xaa
<222> LOCATION: (677)..(677)
<223> OTHER INFORMATION: Xaa is any amino acid or absent
<220> FEATURE:
<221> NAME/KEY: Xaa
<222> LOCATION: (685)..(685)
<223> OTHER INFORMATION: Xaa is any amino acid or absent
<220> FEATURE:
<221> NAME/KEY: Xaa
<222> LOCATION: (690)..(691)
<223> OTHER INFORMATION: Xaa is any amino acid or absent
<220> FEATURE:
<221> NAME/KEY: Xaa
<222> LOCATION: (694)..(696)
<223> OTHER INFORMATION: Xaa is any amino acid or absent
<220> FEATURE:
<221> NAME/KEY: Xaa
<222> LOCATION: (701)..(701)
<223> OTHER INFORMATION: Xaa is any amino acid or absent
<220> FEATURE:
<221> NAME/KEY: Xaa
<222> LOCATION: (705)..(706)
<223> OTHER INFORMATION: Xaa is any amino acid or absent
<220> FEATURE:
<221> NAME/KEY: Xaa
<222> LOCATION: (713)..(713)
<223> OTHER INFORMATION: Xaa is any amino acid or absent
<220> FEATURE:
<221> NAME/KEY: Xaa
<222> LOCATION: (717)..(717)
<223> OTHER INFORMATION: Xaa is any amino acid or absent
<220> FEATURE:
<221> NAME/KEY: Xaa
<222> LOCATION: (724)..(725)
<223> OTHER INFORMATION: Xaa is any amino acid or absent
<220> FEATURE:
<221> NAME/KEY: Xaa
<222> LOCATION: (729)..(729)
<223> OTHER INFORMATION: Xaa is any amino acid or absent
<220> FEATURE:
<221> NAME/KEY: Xaa
<222> LOCATION: (732)..(733)
<223> OTHER INFORMATION: Xaa is any amino acid or absent
<220> FEATURE:
<221> NAME/KEY: Xaa
<222> LOCATION: (747)..(747)
<223> OTHER INFORMATION: Xaa is any amino acid or absent
<220> FEATURE:
<221> NAME/KEY: Xaa
<222> LOCATION: (754)..(757)
<223> OTHER INFORMATION: Xaa is any amino acid or absent
<220> FEATURE:
<221> NAME/KEY: Xaa
<222> LOCATION: (759)..(760)
<223> OTHER INFORMATION: Xaa is any amino acid or absent
<220> FEATURE:
<221> NAME/KEY: Xaa
<222> LOCATION: (762)..(764)
<223> OTHER INFORMATION: Xaa is any amino acid or absent
<220> FEATURE:
<221> NAME/KEY: Xaa
<222> LOCATION: (766)..(766)
<223> OTHER INFORMATION: Xaa is any amino acid or absent
<220> FEATURE:
<221> NAME/KEY: Xaa
<222> LOCATION: (772)..(772)
<223> OTHER INFORMATION: Xaa is any amino acid or absent
<220> FEATURE:
<221> NAME/KEY: Xaa
<222> LOCATION: (775)..(775)
<223> OTHER INFORMATION: Xaa is any amino acid or absent

<400> SEQUENCE: 39

```
Xaa Ile Xaa Asp Thr Asp Tyr Xaa Thr Xaa Asp Gly Xaa Pro Xaa Xaa
1               5                   10                  15

Arg Ile Phe Xaa Lys Xaa Xaa Gly Glu Phe Xaa Xaa Xaa Tyr Asp Xaa
            20                  25                  30

Xaa Phe Glu Pro Tyr Phe Tyr Ala Leu Leu Lys Asp Asp Ser Ala Ile
        35                  40                  45

Xaa Xaa Xaa Xaa Xaa Xaa Xaa Ala Xaa Arg His Gly Thr Val Xaa Thr
    50                  55                  60

Val Lys Arg Xaa Xaa Xaa Xaa Gln Xaa Lys Phe Leu Xaa Arg Xaa Val
65                  70                  75                  80

Glu Val Trp Xaa Leu Xaa Phe Thr His Pro Gln Asp Val Pro Ala Xaa
                85                  90                  95

Xaa Asp Xaa Ile Xaa Xaa His Xaa Xaa Val Ile Asp Ile Tyr Glu Tyr
            100                 105                 110

Asp Ile Pro Phe Ala Lys Arg Tyr Leu Ile Asp Xaa Gly Leu Val Pro
        115                 120                 125

Met Glu Gly Asp Glu Xaa Leu Xaa Met Xaa Xaa Xaa Asp Ile Glu Thr
    130                 135                 140

Xaa Tyr His Glu Gly Xaa Glu Phe Ala Glu Gly Xaa Xaa Leu Met Ile
145                 150                 155                 160

Ser Tyr Ala Asp Xaa Glu Gly Ala Arg Val Ile Thr Trp Lys Xaa Val
                165                 170                 175

Asp Leu Pro Tyr Val Asp Val Val Ser Thr Glu Xaa Glu Met Ile Lys
            180                 185                 190

Arg Xaa Xaa Xaa Val Val Lys Glu Lys Asp Pro Asp Val Leu Ile Xaa
        195                 200                 205

Tyr Xaa Gly Asp Asn Phe Asp Xaa Ala Tyr Leu Lys Xaa Arg Cys Glu
    210                 215                 220

Xaa Leu Gly Xaa Asn Phe Ala Leu Xaa Arg Xaa Xaa Xaa Xaa Xaa Glu
225                 230                 235                 240

Pro Lys Ile Xaa Xaa Met Gly Xaa Arg Phe Ala Val Glu Xaa Lys Gly
                245                 250                 255

Arg Xaa His Phe Asp Leu Xaa Pro Xaa Xaa Arg Xaa Thr Xaa Asn Leu
            260                 265                 270

Pro Thr Tyr Xaa Leu Xaa Xaa Val Tyr Glu Xaa Val Xaa Gly Gln Xaa
        275                 280                 285

Lys Xaa Lys Xaa Xaa Xaa Glu Glu Ile Thr Thr Xaa Trp Glu Thr Xaa
    290                 295                 300

Xaa Xaa Xaa Xaa Xaa Xaa Ala Arg Tyr Ser Met Glu Asp Ala Xaa Val
305                 310                 315                 320

Thr Xaa Glu Leu Gly Xaa Glu Phe Xaa Pro Met Glu Ala Xaa Leu Xaa
                325                 330                 335
```

```
Xaa Leu Val Gly Xaa Pro Xaa Trp Asp Val Xaa Arg Ser Ser Thr Gly
            340                 345                 350

Asn Leu Val Glu Trp Xaa Leu Leu Xaa Xaa Ala Tyr Xaa Arg Asn Glu
        355                 360                 365

Val Ala Pro Asn Lys Pro Ser Xaa Glu Glu Tyr Gln Xaa Arg Xaa Xaa
    370                 375                 380

Glu Xaa Tyr Thr Gly Xaa Phe Val Xaa Glu Pro Glu Lys Gly Leu Trp
385                 390                 395                 400

Xaa Xaa Xaa Xaa Xaa Leu Asp Xaa Xaa Ala Leu Tyr Pro Ser Ile Ile
                405                 410                 415

Xaa Xaa His Asn Val Ser Pro Asp Thr Leu Xaa Leu Glu Xaa Cys Xaa
            420                 425                 430

Asn Tyr Asp Ile Ala Pro Xaa Val Gly Xaa Lys Phe Cys Lys Asp Ile
        435                 440                 445

Pro Gly Phe Ile Pro Ser Xaa Leu Xaa His Leu Xaa Xaa Xaa Arg Gln
    450                 455                 460

Xaa Xaa Lys Thr Xaa Met Xaa Glu Xaa Gln Asp Pro Xaa Glu Lys Ile
465                 470                 475                 480

Xaa Leu Asp Tyr Arg Gln Lys Ala Xaa Lys Leu Leu Xaa Asn Ser Phe
                485                 490                 495

Tyr Gly Tyr Xaa Gly Tyr Xaa Lys Ala Arg Trp Tyr Xaa Xaa Glu Cys
            500                 505                 510

Ala Glu Ser Val Thr Xaa Trp Gly Arg Lys Tyr Ile Glu Leu Val Trp
        515                 520                 525

Xaa Glu Leu Glu Xaa Xaa Phe Gly Phe Lys Xaa Leu Tyr Ile Asp Thr
    530                 535                 540

Asp Gly Leu Tyr Ala Thr Ile Pro Gly Gly Glu Ser Xaa Glu Ile Lys
545                 550                 555                 560

Xaa Xaa Xaa Leu Xaa Phe Leu Xaa Tyr Ile Asn Ala Xaa Leu Pro Gly
                565                 570                 575

Ala Leu Glu Leu Glu Tyr Glu Xaa Phe Tyr Xaa Arg Gly Phe Phe Val
            580                 585                 590

Xaa Lys Lys Lys Tyr Ala Xaa Ile Asp Glu Glu Xaa Xaa Ile Thr Thr
        595                 600                 605

Arg Gly Leu Glu Xaa Val Arg Arg Asp Trp Ser Xaa Xaa Ala Lys Glu
    610                 615                 620

Thr Xaa Ala Xaa Val Leu Glu Ala Leu Leu Xaa Asp Xaa Xaa Val Xaa
625                 630                 635                 640

Lys Ala Val Xaa Xaa Val Xaa Xaa Xaa Thr Glu Xaa Xaa Ser Lys Tyr
                645                 650                 655

Xaa Val Pro Xaa Glu Lys Leu Val Ile His Glu Gln Ile Thr Arg Asp
            660                 665                 670

Xaa Lys Asp Tyr Xaa Ala Thr Gly Pro His Val Ala Xaa Ala Lys Arg
        675                 680                 685

Leu Xaa Xaa Arg Gly Xaa Xaa Xaa Arg Pro Gly Thr Xaa Ile Ser Tyr
    690                 695                 700

Xaa Xaa Leu Lys Gly Ser Gly Arg Xaa Gly Asp Arg Xaa Ile Pro Phe
705                 710                 715                 720

Asp Glu Phe Xaa Xaa Thr Lys His Xaa Tyr Asp Xaa Xaa Tyr Tyr Ile
                725                 730                 735

Glu Asn Gln Val Leu Pro Ala Val Glu Arg Xaa Leu Arg Ala Phe Gly
            740                 745                 750
```

-continued

Tyr Xaa Xaa Xaa Xaa Leu Xaa Xaa Gln Xaa Xaa Xaa Gln Xaa Gly Leu
        755                 760                 765

Ser Ala Trp Xaa Lys Pro Xaa Gly Thr
    770                 775

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
tttggaaaca tctggagtcc t 21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gcccaaaggg aactgatagt c 21

<210> SEQ ID NO 42
<211> LENGTH: 17
<212> TYPE: DNA
<213> ORGANISM: Artificial Sequence
<220> FEATURE:
<223> OTHER INFORMATION: Primer

<400> SEQUENCE: 42
gttttcccag tcacgac 17

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ggtatcttta tagtcctgtc g 21

<210> SEQ ID NO 44
<211> LENGTH: 34
<212> TYPE: DNA
<213> ORGANISM: Artificial Sequence
<220> FEATURE:
<223> OTHER INFORMATION: Primer

<400> SEQUENCE: 44
gttttcccag tcacgacgtt gtaaaacgac ggcc 34

<210> SEQ ID NO 45
<211> LENGTH: 775
<212> TYPE: PRT
<213> ORGANISM: Pyrococcus sp. GB-D

<400> SEQUENCE: 45

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

-continued

```
Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445
```

-continued

```
Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775
```

<210> SEQ ID NO 46
<211> LENGTH: 1829
<212> TYPE: PRT
<213> ORGANISM: Thermococcus aggregans
<220> FEATURE:
<221> NAME/KEY: misc_feature
<222> LOCATION: (1118)..(1118)
<223> OTHER INFORMATION: Xaa can be any naturally occurring amino acid
<220> FEATURE:
<221> NAME/KEY: misc_feature
<222> LOCATION: (1123)..(1123)
<223> OTHER INFORMATION: Xaa can be any naturally occurring amino acid

<400> SEQUENCE: 46

-continued

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Asp Glu Ile Lys Ala Ile Lys Gly Glu Arg His Gly Lys Ile Val Arg
    50                  55                  60

Val Val Asp Ala Val Lys Val Lys Lys Lys Phe Leu Gly Arg Asp Val
65                  70                  75                  80

Glu Val Trp Lys Leu Ile Phe Glu His Pro Gln Asp Val Pro Ala Leu
                85                  90                  95

Arg Gly Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Met Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Ile Val Arg Glu Lys Asp Pro Asp Val Leu Ile Thr
        195                 200                 205

Tyr Asn Gly Asp Asn Phe Asp Leu Pro Tyr Leu Ile Lys Arg Ala Glu
    210                 215                 220

Lys Leu Gly Val Thr Leu Leu Leu Gly Arg Asp Lys Glu His Pro Glu
225                 230                 235                 240

Pro Lys Ile His Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Glu Arg Asn Glu
        355                 360                 365

Leu Ala Pro Asn Lys Pro Asp Glu Glu Glu Tyr Arg Arg Arg Leu Arg
    370                 375                 380

Thr Thr Tyr Leu Gly Gly Tyr Val Lys Glu Pro Glu Arg Gly Leu Trp
385                 390                 395                 400

Glu Asn Ile Ala Tyr Leu Asp Phe Arg Cys His Pro Ala Asp Thr Lys
                405                 410                 415

Val Ile Val Lys Gly Lys Gly Ile Val Asn Ile Ser Asp Val Lys Glu
```

-continued

```
            420                 425                 430

Gly Asp Tyr Ile Leu Gly Ile Asp Gly Trp Gln Arg Val Lys Lys Val
        435                 440                 445

Trp Lys Tyr His Tyr Glu Gly Lys Leu Ile Asn Ile Asn Gly Leu Lys
    450                 455                 460

Cys Thr Pro Asn His Lys Val Pro Val Val Thr Glu Asn Asp Arg Gln
465                 470                 475                 480

Thr Arg Ile Arg Asp Ser Leu Ala Lys Ser Phe Leu Ser Gly Lys Val
                485                 490                 495

Lys Gly Lys Ile Ile Thr Thr Lys Leu Phe Glu Lys Ile Ala Glu Phe
            500                 505                 510

Glu Lys Asn Lys Pro Ser Glu Glu Glu Ile Leu Lys Gly Glu Leu Ser
        515                 520                 525

Gly Ile Ile Leu Ala Glu Gly Thr Leu Leu Arg Lys Asp Ile Glu Tyr
    530                 535                 540

Phe Asp Ser Ser Arg Gly Lys Lys Arg Ile Ser His Gln Tyr Arg Val
545                 550                 555                 560

Glu Ile Thr Ile Gly Glu Asn Glu Lys Glu Leu Leu Glu Arg Ile Leu
                565                 570                 575

Tyr Ile Phe Asp Lys Leu Phe Gly Ile Arg Pro Ser Val Lys Lys Lys
            580                 585                 590

Gly Asp Thr Asn Ala Leu Lys Ile Thr Thr Ala Lys Lys Ala Val Tyr
        595                 600                 605

Leu Gln Ile Glu Glu Leu Leu Lys Asn Ile Glu Ser Leu Tyr Ala Pro
    610                 615                 620

Ala Val Leu Arg Gly Phe Phe Glu Arg Asp Ala Thr Val Asn Lys Ile
625                 630                 635                 640

Arg Ser Thr Ile Val Val Thr Gln Gly Thr Asn Asn Lys Trp Lys Ile
                645                 650                 655

Asp Ile Val Ala Lys Leu Leu Asp Ser Leu Gly Ile Pro Tyr Ser Arg
            660                 665                 670

Tyr Glu Tyr Lys Tyr Ile Glu Asn Gly Lys Glu Leu Thr Lys His Ile
        675                 680                 685

Leu Glu Ile Thr Gly Arg Asp Gly Leu Ile Leu Phe Gln Thr Leu Val
    690                 695                 700

Gly Phe Ile Ser Ser Glu Lys Asn Glu Ala Leu Glu Lys Ala Ile Glu
705                 710                 715                 720

Val Arg Glu Met Asn Arg Leu Lys Asn Asn Ser Phe Tyr Asn Leu Ser
                725                 730                 735

Thr Phe Glu Val Ser Ser Glu Tyr Tyr Lys Gly Glu Val Tyr Asp Leu
            740                 745                 750

Thr Leu Glu Gly Asn Pro Tyr Tyr Phe Ala Asn Gly Ile Leu Thr His
        755                 760                 765

Asn Ser Leu Tyr Pro Ser Ile Ile Val Thr His Asn Val Ser Pro Asp
    770                 775                 780

Thr Leu Glu Arg Glu Gly Cys Lys Asn Tyr Asp Val Ala Pro Ile Val
785                 790                 795                 800

Gly Tyr Lys Phe Cys Lys Asp Phe Pro Gly Phe Ile Pro Ser Ile Leu
                805                 810                 815

Gly Glu Leu Ile Thr Met Arg Gln Glu Ile Lys Lys Lys Met Lys Ala
            820                 825                 830

Thr Ile Asp Pro Ile Glu Lys Lys Met Leu Asp Tyr Arg Gln Arg Ala
        835                 840                 845
```

```
Val Lys Leu Leu Ala Asn Ser Ile Leu Pro Asn Glu Trp Leu Pro Ile
    850                 855                 860

Ile Glu Asn Gly Glu Val Lys Phe Val Lys Ile Gly Glu Phe Ile Asp
865                 870                 875                 880

Arg Tyr Met Glu Glu Gln Lys Asp Lys Val Arg Thr Val Asp Asn Thr
                885                 890                 895

Glu Val Leu Glu Val Asp Asn Ile Phe Ala Phe Ser Leu Asn Lys Glu
            900                 905                 910

Ser Lys Lys Ser Glu Ile Lys Lys Val Lys Ala Leu Ile Arg His Lys
        915                 920                 925

Tyr Lys Gly Glu Ala Tyr Glu Val Glu Leu Asn Ser Gly Arg Lys Ile
    930                 935                 940

His Ile Thr Arg Gly His Ser Leu Phe Thr Ile Arg Asn Gly Lys Ile
945                 950                 955                 960

Lys Glu Ile Trp Gly Glu Glu Val Lys Val Gly Asp Leu Ile Ile Val
                965                 970                 975

Pro Lys Lys Val Lys Leu Asn Glu Lys Glu Ala Val Ile Asn Ile Pro
            980                 985                 990

Glu Leu Ile Ser Lys Leu Pro Asp  Glu Asp Thr Ala Asp  Val Val Met
        995                 1000                1005

Thr Thr  Pro Val Lys Gly Arg  Lys Asn Phe Phe Lys  Gly Met Leu
    1010                1015                1020

Arg Thr  Leu Lys Trp Ile Phe  Gly Glu Glu Ser Lys  Arg Ile Arg
    1025                1030                1035

Thr Phe  Asn Arg Tyr Leu Phe  His Leu Glu Glu Leu  Gly Phe Val
    1040                1045                1050

Lys Leu  Leu Pro Arg Gly Tyr  Glu Val Thr Asp Trp  Glu Gly Leu
    1055                1060                1065

Lys Arg  Tyr Arg Gln Leu Tyr  Glu Lys Leu Val Lys  Asn Leu Arg
    1070                1075                1080

Tyr Asn  Gly Asn Lys Arg Glu  Tyr Leu Val Arg Phe  Asn Asp Ile
    1085                1090                1095

Lys Asp  Ser Val Ser Cys Phe  Pro Arg Lys Glu Leu  Glu Glu Trp
    1100                1105                1110

Lys Ile  Gly Thr Xaa Lys Gly  Phe Arg Xaa Lys Cys  Ile Leu Lys
    1115                1120                1125

Val Asp  Glu Asp Phe Gly Lys  Phe Leu Gly Tyr Tyr  Val Ser Glu
    1130                1135                1140

Gly Tyr  Ala Gly Ala Gln Lys  Asn Lys Thr Gly Gly  Met Ser Tyr
    1145                1150                1155

Ser Val  Lys Leu Tyr Asn Glu  Asn Pro Asn Val Leu  Lys Asp Met
    1160                1165                1170

Lys Asn  Ile Ala Glu Lys Phe  Phe Gly Lys Val Arg  Val Gly Lys
    1175                1180                1185

Asn Cys  Val Asp Ile Pro Lys  Lys Met Ala Tyr Leu  Leu Ala Lys
    1190                1195                1200

Ser Leu  Cys Gly Val Thr Ala  Glu Asn Lys Arg Ile  Pro Ser Ile
    1205                1210                1215

Ile Phe  Asp Ser Ser Glu Pro  Val Arg Trp Ala Phe  Leu Arg Ala
    1220                1225                1230

Tyr Phe  Val Gly Asp Gly Asp  Ile His Pro Ser Lys  Arg Leu Arg
    1235                1240                1245
```

-continued

```
Leu Ser  Thr Lys Ser Glu Leu  Leu Ala Asn Gln Leu  Val Phe Leu
    1250                 1255                 1260

Leu Asn  Ser Leu Gly Val Ser  Ser Ile Lys Ile Gly  Phe Asp Ser
    1265                 1270                 1275

Gly Val  Tyr Arg Val Tyr Ile  Asn Glu Asp Leu Pro  Phe Leu Gln
    1280                 1285                 1290

Thr Ser  Arg Gln Lys Asn Thr  Tyr Tyr Pro Asn Leu  Ile Pro Lys
    1295                 1300                 1305

Glu Val  Leu Glu Glu Ile Phe  Gly Arg Lys Phe Gln  Lys Asn Ile
    1310                 1315                 1320

Thr Phe  Glu Lys Phe Lys Glu  Leu Ala Asp Ser Gly  Lys Leu Asp
    1325                 1330                 1335

Lys Arg  Lys Val Lys Leu Leu  Asp Phe Leu Leu Asn  Gly Asp Ile
    1340                 1345                 1350

Val Leu  Asp Arg Val Lys Asn  Val Glu Lys Arg Glu  Tyr Glu Gly
    1355                 1360                 1365

Tyr Val  Tyr Asp Leu Ser Val  Glu Asp Asn Glu Asn  Phe Leu Val
    1370                 1375                 1380

Gly Phe  Gly Leu Leu Tyr Ala  His Asn Ser Tyr Tyr  Gly Tyr Met
    1385                 1390                 1395

Gly Tyr  Pro Lys Ala Arg Trp  Tyr Ser Lys Glu Cys  Ala Glu Ser
    1400                 1405                 1410

Val Thr  Ala Trp Gly Arg His  Tyr Ile Glu Met Thr  Ile Lys Glu
    1415                 1420                 1425

Ile Glu  Glu Lys Phe Gly Phe  Lys Val Leu Tyr Ala  Asp Ser Val
    1430                 1435                 1440

Thr Gly  Asp Thr Glu Ile Ile  Val Lys Arg Asn Gly  Arg Ile Glu
    1445                 1450                 1455

Phe Val  Pro Ile Glu Lys Leu  Phe Glu Arg Val Asp  Tyr Arg Ile
    1460                 1465                 1470

Gly Glu  Lys Glu Tyr Cys Ile  Leu Glu Asp Val Glu  Ala Leu Thr
    1475                 1480                 1485

Leu Asp  Asn Arg Gly Lys Leu  Ile Trp Lys Lys Val  Pro Tyr Val
    1490                 1495                 1500

Met Arg  His Arg Ala Lys Lys  Lys Val Tyr Arg Ile  Trp Ile Thr
    1505                 1510                 1515

Asn Ser  Trp Tyr Ile Asp Val  Thr Glu Asp His Ser  Leu Ile Val
    1520                 1525                 1530

Ala Glu  Asp Gly Leu Lys Glu  Ala Arg Pro Met Glu  Ile Glu Gly
    1535                 1540                 1545

Lys Ser  Leu Ile Ala Thr Lys  Asp Asp Leu Ser Gly  Val Glu Tyr
    1550                 1555                 1560

Ile Lys  Pro His Ala Ile Glu  Glu Ile Ser Tyr Asn  Gly Tyr Val
    1565                 1570                 1575

Tyr Asp  Ile Glu Val Glu Gly  Thr His Arg Phe Phe  Ala Asn Gly
    1580                 1585                 1590

Ile Leu  Val His Asn Thr Asp  Gly Phe Tyr Ala Thr  Ile Pro Gly
    1595                 1600                 1605

Glu Lys  Pro Glu Thr Ile Lys  Lys Lys Ala Lys Glu  Phe Leu Lys
    1610                 1615                 1620

Tyr Ile  Asn Ser Lys Leu Pro  Gly Leu Leu Glu Leu  Glu Tyr Glu
    1625                 1630                 1635

Gly Phe  Tyr Leu Arg Gly Phe  Phe Val Ala Lys Lys  Arg Tyr Ala
```

-continued

```
    1640                1645                1650

Val Ile  Asp Glu Glu Gly Arg  Ile Thr Thr Arg Gly  Leu Glu Val
    1655                1660                1665

Val Arg  Arg Asp Trp Ser Glu  Ile Ala Lys Glu Thr  Gln Ala Lys
    1670                1675                1680

Val Leu  Glu Ala Ile Leu Lys  Glu Asp Ser Val Glu  Lys Ala Val
    1685                1690                1695

Glu Ile  Val Lys Asp Val Val  Glu Glu Ile Ala Lys  Tyr Gln Val
    1700                1705                1710

Pro Leu  Glu Lys Leu Val Ile  His Glu Gln Ile Thr  Lys Asp Leu
    1715                1720                1725

Ser Glu  Tyr Lys Ala Ile Gly  Pro His Val Ala Ile  Ala Lys Arg
    1730                1735                1740

Leu Ala  Ala Lys Gly Ile Lys  Val Arg Pro Gly Thr  Ile Ile Ser
    1745                1750                1755

Tyr Ile  Val Leu Arg Gly Ser  Gly Lys Ile Ser Asp  Arg Val Ile
    1760                1765                1770

Leu Leu  Ser Glu Tyr Asp Pro  Lys Lys His Lys Tyr  Asp Pro Asp
    1775                1780                1785

Tyr Tyr  Ile Glu Asn Gln Val  Leu Pro Ala Val Leu  Arg Ile Leu
    1790                1795                1800

Glu Ala  Phe Gly Tyr Arg Lys  Glu Asp Leu Lys Tyr  Gln Ser Ser
    1805                1810                1815

Lys Gln  Val Gly Leu Asp Ala  Trp Leu Lys Lys
    1820                1825
```

CHIMERIC DNA POLYMERASES

The present application claims benefit of priority patent application Ser. No. 13/127,420, filed Jul. 19, 2011, as a national phase entry of International Application serial number PCT/US2009/063166, filed Nov. 3, 2009 which claims priority to U.S. Provisional Patent Application Ser. No. 61/110,862, filed Nov. 3, 2008. The entire disclosure of each of these is incorporated herein by reference.

BACKGROUND OF THE INVENTION

DNA polymerases are enzymes that use single-stranded DNA as a template to synthesize the complementary DNA strand. In particular, DNA polymerases can add free nucleotides to the 3' end of a newly-forming strand resulting in elongation of the new strand in a 5'-3' direction. Some DNA polymerases can correct mistakes in newly-synthesized DNA. This process is known as error correction. These polymerases can recognize an incorrectly incorporated nucleotide and the 3'->5' exonuclease activity of the enzyme allows the incorrect nucleotide to be excised (this activity is known as proofreading). Following base excision, the polymerase can re-insert the correct base and replication can continue. The proofreading function gives the DNA replication much higher fidelity than it would have if synthesis were the result of only a base-pairing selection step. Brutlag, D. and Kornberg, A., *J. Biol. Chem.,* 247:241-248 (1972). DNA polymerases with 3'-5' proofreading exonuclease activity have a substantially lower error rate when compared with a non-proofreading exonuclease-possessing polymerase. Chang, L. M. S., *J. Biol. Chem.,* 252:1873-1880 (1977). However, sometimes, the advantage of these polymerases is offset by its relatively low processivity that reduces the yield of DNA amplification products.

The present specification makes reference to a Sequence Listing (submitted electronically as a .txt file named "Sequence Listing.txt" on May 3, 2011). The .txt file was generated on Nov. 12, 2013 and is 235 kb in size. The entire contents of the Sequence Listing are herein incorporated by reference.

SUMMARY OF THE INVENTION

The present invention encompasses the discovery that domain swapping can combine desired functional characteristics (e.g., high processivity, high elongation rate, thermostability, resistance to salt, PCR additives (e.g., PCR enhancers) and other impurities, and high fidelity) of different DNA polymerases in a chimeric enzyme. Thus, the present invention provides, among other things, robust, fast and accurate DNA polymerases for DNA amplification, synthesis, detection, sequencing and other important recombinant DNA techniques.

In one aspect, the present invention provides chimeric polymerases containing a first domain having a sequence at least 80% (e.g., at least 85%, 90%, 91%, 92%, 93%, 94%, 95%, 96%, 97%, 98%, 99%) identical to an amino acid sequence found in a first DNA polymerase characterized with high processivity, elongation rate, salt resistance, thermostability or TMAC tolerance; and a second domain having a sequence at least 80% (e.g., at least 85%, 90%, 91%, 92%, 93%, 94%, 95%, 96%, 97%, 98%, 99%) identical to an amino acid sequence found in a second DNA polymerase characterized with high fidelity, wherein the chimeric polymerases are characterized with both high fidelity and high processivity, elongation rate, or salt resistance. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. As used herein, the term "high elongation rate" refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s). As used herein, the term "high salt resistance" refers to the ability of a DNA polymerase to substantially maintain its enzymatic activity at a salt concentration higher than 30 mM (e.g., higher than 35 mM, 40 mM, 45 mM, or 50 mM). As used herein, the term "high fidelity" refers to an error rate less than $4.45\times10^{-6}$ (e.g., less than $4.0\times10^{-6}$, $3.5\times10^{-6}$, $3.0\times10^{-6}$, $2.5\times10^{-6}$, $2.0\times10^{-6}$, $1.5\times10^{-6}$, $1.0\times10^{-6}$, $0.5\times10^{-6}$) mutations/nt/doubling. As used herein, the term "high TMAC tolerance" refers to the ability of a DNA polymerase to substantially maintain its enzymatic activity at a TMAC (tetra-methyl ammonium chloride) concentration higher than 10 mM (e.g., higher than 15 mM, 20 mM, 25 mM, 30 mM). As used herein, the term "high thermostability" refers to the ability of a DNA polymerase to substantially maintain its enzymatic activity after more than 30 minutes incubation at 98° C. (e.g., 45 min, 60 min, 90 min, 180 min, 210 min, 240 min). The terms of "processivity," "elongation rate," "fidelity," "salt resistance," "TMAC tolerance," and "thermostability" are further defined in the Definitions section.

In some embodiments, exemplary first DNA polymerases suitable for the present invention include, but are not limited to, KOD polymerase, TNA1 polymerase, *Thermococcus* sp. 9 degrees N-7, T4, T7, or phi29. In some embodiments, the first DNA polymerase is KOD polymerase. In some embodiments, exemplary second DNA polymerases suitable for the invention include, but are not limited to, polymerases isolated from *Pyrococcus furiosus, P. abyssi, T. gorgonarius, T. litoralis, T. zilligii, T.* sp. GT, or *P.* sp. GB-D. In some embodiments, the second DNA polymerase is Pfu polymerase. In particular embodiments, the first DNA polymerase is KOD polymerase and the second DNA polymerase is Pfu polymerase.

In some embodiments, suitable first domain is an exonuclease domain, N-terminal domain, and/or a thumb domain. In some embodiments, suitable second domain is palm and/or fingers domain.

In some embodiments, amino acid sequences found in the first DNA polymerase correspond to amino acid residues 26 to 105 of KOD polymerase (SEQ ID NO:11), amino acid residues 156 to 301 of KOD polymerase (SEQ ID NO:11), and/or amino acid residues 612 to 749 of KOD polymerase (SEQ ID NO:11).

In some embodiments, amino acid sequences found in the second DNA polymerase correspond to amino acid residues 394 to 563 of Pfu polymerase (SEQ ID NO:9).

In some embodiments, a chimeric polymerase in accordance with the present invention include a first domain having a consensus sequence selected from the group consisting of XXLXXXXXXXEGXRXXXXXX-
VXXXXXDXXXTXXXXXXXXXXV-
VKXXXXXVLIX XXXXNXXXAXXKXXCXXXXX-
NFALXXXXXXXXXXXXIXXMXXRFXXXXXXXXX
XXXXPXXRXXXXXXXXXXXXXXXXXVXX-
QXXXXXXXEXXTTXXXT (SEQ ID NO:30), wherein X is any amino acid or a peptide bond;

XXEXXXXYXXXXEXXFXXXXKXXX-
AXXXXXXXXAXXXXTVXTVKRXXXXQXXX

XXRXVEXXXXXFTXXXXXXAXXDXIXXXXX (SEQ ID NO:31), wherein X is any amino acid or a peptide bond;

XXXXXXXXXXXXXXXX-
ALXXDXXXXKXXXXXXXXTEXXSKXX-
VXXXXXVXHX XXXXDXKDXXX-
TXXXXXXXXRXXXRXXXXRXXTXXSXXXXKXS
XRXGDXXXPF DXFXX-
TXXXXXXXXXXXXXXXXXEXXXRAXX (SEQ ID NO:32), wherein X is any amino acid or a peptide bond;

NG$X_1$FKIE$X_2$DRTF$X_3$PY$X_4$YALL$X_5$DDS$X_6$IEEVKKIT
$X_7$ERHG$X_8X_9$V$X_{10}X_{11}X_{12}X_{13}$VEK
V$X_{14}$KKFLG$X_{15}$P$X_{16}X_{17}$VWKLY$X_{18}X_{19}$HPQDVP$X_{20}$
IR$X_{21}$K$X_{22}$REHPA (SEQ ID NO:33), wherein $X_1$ is not K; $X_2$ is not H; $X_3$ is not R; $X_4$ is not I; $X_5$ is not R; $X_6$ is not K; $X_7$ is not G; $X_8$ is not K; $X_9$ is not I; $X_{10}$ is not R; $X_{11}$ is not I; $X_{12}$ is not V; $X_{13}$ is not D; $X_{14}$ is not E; $X_{15}$ is not K; $X_{16}$ is not I; $X_{17}$ is not T; $X_{18}$ is not L; $X_{19}$ is not E; $X_{20}$ is not T; $X_{21}$ is not E; and $X_{22}$ is not V;

PI$X_1$MISYADE$X_2X_3$A$X_4$VITWKN$X_5$DLPYV$X_6$VVS$X_7$
EREMIKRFLR$X_8X_9X_{10}$EKDPD$X_{11}X_{12}X_{13}$TYNGD$X_{14}$
FDF$X_{15}$YL$X_{16}$KR$X_{17}$EKLGI$X_{18}X_{19}X_{20}X_{21}$GRDGSEP
K$X_{22}$QR$X_{23}$GD$X_{24}X_{25}$AVEVKGRIHFDLY$X_{26}$VI$X_{27}$R
TINLPTYTLEAVYEA$X_{28}$FG$X_{29}$PKEKVYA$X_{30}$EI$X_{31}$
$X_{32}$AWE$X_{33}$ (SEQ ID NO:34), wherein $X_1$ is not I; $X_2$ is not N; $X_3$ is not E; $X_4$ is not K; $X_5$ is not I; $X_6$ is not E; $X_7$ is not S; $X_8$ is not I; $X_9$ is not I; $X_{10}$ is not R; $X_{11}$ is not I; $X_{12}$ is not I; $X_{13}$ is not V; $X_{14}$ is not S; $X_{15}$ is not P; $X_{16}$ is not A; $X_{17}$ is not A; $X_{18}$ is not K; $X_{19}$ is not L; $X_{20}$ is not T; $X_{21}$ is not I; $X_{22}$ is not M; $X_{23}$ is not I; $X_{24}$ is not M; $X_{25}$ is not T; $X_{26}$ is not H; $X_{27}$ is not T; $X_{28}$ is not I; $X_{29}$ is not K; $X_{30}$ is not D; $X_{31}$ is not A; $X_{32}$ is not K; and $X_{33}$ is not S;

RDWSEIAKETQARVLE$X_1X_2$LK$X_3$GDVE$X_4$AVRIVKE
V$X_5X_6$KL$X_7X_8$YE$X_9$PPEKL$X_{10}$I$X_{11}$EQITR$X_{12}$L$X_{13}$
$X_{14}$YKA$X_{15}$GPHVAVAK$X_{16}$LAA$X_{17}$GVKI$X_{18}$PG$X_{19}$
VI$X_{20}$YIVL$X_{21}$G$X_{22}$G$X_{23}$I$X_{24}X_{25}$RAI$X_{26}X_{27}X_{28}$E$X_{29}$
DP$X_{30}$KHKYDAEYYIENQVLPAV$X_{31}$RIL$X_{32}X_{33}$FG
(SEQ ID NO:35), wherein $X_1$ is not T; $X_2$ is not I; $X_3$ is not H; $X_4$ is not E; $X_5$ is not I; $X_6$ is not Q; $X_7$ is not A; $X_8$ is not N; $X_9$ is not I; $X_{10}$ is not A; $X_{ii}$ is not Y; $X_{12}$ is not P; $X_{13}$ is not H; $X_{14}$ is not E; $X_{15}$ is not I; $X_{16}$ is not K; $X_{17}$ is not K; $X_{18}$ is not K; $X_{19}$ is not M; $X_{20}$ is not G; $X_{21}$ is not R; $X_{22}$ is not D; $X_{23}$ is not P; $X_{24}$ is not S; $X_{25}$ is not N; $X_{26}$ is not L; $X_{27}$ is not A; $X_{28}$ is not E; $X_{29}$ is not Y; $X_{30}$ is not K; $X_{31}$ is not L; $X_{32}$ is not E; and $X_{33}$ is not G;

and combinations thereof;

and a second domain having a consensus sequence selected from the group consisting of XKXXXXXXXXXXXXX-
AXXXXXXXXXXXXXXXXXLXXXXNXX-
IXXXXXXKXXXXI XXXXXXXXXHXXXXXXXXX-
TXXXEXQXXXXKIXXXXXXKXXXLXXXXFXXXX
X XXKXXXXXXXXXXXXXXXXXXKXX-
ELVWXXLXXXFXXXXLXIXXXXLYXXXXXG ESX-
EIXXXXLX (SEQ ID NO:36), wherein X is any amino acid or a peptide bond;

E$X_1$GLWENIVYLDFR$X_2$LYPSIIITHNVSPDTLN$X_3$EGC
K$X_4$YD$X_5$APQVGH$X_6$FCKD$X_7$P
GFIPSLLG$X_8$LLEERQKIK$X_9$KMK$X_{10}$T$X_{11}$DPIE$X_{12}$
$X_{13}$LLDYRQ$X_{14}$AIK$X_{15}$LANS$X_{16}$YG
YYGYA$X_{17}$ARWYCKECAESVTAWGR$X_{18}$YI$X_{19}X_{20}$
$X_{21}X_{22}$KE$X_{23}$EEK$X_{24}$GFKV$X_{25}$Y$X_{26}$DTDG$X_{27}X_{28}$AT
IPG$X_{29}X_{30}X_{31}$E$X_{32}X_{33}$KKKA$X_{34}$E (SEQ ID NO:37), wherein $X_1$ is not R; $X_2$ is not S; $X_3$ is not R; $X_4$ is not E; $X_5$ is not V; $X_6$ is not R; $X_7$ is not F; $X_8$ is not D; $X_9$ is not K; $X_{10}$ is not A; $X_{11}$ is not I; $X_{12}$ is not R; $X_{13}$ is not K; $X_{14}$ is not R; $X_{15}$ is not I; $X_{16}$ is not Y; $X_{17}$ is not R; $X_{18}$ is not E; $X_{19}$ is not T; $X_{20}$ is not M; $X_{21}$ is not T; $X_{22}$ is not I; $X_{23}$ is not I; $X_{24}$ is not Y; $X_{25}$ is not I; $X_{26}$ is not S; $X_{27}$ is not F; $X_{28}$ is not F; $X_{29}$ is not A; $X_{30}$ is not D; $X_{31}$ is not A; $X_{32}$ is not T; $X_{33}$ is not V; $X_{34}$ is not M, and combinations thereof, wherein the chimeric polymerase is characterized with high fidelity and high processivity, elongation rate, salt resistance, TMAC or other PCR enhancer tolerance or thermostability.

In some embodiments, chimeric polymerases in accordance with the present invention are defined by consensus sequence XXXXTXXXXXDXXXXXXIXXXXXX-
EXXXXYXXXXEXXFXXXXKXXXAXXXXXX
XXAXXXXTVXTVKRXXXXQXXXXXRX-
VEXXXXXFTXXXXXXAXXDXIXXXXXXI
XXYXXXXXXXXXXXXXXX-
VXXXXDXXXXMXXXXXXXXXXXXXX-
AEXXXLX XXXXXXEGXRXXXXXX-
VXXXXXDXXXTXXXXXXXXXXVVKXXXXXVLI
XXXXX NXXXAXXKXXCXXXXXN-
FALXXXXXXXXXXIXXMXXR-
FXXXXXXXXXXXXXPX
XRXXXXXXXXXXXXXXXXVXX-
QXXXXXXXXEXXTTXXXTXXXXXXXXRXXXXX
XXVXXXXXXXXXXXXAXXXXXVXX-
PXXXXXXXXXXXXXXXXXXXXXXXXXV
XXXXXSXEXYQXXXXEXX-
TXXFXXXXXKXXXXXXXXXXXX-
AXXXXXXXXXXXX XXXXXLXXXXNXX-
IXXXXXXKXXXXIXXXXXXXXXHXXXXXXXXXT
XXXEXQX XXXKIXXXXXXKXXX-
LXXXXFXXXXXXXKXXXXXXXXXXXXXXXXXK
XXELVW XXLXXXFXXXXLXIXXXX-
LYXXXXXGESXEIXXXXLXXLXXXX-
AXXXXAXXXXX
XXXXXXXXXXXXKXXXXXXXXX-
ITXXXXXXXXXXXXXXXXXXXXXXXALX
XDXXXXKXXXXXXXXTEXXSKXX-
VXXXXXVXHXXXXXDXKDXXXTXXXXXXX
XRXXXRXXXXRXXTXXSXXXXKX-
SXRXGDXXXPFDXFXXTXXXXXXXXXXXXX
XXXXX-
EXXXRAXXXXXXXXXXXXXXXXXX-
SAXXXKPXGT (SEQ ID NO:38), wherein X is any amino acid or a peptide bond, and wherein the chimeric polymerase has a fidelity higher than that of KOD and a processivity, an elongation rate, a salt resistance, a TMAC or other PCR enhancer tolerance or a thermostability higher than that of Pfu.

In some embodiments, chimeric polymerases in accordance with the present invention are defined by consensus sequence XIXDTDYXTXDGX-
PXXRIFXKXXGEFXXXYDXXFEPYFY-
ALLKDDSAIXXXXXXXA XRHGTVXTVKRXXXX-
QXKFLXRXVEVWXLXFTHPQDVPAXXDXMHXXV
IDIYE YDIPFAKRYLIDXGLVPMEGDEX-
LXMXXXDIETXYHEGXEFAEGXXLMISYADXEG
ARVITWKXVDLPYVDVVSTEX-
EMIKRXXXVVKEKDPDVLIXYXGDNFDXAYLKXR
CEXLGXNFALXRXXXXXEPKIXXMGXR-
FAVEXKGRXHFDLXPXXRXTXNLPTYXL
XXVYEXVXGQXKXKXXXEEITTX-
WETXXXXXXXARYSMEDAXVTXELGXEFXPM
EAXLXXLVGXPXWDVXRSSTGNLVEWX-
LLXXAYXRNEVAPNKPSXEEYQXRXXE XYT-
GXFVXEPEKGLWXXXXXLDXXALYPSI- IXXHNVSPDTLXLEXCXNYDIAPXVG XKFCKDIPGFIPSXLXHLXXXRQXXK-TXMXEXQDPXEKIXLDYRQKAXKLLXNSFY GYXGYXKARWYXXECAESVTX-WGRKYIELVWXELEXXFGFKXLYIDTDGLYATIP GGESXEIKXXXLXFLXYINAXLPGALEL-EYEXFYXRGFFVXKKKYAXIDEEXXITTR GLEX-VRRDWSXXAKETXAXVLEALLXDXX-VXKAVXXVXXXTEXXSKYXVPXEKL VIHEQITRDXKDYXATGPHVAX-AKRLXXRGXXXRPGTXISYXXLKGS-GRXGDRXIPF DEFXXTKHXYDXXYYIENQVLPAV-ERXLRAFGYXXXXLXXQXXXQXGLSAWXKP XGT (SEQ ID NO:39), wherein X is any amino acid or a peptide bond.

In some embodiments, the present invention further provides chimeric polymerases containing a first domain having a sequence at least 80% (e.g., at least 85%, 90%, 91%, 92%, 93%, 94%, 95%, 96%, 97%, 98%, 99%) identical to an amino acid sequence found in an exonuclease domain, an N-terminal domain, and/or a thumb domain of a first DNA polymerase; and a second domain having a sequence at least 80% (e.g., at least 85%, 90%, 91%, 92%, 93%, 94%, 95%, 96%, 97%, 98%, 99%) identical to an amino acid sequence found in palm and/or fingers domain of a second DNA polymerase. In some embodiments, the chimeric polymerase has a fidelity higher than that of the second DNA polymerase and a processivity, an elongation rate, a salt resistance, a TMAC or other PCR enhancer tolerance or a thermostability higher than that of the first DNA polymerase.

In another aspect, the present invention provides methods of engineering chimeric polymerases. Inventive methods in accordance with the present invention include steps of: (a) providing an N-terminal domain, an exonuclease domain, and/or a thumb domain based on a first DNA polymerase; (b) providing a palm and/or fingers domain based on a second DNA polymerase; (c) combining the domains from step (a) and step (b) to form a chimeric polymerase; wherein the chimeric polymerase has a fidelity higher than that of the first DNA polymerase and a processivity, an elongation rate, a salt resistance, a TMAC or other PCR enhancer tolerance or a thermostability higher than that of the second DNA polymerase. In some embodiments, a chimeric polymerase engineered according to the present invention has a processivity, an elongation rate, a salt resistance, a TMAC or other PCR enhancer tolerance or a thermostability substantially similar to that of the first DNA polymerase and a fidelity substantially similar to that of the second DNA polymerase.

In some embodiments, exemplary first DNA polymerases suitable for the present invention include, but are not limited to, KOD polymerase, TNA1 polymerase, *Thermococcus* sp. 9 degrees N-7, T4, T7, or phi29. In some embodiments, the first DNA polymerase is KOD polymerase. In some embodiments, exemplary second DNA polymerases suitable for the invention include, but are not limited to, polymerases isolated from *Pyrococcus furiosus, P. abyssi, T. gorgonarius, T. litoralis, T. zilligii, T.* sp. GT, or *P.* sp. GB-D. In some embodiments, the second DNA polymerase is Pfu polymerase.

In some embodiments, the first DNA polymerase is KOD polymerase and the second DNA polymerase is Pfu polymerase. In some embodiments, the first DNA polymerase is Pfu polymerase and the second DNA polymerase is KOD polymerase.

In some embodiments, the present invention provides methods of improving the fidelity of a DNA polymerase. In particular embodiments, inventive methods in accordance with the invention include a step of replacing a sequence within the palm and/or fingers domain of the DNA polymerase of interest with a corresponding sequence from a different DNA polymerase that is characterized with higher fidelity relative to the DNA polymerase of interest.

In some embodiments, the present invention provides methods of improving the processivity, elongation rate, salt resistance, TMAC or other PCR enhancer tolerance or thermostability of a DNA polymerase. In particular embodiments, inventive methods in accordance with the present invention include a step of replacing a sequence within the N-terminal domain, the exonuclease domain and/or the thumb domain of the DNA polymerase of interest with a corresponding sequence from a different DNA polymerase that is characterized with higher processivity, elongation rate, salt resistance, TMAC or other PCR enhancer tolerance or thermostability relative to the DNA polymerase of interest.

The present invention provides various chimeric polymerases described herein including chimeric polymerases engineered and/or improved using inventive methods as described herein. In some embodiments, chimeric polymerases in accordance with the present invention contain an amino acid sequence at least 80% identical to SEQ ID NO:16 (the Kofu amino acid sequence as shown in the Sequences section). In particular embodiments, a chimeric polymerase in accordance with the present invention contains the amino acid sequence of SEQ ID NO:16. In some embodiments, chimeric polymerases in accordance with the present invention contain an amino acid sequence at least 80% identical to SEQ ID NO:15 (the Pod amino acid sequence as shown in the Sequences section). In particular embodiments, a chimeric polymerase in accordance with the present invention contains the amino acid sequence of SEQ ID NO:15.

The present invention also provides kits and compositions containing various chimeric polymerases described herein and uses thereof (e.g., methods of amplifying DNA fragments using chimeric DNA polymerases of the invention). In addition, the present invention provides nucleotide sequences encoding various chimeric polymerases described herein and vectors and/or cells containing the nucleotide sequences according to the invention.

BRIEF DESCRIPTION OF THE DRAWINGS

The drawings are for illustration purposes only, not for limitation.

DEFINITIONS

Figure 1A:
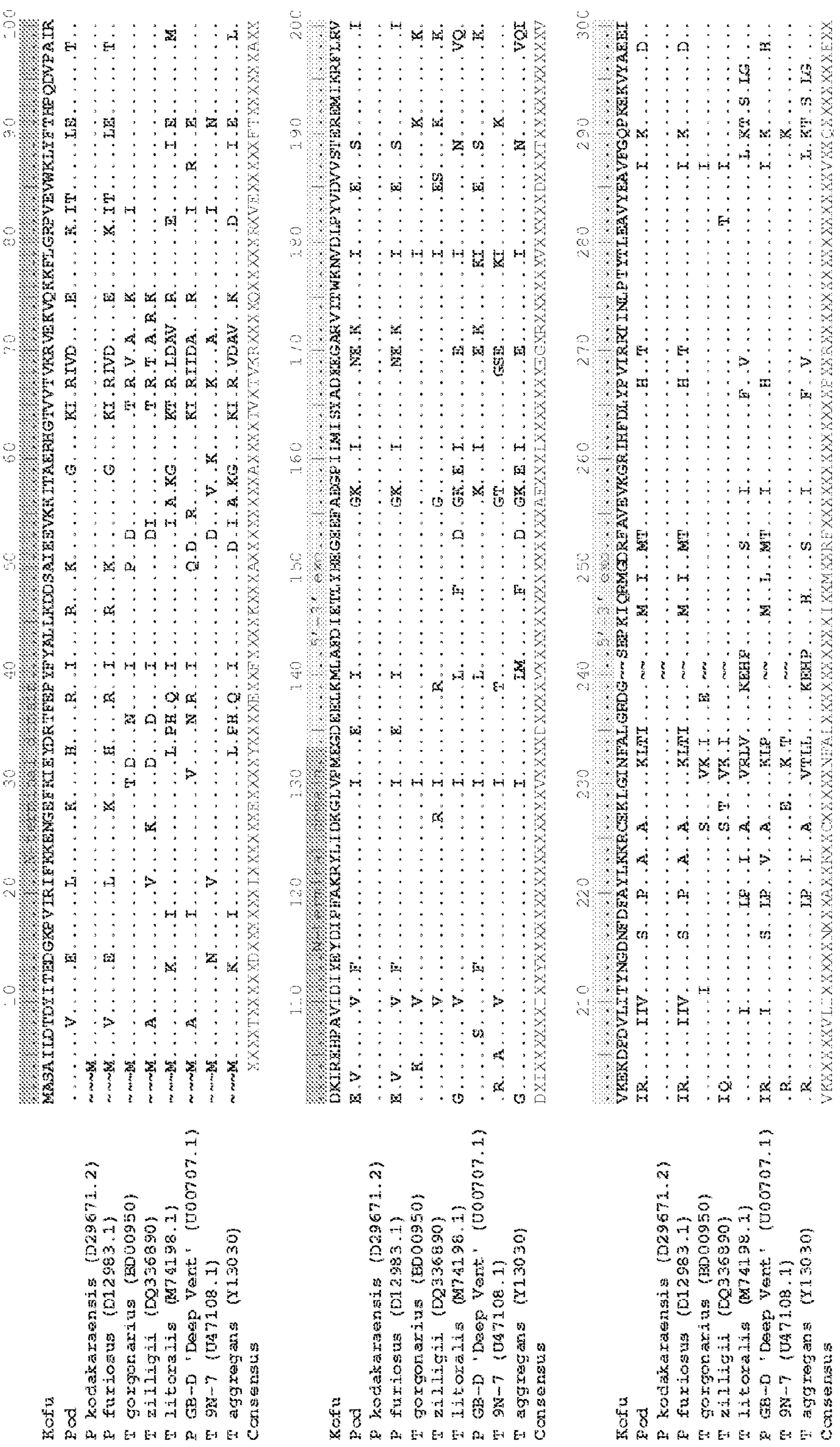
FIGS. 1*a-c* depict an alignment of domains in exemplary naturally-occurring type B DNA polymerases *P. kodakarensis* (SEQ ID NO:11), *P. furiosus* (SEQ ID NO:9), *T. gorgonarius* (SEQ ID NO:22), *T. Zilligii* (SEQ ID NO:23), *T. litoralis* (SEQ ID NO:19), P GN-D 'Deep Vent' (SEQ ID NO:45), T 9N-7 (SEQ ID NO:18), *T. aggregans* (SEQ ID NO:46); and exemplary chimeric DNA polymerases Kofu (SEQ ID NO: 16) and Pod (SEQ ID NO: 15); as compared to the generated consensus sequence (SEQ ID NO:38). The KOD and Pfu polymerase domains that were swapped in the Kofu and Pod chimeras are indicated above the alignment.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions Amino acids, including carboxy- and/or amino-terminal amino acids in peptides, can be modified by methylation, amidation, acetylation, and/or substitution with other chemical groups. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Chimeric polymerase: As used herein, the term "chimeric polymerase" (also referred to as "chimera") refers to any polymerase containing two or more heterologous domains, amino acid sequences, peptides, and/or proteins joined either covalently or non-covalently to produce a polymerase that does not occur in nature. Typically, a chimeric polymerase contains a first domain joined to a second domain, wherein the first and second domains are not found in the same relationship in nature. Typically, the first domain is derived from a first DNA polymerase and a second domain is derived from a second DNA polymerase. Typically, the first and second DNA polymerases are characterized with at least one distinct functional characteristics (e.g., processivity, elongation rate, fidelity, salt tolerance, tolerance to PCR additives or thermostability). As used herein, a sequence derived from a DNA polymerase of interest refers to any sequence found in the DNA polymerase of interest, or any sequence having at least 70% (e.g., at least 75%, 80%, 85%, 90%, 91%, 92%, 93%, 94%, 95%, 96%, 97%, 98%, 99%) identical to an amino acid sequence found in the DNA polymerase of interest. A "chimeric polymerase" according to the invention may contain two or more amino acid sequences from related or similar polymerases (e.g., proteins sharing similar sequences and/or structures), joined to form a new functional protein. A "chimeric polymerase" according to the invention may contain two or more amino acid sequences from unrelated polymerases, joined to form a new functional protein. For example, a chimeric polymerase of the invention may be an "interspecies" or "intergenic" fusion of protein structures expressed by different kinds of organisms.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

DNA binding affinity: As used herein, the term "DNA-binding affinity" typically refers to the activity of a DNA polymerase in binding DNA nucleic acid. In some embodiments, DNA binding activity can be measured in a two band-shift assay. For example, in some embodiments (based on the assay of Guagliardi et al. (1997) *J. Mol. Biol.* 267:841-848), double-stranded nucleic acid (the 452-bp HindIII-EcoRV fragment from the *S. solfataricus* lacS gene) is labeled with $^{32}P$ to a specific activity of at least about $2.5\times10^7$ cpm/μg (or at least about 4000 cpm/fmol) using standard methods. See, e.g., Sambrook et al. (2001) Molecular Cloning: A Laboratory Manual ($3^{rd}$ ed., Cold Spring Harbor Laboratory Press, NY) at 9.63-9.75 (describing end-labeling of nucleic acids). A reaction mixture is prepared containing at least about 0.5 μg of the polypeptide in about 10 μl of binding buffer (50 mM sodium phosphate buffer (pH 8.0), 10% glycerol, 25 mM KCl, 25 mM $MgCl_2$). The reaction mixture is heated to 37° C. for 10 min. About $1\times10^4$ to $5\times10^4$ cpm (or about 0.5-2 ng) of the labeled double-stranded nucleic acid is added to the reaction mixture and incubated for an additional 10 min. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture. Other methods of measuring DNA binding affinity are known in the art (see, e.g., Kong et al. (1993) *J. Biol. Chem.* 268(3): 1965-1975).

Domain: As used herein, the term "Domain" as used herein refers to an amino acid sequence of a polypeptide (e.g., polymerase) comprising one or more defined functions or properties.

Elongation rate: As used herein, the term "elongation rate" refers to the average speed at which a DNA polymerase extends a polymer chain. As used herein, a high elongation rate refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s).

Enzyme activity: As used herein, the term "enzyme activity" refers to the specificity and efficiency of a DNA polymerase. Enzyme activity of a DNA polymerase is also referred to as "polymerase activity," which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer (e.g., 20 mM Tris.Cl, pH 8.0, 50 mM KCl, 0.5% NP 40, and 0.5% Tween-20). For each dilution, 5 μl can be removed and added to 45 μl of a reaction mixture containing 25 mM TAPS (pH 9.25), 50 mM KCl, 2 mM MgCl2, 0.2 mM dATP, 0.2 mM dGTP, 0.2 mM dTTP, 0.1 mM dCTP, 12.5 μg activated DNA, 100 μM [α-$^{32}$P]dCTP (0.05 μCi/nmol) and sterile deionized water.

The reaction mixtures can be incubated at 37° C. (or 74° C. for thermostable DNA polymerases) for 10 minutes and then stopped by immediately cooling the reaction to 4° C. and adding 10 μl of ice-cold 60 mM EDTA. A 25 μl aliquot can be removed from each reaction mixture. Unincorporated radioactively labeled dCTP can be removed from each aliquot by gel filtration (Centri-Sep, Princeton Separations, Adelphia, N.J.). The column eluate can be mixed with scintillation fluid (1 ml). Radioactivity in the column eluate is quantified with a scintillation counter to determine the amount of product synthesized by the polymerase. One unit of polymerase activity can be defined as the amount of polymerase necessary to synthesize 10 nmole of product in 30 minutes (Lawyer et al. (1989) *J. Biol. Chem.* 264:6427-647). Other methods of measuring polymerase activity are known in the art (see, e.g., Sambrook et al. (2001) Molecular Cloning: A Laboratory Manual ($3^{rd}$ ed., Cold Spring Harbor Laboratory Press, NY)).

Fidelity: As used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not complementary to the template nucleotide). The accuracy or fidelity of DNA polymerization is maintained by both the polymerase activity and the 3'-5' exonuclease activity of a DNA polymerase. The term "high fidelity" refers to an error rate less than $4.45\times10^{-6}$ (e.g., less than $4.0\times10^{-6}$, $3.5\times10^{-6}$, $3.0\times10^{-6}$, $2.5\times10^{-6}$, $2.0\times10^{-6}$, $1.5\times10^{-6}$, $1.0\times10^{-6}$, $0.5\times10^{-6}$) mutations/nt/doubling. The fidelity or error rate of a DNA polymerase may be measured using assays known to the art. For example, the error rates of DNA polymerases can be tested using the lacI PCR fidelity assay described in Cline, J. et al. (1996) NAR 24: 3546-3551. Briefly, a 1.9 kb fragment encoding the lacIOlacZα target gene is amplified from pPRIAZ plasmid DNA using 2.5 U DNA polymerase (i.e., amount of enzyme necessary to incorporate 25 nmoles of total dNTPs in 30 min. at 72° C.) in the appropriate PCR buffer. The lacI-containing PCR products are then cloned into lambda GT10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180: 1-8). Error rates are expressed as mutation frequency per by per duplication (MF/bp/d), where bp is the number of detectable sites in the lacI gene sequence (349) and d is the number of effective target doublings. Similar to the above, any plasmid containing the lacIOlacZα target gene can be used as template for the PCR. The PCR product may be cloned into a vector different from lambda GT (e.g., plasmid) that allows for blue/white color screening.

Joined: As used herein, "joined" refers to any method known in the art for functionally connecting polypeptide domains, including without limitation recombinant fusion with or without intervening domains, inter-mediated fusion, non-covalent association, and covalent bonding, including disulfide bonding, hydrogen bonding, electrostatic bonding, and conformational bonding.

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

Oligonucleotide or Polynucleotide: As used herein, the term "oligonucleotide" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed towards the 5' end of the template strand. A "DNA polymerase" catalyzes the polymerization of deoxynucleotides.

Processivity: As used herein, "processivity" refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the length of nucleotides (for example 20 nts, 300 nts, 0.5-1 kb, or more) that are polymerized or modified without intervening dissociation of the DNA polymerase from the growing DNA chain. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Processivity can be measured according the methods defined herein and in WO 01/92501 A1.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes appropriate pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require lower temperatures to form sufficiently stable hybrid complexes with template.

Salt resistance: As used herein, the term "salt resistance" (also referred to as salt tolerance) refers to the ability of a DNA polymerase to substantially maintain its enzymatic activity in the presence of salt or PCR additives (e.g., TMAC). In some embodiments, resistance to salt or PCR additives is measured by the maximum salt concentration at which a DNA polymerase is still active. The maximum salt concentration differs for each polymerase and is known in the art, or can be experimentally determined according to methods in the art. For example, Pfu is inhibited at 30 mM salt (in a PCR reaction).

Synthesis: As used herein, the term "synthesis" refers to any in vitro method for making new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, PCR, the labeling of polynucleotide (i.e., for probes and oligonucleotide primers), polynucleotide sequencing.

Template DNA molecule: As used herein, the term "template DNA molecule" refers to a strand of a nucleic acid from which a complementary nucleic acid strand is synthesized by a DNA polymerase, for example, in a primer extension reaction.

Template dependent manner: As used herein, the term "template dependent manner" refers to a process that involves the template dependent extension of a primer molecule (e.g., DNA synthesis by DNA polymerase). The term "template dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

Thermostable enzyme: As used herein, the term "thermostable enzyme" refers to an enzyme which is stable to heat (also referred to as heat-resistant) and catalyzes (facilitates) polymerization of nucleotides to form primer extension products that are complementary to a polynucleotide template sequence. Typically, thermostable stable polymerases are preferred in a thermocycling process wherein double stranded nucleic acids are denatured by exposure to a high temperature (e.g., about 95 C) during the PCR cycle. A thermostable enzyme described herein effective for a PCR amplification reaction satisfies at least one criteria, i.e., the enzyme do not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° C. to about 98° C. for a time depending mainly on the temperature and the nucleic acid length, typically about 0.2 to four minutes. Higher temperatures may be tolerated as the buffer salt concentration and/or GC composition of the nucleic acid is increased. In some embodiments, thermostable enzymes will not become irreversibly denatured at about 90° C.-100° C. Typically, a thermostable enzyme suitable for the invention has an optimum temperature at which it functions that is higher than about 40° C., which is the temperature below which hybridization of primer to template is promoted, although, depending on (1) magnesium and salt, concentrations and (2) composition and length of primer, hybridization can occur at higher temperature (e.g., 45° C.-70° C.). The higher the temperature optimum for the enzyme, the greater the specificity and/or selectivity of the primer-directed extension process. However, enzymes that are active below 40° C. (e.g., at 37° C.) are also with the scope of this invention provided they are heat-stable. In some embodiments, the optimum temperature ranges from about 50° C. to 90° C. (e.g., 60° C.-80° C.).

TMAC or other PCR enhancer tolerance: As used herein, the term "TMAC or other PCR enhancer tolerance" (also referred to as TMAC or other PCR enhancer resistance) refers to the ability of a DNA polymerase to substantially maintain its enzymatic activity in the presence of TMAC or other PCR enhancers (e.g., glycerol, DMSO, betaine, amides, other tetramethyl ammonium salts).

DETAILED DESCRIPTION OF THE INVENTION

The present invention provides, among other things, chimeric DNA polymerases containing heterologous domains having sequences derived from at least two DNA polymerases that have at least one distinct functional characteristics (e.g., elongation rate, processivity, error rate or fidelity, salt tolerance or resistance) and methods of making and using the same.

DNA Polymerases

Chimeric DNA polymerases in accordance with the present invention may be engineered from any DNA polymerases, in particular, thermostable polymerases. Typically, DNA polymerases are grouped into six families: A, B, C, D, X and Y. Families A, B, C are grouped based on their amino acid sequence homologies to *E. coli* polymerases I, II, and III, respectively. Family X has no homologous *E. coli* polymerases. In some embodiments, DNA polymerases suitable for the present invention are family B DNA polymerases. Family B polymerases include, but are not limited to, *E. coli* pol II, archaeal polymerases, PRD1, phi29, M2, T4 bacteriophage DNA polymerases, eukaryotic polymerases α, Δ, ε, and many viral polymerases. In some embodiments, DNA polymerases suitable for the invention are archaeal polymerases (e.g., euryarchaeal polymerases).

Suitable exemplary archaeal polymerases include, but are not limited to, DNA polymerases from archaea (e.g., *Thermococcus litoralis* (Vent™, GenBank: AAA72101), *Pyrococcus furiosus* (Pfu, GenBank: D12983, BAA02362), *Pyrococcus woesii, Pyrococcus* GB-D (Deep Vent™, GenBank: AAA67131), *Thermococcus kodakaraensis* KODI (KOD, GenBank: BD175553, BAA06142*; Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: O29753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococ-*

*cus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025) and other archaeal B polymerases, such as GenBank AAC62712, P956901, BAAA07579)). Additional representative temperature-stable family A and B polymerases include, e.g., polymerases extracted from the thermophilic bacteria *Thermus* species (e.g., *flavus, ruber, thermophilus, lacteus, rubens, aquaticus*), *Bacillus stearothermophilus, Thermotoga maritima, Methanothermus fervidus*.

DNA polymerases suitable for the present invention include DNA polymerases that have not yet been isolated. Suitable polymerases for the present invention include fusion polymerases. Fusion polymerases generally contain an additional protein domain at the N- or C-terminus that changes the phenotype of the fusion polymerase compared to the polymerase without the extra domain. Exemplary polymerases include, but are not limited to, polymerases with double-stranded DNA-binding domains fused at the C- or N-terminus. Further examples of fusion polymerases include those with dUTPase fused to the N- or C-terminus (U.S. patent application 20070190538).

In some embodiments, chimeric DNA polymerases according to the invention contain sequences derived from two or more DNA polymerases that have at least one distinct functional characteristic. Exemplary functional characteristics include, but are not limited to, processivity, elongation rate, fidelity, resistance to salt or PCR additive (e.g., PCR enhancers), thermostability, strand displacement activity, exonuclease activity, uracil read-ahead function, nucleotide selectivity, ability to incorporate modified analogs, and reverse transcriptase activity. For example, some DNA polymerases are characterized with high fidelity. As used herein, the term "high fidelity" refers to an error rate less than $4.45\times10^{-6}$ (e.g., less than $4.0\times10^{-6}$, $3.5\times10^{-6}$, $3.0\times10^{-6}$, $2.5\times10^{-6}$, $2.0\times10^{-6}$, $1.5\times10^{-6}$, $1.0\times10^{-6}$, $0.5\times10^{-6}$) mutations/nt/doubling. Some DNA polymerases are characterized with high processivity. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Some DNA polymerases are characterized with high elongation rate. As used herein, the term "high elongation rate" refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s). Some enzymes are characterized with high resistance to salt (also referred to as salt tolerance). As used herein, the term "high resistance to salt" (also referred to as high salt tolerance) refers to the ability of a DNA polymerase to substantially maintain its activity at a salt concentration higher than 30 mM (e.g., higher than 35 mM, 40 mM, 45 mM, 50 mM). In addition, some enzymes are characterized with resistance to PCR additives. Certain PCR additives are PCR enhancers. For example, Kovarova et al. showed that TMA salts, DMSO, betaine and formamide act as PCR enhancers (Kovarova and Draber. (2000) *Nucl. Acids. Res.* 28(13), e70). Another example of PCR enhancers is glycerol. Some enzymes are characterized with resistance to PCR enhancers, in particular, TMAC (also referred to as TMAC tolerance). As used herein, the term "high TMAC tolerance" refers to the ability of a DNA polymerase to substantially maintain its enzymatic activity at a TMAC (tetra-methyl ammonium chloride) concentration higher than 10 mM (e.g., higher than 15 mM, 20 mM). Certain characteristics of exemplary DNA polymerases are shown in Table 1.

TABLE 1

Characteristics of exemplary DNA polymerases

| Polymerases | Fidelity/ Error rate | Processivity (nts) | Elongation rate (nts/s) | Salt tolerance |
|---|---|---|---|---|
| Pfu | $2.0\times10^{-6}$ | >20 | 25 | 30 mM |
| KOD | $4.45\times10^{-6}$ | ~300 | 106-138 | |
| TNA1 | | 150 | | |
| *T. zilligii* | $2.0\times10^{-6}$ | | | |
| *P. abyssi* | $0.66\times10^{-6}$ | | | |
| *T. gorgonarius* | $2.2\text{-}3.4\times10^{-6}$ | | | |

Typically, enzymes with high salt tolerance are also characterized with high processivity and/or elongation rate. Without wishing to be bound by any theories, it is thought that salt tolerance affects the binding affinity between polymerase and DNA which, in turn, affects processivity or elongation rate. Typically, binding of polymerases to DNA involves binding interaction between positively charged amino acid residues and negatively charged DNA. At high salt concentrations, competition from the anions of the salt for the positively charged amino acid residues on the polymerases lead to diminished DNA binding affinity. See, Pavlov et al. (2002) *Proc. Natl. Acad. Sci.* 99(21): 13510-13515, which is incorporated by reference herein. On the other hand, increasing the contact points between DNA and polymerase may increase the salt resistance of the polymerase as well as the processivity or elongation rate because the additional contact points between DNA and polymerase may increase binding affinity of the polymerase for DNA and decrease the rate of dissociation so that the polymerase will remain associated with DNA longer, which will in turn lead to an increase in processivity. For example, Pavlov et al. added helix-hairpin-helix (HhH) motifs from topoisomerase V to Taq and Pfu. These motifs are involved in DNA binding in topoisomerase V. Pavlov et al. showed that both Pfu and Taq become more salt resistant when fused to the HhH motifs. Pavlov et al. also showed that HhH fusion to both Taq and Pfu increased the processivity of the polymerases. As another example, dsDNA binding proteins, e.g., Sso7d, can be fused to DNA polymerases to increase the number of contact points between DNA and polymerases (Wang et al. (2004) *Nucl. Acids Res.* 32(3): 1197-1207, which is incorporated by reference herein). Sso7d is a sequence non-specific dsDNA binding protein involved in ensuring DNA stability and/or DNA packing in *Sulfolobus solfataricus*. Fusion of Sso7d to both Taq and Pfu increased the salt resistance and processivity of the polymerases.

Exemplary DNA polymerases characterized with high processivity, elongation rate, thermostability, salt or PCR enhancer tolerance include, but are not limited to, KOD polymerase, TNA1 polymerase, *Thermococcus* sp. 9 degrees N-7, T4, T7, or phi29. Exemplary DNA polymerases characterized with high fidelity include, but are not limited to, polymerases isolated from *Pyrococcus furiosus, P. abyssi, T. gorgonarius, T. litoralis, T. zilligii, T.* sp. GT, or *P.* sp. GB-D.

As non-limiting examples, KOD, Pfu, *T. gorgonarius, T. zilligii, T. litoralis* and *Thermococcus* sp. 9N-7 polymerases are used to engineer chimeric DNA polymerases (see the Example sections).

Domains of DNA Polymerases

Typically, archaeal DNA polymerases include at least the following domains: N-terminal domain, exonuclease domain (e.g., 3'->5' exonuclease domain), palm, fingers, and thumb domain (see FIGS. 1*a-c*). Knowledge of domain structure, function and coordination is primary based on crystal structure studies and site-directed mutagenesis of various DNA polymerases, in particular, archaeal DNA polymerases. For example, among the first crystal structures of family B DNA polymerases obtained was that of bacteriophage RB69 DNA polymerase (Wang et al. (1997) *Cell,* 89:1087-1099, which is incorporated by reference herein). Among the first crystal structures of archaeal DNA polymerases solved was Tgo DNA polymerase (see, Hopfner et al. 1999 *Proc. Natl. Acad. Sci.* 96(7), 3600-3605, which is incorporated by reference herein). Recently, crystal structures of the following archaeal family B DNA polymerases have been reported: DNA polymerase from *Thermococcus* sp. 9° N-7 (Rodriguez et al. (2000) *J. Mol. Biol.* 299:447-462, which is incorporated by reference herein), KOD1 DNA polymerase (Hashimoto et al. 2001 *J. Mol. Biol.* 306(3), 469-477, which is incorporated by reference herein), Pfu DNA polymerase (see, U.S. Pat. Nos. 5,948,663; 5,866,395; 5,545,552; 5,556,772 and Kim et al. (2008) *Int. J. Biol. Macromol.* 42(4), 356-61, all of which are hereby incorporated by reference).

Various functions, such as substrate binding, nucleotide transfer, catalytic activity, proofreading, have been assigned to various domains based on the structural-functional analysis of DNA polymerases. It has also been suggested that the domains tightly coordinate with each other to complete the DNA replication process.

For example, the polymerase activity has been associated with palm, fingers and thumb domains. In particular, the palm subdomain is thought to be the catalytic site of the polymerase. The polymerase catalyzes a phosphoryl transfer reaction in which the alpha phosphate of the incoming dNTP undergoes nucleophilic attack from the OH primer terminus. Typically, three carboxylate side chains are important to this active site. These residues may bind two metal ions (Mg++) which may facilitate deprotonation of the OH terminus and formation of a transition state at the alpha phosphate of the dNTP. The thumb domain is believed to interact with the minor grove of the newly synthesized dsDNA and also with the incoming nucleotide. The thumb domain is less conserved but typically has a largely helical structure. The fingers domain may play a role in template fixation and nucleotide specificity. Like the thumb domain, it is likely to interact with the incoming nucleotide. The thumb domain may contain $\alpha$ helices, and/or $\beta$ strands. It is thought that unbound DNA polymerases form open conformations of the fingers and thumb domains, and when the DNA is bound, the two domains move towards the palm domain to hold the DNA template and primer more tightly and to probe for Watson-Crick base pairing between the incoming nucleotide and the template nucleotide. The presence of a nucleotide that forms a Watson-Crick base pair with the template facilitates formation of an appropriate conformation of the active site of the polymerase and subsequent incorporation of this nuleotide. For review see Hamilton et al. (2001) BioTechniques 31:370-383. It was reported that mutagenesis in the palm/fingers domain may affects the nucleotide selectivity and affinity and mutagenesis in the thumb domain may affect the binding affinity to dsDNA. Important amino acids in the palm, fingers and thumb domain are described in U.S. Application Publication No. 20060281109, which is hereby incorporated by reference.

The uracil read-ahead function has been associated with the N-terminal domain. For example, archaeal family B DNA polymerases are able to recognize unrepaired uracil in a template strand and stall polymerization upstream of the lesion to prevent an A-T mutation. A "pocket" in the N-terminal domains of archaeal DNA polymerases was identified to be positioned to interact with the template strand and provide this uracil read-ahead function (Fogg et al. (2002) Nature Structural Biology 9(12), 922-927).

The exonuclease domain is associated with either 5'->3' exonuclease activity, 3'->5" exonuclease activity or both, which is required to remove incorrectly inserted nucleotide. When a mismatched nucleotide is incorporated, the template/primer strand binds to the polymerase more weakly and/or is misaligned with respect to the polymerase active site causing the mismatched nucleotide to be moved to the active site of the exonuclease domain and excised.

It is thought that the fidelity is affected by the ratio of the polymerase and the exonuclease activity, which may be influenced by the rate of dissociation, conformational change, and the rate of nucleotide incorporation in the presence of mismatched nucleotides. It has also been suggested that the balance between the 3'->5' exonuclease activity and the polymerase activity is mediated by a flexible loop containing the Y-GG/A motif located between the N-terminal and exonuclease domains and the C-terminal polymerase domains (i.e., the palm, fingers and thumb domains). See, Bohlke et al. (2000) *Nucl. Acids Res.* 28(20), 3910-3917. A unique loop of the exonuclease domain, and the tip of the thumb are important for the coordination of proofreading and polymerase activities in DNA polymerases. Site-directed mutagenesis in this loop, especially at H147 in KOD DNA polymerase, suggested that electrostatic and hydrophobic interactions between this loop and the thumb affect the ratio between exonuclease activity and polymerase activity and hence fidelity. See, Kuroita et al. *J. Mol. Biol.* (2005) 351, 291-298.

Domain Swapping

According to the present invention, heterologous domains from different DNA polymerases (e.g., polymerases with at least one distinct functional characteristic) may be combined to form a chimeric polymerase. Suitable domains include naturally-occurring N-terminal domains, exonuclease domains, palm, fingers, and/or thumb domains found in various DNA polymerases. Naturally-occurring N-terminal domains, exonuclease domains, palm, fingers, and/or thumb domains in various DNA polymerases are well defined. For example, an N-terminal domain may include a sequence corresponding to amino acid residues 26 to 105 of KOD polymerase (SEQ ID NO:11); an exonuclease domain may include a region corresponding to amino acid residues 156 to 301 of KOD polymerase (SEQ ID NO:11); a thumb domain may include a region corresponding to amino acid residues 612 to 749 of KOD polymerase (SEQ ID NO:11); and palm and fingers domain may include a region corresponding to amino acid residues 394 to 563 of Pfu polymerase (SEQ ID NO:9).

Figure 1B:
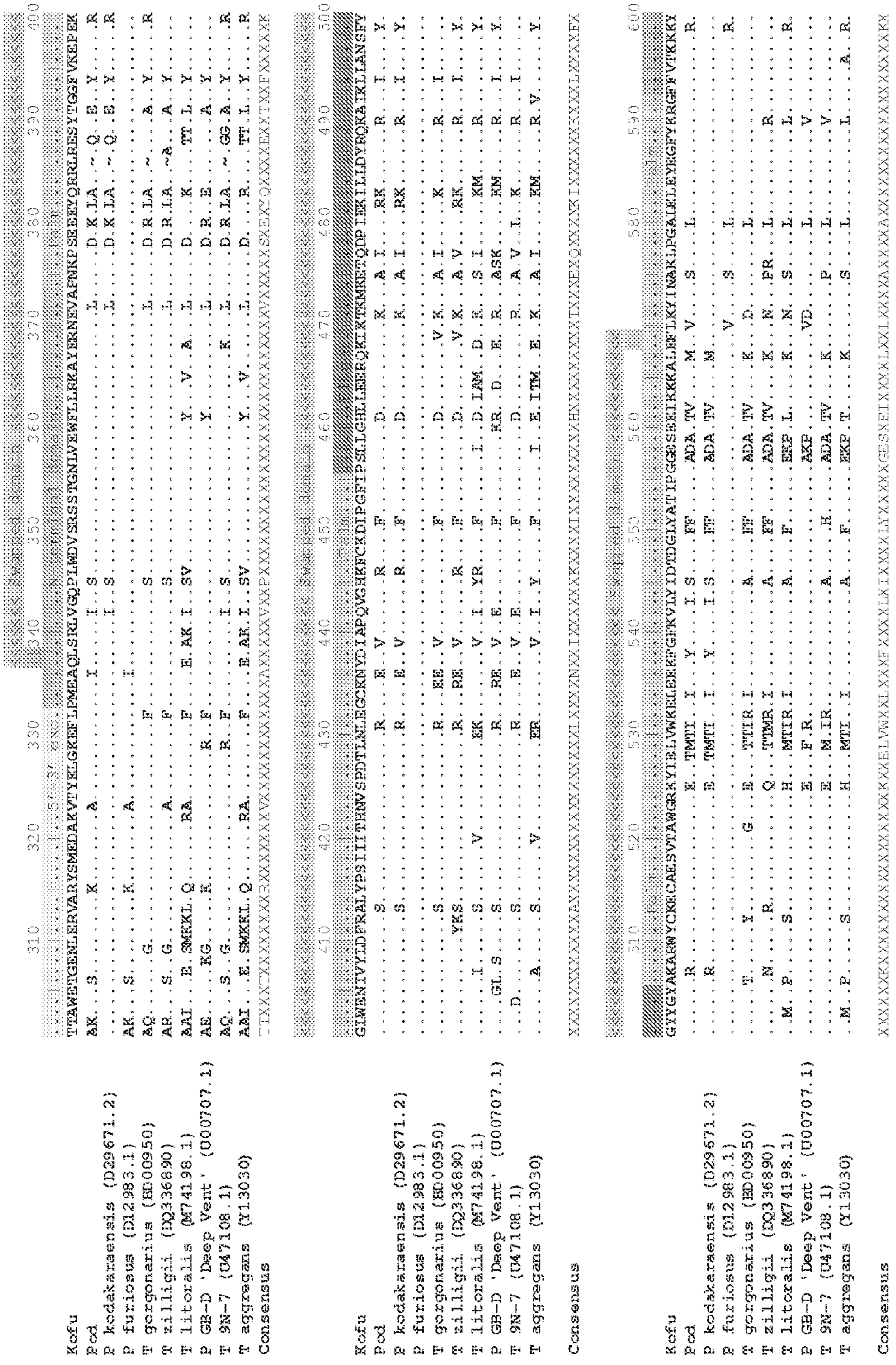
Figure 1C:
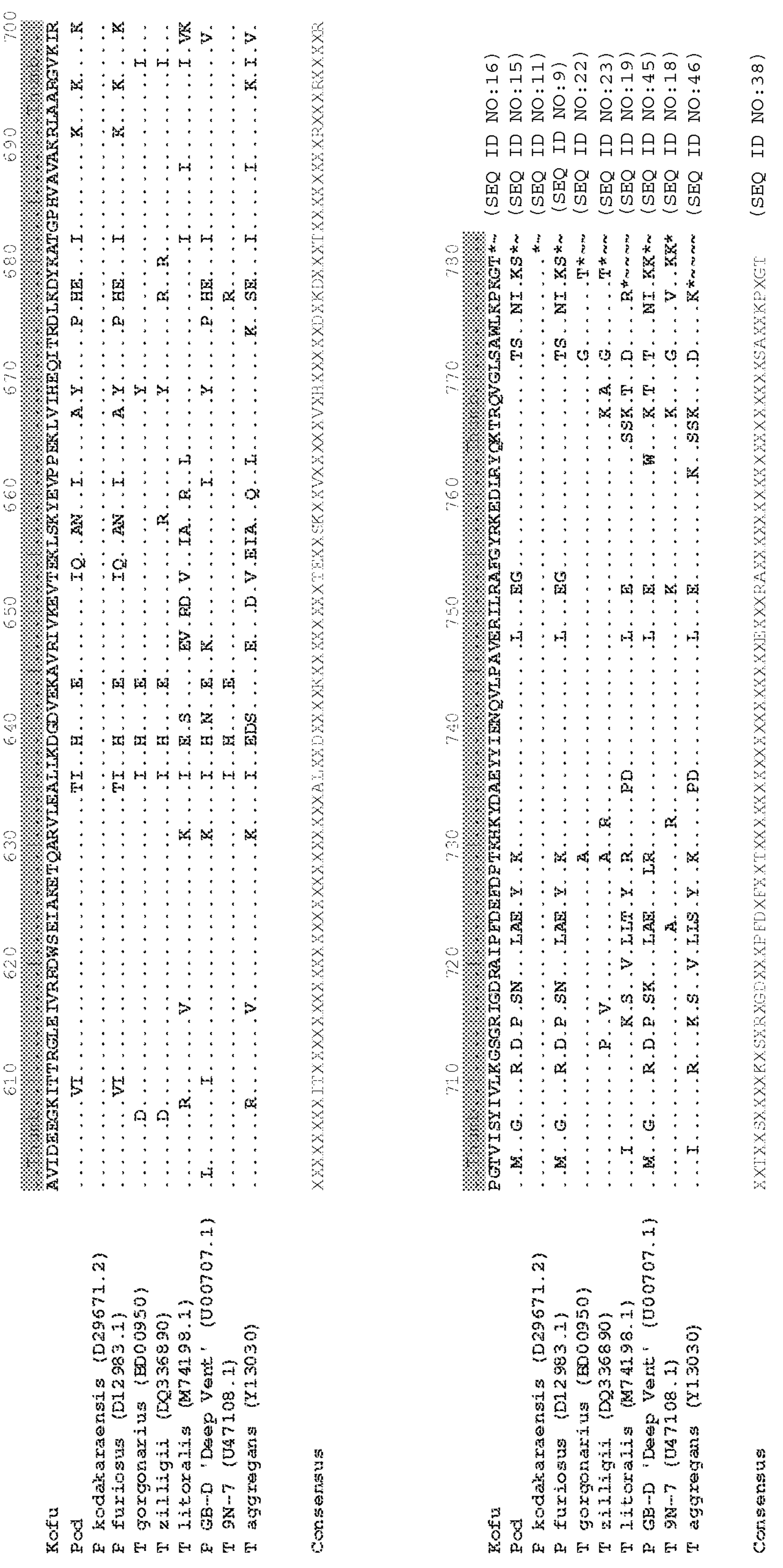

Corresponding domains or positions in various DNA polymerases can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above. An example of an alignment is shown in FIG. 1*a-c*.

In some embodiments, a suitable domain may be a variant (e.g., mutant or fragment) of a naturally-occurring domain sequence. For example, a suitable domain may have a sequence having at least 70% (e.g., at least 75%, 80%, 85%, 90%, 91%, 92%, 93%, 94%, 95%, 96%, 97%, 98%, 99%) identical to an amino acid sequence of a naturally-occurring domain found in a DNA polymerase of interest.

It is further contemplated that sequences defining the N-terminal domain, exonuclease domain, palm, fingers, and/or thumb domains may correlate with certain enzymatic characteristics of DNA polymerases, such as, fidelity or error rate, elongation rate, processivity, and salt resistance. For example, as described in the Examples section, the present inventors have demonstrated that sequences defining the N-terminal, exonuclease, and/or thumb domain may correlate with the characteristics associated with elongation rate, processivity, thermostability, TMAC tolerance and/or salt resistance; and that sequences defining the palm and/or fingers domain may correlate with the characteristics associated with fidelity or error rate of DNA polymerases.

In addition, based on sequence alignments between various DNA polymerases (see, e.g., FIGS. 1 *a-c*), it is further contemplated that domains correlative with high processivity, elongation rate, thermostability, TMAC tolerance and/or salt resistance may be defined by one or more of the following positive consensus sequences:

Positive Consensus Sequence 1 (Defining an N-terminal Domain)

XXLXXXXXXXEGXRXXXXXX-
VXXXXXDXXXTXXXXXXXXXXXV-
VKXXXXXXVLIX XXXXNXXXAXXKXXCXXXXX-
NFALXXXXXXXXXXXXIXXMXXRFXXXXXXXXX
XXXXPXXRXXXXXXXXXXXXXXXXVXX-
QXXXXXXXEXXTTXXXT (SEQ ID NO:30), wherein X is any amino acid or a peptide bond;

Positive Consensus Sequence 2 (Defining an Exonuclease Domain)

XXEXXXXYXXXXEXXFXXXXKXXX-
AXXXXXXXXAXXXXTVXTVKRXXXXQXXX
XXRXVEXXXXXFTXXXXXXAXXDXIXXXXX
(SEQ ID NO:31), wherein X is any amino acid or a peptide bond; and Positive Consensus Sequence 3 (Defining a Thumb Domain)

XXXXXXXXXXXXXXX-
ALXXDXXXXKXXXXXXXXTEXXSKXX-
VXXXXXVXHX XXXXDXKDXXX-
TXXXXXXXXRXXXRXXXXRXXTXXSXXXXKXS
XRXGDXXXPF DXFXX-
TXXXXXXXXXXXXXXXXXXEXXXRAXX (SEQ ID NO:32), wherein X is any amino acid or a peptide bond.

Additionally or alternatively, a domain or domains correlative with high processivity, elongation rate, thermostability, TMAC tolerance and/or salt resistance may be defined by one or more of the following negative consensus sequences:

Negative Consensus Sequence 1 (Defining an N-Terminal Domain)

NG$X_1$FKIE$X_2$DRTF$X_3$PY$X_4$YALL$X_5$DDS$X_6$IEEVKKIT
$X_7$ERHG$X_8X_9$V$X_{10}X_{11}X_{12}X_{13}$VEK
V$X_{14}$KKFLG$X_{15}$P$X_{16}X_{17}$VWKLY$X_{18}X_{19}$HPQDVP$X_{20}$
IR$X_{21}$K$X_{22}$REHPA (SEQ ID NO:33), wherein $X_1$ is not K; $X_2$ is not H; $X_3$ is not R; $X_4$ is not I; $X_5$ is not R; $X_6$ is not K; $X_7$ is not G; $X_8$ is not K; $X_9$ is not I; $X_{10}$ is not R; $X_{11}$ is not I; $X_{12}$ is not V; $X_{13}$ is not D; $X_{14}$ is not E; $X_{15}$ is not K; $X_{16}$ is not I; $X_{17}$ is not T; $X_{18}$ is not L; $X_{19}$ is not E; $X_{20}$ is not T; $X_{21}$ is not E; and $X_{22}$ is not V;

Negative Consensus Sequence 2 (Defining an Exonuclease Domain)

PI$X_1$MISYADE$X_2X_3$A$X_4$VITWKN$X_5$DLPYV$X_6$VVS$X_7$
EREMIKRFLR$X_8X_9X_{10}$EKDPD$X_{11}X_{12}X_{13}$TYNGD$X_{14}$
FDF$X_{15}$YL$X_{16}$KR$X_{17}$EKLGI$X_{18}X_{19}X_{20}X_{21}$GRDGSEP
K$X_{22}$QR$X_{23}$GD$X_{24}X_{25}$AVEVKGRIHFDLY$X_{26}$VI$X_{27}$R
TINLPTYTLEAVYEA$X_{28}$FG$X_{29}$PKEKVYA$X_{30}$EI$X_{31}$
$X_{32}$AWE$X_{33}$ (SEQ ID NO:34), wherein $X_1$ is not I; $X_2$ is not N; $X_3$ is not E; $X_4$ is not K; $X_5$ is not I; $X_6$ is not E; $X_7$ is not S; $X_8$ is not I; $X_9$ is not I; $X_{10}$ is not R; $X_{11}$ is not I; $X_{12}$ is not I; $X_{13}$ is not V; $X_{14}$ is not S; $X_{15}$ is not P; $X_{16}$ is not A; $X_{17}$ is not A; $X_{18}$ is not K; $X_{19}$ is not L; $X_{20}$ is not T; $X_{21}$ is not I; $X_{22}$ is not M; $X_{23}$ is not I; $X_{24}$ is not M; $X_{25}$ is not T; $X_{26}$ is not H; $X_{27}$ is not T; $X_{28}$ is not I; $X_{29}$ is not K; $X_{30}$ is not D; $X_{31}$ is not A; $X_{32}$ is not K; and $X_{33}$ is not S; and Negative Consensus Sequence 3 (Defining a Thumb Domain)

RDWSEIAKETQARVLE$X_1X_2$LK$X_3$GDVE$X_4$AVRIVKEV
$X_5X_6$KL$X_7X_8$YE$X_9$PPEKL$X_{10}$I$X_{11}$EQITR$X_{12}$L$X_{13}X_{14}$
YKA$X_{15}$GPHVAVAK$X_{16}$LAA$X_{17}$GVKI$X_{18}$PG$X_{19}$VI
$X_{20}$YIVL$X_{21}$G$X_{22}$G$X_{23}$I$X_{24}X_{25}$RAI$X_{26}X_{22}X_{28}$E$X_{29}$DP
$X_{30}$KHKYDAEYYIENQVLPAV$X_{31}$RIL$X_{32}X_{33}$FG
(SEQ ID NO:35), wherein $X_1$ is not T; $X_2$ is not I; $X_3$ is not H; $X_4$ is not E; $X_5$ is not I; $X_6$ is not Q; $X_7$ is not A; $X_8$ is not N; $X_9$ is not I; $X_{10}$ is not A; $X_{11}$ is not Y; $X_{12}$ is not P; $X_{13}$ is not H; $X_{14}$ is not E; $X_{15}$ is not I; $X_{16}$ is not K; $X_{17}$ is not K; $X_{18}$ is not K; $X_{19}$ is not M; $X_{20}$ is not G; $X_{21}$ is not R; $X_{22}$ is not D; $X_{23}$ is not P; $X_{24}$ is not S; $X_{25}$ is not N; $X_{26}$ is not L; $X_{27}$ is not A; $X_{28}$ is not E; $X_{29}$ is not Y; $X_{30}$ is not K; $X_{31}$ is not L; $X_{32}$ is not E; and $X_{33}$ is not G.

In some embodiments, a domain correlative with high fidelity may be defined by the following positive consensus sequence (defining palm and fingers domain):

XKXXXXXXXXXXXX-
AXXXXXXXXXXXXXXXXXLXXXXNXX-
IXXXXXXKXXXXI XXXXXXXXXHXXXXXXXXX-
TXXXEXQXXXXKIXXXXXXKXXXLXXXXFXXXX
X XXKXXXXXXXXXXXXXXXXXXKXX-
ELVWXXLXXXFXXXXLXIXXXXLYXXXXXG ESX-
EIXXXXLX (SEQ ID NO:36), wherein X is any amino acid or a peptide bond.

Additionally or alternatively, a domain correlative with high fidelity may be defined by the following negative consensus sequence (defining palm and fingers domain):

E$X_1$GLWENIVYLDFR$X_2$LYPSIIITHNVSPDTLN$X_3$EGC
K$X_4$YD$X_5$APQVGH$X_6$FCKD$X_7$P
GFIPSLLG$X_8$LLEERQKIK$X_9$KMK$X_{10}$T$X_{11}$DPIE$X_{12}$
$X_{13}$LLDYRQ$X_{14}$AIK$X_{15}$LANS$X_{16}$YG
YYGYA$X_{17}$ARWYCKECAESVTAWGR$X_{18}$YI$X_{19}X_{20}$
$X_{21}X_{22}$KE$X_{23}$EEK$X_{24}$GFKV$X_{25}$Y$X_{26}$DTDG$X_{27}X_{28}$ATI
PG$X_{29}X_{30}X_{31}$E$X_{32}X_{33}$KKKA$X_{34}$E (SEQ ID NO:37), wherein $X_1$ is not R; $X_2$ is not S; $X_3$ is not R; $X_4$ is not E; $X_5$ is not V; $X_6$ is not R; $X_7$ is not F; $X_8$ is not D; $X_9$ is not K; $X_{10}$ is not A; $X_{11}$ is not I; $X_{12}$ is not R; $X_{13}$ is not K; $X_{14}$ is not R; $X_{15}$ is not I; $X_{16}$ is not Y; $X_{17}$ is not R; $X_{18}$ is not E; $X_{19}$ is not T; $X_{20}$ is not M; $X_{21}$ is not T; $X_{22}$ is not I; $X_{23}$ is not I; $X_{24}$ is not Y; $X_{25}$ is not I; $X_{26}$ is not S; $X_{27}$ is not F; $X_{28}$ is not F; $X_{29}$ is not A; $X_{30}$ is not D; $X_{31}$ is not A; $X_{32}$ is not T; $X_{33}$ is not V; $X_{34}$ is not M.

Therefore, appropriate domains may be taken or derived from DNA polymerases with distinct functional characteristics to engineer a chimeric DNA polymerase with desirable combinations of functional features. In some embodiments, inventive methods in accordance with the present invention include steps of: (a) providing an N-terminal domain, an exonuclease domain, and/or a thumb domain based on a first DNA polymerase; (b) providing palm and/or fingers domain based on a second DNA polymerase; (c) combining the domains from step (a) and step (b) to form a chimeric polymerase. In some embodiments, the first and the second DNA polymerases are characterized with at least one distinct characteristic. For example, the first DNA polymerase may be characterized with high processivity, elongation rate, thermostability, TMAC tolerance and/or salt resistance and the second DNA polymerase may be characterized with high fidelity. In some embodiments, the first DNA polymerase may be characterized with high fidelity and the second DNA polymerase may be characterized with high processivity, elongation rate, thermostability, TMAC tolerance and/or salt resistance. In some embodiments, a chimeric polymerase engineered according to the invention has a processivity, elongation rate, thermostability, TMAC tolerance or salt resistance substantially similar to that of the first DNA polymerase and a fidelity substantially similar to that of the second DNA polymerase. In some embodiments, a chimeric polymerases engineered according to the present invention has the fidelity higher than that of the first DNA polymerase and the processivity, elongation rate or salt resistance higher than that of the second DNA polymerase.

The present invention further contemplates methods of improving the fidelity, processivity, elongation rate, thermostability, TMAC tolerance and/or salt resistance of a DNA polymerase. In some embodiments, inventive methods in accordance with the invention include a step of replacing a sequence within the palm-fingers domain of the DNA polymerase of interest with a corresponding sequence from a different DNA polymerase that is characterized with higher fidelity relative to the DNA polymerase of interest.

Additionally or alternatively, in some embodiments, inventive methods in accordance with the present invention include a step of replacing a sequence within the N-terminal domain, the exonuclease domain and/or the thumb domain of the DNA polymerase of interest with a corresponding sequence from a different DNA polymerase that is characterized with higher processivity, elongation rate, thermostability, TMAC tolerance or salt resistance relative to the DNA polymerase of interest.

As a non-limiting example, the present inventors have engineered a chimeric DNA polymerase Kofu and its reciprocal chimera POD based on KOD polymerase and Pfu polymerase (see the Examples section). As discussed in the example section, Kofu contains the N-terminal domain, the exonuclease domain and the thumb domain from KOD polymerase and the palm-fingers domain from Pfu polymerase. The sequence of Kofu polymerase is provided in SEQ ID NO:16. The reciprocal chimera POD contains the N-terminal domain, the exonuclease domain and the thumb domain from Pfu polymerase and the palm-fingers domain from KOD polymerase. The sequence of POD polymerase is provided in SEQ ID NO:15.

As discussed in the examples section, the Kofu chimeric polymerase displays the approximate replication fidelity of Pfu but the elongation speed, processivity, thermostability, TMAC tolerance and PCR performance similar to KOD. Alternatively, the Pod chimeric polymerase displays the approximate replication fidelity of KOD but the elongation speed, processivity, thermostability, TMAC tolerance and PCR performance similar to Pfu.

In some embodiments, the present invention provides variants of Kofu chimeric polymerase that contain an amino acid sequence at least 80% (e.g., at least 85%, 90%, 91%, 92%, 93%, 94%, 95%, 96%, 97%, 98%, 99%) identical to SEQ ID NO:16 (Kofu amino acid sequence). In particular embodiments, variants of Kofu chimeric polymerase in accordance with the invention have processivity, elongation rate, thermostability, TMAC tolerance and/or fidelity substantially similar to Kofu.

In some embodiments, variants of Kofu chimeric polymerases in accordance with the present invention are defined by consensus sequence
XXXXTXXXXXDXXXXXXIXXXXXX-
EXXXXYXXXXEXXFXXXXKXXXAXXXXXX
XXAXXXXTVXTVKRXXXXQXXXXXRX-
VEXXXXXFTXXXXXXAXXDXIXXXXXXI
XXYXXXXXXXXXXXXXXXX-
VXXXXDXXXXMXXXXXXXXXXXXXXX-
AEXXXLX XXXXXXEGXRXXXXXX-
VXXXXXDXXXTXXXXXXXXXXVVKXXXXXVLI
XXXXX NXXXAXXKXXCXXXXXN-
FALXXXXXXXXXXIXXMXXR-
FXXXXXXXXXXXXXPX
XRXXXXXXXXXXXXXXXXVXX-
QXXXXXXXEXXTTXXXTXXXXXXXXRXXXXX
XXVXXXXXXXXXXXXAXXXXXVXX-
PXXXXXXXXXXXXXXXXXXXXXXXXXXV
XXXXXSXEXYQXXXXEXX-
TXXFXXXXXKXXXXXXXXXXXX-
AXXXXXXXXXXXX XXXXXLXXXXNXX-
IXXXXXXKXXXXIXXXXXXXXXHXXXXXXXXXT
XXXEXQX XXXKIXXXXXXKXXX-
LXXXXFXXXXXXXKXXXXXXXXXXXXXXXXXK
XXELVW XXLXXXFXXXXLXIXXXX-
LYXXXXXGESXEIXXXXLXXLXXXX-
AXXXXAXXXXX
XXXXXXXXXXXXXKXXXXXXXXX-
ITXXXXXXXXXXXXXXXXXXXXXXXXALX
XDXXXXKXXXXXXXXTEXXSKXX-
VXXXXXVXHXXXXXDXKDXXXTXXXXXXX
XRXXXRXXXXRXXTXXSXXXXKX-
SXRXGDXXXPFDXFXXTXXXXXXXXXXXXX
XXXXX-
EXXXRAXXXXXXXXXXXXXXXXXX-
SAXXKPXGT (SEQ ID NO:38), wherein X is any amino acid or a peptide bond.

In some embodiments, variants of Kofu chimeric polymerases in accordance with the present invention are defined by consensus sequence
XIXDTDYXTXDGX-
PXXRIFXKXXGEFXXXYDXXFEPYFY-
ALLKDDSAIXXXXXXXA XRHGTVXTVKRXXXX-
QXKFLXRXVEVWXLXFTHPQDVPAXXDXMHXXV
IDIYE YDIPFAKRYLIDXGLVPMEGDEX-
LXMXXXDIETXYHEGXEFAEGXXLMISYADXEG
ARVITWKXVDLPYVDVVSTEX- EMIKRXXXVVKEKDPDVLIXYXGDNFDXAYLKXR
CEXLGXNFALXRXXXXXEPKIXXMGXR-
FAVEXKGRXHFDLXPXXRXTXNLPTYXL
XXVYEXVXGQXKXKXXXEEITTX-
WETXXXXXXXARYSMEDAXVTXELGXEFXPM
EAXLXXLVGXPXWDVXRSSTGNLVEWX-
LLXXAYXRNEVAPNKPSXEEYQXRXXE XYT-
GXFVXEPEKGLWXXXXXLDXXALYPSI-
IXXHNVSPDTLXLEXCXNYDIAPXVG
XKFCKDIPGFIPSXLXHLXXXRQXXK-
TXMXEXQDPXEKIXLDYRQKAXKLLXNSFY
GYXGYXKARWYXXECAESVTX-
WGRKYIELVWXELEXXFGFKXLYIDTDGLYATIP
GGESXEIKXXXLXFLXYINAXLPGALEL-
EYEXFYXRGFFVXKKKYAXIDEEXXITTR GLEX-
VRRDWSXXAKETXAXVLEALLXDXX-
VXKAVXXVXXXTEXXSKYXVPXEKL
VIHEQITRDXKDYXATGPHVAX-
AKRLXXRGXXXRPGTXISYXXLKGS-
GRXGDRXIPF DEFXXTKHXYDXXYYIENQVLPAV-
ERXLRAFGYXXXXLXXQXXXQXGLSAWXKP XGT
(SEQ ID NO:39), wherein X is any amino acid or a peptide bond In some embodiments, the present invention provide variants of POD chimeric polymerases that contain an amino acid sequence at least 80% (e.g., at least 85%, 90%, 91%, 92%, 93%, 94%, 95%, 96%, 97%, 98%, 99%) identical to SEQ ID NO:15 (Pod amino acid sequence). In particular embodiments, variants of POD chimeric polymerases in accordance with the present invention have processivity, elongation rate, thermostability, TMAC tolerance and/or fidelity substantially similar to POD.

Expression of Chimeric DNA Polymerases of the Invention

Standard recombinant DNA techniques (e.g., restriction enzyme digestion, ligation, PCR) can be used to engineer chimeric DNA polymerases in accordance with the present invention. Methods well known in the art may be applied to express and isolate chimeric DNA polymerases. Many bacterial expression vectors contain sequence elements or combinations of sequence elements allowing high level inducible expression of the protein encoded by a foreign sequence. Expression vectors are commercially available from, for example, Novagen (http://www.emdbiosciences.com/html/NVG/AllTables.html#).

In addition, bacteria expressing an integrated inducible form of the T7 RNA polymerase gene may be transformed with an expression vector bearing a chimeric DNA polymerase gene linked to the T7 promoter. Induction of the T7 RNA polymerase by addition of an appropriate inducer, for example, isopropyl-p-D-thiogalactopyranoside (IPTG) for a lac-inducible promoter, induces the high level expression of the chimeric gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned chimeric genes (several BL21-CODON PLUS™ cell strains carrying rare-codon tRNAs are available from Stratagene, for example). Additionally or alternatively, genes encoding DNA polymerases may be codon optimized to facilitate expression in *E. coli*. Codon optimized sequences can be chemically synthesized.

There are many methods known to those of skill in the art that are suitable for the purification of a chimeric DNA polymerase of the invention. For example, the method of Lawyer et al. (1993, PCR Meth. & App. 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase.

Further, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

Uses of Chimeric DNA Polymerases of the Invention

Chimeric DNA polymerases of the present invention may be used for any methods involving polynucleotide synthesis. Polynucleotide synthesis methods are well known to a person of ordinary skill in the art and can be found, for example, in Molecular Cloning second edition, Sambrook et al., Cold Spring Harbor Laboratory Press, Cold Spring Harbor, N. Y. (1989). For example, chimeric DNA polymerases of the present invention have a variety of uses in recombinant DNA technology including, but not limited to, labeling of DNA by nick translation, second-strand cDNA synthesis in cDNA cloning, DNA sequencing, and amplifying, detecting, and/or cloning nucleic acid sequences using polymerase chain reaction (PCR).

In some embodiments, the invention provides robust, fast, and accurate enzymes for PCR. PCR refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

Chimeric DNA polymerases with higher processivity, elongation rate and/or fidelity are expected to reduce error rate, improve efficiency and success rate of long-range amplification (higher yield, longer targets amplified), and/or reduce the amount of required DNA template.

Various specific PCR amplification applications are available in the art (for reviews, see for example, Erlich, 1999, Rev Immunogenet., 1: 127-34; Prediger 2001, *Methods Mol. Biol.* 160: 49-63; Jurecic et al., 2000, *Curr. Opin. Microbiol.* 3: 316-21; Triglia, 2000, *Methods Mol. Biol.* 130: 79-83; MaClelland et al., 1994, *PCR Methods Appl.* 4: S66-81; Abramson and Myers, 1993, *Current Opinion in Biotechnology* 4: 41-47; each of which is incorporated herein by references).

As non-limiting examples, the present invention can be used in PCR applications including, but are not limited to, i) hot-start PCR which reduces non-specific amplification; ii) touch-down PCR which starts at high annealing temperature, then decreases annealing temperature in steps to reduce nonspecific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis; xv) DOP-PCR that uses partially degenerate primers for whole-genome amplification; xvi) quantitative PCR using SYBR green or oligonucleotide probes to detect amplification; xvii) whole-genome amplification using adaptor-ligated DNA fragment libraries as template, and xviii) error-prone PCR in which conditions are optimized to give an increased number of mutations in the PCR product.

It should be understood that this invention is not limited to any particular amplification system. As other systems are developed, those systems may benefit by practice of this invention.

Kits

The invention also contemplates kit formats which include a package unit having one or more containers containing chimeric DNA polymerases of the invention and compositions thereof. In some embodiments, the present invention provides kits further including containers of various reagents used for polynucleotide synthesis, including synthesis in PCR.

Inventive kits in accordance with the present invention may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

EXAMPLES

Example 1

Designs of Chimeras of KOD and Pfu DNA Polymerases

The two enzymes we chose to include in this experiment were *Pyroccocus furiosus* DNA polymerase (Pfu) and *Thermococcus Kodarensis* (KOD) DNA polymerases. The two enzymes have similar domain structure and have a 79% identity at the amino acid level using blastP alignments (see Table 2). The domain structures of Pfu and KOD are illustrated in FIGS. 1*a-c*.

TABLE 2

ClustalW alignment of Pfu and KOD

```
PFU    1  MILDVDYITEEGKPVIRLFKKENGKFKIEHDRTFRPYIYALLRDDSKIEEVKKITGERHG   60
KOD    1  ....T.....D......I......E....Y....E..F....K...A........A....   60
PFU   61  KIVRIVDVEKVEKKFLGKPITVWKLYLEHPQDVPTIREKVREHPAVVDIFEYDIPFAKRY  120
KOD   61  TV.TVKR....Q.....R.VE.....FT......A..D.I......I..Y..........  120
PFU  121  LIDKGLIPMEGEEELKILAFDIETLYHEGEEFGKGPIIMISYADENEAKVITWKNIDLPY  180
KOD  121  ......V....D....M...............AE...L.......EG.R......V....  180
PFU  181  VEVVSSEREMIKRFLRIIREKDPDIIVTYNGDSFDFPYLAKRAEKLGIKLTIGRDGSEPK  240
KOD  181  .D...T..........VVK.....VLI.....N...A..K..C.....NFAL........  240
PFU  241  MQRIGDMTAVEVKGRIHFDLYHVITRTINLPTYTLEAVYEAIFGKPKEKVYADEIAKAWE  300
KOD  241  I..M..RF.............P..R................V..Q.......E..TT...  300
PFU  301  SGENLERVAKYSMEDAKATYELGKEFLPMEIQLSRLVGQPLWDVSRSSTGNLVEWFLLRK  360
KOD  301  T........R.......V............A.....I..S....................  360
PFU  361  AYERNEVAPNKPSEEEYQRRLRESYTGGFVKEPEKGLWENIVYLDFRALYPSIIITHNVS  420
KOD  361  ......L.....D.K.LA..~.Q..E.. Y.....R............S............  419
```

TABLE 2-continued

ClustalW alignment of Pfu and KOD

| PFU | 421 | PDTLNLEGCKNYDIAPQVGHKFCKDIPGFIPSLLGHLLEERQKIKTKMKETQDPIEKILL | 480 |
|---|---|---|---|
| KOD | 420 | .....R....E..V......R....F.........D.........K...A.I....RK.. | 479 |
| PFU | 481 | DYRQKAIKLLANSFYGYYGYAKARWYCKECAESVTAWGRKYIELVWKELEEKFGFKVLYI | 540 |
| KOD | 480 | ....R...I....Y.......R.................E..TMTI..I...Y....I.S | 539 |
| PFU | 541 | DTDGLYATIPGGESEEIKKKALEFVKYINSKLPGLLELEYEGFYKRGFFVTKKRYAVIDE | 600 |
| KOD | 540 | ....FF.....ADA.TV....M..L....A....A..................K...... | 599 |
| PFU | 601 | EGKVITRGLEIVRRDWSEIAKETQARVLETILKHGDVEEAVRIVKEVIQKLANYEIPPEK | 660 |
| KOD | 600 | ...IT........................AL..D....K........TE...SK..V.... | 659 |
| PFU | 661 | LAIYEQITRPLHEYKAIGPHVAVAKKLAAKGVKIKPGMVIGYIVLRGDGPISNRAILAEE | 720 |
| KOD | 660 | .V.H.....D.KD...T........R...R....R..T..S....K.S.R.GD...PFD. | 719 |
| PFU | 721 | YDPKKHKYDAEYYIENQVLPAVLRILEGFGYRKEDLRYQKTRQVGLTSWLNIKKS* | 776 |
| KOD | 720 | F..T..................E...RA..................SA..KP.GT* | 775 |
| PFU | (SEQ ID NO: 9) | | |
| KOD | (SEQ ID NO: 11) | | |

Pfu and KOD have very distinct phenotypic characteristics, in particular, with respect to elongation rate, processivity and error rate (See Table 3):

TABLE 3

| | Pfu | KOD |
|---|---|---|
| Elongation Rate: | 25 nt/s | 106-138 nt/s (Takagi et al. 1997) |
| Processivity: | >20 nt | ~300 nt (Takagi et al. 1997) |
| Error Rate (mutations/nt/doubling): | $1.5 \times 10^{-6}$ | $4.45 \times 10^{-6}$ (internal data) |

Thus, the goal was to find chimeric combinations of these two enzymes which exhibited the error rate comparable to Pfu ($2.0 \times 10^{-6}$) with the processivity and/or elongation rate comparable to KOD (~300 nt/s and 106-138 nt/s respectively). An enzyme with the above mentioned characteristics has utility as a robust, fast, and accurate enzyme for PCR.

Figure 2:
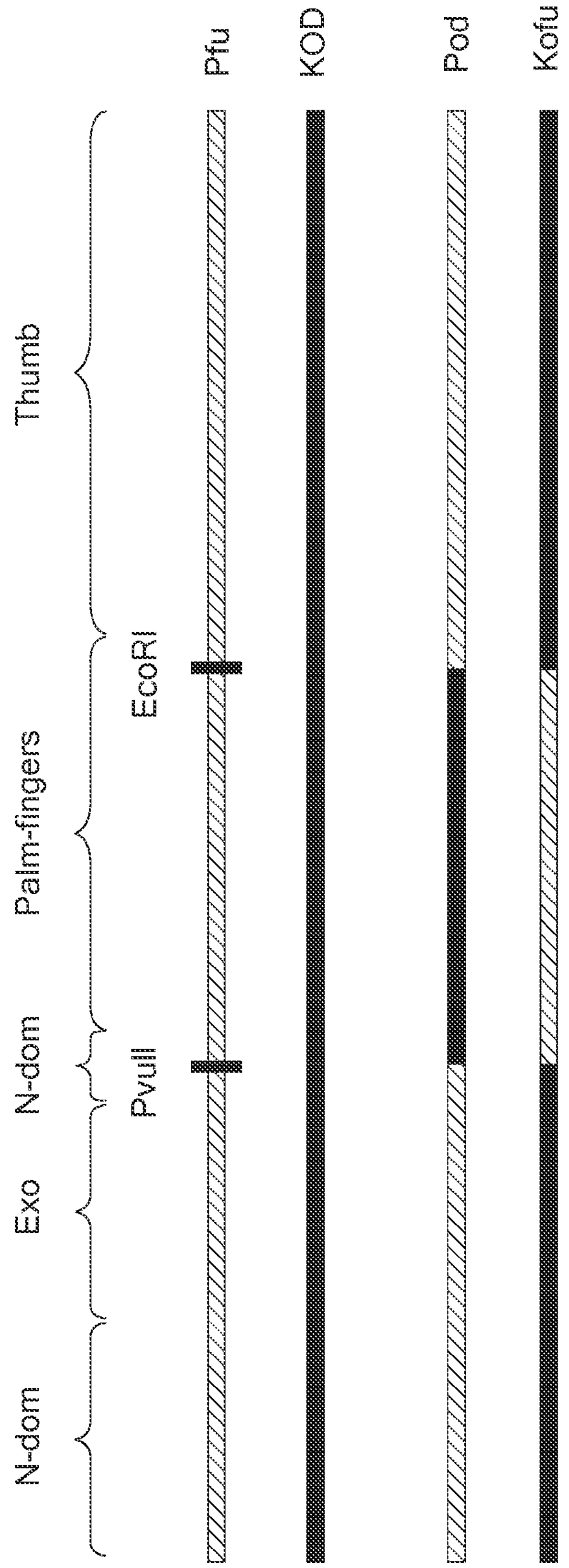
FIG. 2 depicts that an exemplary chimeric polymerase Pod contains the N-terminal domain, the 3'-5' exonuclease domain and the thumb domain of Pfu and the palm and fingers domain of KOD and the reciprocal chimeric polymerase Kofu contains the N-terminal domain, the 3'-5' exonuclease domain and the thumb domain of KOD and the palm and fingers domain of Pfu.

Restriction sites were inserted into the codon-optimized nucleotide sequence of KOD and Pfu polymerases at positions that approximately flank the polymerase domain of the enzymes (see Example 2). For example, PvuII and EcoRI sites flanking the polymerase domain (the palm and fingers domain) were used to replace the polymerase domain of Pfu with that of KOD to generate the chimera deemed Pod (FIG. 2). This chimera contains the N-terminal domain, the 3'-5' exonuclease domain and the thumb domain of Pfu and the palm and fingers domain of KOD. The reciprocal swap, yielding the chimera Kofu, was generated by replacing the polymerase domain (palm and fingers) of KOD with that of Pfu.

Example 2

Codon Optimization and Synthesis of *Pyrococcus furiosus* and *Thermococcus kodakarensis* DNA Polymerases Native DNA sequences for *Pyrococcus furiosus* polymerase I (SEQ ID NO:1) and *Thermococcus kodakarensis* polymerase I (SEQ ID NO:2) were retrieved from Genbank. These two DNA sequences were in silico codon optimized by Codon Devices (Cambridge, Mass.) for expression in *E. coli* resulting in SEQ ID NO:3 for the Pfu polymerase I codon optimized gene DNA sequence and SEQ ID NO:4 for the KOD polymerase I codon optimized gene DNA sequence. The two codon optimized genes were chemically synthesized and cloned into pUC19 by Codon Devices (Cambridge, Mass.) resulting in SEQ ID NO:7 for Pfu polymerase I and SEQ ID NO:8 for KOD polymerase I.

Example 3

Cloning of Codon Optimized KOD and Pfu Polymerase I Sequences into Expression Vector pKBexp KOD (SEQ ID NO:8) and Pfu (SEQ ID NO:7) polymerase codon optimized pUC 19 constructs were cloned into the pKBexp vector as follows:

The pKBexp vector contains two Eco31I sites with non-complementary overhangs enabling directional cloning of inserts using a single restriction enzyme. KOD and Pfu polymerase genes were designed with two flanking Eco31I sites that enabled directional and in-frame cloning into pKBexp.

Purified DNA from the pKBexp vector was digested with Eco31I and purified from an agarose gel. KOD and Pfu codon optimized pUC DNA constructs (SEQ ID NO.8 and SEQ ID NO.7) were likewise digested with Eco31I and the roughly 2.3 kilobase insert fragments were cut out from an agarose gel and purified. 30 ng of KOD or Pfu polymerase genes were ligated with 15 ng of digested pKBexp using T4 DNA ligase. The ligation reactions were purified and used to transform competent *E. coli* DH10B. DNA minipreps were made of ampicillin resistant clones. The presence of inserts was confirmed by digestion of the minipreps with XbaI and HindIII, two enzymes that flank the insert. The cloning of the KOD polymerase gene sequence in pKBexp deemed pKB11 and the Pfu polymerase gene in pKBexp deemed pKB14 were confirmed by DNA sequencing.

Example 4

Domain Swapping of DNA Sequences from KOD and Pfu Polymerase I Genes

The codon-optimized sequences of KOD (SEQ ID NO:5) and Pfu (SEQ ID NO:3) polymerase I genes were designed with restriction sites that approximately flank the finger and palm domains of KOD and Pfu polymerases. The KOD codon optimized sequence contains a PvuII restriction site and an EcoRI restriction site. The Pfu codon optimized sequence contains a PvuII restricition site and an EcoRI restriction site.

Purified DNA from pKB11 and pKB14 were each digested the restriction enzymes EcoRI and Pvuii. The large fragment (4.7 kb) and small fragment (0.7 kb) from each digest were separately extracted and purified from an agarose gel. The small fragments from each restriction digest contained the finger and palm domains of KOD and Pfu respectively. The digested and purified large fragments (containing the expression vector and remaining polymerase fragments) were dephosphorylated using Shrimp Alkaline Phospate. The construct deemed POD was created by ligation of 30 ng of the 4.7 kb Pfu large fragment (aa residues 1 to 335 and 567 to 778 of Pfu DNA polymerase with 10 ng of the 0.7 kb KOD small fragment (corresponding to amino acid residues 336 to 565 of KOD DNA polymerase SEQ ID NO: 11). POD thus includes N-terminal, exonuclease and thumb domains from Pfu DNA polymerase and palm and finger domains from KOD. The construct deemed Kofu was made by ligation of 30 ng of the 4.7 kb KOD large fragment (corresponding to amino acid residues 1 to 335 and 566 to 777 of KOD DNA polymerase SEQ ID NO: 11) with 10 ng of the 0.7 kb Pfu small fragment (corresponding to amino acid residues 336 to 566 of Pfu DNA polymerase SEQ ID NO: 9). Kofu thus includes N-terminal, exonuclease and thumb domains from KOD DNA polymerase and palm and finger domains from Pfu. The ligation reactions were used to transform *E. coli* DH10B. The construction of Pod (SEQ ID NO:13) and Kofu (SEQ ID NO:14) was confirmed by DNA sequencing. The domain structures of POD and Kofu are illustrated in FIGS. 1*a-c*. Expression and purification of chimeric polymerases are done using methods known in the art, for example, as reviewed in "Detailed description of the invention."

Example 5

Figure 3:
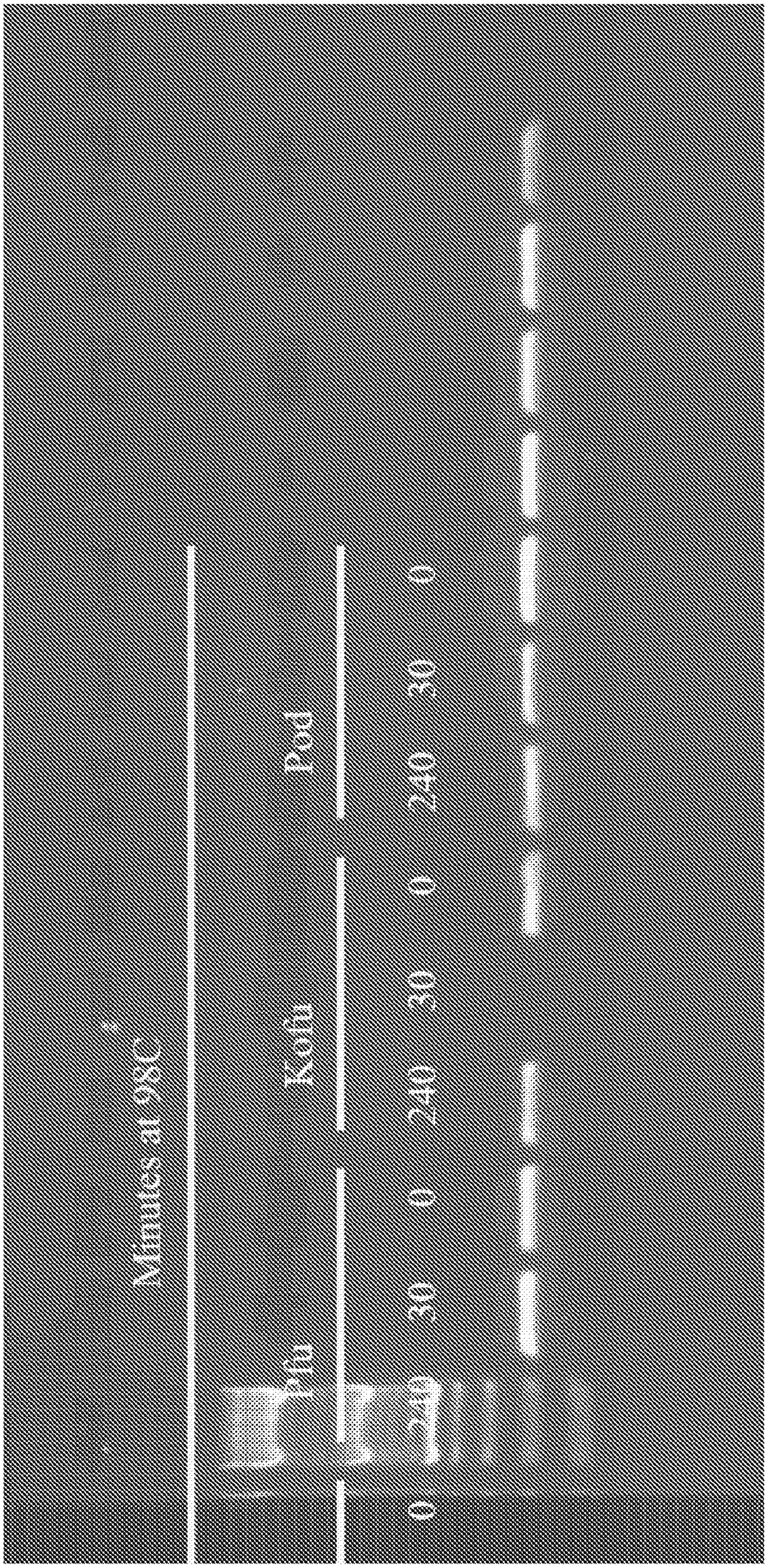
FIG. 3 depicts exemplary results showing the thermostability of KOD, Pfu, Kofu and Pod.

Thermostability of KOD, Pfu, Kofu and Pod 10 ng of each enzyme was incubated at 98° C. for 240, 120, 60, 30, 15, 8, 4, 2, 1 or 0 min in a 10 μl volume containing the following: 20 mM Tris-HCl pH 8.0, 2 mM $MgCl_2$, 6 mM $(NH4)_2SO_4$, 25 or 50 mM KCl (25 mM for Pfu and Pod, 50 mM for KOD and Kofu). 10 μl of primer/template mix was added to each tube after the heat incubation. The primer template mix contained the following: 20 mM Tris-HCl pH 8.0, 2 mM $MgCl_2$, 6 mM $(NH4)_2SO_4$, 0.6 mM dNTP, 0.6 μM each of primers HPRT1-F1 (5'-tttggaaacatctggagtcct-3' (SEQ ID NO:40)) and HPRT1-R1 (5'-gcccaaagggaactgatagtc-3' (SEQ ID NO:41)), 2 ng human genomic DNA per μl, and 25 or 50 mM KCl (25 mM for Pfu and Pod, 50 mM for KOD and Kofu). The amplifications were performed with the following cycling protocol: 3 minutes at 95° C., 35×(20 seconds at 98° C., 20 seconds at 60° C., 20 seconds at 72° C.), 20 seconds at 72° C. The PCR products were analysed on an agarose gel (see FIG. 3). As illustrated in FIG. 3, no amplification was observed for Pfu after pre-incubation of the enzyme for 4 hours at 98° C. In contrast, KOD, Kofu and Pod were able to amplify a PCR product for all time points tested.

Example 6

Fidelity Assays

The fidelity of enzymes was determined by a method similar to that described by Cline et al. and references therein (*Nucl. Acids Res.,* 1996, 24(18): 3546-3551). LacI was PCR amplified from *E. coli* and cloned into pUC19 to degenerate plasmid pKB-LacIQZalpha (SEQ ID NO:17). pKB-LacIQZalpha served both as template for PCR amplification of LacI in the fidelity assays and as vector for cloning the amplified LacI into for blue/white colony screening.

2×50 μl PCR reactions (for each enzyme) were set-up, using 70 ng of pKB-LacIQZalfa plasmid template (equivalent to 25 ng of lacI target) and 2.5 U of each enzyme to amplify the 1.386 Kb lacIOZalpha fragment. The PCR conditions were as follows: amplification with Pfu and Pod were done in Pfu buffer (Fermentas); KOD and Kofu in Novagen KOD buffer 1. Final concentrations of 2 mM MgCl2, 0.4 μM each of primers M13-40 (GTTTTCCCAGTCACGAC (SEQ ID NO:42)) and PKBlac-1R (GGTATCTTTATAGTCCTGTCG (SEQ ID NO:43)) and 0.2 mM each dNTP. Cycling parameters for Pfu and Pod were: 94° C. 4 minutes, 30×(94° C. 15 seconds, 55° C. 15 seconds, 72° C. 3 minutes), 72° C. 6 minutes. Cycling parameters for KOD and Kofu were: 94° C. 2 minutes, 30×(98° C. 15 seconds, 55° C. 2 seconds, 72° C. 20 seconds), 72° C. 30 seconds.

PCR product yields were quantitated by means of gel electrophoresis and the number of template doublings were calculated. PCR products were digested with XbaI, NcoI and DpnI, gel-purified (without exposure to UV light) and ligated into XbaI-NcoI-digested pKB-LacIQZalpha. *E. coli* was transformed with the ligation mixtures and the cells were plated onto LB-Amp-X-gal plates. The number of blue colonies, white colonies and total number of colonies were recorded. The error rate f was calculated as f=−1n(F)/(d×(bp)), where F=fraction of white colonies ((total colonies minus blue colonies)/total colonies), d=number of template doublings and b=349 (only 349 bp of the lacI amplicon are scored). Exemplary results are summarized in Table 4. As shown in Table 4, Pfu and Kofu have similar fidelity and that their fidelity is higher than that of KOD and Pod.

TABLE 4

Fidelity of KOD, Pfu, Kofu and Pod

| | White colonies | Doublings d | Blue colonies | Total colonies | Fidelity f ($\times 10^{-6}$) |
|---|---|---|---|---|---|
| KOD | 21130 | 7.77 | 246 | 21376 | 4.27 |
| Pfu | 19270 | 7.76 | 77 | 19347 | 1.47 |
| Kofu | 12817 | 5.8 | 39 | 12856 | 1.50 |
| Pod | 22039 | 7.19 | 221 | 22260 | 3.98 |

Example 7

Processivity Assays

Processivity can be determined and calculated using assays described in (Wang et al. *Nucl. Acids Res,* 2004, 32(3): 1197-1207; and Von Hippel et al. *NY Acad Sci* 1994; 726:118-131).

Briefly, 0.8 pmoles of a 5'FAM-labelled primer (−40M13LFF, 5'FAM-GTTTTCCCAGTCACGACGTTG-TAAAACGACGGCC-3' (SEQ ID NO:44)) is added to 1.6 pmoles of ssM13mpl8 DNA in the presence of 20 mM Tris-HCl pH 8.0, 25 mM KCl, 2.5 mM MgCl2, 0.3 mM dNTP in a 16 microL volume. The primer is annealed to the template by heating to 95° C. for 2 minutes followed by slow cooling to 72° C. in a thermocycler at a rate of 0.1° C./second, incubation for 10 minutes at 72° C. and further cooling at 0.1° C./second to 4° C. The polymerases are diluted in 20 mM Tris-HCl pH 8.0, 25 mM KCl. The primed template and the diluted polymerases are heated to 72° C. and the reaction is started by adding 4 μl diluted polymerase to 16 μl of primed template. The polymerases are diluted to give polymerase: template ratios of 1:10-1:10000. The reactions are terminated after various timepoints by adding EDTA to a final concentration of 10 mM.

The extension reactions are analyzed on an ABI 3130XL Genetic Analyzer. The median product length is determined for each reaction. The median product length is defined as the length of the product at which the total fluorescence intensity of all products up to that length equals 50% of the sum of fluorescence intensities of all detectable products. The traces for those samples where the median product length does not change with a change in polymerase concentration or incubation time are used to calculate the processivity according to Von Hippel et al. (Von Hippel et al. *NY Acad Sci* 1994; 726:118-131). Each peak (I) with a fluorescence level significantly above background level is integrated to give the fluorescence intensity of that peak (ni). The total fluorescence intensity (nT) is the sum of the fluorescence of all peaks. The integration data are plotted as log(ni/nT) vs n−1, where n is the number of nucleotides incorporated. The data is fitted to the following equation: log(ni/nT)=(n−1)log Pi+log(1−Pi). Pi, the microscopic processivity factor, is defined as the probability of not terminating extension at position i. The average primer extension length is determined from 1/(1−Pi).

Example 8

Salt Resistance of KOD, Pfu, Kofu and Pod

Previous studies (Pavlov et al. (2002) *Proc Natl Acad Sci.* 99(21), 13510-13515; Wang et al. (2004) *Nucl Acids Res.* 32(3), 1197-1207) have shown that there is a direct correlation between increased tolerance of polymerases to salt and the processivity of polymerases. For all polymerases tested (from family A or family B), it was found that polymerases with increased salt tolerance also have increased processivity. We therefore compared the salt tolerance of our chimeras with that of the parental polymerases as a proxy for processivity.

Figure 4:
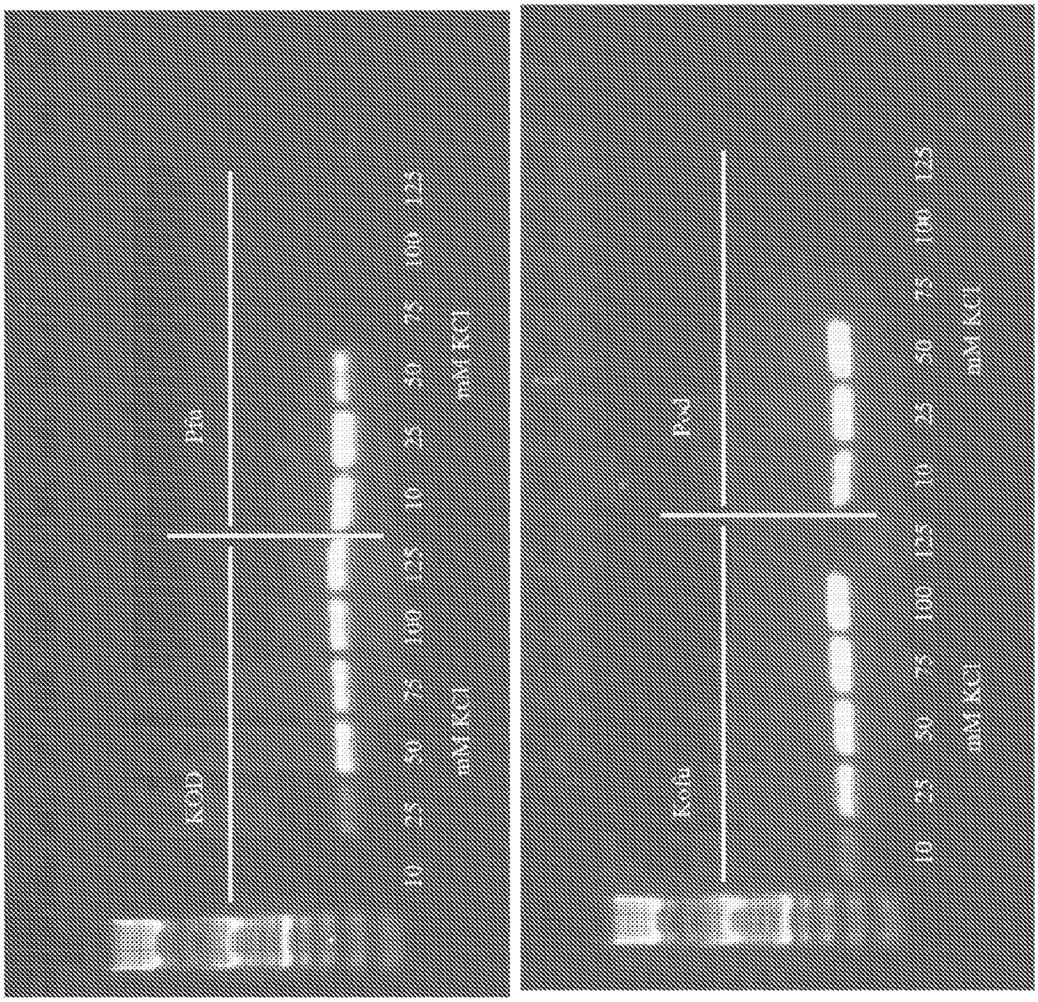
FIG. 4 depicts exemplary results showing the salt resistance of KOD, Pfu, Kofu and Pod.

The protein concentration of the purified KOD, Pfu, Kofu and Pod where determined using a Bioanalyzer 2100 (Agilent, Santa Clara, Calif., USA) with the Protein 230 Kit from the same supplier. The polymerases were tested in real-time PCR with increasing amounts of KCl added. The reactions were performed in a 20 μl volume containing 20 mM Tris-HCl pH 8.0, 6 mM $(NH_4)_2SO_4$, 2 mM $MgCl_2$, 3% DMSO, 10 ng polymerase, 20 ng human genomic DNA, 0.3 mM each dNTP, 0.25×SYBR Green (Invitrogen, Carlsbad, Calif., USA). A diluted stock 20×SYBR Green in DMSO was made), 0.3 μM forward primer HPRT1-F1 (5'-tttggaaacatctg-gagtcct-3' (SEQ ID NO:40)) and 0.3 μM reverse primer HPRT1-R1(5'-gcccaaagggaactgatagtc-3' (SEQ ID NO:41)). KCl was added to final concentrations of 10, 25, 50, 75, 100 or 125 mM. PCR amplification was performed in a Corbett 6000 HRM real-time thermocycler (Corbett Life Science, Sidney, Australia) with the following cycling protocol: 3 minutes at 95° C., 40 cycles of (10 seconds at 95° C., 20 seconds at 60° C., 20 seconds at 72° C., data acquisition), followed by a melting curve analysis step of: ramp from 72° C. to 95° C. in 1° C. steps, wait for 5 seconds before data acquisition at the end of each step. 8 μl of each sample was analysed on a 1.5% agarose gel. 5 μl of Fermentas GeneRuler™ Mix, cat no. SM0333 (Fermentas, Vilnius, Lithuania) was loaded onto the gel as a DNA marker. Exemplary results are shown in FIG. 4.

Example 9

TMAC Tolerance of KOD, Pfu, Kofu and Pod

Tetra-methyl ammonium-containing salts enhance PCR reactions as shown by Kovarova et al. (Kovarova, M. and Draber, P.; *Nucl. Acids Res.* (2000) 28(13) e70-). One such salt is tetra-methyl ammonium chloride (TMAC). We therefore compared the TMAC tolerance of our chimeras with that of the parental polymerases.

Figure 5:
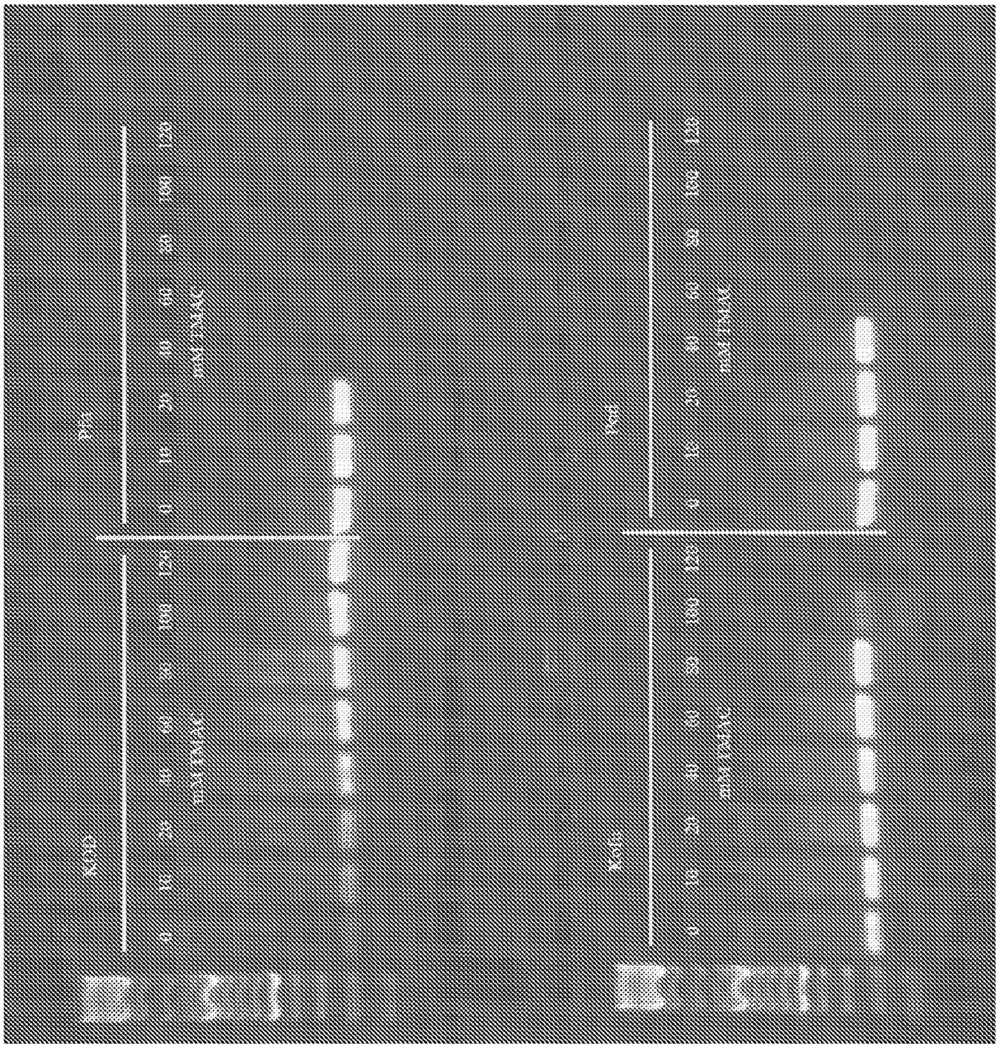
FIG. 5 depicts exemplary results showing the TMAC tolerance of KOD, Pfu, Kofu and Pod.

The polymerases were tested in real-time PCR with increasing amounts of TMAC added. The reactions were performed in a 20 μl volume containing 20 mM Tris-HCl pH 8.0, 6 mM $(NH_4)_2SO_4$, 2 mM $MgCl_2$, 25 mM KCl, 10 ng polymerase, 20 ng human genomic DNA, 0.3 mM each dNTP, 0.25×SYBR Green (Invitrogen, Carlsbad, Calif., USA. A diluted stock 20×SYBR Green in DMSO was made), 0.3 μM forward primer HPRT1-F1 (5'-tttggaaacatctggagtcct-3' (SEQ ID NO:40)) and 0.3 μM reverse primer HPRT1-R1 (5'-gcccaaagggaactgatagtc-3' (SEQ ID NO:41)). TMAC was added to final concentrations of 0, 10, 20, 40, 60, 80, 100 or 120 mM. PCR amplification was performed in a Corbett 6000 HRM real-time thermocycler (Corbett Life Science, Sidney, Australia) with the following cycling protocol: 3 minutes at 95° C., 40 cycles of (10 seconds at 95° C., 20 seconds at 50° C., 20 seconds at 72° C., data acquisition), followed by a melting curve analysis step of: ramp from 72° C. to 95° C. in 1° C. steps, wait for 5 seconds before data acquisition at the end of each step. 8 μl of each sample was analysed on a 1.5% agarose gel. 5 μl of Fermentas GeneRuler™ Mix, cat no. SM0333 (Fermentas, Vilnius, Lithuania) was loaded onto the gel as a DNA marker. Exemplary results are shown in FIG. 5.

Example 10

Additional Chimeras of KOD and Pfu Polymerases

This example is designed to show that the positions where the swapping between domains take place may vary.

Additional chimeras are made by swapping the palm and finger domains of KOD and Pfu polymerases where the exact position of the swap varies slightly compared to positions for Kofu and Pod. Kofu-II (SEQ ID NO:26) is made by replacing amino acid residues 305 to 615 of KOD (SEQ ID NO: 12) with amino acids 305 to 616 of Pfu (SEQ ID NO:10). Pod-II (SEQ ID NO:27) is made by replacing amino acids 305 to 616 of Pfu (SEQ ID NO:10) with amino acids 305 to 615 of KOD (SEQ ID NO:12).

Kofu-III (SEQ ID NO:28) is made by replacing amino acid residues 396 to 564 of KOD (SEQ ID NO: 12) with amino acids 397 to 565 of Pfu (SEQ ID NO:10). Pod-III (SEQ ID NO:29) is made by replacing amino acids 397 to 565 of Pfu (SEQ ID NO:10) whith amino acids 396 to 564 of KOD (SEQ ID NO:12).

The amino acid sequence of chimeras Kofu-II, Pod-II, Kofu-III and Pod-III are reverse translated and codon-optimized for expression in *E. coli*. Additional nucleotide sequences containing Eco31I restriction sites are added to the 5' and 3' ends of the construct to facilitate cloning into an expression vector. More specifically, the 5' and 3' sequences can be designed so that the overhangs, after digestion of the DNA with Eco31I, are complementary to the overhangs in a particular expression vector (e.g., pKB). Codon optimization and gene synthesis is performed by GeneArt Gmbh. Expression and purification of chimeric polymerases are done using methods known in the art, for example, as reviewed in "Detailed description of the invention". The thermostability, fidelity, processivity, salt resistance and TMAC resistance of the chimeric polymerses are determined as described in Examples 5 through 9.

Example 11

Chimeras of *T. litoralis* and 9 Degrees N-7 Polymerases

Chimeras 9Nli and Li9N are designed based on the alignment in FIGS. 1*a-c*. They are made by swapping the palm and finger domains between the DNA polymerases of *T. litoralis* and *Thermococcus* sp. 9 degrees N-7. The overall sequence identity between these two polymerases are 77% on the amino acid level.

Chimera 9Nli can be made by replacing the palm and finger region of the 9N polymerase with the palm and finger region of the *T. litoralis* polymerase. In this particular example, 9Nli is made by replacing amino acids 347 to 580 of 9N polymerase (SEQ ID NO:18) with amino acids 349 to 583 of *T. litoralis* polymerase (SEQ ID NO:19). The sequence of the coding region of 9Nli is provided as SEQ ID NO:20.

Chimera LiN9 can be made by replacing the palm and finger domain of the DNA polymerase of *T. litoralis* with the finger domain of the DNA polymerase of 9 degrees North. In this particular example, LiN9 is made by replacing amino acids 349 to 583 of *T. litoralis* polymerase (SEQ ID NO:19) with amino acids 347 to 580 of 9 degrees N-7 polymerase (SEQ ID NO:18). The sequence of the coding region of LiN9 is provided as SEQ ID NO:21.

Example 12

Chimeras of *T. gorgonarius* and *T. zilligii* Type B DNA Polymerases

Chimerase GoZi and ZiGo are designed based on the alignment in FIGS. 1*a-c*. They are made by swapping the palm and finger domains between the DNA polymerases of *T. gorgonarius* and *T. zilligii*. The overall sequence identity between these two polymerases are 94% on the amino acid level.

Chimera GoZi can be made by replacing the palm and finger region of the *T. gorgonarius* polymerase with the palm and finger region of the *T. zilligii* polymerase. In this particular example, GoZi is made by replacing amino acids 391 to 559 of *T. gorgonarius* polymerase (SEQ ID NO:22) with amino acids 391 to 559 of *T. zilligii* polymerase (SEQ ID NO:23). The sequence of the resulting chimera GoZi is provided as SEQ ID NO:24.

Chimera ZiGo can be made by replacing the palm and finger domain of the DNA polymerase of *T. zilligii* with the finger domain of the DNA polymerase of *T. gorgonarius*. In this particular example, ZiGo is made by replacing amino acids 391 to 559 of *T. zilligii* polymerase (SEQ ID NO:23) with amino acids 391 to 559 of *T. gorgonarius* polymerase (SEQ ID NO:22). The sequence of the coding region of ZiGo is provided as SEQ ID NO:25.

TABLE 5

| Sequences |
|---|
| Native DNA sequences of Pfu and KOD<br>Sequence 1<br>>Native Pfu nucleotide sequence from genomic sequence<br>(Acc. No. AE010147) |

```
                                                 (SEQ ID NO: 1)
  1 ATGATTTTAG ATGTGGATTA CATAACTGAA GAAGGAAAAC CTGTTATTAG GCTATTCAAA

 61 AAAGAGAACG GAAAATTTAA GATAGAGCAT GATAGAACTT TTAGACCATA CATTTACGCT

121 CTTCTCAGGG ATGATTCAAA GATTGAAGAA GTTAAGAAAA TAACGGGGGA AAGGCATGGA

181 AAGATTGTGA GAATTGTTGA TGTAGAGAAG GTTGAGAAAA AGTTTCTCGG CAAGCCTATT

241 ACCGGCGAGA AACTTTATTT GGAACATCCC CAAGATGTTC CCACTATTAG AGAAAAAGTT

301 AGAGAACATC CAGCAGTTGT GGACATCTTC GAATACGATA TTCCATTTGC AAAGAGATAC

361 CTCATCGACA AAGGCCTAAT ACCTTGAGAG GGGGAAGAAG AGCTAAAGAT TCTTGCCTTC

421 GATATAGAAA CCCTCTATCA CGAAGGAGAA GAGTTTGGAA AAGGCCCAAT TATAATGATT

481 AGTTATGCAG ATGAAAATGA AGCAAAGGTG ATTACTTGGA AAAACATAGA TCTTCCATAC

541 GTTGAGGTTG TATCAAGCGA GAGAGAGATG ATAAAGAGAT TTCTCAGGAT TATCAGGGAG

601 AAGGATCCTG ACATTATAGT TACTTATAAT GGAGACTCAT TCGACTTCCC ATATTTAGCG

661 AAAAGGGCAG AAAAACTTGG GATTAAATTA ACCATTGGAA GAGATGGAAG CGAGCCCAAG

721 ATGCAGAGAA TAGGCGATAT GACGGCTGTA GAAGTCAAGG GAAGAATACA TTTCGACTTG

781 TATCATGTAA TAACAAGGAC AATAAATCTC CCAACATACA CACTAGAGGC TGTATATGAA

841 GCAATTTTTG GAAAGCCAAA GGAGAAGGTA TACGCCGACG AGATAGCAAA AGCCTGGGAA
```

TABLE 5-continued

| Sequences |
|---|
| 901 AGTGGAGAGA ACCTTGAGAG AGTTGCCAAA TACTCGATGG AAGATGCAAA GGCAACTTAT |
| 961 GAACTCGGGA AAGAATTCCT TCCAATGGAA ATTCAGCTTT CAAGATTAGT TGGACAACCT |
| 1021 TTATGGGATG TTTCAAGGTC AAGCACAGGG AACCTTGTAG AGTGGTTCTT ACTTAGGAAA |
| 1081 GCCTACGAAA GAAACGAAGT AGCTCCAAAC AAGCCAAGTG AAGAGGAGTA TCAAAGAAGG |
| 1141 CTCAGGGAGA GCTACACAGG TGGATTCGTT AAAGAGCCAG AAAAGGGGTT GTGGGAAAAC |
| 1201 ATAGTATACC TAGATTTTAG AGCCCTATAT CCCTCGATTA TAATTACCCA CAATGTTTCT |
| 1261 CCCGATACTC TAAATCTTGA GGGATGCAAG AACTATGATA TCGCTCCTCA AGTAGGCCAC |
| 1321 AAGTTCTGCA AGGACATCCC TGGTTTTATA CCAAGTCTCT TGGGACATTT GTTAGAGGAA |
| 1381 AGACAAAAGA TTAAGACAAA AATGAAGGAA ACTCAAGATC CTATAGAAAA AATACTCCTT |
| 1441 GACTATAGAC AAAAAGCGAT AAAACTCTTA GCAAATTCTT TCTACGGATA TTATGGCTAT |
| 1501 GCAAAAGCAA GATGGTACTG TAAGGAGTGT GCTGAGAGCG TTACTGCCTG GGGAAGAAAG |
| 1561 TACATCGAGT TAGTATGGAA GGAGCTCGAA GAAAAGTTTG GATTTAAAGT CCTCTACATT |
| 1621 GACACTGATG GTCTCTATGC AACTATCCCA GGAGGAGAAA GTGAGGAAAT AAAGAAAAAG |
| 1681 GCTCTAGAAT TTGTAAAATA CATAAATTCA AAGCTCCCTG GACTGCTAGA GCTTGAATAT |
| 1741 GAAGGGTTTT ATAAGAGGGG ATTCTTCGTT ACGAAGAAGA GGTATGCAGT AATAGATGAA |
| 1801 GAAGGAAAAG TCATTACTCG TGGTTTAGAG ATAGTTAGGA GAGATTGGAG TGAAATTGCA |
| 1861 AAAGAAACTC AAGCTAGAGT TTTGGAGACA ATACTAAAAC ACGGAGATGT TGAAGAAGCT |
| 1921 GTGAGAATAG TAAAAGAAGT AATACAAAAG CTTGCCAATT ATGAAATTCC ACCAGAGAAG |
| 1981 CTCGCAATAT ATGAGCAGAT AACAAGACCA TTACATGAGT ATAAGGCGAT AGGTCCTCAC |
| 2041 GTAGCTGTTG CAAAGAAACT AGCTGCTAAA GGAGTTAAAA TAAAGCCAGG AATGGTAATT |
| 2101 GGATACATAG TACTTAGAGG CGATGGTCCA ATTAGCAATA GGGCAATTCT AGCCTGGGAA |
| 2161 TACGATCCCA AAAAGCACAA GTATGACGCA GAATATTACA TTGAGAACCA GGTTCTTCCA |
| 2221 GCGGTACTTA GGATATTGGA GGGATTTGGA TACAGAAAGG AAGACCTCAG ATACCAAAAG |
| 2281 ACAAGACAAG TCGGCCTAAC TTCCTGGCTT AACATTAAAA AATCCTAG |
| Sequence 2<br>>Native KOD nucleotide sequence (from genomic sequence,<br>Acc. no. AP006878)<br>(SEQ ID NO: 2) |
| 1 ATGATCCTCG ACACTGACTA CATAACCGAG GATGGAAAGC CTGTCATAAG AATTTTCAAG |
| 61 AAGGAAAACG GCGAGTTTAA GATTGAGTAC GACCGGACTT TTGAACCCTA CTTCTACGCC |
| 121 CTCCTGAAGG ACGATTCTGC CATTGAGGAA GTCAAGAAGA TAACCGCCGA GAGGCACGGG |
| 181 ACGGTTGTAA CGGTTAAGCG GGTTGAAAAG GTTCAGAAGA AGTTCCTCGG GAGACCAGTT |
| 241 GAGGTCTGGA AACTCTACTT TACTCGATGG CAGGACGTCC CAGCGATAAG GGACAAGATA |
| 301 CGAGAGCATC CAGCAGTTAT TGACATCTAC GAGTACGACA TACCCTTCGC CAAGCGCTAC |
| 361 CTCATAGACA AGGGATTAGT GCCAATGGAA GGCGACGAGG AGCTGAAAAT GCTCGCCTTC |
| 421 GACATTGAAA CTCTCTACCA TGAGGGCGAG GAGTTCGCCG AGGGGCCAAT CCTTATGATA |
| 481 AGCTACGCCG ACGAGGAAGG GGCCAGGGTG ATAACTTGGA AGAACGTGGA TCTCCCCTAC |
| 541 GTTGACGTCG TCTCGACGGA GAGGGAGATG ATAAAGCGCT TCCTCCGTGT TGTGAAGGAG |
| 601 AAAGACCCGG ACGTTCTCAT AACCTACAAC GGCGACAACT TCGACTTCGC CTATCTGAAA |
| 661 AAGCGCTGTG AAAAGCTCGG AATAAACTTC GCCCTCGGAA GGGATGGAAG CGAGCCGAAG |
| 721 ATTCAGAGGA TGGGCGACAG GTTTGCCGTC GAAGTGAAGG GACGGATACA CTTCGATCTC |

TABLE 5-continued

| Sequences |
|---|
| 781 TATCCTGTGA TAAGACGGAC GATAAACCTG CCCACATACA CGCTTGAGGC CGTTTATGAA |
| 841 GCCGTCTTCG GTCAGCCGAA GGAGAAGGTT TACTCGATGG AAATAACCAC AGCCTGGGAA |
| 901 ACCGGCGAGA ACCTTGAGAG AGTCGCCCGC TACTCGATGG AAGATGCGAA GGTCACATAC |
| 961 GAGCTTGGGA AGGAGTTCCT TCCGATGGAG GCCCAGCTTT CTCGCTTAAT CGGCCAGTCC |
| 1021 CTCTGGGACG TCTCCCGCTC CAGCACTGGC AACCTCGTTG AGTGGTTCCT CCTCAGGAAG |
| 1081 GCCTATGAGA GGAATGAGCT GGCCCCGAAC AAGCCCGATG AAAAGGAGCT GGCCAGAAGA |
| 1141 CGGCAGAGCT ATGAAGGAGG CTATGTAAAA GAGCCCGAGA GAGGGTTGTG GGAGAACATA |
| 1201 GTGTACCTAG ATTTTAGATC CCTGTACCCC TCAATCATCA TCACCCACAA CGTCTCGCCG |
| 1261 GATACGCTCA ACAGAGAAGG ATGCAAGGAA TATGACGTTG CCCCACAGGT CGGCCACCGC |
| 1321 TTCTGCAAGG ACTTCCCAGG ATTTATCCCG AGCCTGCTTG GAGACCTCCT AGAGGAGAGG |
| 1381 CAGAAGATAA AGAAGAAGAT GAAGGCCACG ATTGACCCGA TCGAGAGGAA GCTCCTCGAT |
| 1441 TACAGGCAGA GGGCCATCAA GATCCTGGCA AACAGCTACT ACGGTTACTA CGGCTATGCA |
| 1501 AGGGCGCGCT GGTACTGCAA GGAGTGTGCA GAGAGCGTAA CGGCCTGGGG AAGGGAGTAC |
| 1561 ATAACGATGA CCATCAAGGA GATAGAGGAA AAGTACGGCT TTAAGGTAAT CTACAGCGAC |
| 1621 ACCGACGGAT TTTTTGCCAC AATACCTGGA GCCGATGCTG AAACCGTCAA AAAGAAGGCT |
| 1681 ATGGAGTTCC TCAAGTATAT CAACGCCAAA CTTCCGGGCG CGCTTGAGCT CGAGTACGAG |
| 1741 GGCTTCTACA AACGCGGCTT CTTCGTCACG AAGAAGAAGT ATGCGGTGAT AGACGAGGAA |
| 1801 GGCAAGATAA CAACGCGCGG ACTTGAGATT GTGAGGCGTG ACTGGAGCGA GATAGCGAAA |
| 1861 GAGACGCAGG CGAGGGTTCT TGAAGCTTTG CTAAAGGACG GTGACGTCGA GAAGGCCGTG |
| 1921 AGGATAGTCA AAGAAGTTAC CGAAAAGCTG AGCAAGTACG AGGTTCCGCC GGAGAAGCTG |
| 1981 GTGATCCACG AGCAGATAAC GAGGGATTTA AAGGACTACA AGGCAACCGG TCCCCACGTT |
| 2041 GCCGTTGCCA AGAGGTTGGC CGCGAGAGGA GTCAAAATAC GCCCTGGAAC GGTGATAAGC |
| 2101 TACATCGTGC TCAAGGGCTC TGGGAGGATA GGCGACAGGG CGATACCGTT CGACGAGTTC |
| 2161 GACCCGACGA AGCACAAGTA CGACGCCGAG TACTACATTG AGAACCAGGT TCTCCCAGCC |
| 2221 GTTGAGAGAA TTCTGAGAGC CTTCGGTTAC CGCAAGGAAG ACCTGCGCTA CCAGAAGACG |
| 2281 AGACAGGTTG GTTTGAGTGC TTGGCTGAAG CCGAAGGGAA CTTGA |
| Codon optimized sequences of Pfu and KOD<br>Sequence 3<br>>Pfu codon optimized nucleotide sequence<br>(SEQ ID NO: 3) |
| 1 ATGATTCTGG ATGTGGACTA TATCACCGAA GAGGGCAAAC CGGTTATACG TTTATTTAAG |
| 61 AAAGAGAATG GTAAATTCAA GATCGAGCAT GACCGCACGT TCCGTCCATA CATTTACGCG |
| 121 TTGCTTCGGG ATGATAGCAA AATTGAGGAA GTCAAAAAGA TCACCGGGGA ACGTCATGGA |
| 181 AAAATAGTAA GAATTGTGGA CGTTGAAAAA GTCGAAAAGA AATTTCTGGG CAAACCGATC |
| 241 ACTGTATGGA AGCTCTATCT GGAACATCCT CAGGATGTGC CCACAATTCG AGAAAAAGTT |
| 301 CGTGAGCACC CAGCCGTCGT GGATATATTT GAATATGACA TCCCTTTTGC AAAACGCTAC |
| 361 TTAATTGATA AAGGCCTGAT CCCGATGGAG GGGGAAGAAG AACTTAAAAT TCTGGCTTTT |
| 421 GACATAGAAA CGCTCTATCA TGAGGGAGAA GAATTTGGCA AAGGTCCCAT CATTATGATT |
| 481 TCTTACGCGG ATGAGAACGA AGCCAAGGTA ATCACTTGGA AAAATATTGA CCTGCCGTAC |
| 541 GTTGAAGTGG TCAGTTCAGA GCGGGAAATG ATTAAACGTT TTTTACGCAT CATTAGAGAG |
| 601 AAAGATCCAG ATATAATCGT TACATATAAC GGCGACTCCT TCGATTTTCC TTACCTGGCA |

TABLE 5-continued

| Sequences |
|---|
| 661 AAACGAGCTG AAAAATTGGG TATTAAACTT ACCATCGGGC GTGACGGATC GGAACCGAAA |
| 721 ATGCAACGCA TTGGCGATAT GACGGCGGTA GAGGTGAAAG GTCGGATACA CTTTGATCTG |
| 781 TATCATGTCA TCACCCGTAC TATTAATCTC CCCACATACA CGTTAGAAGC CGTTTATGAG |
| 841 GCAATATTCG GCAAGCCGAA AGAAAAAGTG TACGCTGACG AAATCGCGAA GGCATGGGAG |
| 901 AGCGGCGAAA ACCTGGAGCG CGTAGCAAAA TATTCTATGG AAGATGCTAA AGCGACCTAC |
| 961 GAATTGGGGA AAGAATTTCT TCCAATGGAA ATTCAGCTGA GTCGTTTAGT CGGACAACCT |
| 1021 CTGTGGGACG TTTCACGCTC CTCGACTGGC AATCTCGTGG AGTGGTTCCT GTTGAGAAAA |
| 1081 GCCTATGAAC GAAACGAAGT AGCACCGAAT AAACCAAGCG AGGAAGAATA TCAGCGTCGC |
| 1141 CTTCGCGAGT CTTACACAGG TGGGTTTGTT AAGGAACCGG AGAAAGGTCT TTGGGAAAAC |
| 1201 ATCGTGTATT TAGATTTCCG TGCGCTGTAC CCCAGTATTA TAATCACCCA CAATGTCTCA |
| 1261 CCTGACACGC TCAACTTGGA AGGTTGCAAA AATTATGATA TTGCTCCGCA AGTTGGACAT |
| 1321 AAGTTTTGTA AAGATATTCC GGGCTTCATC CCGTCCCTGC TTGGTCACTT ACTGGAAGAG |
| 1381 CGCCAAAAAA TTAAGACCAA AATGAAAGAG ACTCAGGATC CCATTGAAAA GATCCTGCTC |
| 1441 GATTACCGGC AAAAAGCCAT TAAATTGCTT GCAAACTCGT TTTATGGGTA CTATGGCTAT |
| 1501 GCGAAGGCTC GTTGGTACTG CAAAGAATGT GCCGAGAGCG TGACAGCATG GGGTCGCAAA |
| 1561 TATATAGAAT TAGTATGGAA GGAGCTGGAA GAAAAATTCG GATTCAAAGT CCTGTACATC |
| 1621 GATACGGATG GCCTCTATGC GACCATTCCT GGTGGGGAGT CTGAAGAAAT CAAGAAAAAA |
| 1681 GCCTTGGAAT TCGTTAAGTA CATTAATAGT AAATTACCGG GACTGCTTGA ACTGGAGTAT |
| 1741 GAAGGCTTCT ACAAAAGAGG TTTTTTCGTT ACTAAGAAAC GATATGCCGT AATAGATGAA |
| 1801 GAGGGGAAAG TCATCACACG TGGCCTCGAG ATTGTTCGCC GGGACTGGTC AGAGATAGCA |
| 1861 AAGGAAACGC AGGCGCGCGT GCTCGAAACC ATCTTGAAAC ATGGTGATGT AGAGGAAGCC |
| 1921 GTCCGCATTG TTAAAGAGGT GATCCAGAAG TTAGCAAACT ATGAAATTCC ACCGGAAAAA |
| 1981 CTGGCGATAT ACGAGCAAAT CACTCGTCCC CTTCACGAAT ATAAAGCTAT TGGACCTCAT |
| 2041 GTAGCCGTCG CGAAGAAACT GGCTGCAAAA GGCGTTAAGA TAAAACCAGG TATGGTGATC |
| 2101 GGGTACATTG TACTCCGCGG CGACGGTCCG ATTTCCAATA GAGCCATCTT GGCGGAGGAA |
| 2161 TATGATCCTA AAAAGCATAA ATACGACGCT GAATATTACA TTGAGAACCA GGTCTTGCCG |
| 2221 GCAGTTCTGC GGATACTTGA AGGATTTGGC TATCGTAAAG AAGATCTGCG CTATCAAAAG |
| 2281 ACGCGACAGG TGGGTCTGAC TAGCTGGTTG AATATCAAAA AATCGTAA |
| Sequence 4<br>>Pfu codon optimized nucleotide sequence,extra 9 nt in 5' area.<br>(SEQ ID NO: 4) |
| 1 ATGGCTAGCG CCATTCTGGA TGTGGACTAT ATCACCGAAG AGGGCAAACC GGTTATACGT |
| 61 TTATTTAAGA AAGAGAATGG TAAATTCAAG ATCGAGCATG ACCGCACGTT CCGTCCATAC |
| 121 ATTTACGCGT TGCTTCGGGA TGATAGCAAA ATTGAGGAAG TCAAAAAGAT CACCGGGGAA |
| 181 CGTCATGGAA AAATAGTAAG AATTGTGGAC GTTGAAAAAG TCGAAAAGAA ATTTCTGGGC |
| 241 AAACCGATCA CTGTATGGAA GCTCTATCTG GAACATCCTC AGGATGTGCC CACAATTCGA |
| 301 GAAAAAGTTC GTGAGCACCC AGCCGTCGTG GATATATTTG AATATGACAT CCCTTTTGCA |
| 361 AAACGCTACT TAATTGATAA AGGCCTGATC CCGATGGAGG GGGAAGAAGA ACTTAAAATT |
| 421 CTGGCTTTTG ACATAGAAAC GCTCTATCAT GAGGGAGAAG AATTTGGCAA AGGTCCCATC |
| 481 ATTATGATTT CTTACGCGGA TGAGAACGAA GCCAAGGTAA TCACTTGGAA AAATATTGAC |
| 541 CTGCCGTACG TTGAAGTGGT CAGTTCAGAG CGGGAAATGA TTAAACGTTT TTTACGCATC |

TABLE 5-continued

| Sequences |
|---|
| 601 ATTAGAGAGA AAGATCCAGA TATAATCGTT ACATATAACG GCGACTCCTT CGATTTTCCT |
| 661 TACCTGGCAA AACGAGCTGA AAAATTGGGT ATTAAACTTA CCATCGGGCG TGACGGATCG |
| 721 GAACCGAAAA TGCAACGCAT TGGCGATATG ACGGCGGTAG AGGTGAAAGG TCGGATACAC |
| 781 TTTGATCTGT ATCATGTCAT CACCCGTACT ATTAATCTCC CCACATACAC GTTAGAAGCC |
| 841 GTTTATGAGG CAATATTCGG CAAGCCGAAA GAAAAAGTGT ACGCTGACGA AATCGCGAAG |
| 901 GCATGGGAGA GCGGCGAAAA CCTGGAGCGC GTAGCAAAAT ATTCTATGGA AGATGCTAAA |
| 961 GCGACCTACG AATTGGGGAA AGAATTTCTT CCAATGGAAA TTCAGCTGAG TCGTTTAGTC |
| 1021 GGACAACCTC TGTGGGACGT TTCACGCTCC TCGACTGGCA ATCTCGTGGA GTGGTTCCTG |
| 1081 TTGAGAAAAG CCTATGAACG AAACGAAGTA GCACCGAATA AACCAAGCGA GGAAGAATAT |
| 1141 CAGCGTCGCC TTCGCGAGTC TTACACAGGT GGGTTTGTTA AGGAACCGGA GAAAGGTCTT |
| 1201 TGGGAAAACA TCGTGTATTT AGATTTCCGT GCGCTGTACC CCAGTATTAT AATCACCCAC |
| 1261 AATGTCTCAC CTGACACGCT CAACTTGGAA GGTTGCAAAA ATTATGATAT TGCTCCGCAA |
| 1321 GTTGGACATA AGTTTTGTAA AGATATTCCG GGCTTCATCC CGTCCCTGCT TGGTCACTTA |
| 1381 CTGGAAGAGC GCCAAAAAAT TAAGACCAAA ATGAAAGAGA CTCAGGATCC CATTGAAAAG |
| 1441 ATCCTGCTCG ATTACCGGCA AAAAGCCATT AAATTGCTTG CAAACTCGTT TTATGGGTAC |
| 1501 TATGGCTATG CGAAGGCTCG TTGGTACTGC AAAGAATGTG CCGAGAGCGT GACAGCATGG |
| 1561 GGTCGCAAAT ATATAGAATT AGTATGGAAG GAGCTGGAAG AAAAATTCGG ATTCAAAGTC |
| 1621 CTGTACATCG ATACGGATGG CCTCTATGCG ACCATTCCTG GTGGGGAGTC TGAAGAAATC |
| 1681 AAGAAAAAAG CCTTGGAATT CGTTAAGTAC ATTAATAGTA AATTACCGGG ACTGCTTGAA |
| 1741 CTGGAGTATG AAGGCTTCTA CAAAAGAGGT TTTTTCGTTA CTAAGAAACG ATATGCCGTA |
| 1801 ATAGATGAAG AGGGGAAAGT CATCACACGT GGCCTCGAGA TTGTTCGCCG GGACTGGTCA |
| 1861 GAGATAGCAA AGGAAACGCA GGCGCGCGTG CTCGAAACCA TCTTGAAACA TGGTGATGTA |
| 1921 GAGGAAGCCG TCCGCATTGT TAAAGAGGTG ATCCAGAAGT TAGCAAACTA TGAAATTCCA |
| 1981 CCGGAAAAAC TGGCGATATA CGAGCAAATC ACTCGTCCCC TTCACGAATA TAAAGCTATT |
| 2041 GGACCTCATG TAGCCGTCGC GAAGAAACTG GCTGCAAAAG GCGTTAAGAT AAAACCAGGT |
| 2101 ATGGTGATCG GGTACATTGT ACTCCGCGGC GACGGTCCGA TTTCCAATAG AGCCATCTTG |
| 2161 GCGGAGGAAT ATGATCCTAA AAAGCATAAA TACGACGCTG AATATTACAT TGAGAACCAG |
| 2221 GTCTTGCCGG CAGTTCTGCG GATACTTGAA GGATTTGGCT ATCGTAAAGA AGATCTGCGC |
| 2281 TATCAAAAGA CGCGACAGGT GGGTCTGACT AGCTGGTTGA ATATCAAAAA ATCGTAA |
| Sequence 5<br>>KOD codon optimized nucleotide sequence<br>(SEQ ID NO: 5) |
| 1 ATGATTCTGG ATACCGACTA TATCACGGAA GATGGCAAAC CGGTGATACG TATTTTTAAG |
| 61 AAAGAGAATG GTGAGTTCAA AATCGAGTAC GACCGCACTT TTGAGCCATA TTTCTACGCG |
| 121 TTACTGAAGG ACGATAGCGC CATTGAAGAA GTTAAAAAAA TCACCGCAGA GCGGCATGGG |
| 181 ACAGTGGTAA CCGTGAAGAG AGTTGAAAAA GTCCAGAAAA AATTTTTGGG ACGACCTGTA |
| 241 GAAGTGTGGA AACTTTATTT CACTCACCCC CAAGATGTTC CGGCTATACG TGATAAAATT |
| 301 CGCGAACATC CAGCGGTCAT TGATATTTAC GAATATGATA TACCTTTTGC CAAGCGTTAC |
| 361 CTCATCGACA AAGGCCTGGT GCCGATGGAA GGTGATGAAG AATTAAAAAT GTTGGCATTC |
| 421 GACATTGAAA CACTTTATCA CGAGGGGGAA GAGTTTGCTG AGGGTCCCAT CCTGATGATT |

TABLE 5-continued

| Sequences |
|---|
| 481 TCTTATGCGG ATGAAGAGGG TGCCCGCGTA ATAACCTGGA AGAACGTTGA TCTCCCGTAC |
| 541 GTGGACGTCG TTAGTACGGA ACGGGAAATG ATCAAACGTT TCCTGCGCGT AGTGAAAGAG |
| 601 AAAGATCCAG ACGTCTTAAT TACCTATAAT GGTGATAACT TTGATTTTGC ATACCTGAAA |
| 661 AAAAGATGCG AAAAGTTGGG CATAAATTTC GCTCTTGGTC GAGACGGGTC AGAGCCTAAA |
| 721 ATCCAGCGTA TGGGAGATCG CTTTGCGGTT GAAGTGAAAG GCCGGATTCA TTTCGACCTG |
| 781 TATCCGGTAA TTCGTCGCAC TATCAACCTC CCCACATACA CGTTAGAAGC CGTCTATGAG |
| 841 GCAGTTTTTG GTCAACCGAA GGAAAAAGTT TACGCTGAGG AAATTACCAC TGCGTGGGAA |
| 901 ACAGGCGAGA ATCTGGAACG TGTAGCCCGC TATTCTATGG AGGATGCAAA AGTTACCTAT |
| 961 GAATTGGGTA AGGAATTTCT TCCAATGGAG GCGCAGCTGT CGAGATTAAT AGGGCAGAGC |
| 1021 CTGTGGGACG TGTCTCGAAG TTCAACGGGA AACCTCGTCG AATGGTTTCT GTTGCGGAAA |
| 1081 GCATACGAGC GTAATGAACT TGCCCCTAAC AAACCGGATG AAAAGGAGCT GGCACGCCGT |
| 1141 CGCCAATCCT ATGAAGGCGG TTACGTTAAA GAACCAGAGC GGGGGTTATG GGAAAATATC |
| 1201 GTGTATCTGG ATTTCCGTTC GCTCTACCCG AGCATTATCA TTACCCACAA CGTATCTCCC |
| 1261 GACACTTTGA ATCGCGAGGG CTGTAAAGAA TATGATGTCG CGCCGCAGGT TGGTCATAGA |
| 1321 TTTTGCAAGG ACTTCCCGGG ATTTATACCA AGTCTGCTTG GCGATTTACT GGAAGAGCGA |
| 1381 CAAAAAATCA AAAAGAAAAT GAAAGCTACA ATCGATCCGA TAGAACGTAA GCTGCTCGAC |
| 1441 TACCGCCAGC GGGCCATCAA AATTTTGGCA AACTCATATT ATGGTTACTA TGGGTACGCG |
| 1501 CGTGCTCGCT GGTATTGTAA AGAGTGCGCC GAATCCGTGA CGGCATGGGG CCGTGAATAC |
| 1561 ATCACCATGA CTATTAAGGA GATAGAAGAG AAATATGGTT TCAAAGTAAT CTACTCGGAT |
| 1621 ACAGACGGAT TCTTTGCGAC GATTCCCGGT GCCGATGCAG AAACCGTCAA GAAAAAAGCG |
| 1681 ATGGAATTCC TTAAGTATAT AAATGCTAAA TTACCTGGTG CCCTGGAGCT GGAATACGAA |
| 1741 GGGTTTTACA AACGCGGATT CTTTGTTACT AAGAAAAAAT ATGCGGTGAT CGACGAGGAA |
| 1801 GGCAAGATTA CGACCAGAGG CCTCGAGATT GTACGGCGTG ATTGGAGCGA AATCGCTAAA |
| 1861 GAAACACAGG CACGTGTCTT GGAGGCATTA CTGAAAGATG GGGACGTTGA AAAGGCGGTG |
| 1921 CGAATTGTAA AAGAAGTCAC CGAAAAACTT TCTAAGTACG AAGTTCCGCC AGAGAAACTG |
| 1981 GTGATACACG AACAAATCAC TCGTGATCTG AAAGACTATA AGGCTACAGG CCCGCATGTA |
| 2041 GCAGTCGCCA AACGCCTCGC GGCTCGGGGT GTTAAAATTC GTCCCGGAAC GGTGATCAGT |
| 2101 TACATTGTAT TGAAGGGCTC AGGTCGCATA GGGGATAGAG CAATCCCTTT CGACGAGTTT |
| 2161 GATCCAACCA AACACAAATA TGATGCCGAA TACTATATTG AAAACCAGGT CTTGCCGGCG |
| 2221 GTTGAGCGTA TACTGCGCGC TTTCGGCTAT CGAAAGGAAG ATCTTCGTTA CCAAAAAACT |
| 2281 AGACAGGTGG GTCTGTCCGC ATGGCTCAAA CCTAAGGGAA CGTAA |
| Sequence 6<br>>KOD codon optimized nucleotide sequence, extra 9 nt in 5' area.<br>(SEQ ID NO: 6) |
| 1 ATGGCTAGCG CCATTCTGGA TACCGACTAT ATCACGGAAG ATGGCAAACC GGTGATACGT |
| 61 ATTTTTAAGA AAGAGAATGG TGAGTTCAAA ATCGAGTACG ACCGCACTTT TGAGCCATAT |
| 121 TTCTACGCGT TACTGAAGGA CGATAGCGCC ATTGAAGAAG TTAAAAAAAT CACCGCAGAG |
| 181 CGGCATGGGA CAGTGGTAAC CGTGAAGAGA GTTGAAAAAG TCCAGAAAAA ATTTTTGGGA |
| 241 CGACCTGTAG AAGTGTGGAA ACTTTATTTC ACTCACCCCC AAGATGTTCC GGCTATACGT |
| 301 GATAAAATTC GCGAACATCC AGCGGTCATT GATATTTACG AATATGATAT ACCTTTTGCC |
| 361 AAGCGTTACC TCATCGACAA AGGCCTGGTG CCGATGGAAG GTGATGAAGA ATTAAAAATG |

TABLE 5-continued

| Sequences |
|---|
| 421 TTGGCATTCG ACATTGAAAC ACTTTATCAC GAGGGGGAAG AGTTTGCTGA GGGTCCCATC |
| 481 CTGATGATTT CTTATGCGGA TGAAGAGGGT GCCCGCGTAA TAACCTGGAA GAACGTTGAT |
| 541 CTCCCGTACG TGGACGTCGT TAGTACGGAA CGGGAAATGA TCAAACGTTT CCTGCGCGTA |
| 601 GTGAAAGAGA AAGATCCAGA CGTCTTAATT ACCTATAATG GTGATAACTT TGATTTTGCA |
| 661 TACCTGAAAA AAAGATGCGA AAAGTTGGGC ATAAATTTCG CTCTTGGTCG AGACGGGTCA |
| 721 GAGCCTAAAA TCCAGCGTAT GGGAGATCGC TTTGCGGTTG AAGTGAAAGG CCGGATTCAT |
| 781 TTCGACCTGT ATCCGGTAAT TCGTCGCACT ATCAACCTCC CCACATACAC GTTAGAAGCC |
| 841 GTCTATGAGG CAGTTTTTGG TCAACCGAAG GAAAAAGTTT ACGCTGAGGA AATTACCACT |
| 901 GCGTGGGAAA CAGGCGAGAA TCTGGAACGT GTAGCCCGCT ATTCTATGGA GGATGCAAAA |
| 961 GTTACCTATG AATTGGGTAA GGAATTTCTT CCAATGGAGG CGCAGCTGTC GAGATTAATA |
| 1021 GGGCAGAGCC TGTGGGACGT GTCTCGAAGT TCAACGGGAA ACCTCGTCGA ATGGTTTCTG |
| 1081 TTGCGGAAAG CATACGAGCG TAATGAACTT GCCCCTAACA AACCGGATGA AAAGGAGCTG |
| 1141 GCACGCCGTC GCCAATCCTA TGAAGGCGGT TACGTTAAAG AACCAGAGCG GGGGTTATGG |
| 1201 GAAAATATCG TGTATCTGGA TTTCCGTTCG CTCTACCCGA GCATTATCAT TACCCACAAC |
| 1261 GTATCTCCCG ACACTTTGAA TCGCGAGGGC TGTAAAGAAT ATGATGTCGC GCCGCAGGTT |
| 1321 GGTCATAGAT TTTGCAAGGA CTTCCCGGGA TTTATACCAA GTCTGCTTGG CGATTTACTG |
| 1381 GAAGAGCGAC AAAAAATCAA AAAGAAAATG AAAGCTACAA TCGATCCGAT AGAACGTAAG |
| 1441 CTGCTCGACT ACCGCCAGCG GGCCATCAAA ATTTTGGCAA ACTCATATTA TGGTTACTAT |
| 1501 GGGTACGCGC GTGCTCGCTG GTATTGTAAA GAGTGCGCCG AATCCGTGAC GGCATGGGGC |
| 1561 CGTGAATACA TCACCATGAC TATTAAGGAG ATAGAAGAGA AATATGGTTT CAAAGTAATC |
| 1621 TACTCGGATA CAGACGGATT CTTTGCGACG ATTCCCGGTG CCGATGCAGA AACCGTCAAG |
| 1681 AAAAAAGCGA TGGAATTCCT TAAGTATATA AATGCTAAAT TACCTGGTGC CCTGGAGCTG |
| 1741 GAATACGAAG GGTTTTACAA ACGCGGATTC TTTGTTACTA AGAAAAAATA TGCGGTGATC |
| 1801 GACGAGGAAG GCAAGATTAC GACCAGAGGC CTCGAGATTG TACGGCGTGA TTGGAGCGAA |
| 1861 ATCGCTAAAG AAACACAGGC ACGTGTCTTG GAGGCATTAC TGAAAGATGG GGACGTTGAA |
| 1921 AAGGCGGTGC GAATTGTAAA AGAAGTCACC GAAAAACTTT CTAAGTACGA AGTTCCGCCA |
| 1981 GAGAAACTGG TGATACACGA ACAAATCACT CGTGATCTGA AAGACTATAA GGCTACAGGC |
| 2041 CCGCATGTAG CAGTCGCCAA ACGCCTCGCG GCTCGGGGTG TTAAAATTCG TCCCGGAACG |
| 2101 GTGATCAGTT ACATTGTATT GAAGGGCTCA GGTCGCATAG GGGATAGAGC AATCCCTTTC |
| 2161 GACGAGTTTG ATCCAACCAA ACACAAATAT GATGCCGAAT ACTATATTGA AAACCAGGTC |
| 2221 TTGCCGGCGG TTGAGCGTAT ACTGCGCGCT TTCGGCTATC GAAAGGAAGA TCTTCGTTAC |
| 2281 CAAAAAACTA GACAGGTGGG TCTGTCCGCA TGGCTCAAAC CTAAGGGAAC GTAA |
| Sequence 7<br>>pKB13 - Pfu codon optimized nucleotide sequence in pUC19 vector<br>(SEQ ID NO: 7) |
| 1 TCGCGCGTTT CGGTGATGAC GGTGAAAACC TCTGACACAT GCAGCTCCCG GAGACGGTCA |
| 61 CAGCTTGTCT GTAAGCGGAT GCCGGGAGCA GACAAGCCCG TCAGGGCGCG TCAGCGGGTG |
| 121 TTGGCGGGTG TCGGGGCTGG CTTAACTATG CGGCATCAGA GCAGATTGTA CTGAGAGTGC |
| 181 ACCATATGCG GTGTGAAATA CCGCACAGAT GCGTAAGGAG AAAATACCGC ATCAGGCGCC |
| 241 ATTCGCCATT CAGGCTGCGC AACTGTTGGG AAGGGCGATC GGTGCGGGCC TCTTCGCTAT |

TABLE 5-continued

| Sequences |
|---|
| 301 TACGCCAGCT GGCGAAAGGG GGATGTGCTG CAAGGCGATT AAGTTGGGTA ACGCCAGGGT |
| 361 TTTCCCAGTC ACGACGTTGT AAAACGACGG CCAGTGAATT CGGTCTCAGC GCCATTCTGG |
| 421 ATACCGACTA TATCACGGAA GATGGCAAAC CGGTGATACG TATTTTTAAG AAAGAGAATG |
| 481 GTGAGTTCAA AATCGAGTAC GACCGCACTT TTGAGCCATA TTTCTACGCG TTACTGAAGG |
| 541 ACGATAGCGC CATTGAAGAA GTTAAAAAAA TCACCGCAGA GCGGCATGGG ACAGTGGTAA |
| 601 CCGTGAAGAG AGTTGAAAAA GTCCAGAAAA AATTTTTGGG ACGACCTGTA GAAGTGTGGA |
| 661 AACTTTATTT CACTCACCCC CAAGATGTTC CGGCTATACG TGATAAAATT CGCGAACATC |
| 721 CAGCGGTCAT TGATATTTAC GAATATGATA TACCTTTTGC CAAGCGTTAC CTCATCGACA |
| 781 AAGGCCTGGT GCCGATGGAA GGTGATGAAG AATTAAAAAT GTTGGCATTC GACATTGAAA |
| 841 CACTTTATCA CGAGGGGGAA GAGTTTGCTG AGGGTCCCAT CCTGATGATT TCTTATGCGG |
| 901 ATGAAGAGGG TGCCCGCGTA ATAACCTGGA AGAACGTTGA TCTCCCGTAC GTGGACGTCG |
| 961 TTAGTACGGA ACGGGAAATG ATCAAACGTT TCCTGCGCGT AGTGAAAGAG AAAGATCCAG |
| 1021 ACGTCTTAAT TACCTATAAT GGTGATAACT TTGATTTTGC ATACCTGAAA AAAGATGCG |
| 1081 AAAAGTTGGG CATAAATTTC GCTCTTGGTC GAGACGGGTC AGAGCCTAAA ATCCAGCGTA |
| 1141 TGGGAGATCG CTTTGCGGTT GAAGTGAAAG GCCGGATTCA TTTCGACCTG TATCCGGTAA |
| 1201 TTCGTCGCAC TATCAACCTC CCCACATACA CGTTAGAAGC CGTCTATGAG GCAGTTTTTG |
| 1261 GTCAACCGAA GGAAAAAGTT TACGCTGAGG AAATTACCAC TGCGTGGGAA ACAGGCGAGA |
| 1321 ATCTGGAACG TGTAGCCCGC TATTCTATGG AGGATGCAAA AGTTACCTAT GAATTGGGTA |
| 1381 AGGAATTTCT TCCAATGGAG GCGCAGCTGT CGAGATTAAT AGGGCAGAGC CTGTGGGACG |
| 1441 TGTCTCGAAG TTCAACGGGA AACCTCGTCG AATGGTTTCT GTTGCGGAAA GCATACGAGC |
| 1501 GTAATGAACT TGCCCCTAAC AAACCGGATG AAAAGGAGCT GGCACGCCGT CGCCAATCCT |
| 1561 ATGAAGGCGG TTACGTTAAA GAACCAGAGC GGGGGTTATG GGAAAATATC GTGTATCTGG |
| 1621 ATTTCCGTTC GCTCTACCCG AGCATTATCA TTACCCACAA CGTATCTCCC GACACTTTGA |
| 1681 ATCGCGAGGG CTGTAAAGAA TATGATGTCG CGCCGCAGGT TGGTCATAGA TTTTGCAAGG |
| 1741 ACTTCCCGGG ATTTATACCA AGTCTGCTTG GCGATTTACT GGAAGAGCGA CAAAAAATCA |
| 1801 AAAAGAAAAT GAAAGCTACA ATCGATCCGA TAGAACGTAA GCTGCTCGAC TACCGCCAGC |
| 1861 GGGCCATCAA AATTTTGGCA AACTCATATT ATGGTTACTA TGGGTACGCG CGTGCTCGCT |
| 1921 GGTATTGTAA AGAGTGCGCC GAATCCGTGA CGGCATGGGG CCGTGAATAC ATCACCATGA |
| 1981 CTATTAAGGA GATAGAAGAG AAATATGGTT TCAAAGTAAT CTACTCGGAT ACAGACGGAT |
| 2041 TCTTTGCGAC GATTCCCGGT GCCGATGCAG AAACCGTCAA GAAAAAAGCG ATGGAATTCC |
| 2101 TTAAGTATAT AAATGCTAAA TTACCTGGTG CCCTGGAGCT GGAATACGAA GGGTTTTACA |
| 2161 AACGCGGATT CTTTGTTACT AAGAAAAAAT ATGCGGTGAT CGACGAGGAA GGCAAGATTA |
| 2221 CGACCAGAGG CCTCGAGATT GTACGGCGTG ATTGGAGCGA AATCGCTAAA GAAACACAGG |
| 2281 CACGTGTCTT GGAGGCATTA CTGAAAGATG GGGACGTTGA AAAGGCGGTG CGAATTGTAA |
| 2341 AAGAAGTCAC CGAAAAACTT TCTAAGTACG AAGTTCCGCC AGAGAAACTG GTGATACACG |
| 2401 AACAAATCAC TCGTGATCTG AAAGACTATA AGGCTACAGG CCCGCATGTA GCAGTCGCCA |
| 2461 AACGCCTCGC GGCTCGGGGT GTTAAAATTC GTCCCGGAAC GGTGATCAGT TACATTGTAT |
| 2521 TGAAGGGCTC AGGTCGCATA GGGGATAGAG CAATCCCTTT CGACGAGTTT GATCCAACCA |

TABLE 5-continued

| Sequences |
|---|
| 2581 AACACAAATA TGATGCCGAA TACTATATTG AAAACCAGGT CTTGCCGGCG GTTGAGCGTA |
| 2641 TACTGCGCGC TTTCGGCTAT CGAAAGGAAG ATCTTCGTTA CCAAAAAACT AGACAGGTGG |
| 2701 GTCTGTCCGC ATGGCTCAAA CCTAAGGGAA CGTAATGATA TGAGACCGGA TCCTCTAGAG |
| 2761 TCGACCTGCA GGCATGCAAG CTTGGCGTAA TCATGGTCAT AGCTGTTTCC TGTGTGAAAT |
| 2821 TGTTATCCGC TCACAATTCC ACACAACATA CGAGCCGGAA GCATAAAGTG TAAAGCCTGG |
| 2881 GGTGCCTAAT GAGTGAGCTA ACTCACATTA ATTGCGTTGC GCTCACTGCC CGCTTTCCAG |
| 2941 TCGGGAAACC TGTCGTGCCA GCTGCATTAA TGAATCGGCC AACGCGCGGG GAGAGGCGGT |
| 3001 TTGCGTATTG GGCGCTCTTC CGCTTCCTCG CTCACTGACT CGCTGCGCTC GGTCGTTCGG |
| 3061 CTGCGGCGAG CGGTATCAGC TCACTCAAAG GCGGTAATAC GGTTATCCAC AGAATCAGGG |
| 3121 GATAACGCAG GAAAGAACAT GTGAGCAAAA GGCCAGCAAA AGGCCAGGAA CCGTAAAAAG |
| 3181 GCCGCGTTGC TGGCGTTTTT CCATAGGCTC CGCCCCCCTG ACGAGCATCA CAAAAATCGA |
| 3241 CGCTCAAGTC AGAGGTGGCG AAACCCGACA GGACTATAAA GATACCAGGC GTTTCCCCCT |
| 3301 GGAAGCTCCC TCGTGCGCTC TCCTGTTCCG ACCCTGCCGC TTACCGGATA CCTGTCCGCC |
| 3361 TTTCTCCCTT CGGGAAGCGT GGCGCTTTCT CATAGCTCAC GCTGTAGGTA TCTCAGTTCG |
| 3421 GTGTAGGTCG TTCGCTCCAA GCTGGGCTGT GTGCACGAAC CCCCCGTTCA GCCCGACCGC |
| 3481 TGCGCCTTAT CCGGTAACTA TCGTCTTGAG TCCAACCCGG TAAGACACGA CTTATCGCCA |
| 3541 CTGGCAGCAG CCACTGGTAA CAGGATTAGC AGAGCGAGGT ATGTAGGCGG TGCTACAGAG |
| 3601 TTCTTGAAGT GGTGGCCTAA CTACGGCTAC ACTAGAAGAA CAGTATTTGG TATCTGCGCT |
| 3661 CTGCTGAAGC CAGTTACCTT CGGAAAAAGA GTTGGTAGCT CTTGATCCGG CAAACAAACC |
| 3721 ACCGCTGGTA GCGGTGGTTT TTTTGTTTGC AAGCAGCAGA TTACGCGCAG AAAAAAAGGA |
| 3781 TCTCAAGAAG ATCCTTTGAT CTTTTCTACG GGGTCTGACG CTCAGTGGAA CGAAAACTCA |
| 3841 CGTTAAGGGA TTTTGGTCAT GAGATTATCA AAAAGGATCT TCACCTAGAT CCTTTTAAAT |
| 3901 TAAAAATGAA GTTTTAAATC AATCTAAAGT ATATATGAGT AAACTTGGTC TGACAGTTAC |
| 3961 CAATGCTTAA TCAGTGAGGC ACCTATCTCA GCGATCTGTC TATTTCGTTC ATCCATAGTT |
| 4021 GCCTGACTCC CCGTCGTGTA GATAACTACG ATACGGGAGG GCTTACCATC TGGCCCCAGT |
| 4081 GCTGCAATGA TACCGCGAGA CCCACGCTCA CCGGCTCCAG ATTTATCAGC AATAAACCAG |
| 4141 CCAGCCGGAA GGGCCGAGCG CAGAAGTGGT CCTGCAACTT TATCCGCCTC CATCCAGTCT |
| 4201 ATTAATTGTT GCCGGGAAGC TAGAGTAAGT AGTTCGCCAG TTAATAGTTT GCGCAACGTT |
| 4261 GTTGCCATTG CTACAGGCAT CGTGGTGTCA CGCTCGTCGT TTGGTATGGC TTCATTCAGC |
| 4321 TCCGGTTCCC AACGATCAAG GCGAGTTACA TGATCCCCCA TGTTGTGCAA AAAAGCGGTT |
| 4381 AGCTCCTTCG GTCCTCCGAT CGTTGTCAGA AGTAAGTTGG CCGCAGTGTT ATCACTCATG |
| 4441 GTTATGGCAG CACTGCATAA TTCTCTTACT GTCATGCCAT CCGTAAGATG CTTTTCTGTG |
| 4501 ACTGGTGAGT ACTCAACCAA GTCATTCTGA GAATAGTGTA TGCGGCGACC GAGTTGCTCT |
| 4561 TGCCCGGCGT CAATACGGGA TAATACCGCG CCACATAGCA GAACTTTAAA AGTGCTCATC |
| 4621 ATTGGAAAAC GTTCTTCGGG GCGAAAACTC TCAAGGATCT TACCGCTGTT GAGATCCAGT |
| 4681 TCGATGTAAC CCACTCGTGC ACCCAACTGA TCTTCAGCAT CTTTTACTTT CACCAGCGTT |
| 4741 TCTGGGTGAG CAAAAACAGG AAGGCAAAAT GCCGCAAAAA AGGGAATAAG GGCGACACGG |
| 4801 AAATGTTGAA TACTCATACT CTTCCTTTTT CAATATTATT GAAGCATTTA TCAGGGTTAT |
| 4861 TGTCTCATGA GCGGATACAT ATTTGAATGT ATTTAGAAAA ATAAACAAAT AGGGGTTCCG |

TABLE 5-continued

| Sequences |
|---|
| 4921 CGCACATTTC CCCGAAAAGT GCCACCTGAC GTCTAAGAAA CCATTATTAT CATGACATTA |
| 4981 ACCTATAAAA ATAGGCGTAT CACGAGGCCC TTTCGTC |
| Sequence 8<br>>pKB8 - KOD codon optimized nucleotide sequence in pUC19 vector<br>(SEQ ID NO: 8) |
| 1 TCGCGCGTTT CGGTGATGAC GGTGAAAACC TCTGACACAT GCAGCTCCCG GAGACGGTCA |
| 61 CAGCTTGTCT GTAAGCGGAT GCCGGGAGCA GACAAGCCCG TCAGGGCGCG TCAGCGGGTG |
| 121 TTGGCGGGTG TCGGGGCTGG CTTAACTATG CGGCATCAGA GCAGATTGTA CTGAGAGTGC |
| 181 ACCATATGCG GTGTGAAATA CCGCACAGAT GCGTAAGGAG AAAATACCGC ATCAGGCGCC |
| 241 ATTCGCCATT CAGGCTGCGC AACTGTTGGG AAGGGCGATC GGTGCGGGCC TCTTCGCTAT |
| 301 TACGCCAGCT GGCGAAAGGG GGATGTGCTG CAAGGCGATT AAGTTGGGTA ACGCCAGGGT |
| 361 TTTCCCAGTC ACGACGTTGT AAAACGACGG CCAGTGAATT CGGTCTCAGC GCCATTCTGG |
| 421 ATACCGACTA TATCACGGAA GATGGCAAAC CGGTGATACG TATTTTTAAG AAAGAGAATG |
| 481 GTGAGTTCAA AATCGAGTAC GACCGCACTT TTGAGCCATA TTTCTACGCG TTACTGAAGG |
| 541 ACGATAGCGC CATTGAAGAA GTTAAAAAAA TCACCGCAGA GCGGCATGGG ACAGTGGTAA |
| 601 CCGTGAAGAG AGTTGAAAAA GTCCAGAAAA AATTTTTGGG ACGACCTGTA GAAGTGTGGA |
| 661 AACTTTATTT CACTCACCCC CAAGATGTTC CGGCTATACG TGATAAAATT CGCGAACATC |
| 721 CAGCGGTCAT TGATATTTAC GAATATGATA TACCTTTTGC CAAGCGTTAC CTCATCGACA |
| 781 AAGGCCTGGT GCCGATGGAA GGTGATGAAG AATTAAAAAT GTTGGCATTC GACATTGAAA |
| 841 CACTTTATCA CGAGGGGGAA GAGTTTGCTG AGGGTCCCAT CCTGATGATT TCTTATGCGG |
| 901 ATGAAGAGGG TGCCCGCGTA ATAACCTGGA AGAACGTTGA TCTCCCGTAC GTGGACGTCG |
| 961 TTAGTACGGA ACGGGAAATG ATCAAACGTT TCCTGCGCGT AGTGAAAGAG AAAGATCCAG |
| 1021 ACGTCTTAAT TACCTATAAT GGTGATAACT TTGATTTTGC ATACCTGAAA AAAAGATGCG |
| 1081 AAAAGTTGGG CATAAATTTC GCTCTTGGTC GAGACGGGTC AGAGCCTAAA ATCCAGCGTA |
| 1141 TGGGAGATCG CTTTGCGGTT GAAGTGAAAG GCCGGATTCA TTTCGACCTG TATCCGGTAA |
| 1201 TTCGTCGCAC TATCAACCTC CCCACATACA CGTTAGAAGC CGTCTATGAG GCAGTTTTTG |
| 1261 GTCAACCGAA GGAAAAAGTT TACGCTGAGG AAATTACCAC TGCGTGGGAA ACAGGCGAGA |
| 1321 ATCTGGAACG TGTAGCCCGC TATTCTATGG AGGATGCAAA AGTTACCTAT GAATTGGGTA |
| 1381 AGGAATTTCT TCCAATGGAG GCGCAGCTGT CGAGATTAAT AGGGCAGAGC CTGTGGGACG |
| 1441 TGTCTCGAAG TTCAACGGGA AACCTCGTCG AATGGTTTCT GTTGCGGAAA GCATACGAGC |
| 1501 GTAATGAACT TGCCCCTAAC AAACCGGATG AAAAGGAGCT GGCACGCCGT CGCCAATCCT |
| 1561 ATGAAGGCGG TTACGTTAAA GAACCAGAGC GGGGGTTATG GGAAAATATC GTGTATCTGG |
| 1621 ATTTCCGTTC GCTCTACCCG AGCATTATCA TTACCCACAA CGTATCTCCC GACACTTTGA |
| 1681 ATCGCGAGGG CTGTAAAGAA TATGATGTCG CGCCGCAGGT TGGTCATAGA TTTTGCAAGG |
| 1741 ACTTCCCGGG ATTTATACCA AGTCTGCTTG GCGATTTACT GGAAGAGCGA CAAAAAATCA |
| 1801 AAAAGAAAAT GAAAGCTACA ATCGATCCGA TAGAACGTAA GCTGCTCGAC TACCGCCAGC |
| 1861 GGGCCATCAA AATTTTGGCA AACTCATATT ATGGTTACTA TGGGTACGCG CGTGCTCGCT |
| 1921 GGTATTGTAA AGAGTGCGCC GAATCCGTGA CGGCATGGGG CCGTGAATAC ATCACCATGA |
| 1981 CTATTAAGGA GATAGAAGAG AAATATGGTT TCAAAGTAAT CTACTCGGAT ACAGACGGAT |
| 2041 TCTTTGCGAC GATTCCCGGT GCCGATGCAG AAACCGTCAA GAAAAAAGCG ATGGAATTCC |
| 2101 TTAAGTATAT AAATGCTAAA TTACCTGGTG CCCTGGAGCT GGAATACGAA GGGTTTTACA |

TABLE 5-continued

| Sequences |
|---|
| 2161 AACGCGGATT CTTTGTTACT AAGAAAAAAT ATGCGGTGAT CGACGAGGAA GGCAAGATTA |
| 2221 CGACCAGAGG CCTCGAGATT GTACGGCGTG ATTGGAGCGA AATCGCTAAA GAAACACAGG |
| 2281 CACGTGTCTT GGAGGCATTA CTGAAAGATG GGGACGTTGA AAAGGCGGTG CGAATTGTAA |
| 2341 AAGAAGTCAC CGAAAAACTT TCTAAGTACG AAGTTCCGCC AGAGAAACTG GTGATACACG |
| 2401 AACAAATCAC TCGTGATCTG AAAGACTATA AGGCTACAGG CCCGCATGTA GCAGTCGCCA |
| 2461 AACGCCTCGC GGCTCGGGGT GTTAAAATTC GTCCCGGAAC GGTGATCAGT TACATTGTAT |
| 2521 TGAAGGGCTC AGGTCGCATA GGGGATAGAG CAATCCCTTT CGACGAGTTT GATCCAACCA |
| 2581 AACACAAATA TGATGCCGAA TACTATATTG AAAACCAGGT CTTGCCGGCG GTTGAGCGTA |
| 2641 TACTGCGCGC TTTCGGCTAT CGAAAGGAAG ATCTTCGTTA CCAAAAAACT AGACAGGTGG |
| 2701 GTCTGTCCGC ATGGCTCAAA CCTAAGGGAA CGTAATGATA TGAGACCGGA TCCTCTAGAG |
| 2761 TCGACCTGCA GGCATGCAAG CTTGGCGTAA TCATGGTCAT AGCTGTTTCC TGTGTGAAAT |
| 2821 TGTTATCCGC TCACAATTCC ACACAACATA CGAGCCGGAA GCATAAAGTG TAAAGCCTGG |
| 2881 GGTGCCTAAT GAGTGAGCTA ACTCACATTA ATTGCGTTGC GCTCACTGCC CGCTTTCCAG |
| 2941 TCGGGAAACC TGTCGTGCCA GCTGCATTAA TGAATCGGCC AACGCGCGGG GAGAGGCGGT |
| 3001 TTGCGTATTG GGCGCTCTTC CGCTTCCTCG CTCACTGACT CGCTGCGCTC GGTCGTTCGG |
| 3061 CTGCGGCGAG CGGTATCAGC TCACTCAAAG GCGGTAATAC GGTTATCCAC AGAATCAGGG |
| 3121 GATAACGCAG GAAAGAACAT GTGAGCAAAA GGCCAGCAAA AGGCCAGGAA CCGTAAAAAG |
| 3181 GCCGCGTTGC TGGCGTTTTT CCATAGGCTC CGCCCCCCTG ACGAGCATCA CAAAAATCGA |
| 3241 CGCTCAAGTC AGAGGTGGCG AAACCCGACA GGACTATAAA GATACCAGGC GTTTCCCCCT |
| 3301 GGAAGCTCCC TCGTGCGCTC TCCTGTTCCG ACCCTGCCGC TTACCGGATA CCTGTCCGCC |
| 3361 TTTCTCCCTT CGGGAAGCGT GGCGCTTTCT CATAGCTCAC GCTGTAGGTA TCTCAGTTCG |
| 3421 GTGTAGGTCG TTCGCTCCAA GCTGGGCTGT GTGCACGAAC CCCCCGTTCA GCCCGACCGC |
| 3481 TGCGCCTTAT CCGGTAACTA TCGTCTTGAG TCCAACCCGG TAAGACACGA CTTATCGCCA |
| 3541 CTGGCAGCAG CCACTGGTAA CAGGATTAGC AGAGCGAGGT ATGTAGGCGG TGCTACAGAG |
| 3601 TTCTTGAAGT GGTGGCCTAA CTACGGCTAC ACTAGAAGAA CAGTATTTGG TATCTGCGCT |
| 3661 CTGCTGAAGC CAGTTACCTT CGGAAAAAGA GTTGGTAGCT CTTGATCCGG CAAACAAACC |
| 3721 ACCGCTGGTA GCGGTGGTTT TTTTGTTTGC AAGCAGCAGA TTACGCGCAG AAAAAAAGGA |
| 3781 TCTCAAGAAG ATCCTTTGAT CTTTTCTACG GGGTCTGACG CTCAGTGGAA CGAAAACTCA |
| 3841 CGTTAAGGGA TTTTGGTCAT GAGATTATCA AAAAGGATCT TCACCTAGAT CCTTTTAAAT |
| 3901 TAAAAATGAA GTTTTAAATC AATCTAAAGT ATATATGAGT AAACTTGGTC TGACAGTTAC |
| 3961 CAATGCTTAA TCAGTGAGGC ACCTATCTCA GCGATCTGTC TATTTCGTTC ATCCATAGTT |
| 4021 GCCTGACTCC CCGTCGTGTA GATAACTACG ATACGGGAGG GCTTACCATC TGGCCCCAGT |
| 4081 GCTGCAATGA TACCGCGAGA CCCACGCTCA CCGGCTCCAG ATTTATCAGC AATAAACCAG |
| 4141 CCAGCCGGAA GGGCCGAGCG CAGAAGTGGT CCTGCAACTT TATCCGCCTC CATCCAGTCT |
| 4201 ATTAATTGTT GCCGGGAAGC TAGAGTAAGT AGTTCGCCAG TTAATAGTTT GCGCAACGTT |
| 4261 GTTGCCATTG CTACAGGCAT CGTGGTGTCA CGCTCGTCGT TTGGTATGGC TTCATTCAGC |
| 4321 TCCGGTTCCC AACGATCAAG GCGAGTTACA TGATCCCCCA TGTTGTGCAA AAAAGCGGTT |
| 4381 AGCTCCTTCG GTCCTCCGAT CGTTGTCAGA AGTAAGTTGG CCGCAGTGTT ATCACTCATG |
| 4441 GTTATGGCAG CACTGCATAA TTCTCTTACT GTCATGCCAT CCGTAAGATG CTTTTCTGTG |

TABLE 5-continued

| Sequences |
|---|
| 4501 ACTGGTGAGT ACTCAACCAA GTCATTCTGA GAATAGTGTA TGCGGCGACC GAGTTGCTCT |
| 4561 TGCCCGGCGT CAATACGGGA TAATACCGCG CCACATAGCA GAACTTTAAA AGTGCTCATC |
| 4621 ATTGGAAAAC GTTCTTCGGG GCGAAAACTC TCAAGGATCT TACCGCTGTT GAGATCCAGT |
| 4681 TCGATGTAAC CCACTCGTGC ACCCAACTGA TCTTCAGCAT CTTTTACTTT CACCAGCGTT |
| 4741 TCTGGGTGAG CAAAAACAGG AAGGCAAAAT GCCGCAAAAA AGGGAATAAG GGCGACACGG |
| 4801 AAATGTTGAA TACTCATACT CTTCCTTTTT CAATATTATT GAAGCATTTA TCAGGGTTAT |
| 4861 TGTCTCATGA GCGGATACAT ATTTGAATGT ATTTAGAAAA ATAAACAAAT AGGGGTTCCG |
| 4921 CGCACATTTC CCCGAAAAGT GCCACCTGAC GTCTAAGAAA CCATTATTAT CATGACATTA |
| 4981 ACCTATAAAA ATAGGCGTAT CACGAGGCCC TTTCGTC |
| Amino acid sequences of Pfu and KOD |
| Sequence 9 |
| >Pfu amino acid sequence |
| (SEQ ID NO: 9) |
| 1 MILDVDYITE EGKPVIRLFK KENGKFKIEH DRTFRPYIYA LLRDDSKIEE VKKITGERHG |
| 61 KIVRIVDVEK VEKKFLGKPI TVWKLYLEHP QDVPTIREKV REHPAVVDIF EYDIPFAKRY |
| 121 LIDKGLIPME GEEELKILAF DIETLYHEGE EFGKGPIIMI SYADENEAKV ITWKNIDLPY |
| 181 VEVVSSEREM IKRFLRIIRE KDPDIIVTYN GDSFDFPYLA KRAEKLGIKL TIGRDGSEPK |
| 241 MQRIGDMTAV EVKGRIHFDL YHVITRTINL PTYTLEAVYE AIFGKPKEKV YADEIAKAWE |
| 301 SGENLERVAK YSMEDAKATY ELGKEFLPME IQLSRLVGQP LWDVSRSSTG NLVEWFLLRK |
| 361 AYERNEVAPN KPSEEEYQRR LRESYTGGFV KEPEKGLWEN IVYLDFRALY PSIIITHNVS |
| 421 PDTLNLEGCK NYDIAPQVGH KFCKDIPGFI PSLLGHLLEE RQKIKTKMKE TQDPIEKILL |
| 481 DYRQKAIKLL ANSFYGYYGY AKARWYCKEC AESVTAWGRK YIELVWKELE EKFGFKVLYI |
| 541 DTDGLYATIP GGESEEIKKK ALEFVKYINS KLPGLLELEY EGFYKRGFFV TKKRYAVIDE |
| 601 EGKVITRGLE IVRRDWSEIA KETQARVLET ILKHGDVEEA VRIVKEVIQK LANYEIPPEK |
| 661 LAIYEQITRP LHEYKAIGPH VAVAKKLAAK GVKIKPGMVI GYIVLRGDGP ISNRAILAEE |
| 721 YDPKKHKYDA EYYIENQVLP AVLRILEGFG YRKEDLRYQK TRQVGLTSWL NIKKS* |
| Sequence 10 |
| >Pfu amino acid sequence, extra 3 aa in 5' area. |
| (SEQ ID NO: 10) |
| 1 MASAILDVDY ITEEGKPVIR LFKKENGKFK IEHDRTFRPY IYALLRDDSK IEEVKKITGE |
| 61 RHGKIVRIVD VEKVEKKFLG KPITVWKLYL EHPQDVPTIR EKVREHPAVV DIFEYDIPFA |
| 121 KRYLIDKGLI PMEGEEELKI LAFDIETLYH EGEEFGKGPI IMISYADENE AKVITWKNID |
| 181 LPYVEVVSSE REMIKRFLRI IREKDPDIIV TYNGDSFDFP YLAKRAEKLG IKLTIGRDGS |
| 241 EPKMQRIGDM TAVEVKGRIH FDLYHVITRT INLPTYTLEA VYEAIFGKPK EKVYADEIAK |
| 301 AWESGENLER VAKYSMEDAK ATYELGKEFL PMEIQLSRLV GQPLWDVSRS STGNLVEWFL |
| 361 LRKAYERNEV APNKPSEEEY QRRLRESYTG GFVKEPEKGL WENIVYLDFR ALYPSIIITH |
| 421 NVSPDTLNLE GCKNYDIAPQ VGHKFCKDIP GFIPSLLGHL LEERQKIKTK MKETQDPIEK |
| 481 ILLDYRQKAI KLLANSFYGY YGYAKARWYC KECAESVTAW GRKYIELVWK ELEEKFGFKV |
| 541 LYIDTDGLYA TIPGGESEEI KKKALEFVKY INSKLPGLLE LEYEGFYKRG FFVTKKRYAV |
| 601 IDEEGKVITR GLEIVRRDWS EIAKETQARV LETILKHGDV EEAVRIVKEV IQKLANYEIP |
| 661 PEKLAIYEQI TRPLHEYKAI GPHVAVAKKL AAKGVKIKPG MVIGYIVLRG DGPISNRAIL |
| 721 AEEYDPKKHK YDAEYYIENQ VLPAVLRILE GFGYRKEDLR YQKTRQVGLT SWLNIKKS* |

TABLE 5-continued

| Sequences |
|---|
| Sequence 11<br>>KOD amino acid sequence<br>(SEQ ID NO: 11)<br>1 MILDTDYITE DGKPVIRIFK KENGEFKIEY DRTFEPYFYA LLKDDSAIEE VKKITAERHG<br>61 TVVTVKRVEK VQKKFLGRPV EVWKLYFTHP QDVPAIRDKI REHPAVIDIY EYDIPFAKRY<br>121 LIDKGLVPME GDEELKMLAF DIETLYHEGE EFAEGPILMI SYADEEGARV ITWKNVDLPY<br>181 VDVVSTEREM IKRFLRVVKE KDPDVLITYN GDNFDFAYLK KRCEKLGINF ALGRDGSEPK<br>241 IQRMGDRFAV EVKGRIHFDL YPVIRRTINL PTYTLEAVYE AVFGQPKEKV YAEEITTAWE<br>301 TGENLERVAR YSMEDAKVTY ELGKEFLPME AQLSRLIGQS LWDVSRSSTG NLVEWFLLRK<br>361 AYERNELAPN KPDEKELARR RQSYEGGYVK EPERGLWENI VYLDFRSLYP SIIITHNVSP<br>421 DTLNREGCKE YDVAPQVGHR FCKDFPGFIP SLLGDLLEER QKIKKKMKAT IDPIERKLLD<br>481 YRQRAIKILA NSYYGYYGYA RARWYCKECA ESVTAWGREY ITMTIKEIEE KYGFKVIYSD<br>541 TDGFFATIPG ADAETVKKKA MEFLKYINAK LPGALELEYE GFYKRGFFVT KKKYAVIDEE<br>601 GKITTRGLEI VRRDWSEIAK ETQARVLEAL LKDGDVEKAV RIVKEVTEKL SKYEVPPEKL<br>661 VIHEQITRDL KDYKATGPHV AVAKRLAARG VKIRPGTVIS YIVLKGSGRI GDRAIPFDEF<br>721 DPTKHKYDAE YYIENQVLPA VERILRAFGY RKEDLRYQKT RQVGLSAWLK PKGT |
| Sequence 12<br>>KOD amino acid sequence, extra 3 aa in 5' area.<br>(SEQ ID NO: 12)<br>1 MASAILDTDY ITEDGKPVIR IFKKENGEFK IEYDRTFEPY FYALLKDDSA IEEVKKITAE<br>61 RHGTVVTVKR VEKVQKKFLG RPVEVWKLYF THPQDVPAIR DKIREHPAVI DIYEYDIPFA<br>121 KRYLIDKGLV PMEGDEELKM LAFDIETLYH EGEEFAEGPI LMISYADEEG ARVITWKNVD<br>181 LPYVDVVSTE REMIKRFLRV VKEKDPDVLI TYNGDNFDFA YLKKRCEKLG INFALGRDGS<br>241 EPKIQRMGDR FAVEVKGRIH FDLYPVIRRT INLPTYTLEA VYEAVFGQPK EKVYAEEITT<br>301 AWETGENLER VARYSMEDAK VTYELGKEFL PMEAQLSRLI GQSLWDVSRS STGNLVEWFL<br>361 LRKAYERNEL APNKPDEKEL ARRRQSYEGG YVKEPERGLW ENIVYLDFRS LYPSIIITHN<br>421 VSPDTLNREG CKEYDVAPQV GHRFCKDFPG FIPSLLGDLL EERQKIKKKM KATIDPIERK<br>481 LLDYRQRAIK ILANSYYGYY GYARARWYCK ECAESVTAWG REYITMTIKE IEEKYGFKVI<br>541 YSDTDGFFAT IPGADAETVK KKAMEFLKYI NAKLPGALEL EYEGFYKRGF FVTKKKYAVI<br>601 DEEGKITTRG LEIVRRDWSE IAKETQARVL EALLKDGDVE KAVRIVKEVT EKLSKYEVPP<br>661 EKLVIHEQIT RDLKDYKATG PHVAVAKRLA ARGVKIRPGT VISYIVLKGS GRIGDRAIPF<br>721 DEFDPTKHKY DAEYYIENQV LPAVERILRA FGYRKEDLRY QKTRQVGLSA WLKPKGT* |
| DNA sequences of chimeras Pod and Kofu<br>Sequence 13<br>>Pod codon optimized nucleotide sequence<br>(SEQ ID NO: 13)<br>1 ATGGCTAGCG CCATTCTGGA TGTGGACTAT ATCACCGAAG AGGGCAAACC GGTTATACGT<br>61 TTATTTAAGA AAGAGAATGG TAAATTCAAG ATCGAGCATG ACCGCACGTT CCGTCCATAC<br>121 ATTTACGCGT TGCTTCGGGA TGATAGCAAA ATTGAGGAAG TCAAAAAGAT CACCGGGGAA<br>181 CGTCATGGAA AAATAGTAAG AATTGTGGAC GTTGAAAAAG TCGAAAAGAA ATTTCTGGGC<br>241 AAACCGATCA CTGTATGGAA GCTCTATCTG GAACATCCTC AGGATGTGCC CACAATTCGA<br>301 GAAAAAGTTC GTGAGCACCC AGCCGTCGTG GATATATTTG AATATGACAT CCCTTTTGCA<br>361 AAACGCTACT TAATTGATAA AGGCCTGATC CCGATGGAGG GGGAAGAAGA ACTTAAAATT<br>421 CTGGCTTTTG ACATAGAAAC GCTCTATCAT GAGGGAGAAG AATTTGGCAA AGGTCCCATC |

TABLE 5-continued

| Sequences |
|---|
| 481 ATTATGATTT CTTACGCGGA TGAGAACGAA GCCAAGGTAA TCACTTGGAA AAATATTGAC |
| 541 CTGCCGTACG TTGAAGTGGT CAGTTCAGAG CGGGAAATGA TTAAACGTTT TTTACGCATC |
| 601 ATTAGAGAGA AAGATCCAGA TATAATCGTT ACATATAACG GCGACTCCTT CGATTTTCCT |
| 661 TACCTGGCAA AACGAGCTGA AAAATTGGGT ATTAAACTTA CCATCGGGCG TGACGGATCG |
| 721 GAACCGAAAA TGCAACGCAT TGGCGATATG ACGGCGGTAG AGGTGAAAGG TCGGATACAC |
| 781 TTTGATCTGT ATCATGTCAT CACCCGTACT ATTAATCTCC CCACATACAC GTTAGAAGCC |
| 841 GTTTATGAGG CAATATTCGG CAAGCCGAAA GAAAAAGTGT ACGCTGACGA AATCGCGAAG |
| 901 GCATGGGAGA GCGGCGAAAA CCTGGAGCGC GTAGCAAAAT ATTCTATGGA AGATGCTAAA |
| 961 GCGACCTACG AATTGGGGAA AGAATTTCTT CCAATGGAAA TTCAGCTGTC GAGATTAATA |
| 1021 GGGCAGAGCC TGTGGGACGT GTCTCGAAGT TCAACGGGAA ACCTCGTCGA ATGGTTTCTG |
| 1081 TTGCGGAAAG CATACGAGCG TAATGAACTT GCCCCTAACA AACCGGATGA AAAGGAGCTG |
| 1141 GCACGCCGTC GCCAATCCTA TGAAGGCGGT TACGTTAAAG AACCAGAGCG GGGGTTATGG |
| 1201 GAAAATATCG TGTATCTGGA TTTCCGTTCG CTCTACCCGA GCATTATCAT TACCCACAAC |
| 1261 GTATCTCCCG ACACTTTGAA TCGCGAGGGC TGTAAAGAAT ATGATGTCGC GCCGCAGGTT |
| 1321 GGTCATAGAT TTTGCAAGGA CTTCCCGGGA TTTATACCAA GTCTGCTTGG CGATTTACTG |
| 1381 GAAGAGCGAC AAAAAATCAA AAAGAAAATG AAAGCTACAA TCGATCCGAT AGAACGTAAG |
| 1441 CTGCTCGACT ACCGCCAGCG GGCCATCAAA ATTTTGGCAA ACTCATATTA TGGTTACTAT |
| 1501 GGGTACGCGC GTGCTCGCTG GTATTGTAAA GAGTGCGCCG AATCCGTGAC GGCATGGGGC |
| 1561 CGTGAATACA TCACCATGAC TATTAAGGAG ATAGAAGAGA AATATGGTTT CAAAGTAATC |
| 1621 TACTCGGATA CAGACGGATT CTTTGCGACG ATTCCCGGTG CCGATGCAGA AACCGTCAAG |
| 1681 AAAAAAGCGA TGGAATTCGT TAAGTACATT AATAGTAAAT TACCGGGACT GCTTGAACTG |
| 1741 GAGTATGAAG GCTTCTACAA AAGAGGTTTT TTCGTTACTA AGAAACGATA TGCCGTAATA |
| 1801 GATGAAGAGG GGAAAGTCAT CACACGTGGC CTCGAGATTG TTCGCCGGGA CTGGTCAGAG |
| 1861 ATAGCAAAGG AAACGCAGGC GCGCGTGCTC GAAACCATCT TGAAACATGG TGATGTAGAG |
| 1921 GAAGCCGTCC GCATTGTTAA AGAGGTGATC CAGAAGTTAG CAAACTATGA AATTCCACCG |
| 1981 GAAAAACTGG CGATATACGA GCAAATCACT CGTCCCCTTC ACGAATATAA AGCTATTGGA |
| 2041 CCTCATGTAG CCGTCGCGAA GAAACTGGCT GCAAAAGGCG TTAAGATAAA ACCAGGTATG |
| 2101 GTGATCGGGT ACATTGTACT CCGCGGCGAC GGTCCGATTT CCAATAGAGC CATCTTGGCG |
| 2161 GAGGAATATG ATCCTAAAAA GCATAAATAC GACGCTGAAT ATTACATTGA GAACCAGGTC |
| 2221 TTGCCGGCAG TTCTGCGGAT ACTTGAAGGA TTTGGCTATC GTAAAGAAGA TCTGCGCTAT |
| 2281 CAAAAGACGC GACAGGTGGG TCTGACTAGC TGGTTGAATA TCAAAAAATC GTAA |
| Sequence 14<br>>Kofu codon optimized nucleotide sequence<br>(SEQ ID NO: 14) |
| 1 ATGGCTAGCG CCATTCTGGA TACCGACTAT ATCACGGAAG ATGGCAAACC GGTGATACGT |
| 61 ATTTTTAAGA AAGAGAATGG TGAGTTCAAA ATCGAGTACG ACCGCACTTT TGAGCCATAT |
| 121 TTCTACGCGT TACTGAAGGA CGATAGCGCC ATTGAAGAAG TTAAAAAAAT CACCGCAGAG |
| 181 CGGCATGGGA CAGTGGTAAC CGTGAAGAGA GTTGAAAAAG TCCAGAAAAA ATTTTTGGGA |
| 241 CGACCTGTAG AAGTGTGGAA ACTTTATTTC ACTCACCCCC AAGATGTTCC GGCTATACGT |
| 301 GATAAAATTC GCGAACATCC AGCGGTCATT GATATTTACG AATATGATAT ACCTTTTGCC |
| 361 AAGCGTTACC TCATCGACAA AGGCCTGGTG CCGATGGAAG GTGATGAAGA ATTAAAAATG |

TABLE 5-continued

| Sequences |
|---|
| 421 TTGGCATTCG ACATTGAAAC ACTTTATCAC GAGGGGGAAG AGTTTGCTGA GGGTCCCATC |
| 481 CTGATGATTT CTTATGCGGA TGAAGAGGGT GCCCGCGTAA TAACCTGGAA GAACGTTGAT |
| 541 CTCCCGTACG TGGACGTCGT TAGTACGGAA CGGGAAATGA TCAAACGTTT CCTGCGCGTA |
| 601 GTGAAAGAGA AAGATCCAGA CGTCTTAATT ACCTATAATG GTGATAACTT TGATTTTGCA |
| 661 TACCTGAAAA AAAGATGCGA AAAGTTGGGC ATAAATTTCG CTCTTGGTCG AGACGGGTCA |
| 721 GAGCCTAAAA TCCAGCGTAT GGGAGATCGC TTTGCGGTTG AAGTGAAAGG CCGGATTCAT |
| 781 TTCGACCTGT ATCCGGTAAT TCGTCGCACT ATCAACCTCC CCACATACAC GTTAGAAGCC |
| 841 GTCTATGAGG CAGTTTTTGG TCAACCGAAG GAAAAAGTTT ACGCTGAGGA AATTACCACT |
| 901 GCGTGGGAAA CAGGCGAGAA TCTGGAACGT GTAGCCCGCT ATTCTATGGA GGATGCAAAA |
| 961 GTTACCTATG AATTGGGTAA GGAATTTCTT CCAATGGAGG CGCAGCTGAG TCGTTTAGTC |
| 1021 GGACAACCTC TGTGGGACGT TTCACGCTCC TCGACTGGCA ATCTCGTGGA GTGGTTCCTG |
| 1081 TTGAGAAAAG CCTATGAACG AAACGAAGTA GCACCGAATA AACCAAGCGA GGAAGAATAT |
| 1141 CAGCGTCGCC TTCGCGAGTC TTACACAGGT GGGTTTGTTA AGGAACCGGA GAAAGGTCTT |
| 1201 TGGGAAAACA TCGTGTATTT AGATTTCCGT GCGCTGTACC CCAGTATTAT AATCACCCAC |
| 1261 AATGTCTCAC CTGACACGCT CAACTTGGAA GGTTGCAAAA ATTATGATAT TGCTCCGCAA |
| 1321 GTTGGACATA AGTTTTGTAA AGATATTCCG GGCTTCATCC CGTCCCTGCT TGGTCACTTA |
| 1381 CTGGAAGAGC GCCAAAAAAT TAAGACCAAA ATGAAAGAGA CTCAGGATCC CATTGAAAAG |
| 1441 ATCCTGCTCG ATTACCGGCA AAAAGCCATT AAATTGCTTG CAAACTCGTT TTATGGGTAC |
| 1501 TATGGCTATG CGAAGGCTCG TTGGTACTGC AAAGAATGTG CCGAGAGCGT GACAGCATGG |
| 1561 GGTCGCAAAT ATATAGAATT AGTATGGAAG GAGCTGGAAG AAAAATTCGG ATTCAAAGTC |
| 1621 CTGTACATCG ATACGGATGG CCTCTATGCG ACCATTCCTG GTGGGGAGTC TGAAGAAATC |
| 1681 AAGAAAAAAG CCTTGGAATT CCTTAAGTAT ATAAATGCTA AATTACCTGG TGCCCTGGAG |
| 1741 CTGGAATACG AAGGGTTTTA CAAACGCGGA TTCTTTGTTA CTAAGAAAAA ATATGCGGTG |
| 1801 ATCGACGAGG AAGGCAAGAT TACGACCAGA GGCCTCGAGA TTGTACGGCG TGATTGGAGC |
| 1861 GAAATCGCTA AAGAAACACA GGCACGTGTC TTGGAGGCAT TACTGAAAGA TGGGGACGTT |
| 1921 GAAAAGGCGG TGCGAATTGT AAAAGAAGTC ACCGAAAAAC TTTCTAAGTA CGAAGTTCCG |
| 1981 CCAGAGAAAC TGGTGATACA CGAACAAATC ACTCGTGATC TGAAAGACTA TAAGGCTACA |
| 2041 GGCCCGCATG TAGCAGTCGC CAAACGCCTC GCGGCTCGGG GTGTTAAAAT TCGTCCCGGA |
| 2101 ACGGTGATCA GTTACATTGT ATTGAAGGGC TCAGGTCGCA TAGGGGATAG AGCAATCCCT |
| 2161 TTCGACGAGT TTGATCCAAC CAAACACAAA TATGATGCCG AATACTATAT TGAAAACCAG |
| 2221 GTCTTGCCGG CGGTTGAGCG TATACTGCGC GCTTTCGGCT ATCGAAAGGA AGATCTTCGT |
| 2281 TACCAAAAAA CTAGACAGGT GGGTCTGTCC GCATGGCTCA AACCTAAGGG AACGTAA |
| Amino acid sequences of chimeras Pod and Kofu<br>Sequence 15<br>>Pod amino acid sequence<br>(SEQ ID NO: 15) |
| 1 MASAILDVDY ITEEGKPVIR LEKKENGKFK IEHDRTFRPY IYALLRDDSK IEEVKKITGE |
| 61 RHGKIVRIVD VEKVEKKFLG KPITVWKLYL EHPQDVPTIR EKVREHPAVV DIFEYDIPFA |
| 121 KRYLIDKGLI PMEGEEELKI LAFDIETLYH EGEEFGKGPI IMISYADENE AKVITWKNID |
| 181 LPYVEVVSSE REMIKRFLRI IREKDPDIIV TYNGDSFDFP YLAKRAEKLG IKLTIGRDGS |
| 241 EPKMQRIGDM TAVEVKGRIH FDLYHVITRT INLPTYTLEA VYEAIFGKPK EKVYADEIAK |

TABLE 5-continued

| Sequences |
|---|
| 301 AWESGENLER VAKYSMEDAK ATYELGKEFL PMEIQLSRLI GQSLWDVSRS STGNLVEWEL |
| 361 LRKAYERNEL APNKPDEKEL ARRRQSYEGG YVKEPERGLW ENIVYLDFRS LYPSIIITHN |
| 421 VSPDTLNREG CKEYDVAPQV GHRFCKDFPG FIPSLLGDLL EERQKIKKKM KATIDPIERK |
| 481 LLDYRQRAIK ILANSYYGYY GYARARWYCK ECAESVTAWG REYITMTIKE IEEKYGFKVI |
| 541 YSDTDGFFAT IPGADAETVK KKAMEFVKYI NSKLPGLLEL EYEGFYKRGF FVTKKRYAVI |
| 601 DEEGKVITRG LEIVRRDWSE IAKETQARVL ETILKHGDVE EAVRIVKEVI QKLANYEIPP |
| 661 EKLAIYEQIT RPLHEYKAIG PHVAVAKKLA AKGVKIKPGM VIGYIVLRGD GPISNRAILA |
| 721 EEYDPKKHKY DAEYYIENQV LPAVLRILEG FGYRKEDLRY QKTRQVGLTS WLNIKKS* |
| Sequence 16<br>>Kofu amino acid sequence<br>(SEQ ID NO: 16) |
| 1 MASAILDTDY ITEDGKPVIR IFKKENGEFK IEYDRTFEPY FYALLKDDSA IEEVKKITAE |
| 61 RHGTVVIVKR VEKVQKKFLG RPVEVWKLYF THPQDVPAIR DKIREHPAVI DIYEYDIPFA |
| 121 KRYLIDKGLV PMEGDEELKM LAFDIETLYH EGEEFAEGPI LMISYADEEG ARVITWKNVD |
| 181 LPYVDVVSTE REMIKRFLRV VKEKDPDVLI TYNGDNFDFA YLKKRCEKLG INFALGRDGS |
| 241 EPKIQRMGDR FAVEVKGRIH FDLYPVIRRT INLPTYTLEA VYEAVFGQPK EKVYAEEITT |
| 301 AWETGENLER VARYSMEDAK VTYELGKEFL PMEAQLSRLV GQPLWDVSRS STGNLVEWFL |
| 361 LRKAYERNEV APNKPSEEEY QRRLRESYTG GFVKEPEKGL WENIVYLDFR ALYPSIIITH |
| 421 NVSPDTLNLE GCKNYDIAPQ VGHKFCKDIP GFIPSLLGHL LEERQKIKTK MKETQDPIEK |
| 481 ILLDYRQKAI KLLANSFYGY YGYAKARWYC KECAESVTAW GRKYIELVWK ELEEKFGFKV |
| 541 LYIDTDGLYA TIPGGESEEI KKKALEFLKY INAKLPGALE LEYEGFYKRG FFVTKKKYAV |
| 601 IDEEGKITTR GLEIVRRDWS EIAKETQARV LEALLKDGDV EKAVRIVKEV TEKLSKYEVP |
| 661 PEKLVIHEQI TRDLKDYKAT GPHVAVAKRL AARGVKIRPG TVISYIVLKG SGRIGDRAIP |
| 721 FDEFDPTKHK YDAEYYIENQ VLPAVERILR AFGYRKEDLR YQKTRQVGLS AWLKPKGT* |
| Sequence 17<br>>pLACIQZa<br>(SEQ ID NO: 17) |
| 1 TCGCGCGTTTCGGTGATGACGGTGAAAACCTCTGACACATGCAGCTCCCGGAGACGGTCA |
| 61 CAGCTTGTCTGTAAGCGGATGCCGGGAGCAGACAAGCCCGTCAGGGCGCGTCAGCGGGTG |
| 121 TTGGCGGGTGTCGGGGCTGGCTTAACTATGCGGCATCAGAGCAGATTGTACTGAGAGTGC |
| 181 ACCATATGCGGTGTGAAATACCGCACAGATGCGTAAGGAGAAAATACCGCATCAGGCGCC |
| 241 ATTCGCCATTCAGGCTGCGCAACTGTTGGGAAGGGCGATCGGTGCGGGCCTCTTCGCTAT |
| GT<br>301 TACGCCAGCTGGCGAAAGGGGGATGTGCTGCAAGGCGATTAAGTTGGGTAACGCCAGGGT |
| TTTCCCAGTCACGAC >>> Primer M13-40 (SEQ ID NO: 42)<br>361 TTTCCCAGTCACGACGTTGTAAAACGACGGCCAGTGAATTCGAGCTCGGTACCCGGGGAT |
| XbaI<br>421 CCTCTAGAGCCGTAATCATGGTCATAGCTGTTTCCTGTGTGAAATTGTTATCCGCTCACA |
| 481 ATTCCACACAACATACGAGCCGGAAGCATAAAGTGTAAAGCCTGGGGTGCCTAATGAGTG |
| 541 AGCTAACTCACATTAATTGCGTTGCGCTCACTGCCCGCTTTCCAGTCGGGAAACCTGTCG |
| 601 TGCCAGCTGCATTAATGAATCGGCCAACGCGCGGGGAGAGGCGGTTTGCGTATTGGGCGC |
| 661 CAGGGTGGTTTTTCTTTTCACCAGTGAGACGGGCAACAGCTGATTGCCCTTCACCGCCTG |
| 721 GCCCTGAGAGAGTTGCAGCAAGCGGTCCACGCTGGTTTGCCCCAGCAGGCGAAAATCCTG |

TABLE 5-continued

| Sequences |
|---|
| 781 TTTGATGGTGGTTGACGGCGGGATATAACATGAGCTGTCTTCGGTATCGTCGTATCCCAC |
| 841 TACCGAGATATCCGCACCAACGCGCAGCCCGGACTCGGTAATGGCGCGCATTGCGCCCAG |
| 901 CGCCATCTGATCGTTGGCAACCAGCATCGCAGTGGGAACGATGCCCTCATTCAGCATTTG |
| 961 CATGGTTTGTTGAAAACCGGACATGGCACTCCAGTCGCCTTCCCGTTCCGCTATCGGCTG |
| 1021 AATTTGATTGCGAGTGAGATATTTATGCCAGCCAGCCAGACGCAGACGCGCCGAGACAGA |
| 1081 ACTTAATGGGCCCGCTAACAGCGCGATTTGCTGGTGACCCAATGCGACCAGATGCTCCAC |
| 1141 GCCCAGTCGCGTACCGTCTTCATGGGAGAAAATAATACTGTTGATGGGTGTCTGGTCAGA |
| 1201 GACATCAAGAAATAACGCCGGAACATTAGTGCAGGCAGCTTCCACAGCAATGGCATCCTG |
| 1261 GTCATCCAGCGGATAGTTAATGATCAGCCCACTGACGCGTTGCGCGAGAAGATTGTGCAC |
| 1321 CGCCGCTTTACAGGCTTCGACGCCGCTTCGTTCTACCATCGACACCACCACGCTGGCACC |
| 1381 CAGTTGATCGGCGCGAGATTTAATCGCCGCGACAATTTGCGACGGCGCGTGCAGGGCCAG |
| 1441 ACTGGAGGTGGCAACGCCAATCAGCAACGACTGTTTGCCCGCCAGTTGTTGTGCCACGCG |
| 1501 GTTGGGAATGTAATTCAGCTCCGCCATCGCCGCTTCCACTTTTTCCCGCGTTTTCGCAGA |
| 1561 AACGTGGCTGGCCTGGTTCACCACGCGGGAAACGGTCTGATAAGAGACACCGGCATACTC |
| 1621 TGCGACATCGTATAACGTTACTGGTTTCACATTCACCACCCTGAATTGACTCTCTTCCGG |
| 1681 GCGCTATCATGCCATACCGCGAAAGGTTTTGCGCCATTCGATGGTGTCAACGTAAATGCA |
| NcoI |
| 1741 TGCCGCTTCGCCTTCCGGCCACCAGAATAGCCTGCGCCATGGGCTTCCTCGCTCACTGAC |
| 1801 TCGCTGCGCTCGGTCGTTCGGCTGCGGCGAGCGGTATCAGCTCACTCAAAGGCGGTAATA |
| 1861 CGGTTATCCACAGAATCAGGGGATAACGCAGGAAAGAACATGTGAGCAAAAGGCCAGCAA |
| 1921 AAGGCCAGGAACCGTAAAAAGGCCGCGTTGCTGGCGTTTTTCCATAGGCTCCGCCCCCCT |
| 1981 GACGAGCATCACAAAAATCGACGCTCAAGTCAGAGGTGGCGAAACCCGACAGGACTATAA |
| PRIMER PKBLACIR <<< GCTGTCCTGATATT TCTATGG (SEQ ID NO: 43) |
| 2041 AGATACCAGGCGTTTCCCCCTGGAAGCTCCCTCGTGCGCTCTCCTGTTCCGACCCTGCCG |
| 2101 CTTACCGGATACCTGTCCGCCTTTCTCCCTTCGGGAAGCGTGGCGCTTTCTCATAGCTCA |
| 2161 CGCTGTAGGTATCTCAGTTCGGTGTAGGTCGTTCGCTCCAAGCTGGGCTGTGTGCACGAA |
| 2221 CCCCCCGTTCAGCCCGACCGCTGCGCCTTATCCGGTAACTATCGTCTTGAGTCCAACCCG |
| 2281 GTAAGACACGACTTATCGCCACTGGCAGCAGCCACTGGTAACAGGATTAGCAGAGCGAGG |
| 2341 TATGTAGGCGGTGCTACAGAGTTCTTGAAGTGGTGGCCTAACTACGGCTACACTAGAAGA |
| 2401 ACAGTATTTGGTATCTGCGCTCTGCTGAAGCCAGTTACCTTCGGAAAAAGAGTTGGTAGC |
| 2461 TCTTGATCCGGCAAACAAACCACCGCTGGTAGCGGTGGTTTTTTTGTTTGCAAGCAGCAG |
| 2521 ATTACGCGCAGAAAAAAAGGATCTCAAGAAGATCCTTTGATCTTTTCTACGGGGTCTGAC |
| 2581 GCTCAGTGGAACGAAAACTCACGTTAAGGGATTTTGGTCATGAGATTATCAAAAAGGATC |
| 2641 TTCACCTAGATCCTTTTAAATTAAAAATGAAGTTTTAAATCAATCTAAAGTATATATGAG |
| 2701 TAAACTTGGTCTGACAGTTACCAATGCTTAATCAGTGAGGCACCTATCTCAGCGATCTGT |
| 2761 CTATTTCGTTCATCCATAGTTGCCTGACTCCCCGTCGTGTAGATAACTACGATACGGGAG |
| 2821 GGCTTACCATCTGGCCCCAGTGCTGCAATGATACCGCGAGACCCACGCTCACCGGCTCCA |
| 2881 GATTTATCAGCAATAAACCAGCCAGCCGGAAGGGCCGAGCGCAGAAGTGGTCCTGCAACT |
| 2941 TTATCCGCCTCCATCCAGTCTATTAATTGTTGCCGGGAAGCTAGAGTAAGTAGTTCGCCA |
| 3001 GTTAATAGTTTGCGCAACGTTGTTGCCATTGCTACAGGCATCGTGGTGTCACGCTCGTCG |

TABLE 5-continued

| Sequences |
|---|
| 3061 TTTGGTATGGCTTCATTCAGCTCCGGTTCCCAACGATCAAGGCGAGTTACATGATCCCCC |
| 3121 ATGTTGTGCAAAAAAGCGGTTAGCTCCTTCGGTCCTCCGATCGTTGTCAGAAGTAAGTTG |
| 3181 GCCGCAGTGTTATCACTCATGGTTATGGCAGCACTGCATAATTCTCTTACTGTCATGCCA |
| 3241 TCCGTAAGATGCTTTTCTGTGACTGGTGAGTACTCAACCAAGTCATTCTGAGAATAGTGT |
| 3301 ATGCGGCGACCGAGTTGCTCTTGCCCGGCGTCAATACGGGATAATACCGCGCCACATAGC |
| 3361 AGAACTTTAAAAGTGCTCATCATTGGAAAACGTTCTTCGGGGCGAAAACTCTCAAGGATC |
| 3421 TTACCGCTGTTGAGATCCAGTTCGATGTAACCCACTCGTGCACCCAACTGATCTTCAGCA |
| 3481 TCTTTTACTTTCACCAGCGTTTCTGGGTGAGCAAAAACAGGAAGGCAAAATGCCGCAAAA |
| 3541 AAGGGAATAAGGGCGACACGGAAATGTTGAATACTCATACTCTTCCTTTTTCAATATTAT |
| 3601 TGAAGCATTTATCAGGGTTATTGTCTCATGAGCGGATACATATTTGAATGTATTTAGAAA |
| 3661 AATAAACAAATAGGGGTTCCGCGCACATTTCCCCGAAAAGTGCCACCTGACGTCTAAGAA |
| 3721 ACCATTATTATCATGACATTAACCTATAAAAATAGGCGTATCACGAGGCCCTTTCGTC |
| Amino acid sequences of DNA polymerases from *T. litoralis*, *Thermococcus sp.* 9 degrees N-7 and chimeras thereof.<br>Sequence 18<br>*Thermococcus sp.* 9 degrees N-7 DNA polymerase amino acid sequence (acc no. U47108)<br>(SEQ ID NO: 18) |
| 1 MILDTDYITE NGKPVIRVFK KENGEFKIEY DRTFEPYFYA LLKDDSAIED VKKVTAKRHG |
| 61 TVVKVKRAEK VQKKFLGRPI EVWKLYFNHP QDVPAIRDRI RAHPAVVDIY EYDIPFAKRY |
| 121 LIDKGLIPME GDEELTMLAF DIETLYHEGE EFGTGPILMI SYADGSEARV ITWKKIDLPY |
| 181 VDVVSTEKEM IKRFLRVVRE KDPDVLITYN GDNFDFAYLK KRCEELGIKF TLGRDGSEPK |
| 241 IQRMGDRFAV EVKGRIHFDL YPVIRRTINL PTYTLEAVYE AVFGKPKEKV YAEEIAQAWE |
| 301 SGEGLERVAR YSMEDAKVTY ELGREFFPME AQLSRLIGQS LWDVSRSSTG NLVEWFLLRK |
| 361 AYKRNELAPN KPDERELARR RGGYAGGYVK EPERGLWDNI VYLDFRSLYP SIIITHNVSP |
| 421 DTLNREGCKE YDVAPEVGHK FCKDFPGFIP SLLGDLLEER QKIKRKMKAT VDPLEKKLLD |
| 481 YRQRAIKILA NSFYGYYGYA KARWYCKECA ESVTAWGREY IEMVIRELEE KFGFKVLYAD |
| 541 TDGLHATIPG ADAETVKKKA KEFLKYINPK LPGLLELEYE GFYVRGFFVT KKKYAVIDEE |
| 601 GKITTRGLEI VRRDWSEIAK ETQARVLEAI LKHGDVEEAV RIVKEVTEKL SKYEVPPEKL |
| 661 VIHEQITRDL RDYKATGPHV AVAKRLAARG VKIRPGTVIS YIVLKGSGRI GDRAIPADEF |
| 721 DPTKHRYDAE YYIENQVLPA VERILKAFGY RKEDLRYQKT KQVGLGAWLK VKGKK |
| Sequence 19<br>*T. litoralis* DNA polymerase amino acid sequence (acc no. M74198.1)<br>(SEQ ID NO: 19) |
| 1 MILDTDYITK DGKPIIRIFK KENGEFKIEL DPHFQPYIYA LLKDDSAIEE IKAIKGERHG |
| 61 KTVRVLDAVK VRKKFLGREV EVWKLIFEHP QDVPAMRGKI REHPAVVDIY EYDIPFAKRY |
| 121 LIDKGLIPME GDEELKLLAF DIETFYHEGD EFGKGEIIMI SYADEEEARV ITWKNIDLPY |
| 181 VDVVSNEREM IKRFVQVVKE KDPDVIITYN GDNFDLPYLI KRAEKLGVRL VLGRDKEHPE |
| 241 PKIQRMGDSF AVEIKGRIHF DLFPVVRRTI NLPTYTLEAV YEAVLGKTKS KLGAEEIAAI |
| 301 WETEESMKKL AQYSMEDARA TYELGKEFFP MEAELAKLIG QSVWDVSRSS TGNLVEWYLL |
| 361 RVAYARNELA PNKPDEEEYK RRLRTTYLGG YVKEPEKGLW ENIIYLDFRS LYPSIIVTHN |
| 421 VSPDTLEKEG CKNYDVAPIV GYRFCKDFPG FIPSILGDLI AMRQDIKKKM KSTIDPIEKK |
| 481 MLDYRQRAIK LLANSYYGYM GYPKARWYSK ECAESVTAWG RHYIEMTIRE IEEKFGFKVL |

TABLE 5-continued

| Sequences |
|---|
| 541 YADTDGFYAT IPGEKPELIK KKAKEFLNYI NSKLPGLLEL EYEGFYLRGF FVTKKRYAVI |
| 601 DEEGRITTRG LEVVRRDWSE IAKETQAKVL EAILKEGSVE KAVEVVRDVV EKIAKYRVPL |
| 661 EKLVIHEQIT RDLKDYKAIG PHVAIAKRLA ARGIKVKPGT IISYIVLKGS GKISDRVILL |
| 721 TEYDPRKHKY DPDYYIENQV LPAVLRILEA FGYRKEDLRY QSSKQTGLDA WLKR |
| Sequence 20<br>Amino acid sequence of chimeric DNA polymerase 9Nli<br>(SEQ ID NO: 20) |
| 1 MILDTDYITE NGKPVIRVFK KENGEFKIEY DRTFEPYFYA LLKDDSAIED VKKVTAKRHG |
| 61 TVVKVKRAEK VQKKFLGRPI EVWKLYFNHP QDVPAIRDRI RAHPAVVDIY EYDIPFAKRY |
| 121 LIDKGLIPME GDEELTMLAF DIETLYHEGE EFGTGPILMI SYADGSEARV ITWKKIDLPY |
| 181 VDVVSTEKEM IKRFLRVVRE KDPDVLITYN GDNFDFAYLK KRCEELGIKF TLGRDGSEPK |
| 241 IQRMGDRFAV EVKGRIHFDL YPVIRRTINL PTYTLEAVYE AVFGKPKEKV YAEEIAQAWE |
| 301 SGEGLERVAR YSMEDAKVTY ELGREFFPME AQLSRLIGQS LWDVSRSSTG NLVEWYLLRV |
| 361 AYARNELAPN KPDEEEYKRR LRTTYLGGYV KEPEKGLWEN IIYLDFRSLY PSIIVTHNVS |
| 421 PDTLEKEGCK NYDVAPIVGY RFCKDFPGFI PSILGDLIAM RQDIKKKMKS TIDPIEKKML |
| 481 DYRQRAIKLL ANSYYGYMGY PKARWYSKEC AESVTAWGRH YIEMTIREIE EKFGFKVLYA |
| 541 DTDGFYATIP GEKPELIKKK AKEFLNYINS KLPGLLELEY EGFYVRGFFV TKKKYAVIDE |
| 601 EGKITTRGLE IVRRDWSEIA KETQARVLEA ILKHGDVEEA VRIVKEVTEK LSKYEVPPEK |
| 661 LVIHEQITRD LRDYKATGPH VAVAKRLAAR GVKIRPGTVI SYIVLKGSGR IGDRAIPADE |
| 721 FDPTKHRYDA EYYIENQVLP AVERILKAFG YRKEDLRYQK TKQVGLGAWL KVKGKK |
| Sequence 21<br>Amino acid sequence of chimeric DNA polymerase Li9N<br>(SEQ ID NO: 21) |
| 1 MILDTDYITK DGKPIIRIFK KENGEFKIEL DPHFQPYIYA LLKDDSAIEE IKAIKGERHG |
| 61 KTVRVLDAVK VRKKFLGREV EVWKLIFEHP QDVPAMRGKI REHPAVVDIY EYDIPFAKRY |
| 121 LIDKGLIPME GDEELKLLAF DIETFYHEGD EFGKGEIIMI SYADEEEARV ITWKNIDLPY |
| 181 VDVVSNEREM IKRFVQVVKE KDPDVIITYN GDNFDLPYLI KRAEKLGVRL VLGRDKEHPE |
| 241 PKIQRMGDSF AVEIKGRIHF DLFPVVRRTI NLPTYTLEAV YEAVLGKTKS KLGAEEIAAI |
| 301 WETEESMKKL AQYSMEDARA TYELGKEFFP MEAELAKLIG QSVWDVSRSS TGNLVEWFLL |
| 361 RKAYKRNELA PNKPDERELA RRRGGYAGGY VKEPERGLWD NIVYLDFRSL YPSIIITHNV |
| 421 SPDTLNREGC KEYDVAPEVG HKFCKDFPGF IPSLLGDLLE ERQKIKRKMK ATVDPLEKKL |
| 481 LDYRQRAIKI LANSFYGYYG YAKARWYCKE CAESVTAWGR EYIEMVIREL EEKFGFKVLY |
| 541 ADTDGLHATI PGADAETVKK KAKEFLKYIN PKLPGLLELE YEGFYLRGFF VTKKRYAVID |
| 601 EEGRITTRGL EVVRRDWSEI AKETQAKVLE AILKEGSVEK AVEVVRDVVE KIAKYRVPLE |
| 661 KLVIHEQITR DLKDYKAIGP HVAIAKRLAA RGIKVKPGTI ISYIVLKGSG KISDRVILLT |
| 721 EYDPRKHKYD PDYYIENQVL PAVLRILEAF GYRKEDLRYQ SSKQTGLDAW LKR |
| Amino acid sequences of DNA polymerases from *T. gorgonarius*,<br>*T. zilligii* and chimeras thereof.<br>Sequence 22<br>*T. gorgonarius* DNA polymerase amino acid sequence (acc no. 4699806)<br>(SEQ ID NO: 22) |
| 1 MILDTDYITE DGKPVIRIFK KENGEFKIDY DRNFEPYIYA LLKDDSAIED VKKITAERHG |
| 61 TTVRVVRAEK VKKKFLGRPI EVWKLYFTHP QDVPAIRDKI KEHPAVVDIY EYDIPFAKRY |
| 121 LIDKGLIPME GDEELKMLAF DIETLYHEGE EFAEGPILMI SYADEEGARV ITWKNIDLPY |
| 181 VDVVSTEKEM IKRFLKVVKE KDPDVLITYN GDNFDFAYLK KRSEKLGVKF ILGREGSEPK |

TABLE 5-continued

| Sequences |
|---|
| 241 IQRMGDRFAV EVKGRIHFDL YPVIRRTINL PTYTLEAVYE AIFGQPKEKV YAEEIAQAWE |
| 301 TGEGLERVAR YSMEDAKVTY ELGKEFFPME AQLSRLVGQS LWDVSRSSTG NLVEWFLLRK |
| 361 AYERNELAPN KPDERELARR RESYAGGYVK EPERGLWENI VYLDFRSLYP SIIITHNVSP |
| 421 DTLNREGCEE YDVAPQVGHK FCKDFPGFIP SLLGDLLEER QKVKKKMKAT IDPIEKKLLD |
| 481 YRQRAIKILA NSFYGYYGYA KARWYCKECA ESVTAWGRQY IETTIREIEE KFGFKVLYAD |
| 541 TDGFFATIPG ADAETVKKKA KEFLDYINAK LPGLLELEYE GFYKRGFFVT KKKYAVIDEE |
| 601 DKITTRGLEI VRRDWSEIAK ETQARVLEAI LKHGDVEEAV RIVKEVTEKL SKYEVPPEKL |
| 661 VIYEQITRDL KDYKATGPHV AVAKRLAARG IKIRPGTVIS YIVLKGSGRI GDRAIPFDEF |
| 721 DPAKHKYDAE YYIENQVLPA VERILRAFGY RKEDLRYQKT RQVGLGAWLK PKT |
| Sequence 23<br>*T. zilligii* DNA polymerase amino acid sequence<br>(SEQ ID NO: 23) |
| 1 MILDADYITE DGKPVIRVFK KEKGEFKIDY DRDFEPYIYA LLKDDSAIED IKKITAERHG |
| 61 TTVRVTRAER VKKKFLGRPV EVWKLYFTHP QDVPAIRDKI REHPAVVDIY EYDIPFAKRY |
| 121 LIDRGLIPME GDEELRMLAF DIETLYHEGE EFGEGPILMI SYADEEGARV ITWKNIDLPY |
| 181 VESVSTEKEM IKRFLKVIQE KDPDVLITYN GDNFDFAYLK KRSETLGVKF ILGRDGSEPK |
| 241 IQRMGDRFAV EVKGRIHFDL YPVIRRTINL PTYTLETVYE AIFGQPKEKV YAEEIARAWE |
| 301 SGEGLERVAR YSMEDAKATY ELGKEFFPME AQLSRLVGQS LWDVSRSSTG NLVEWFLLRK |
| 361 AYERNELAPN KPDERELARR AESYAGGYVK EPEKGLWENI VYLDYKSLYP SIIITHNVSP |
| 421 DTLNREGCRE YDVAPQVGHR FCKDFPGFIP SLLGDLLEER QKVKKKMKAT VDPIERKLLD |
| 481 YRQRAIKILA NSYYGYYGYA NARWYCRECA ESVTAWGRQY IETTMREIEE KFGFKVLYAD |
| 541 TDGFFATIPG ADAETVKKKA KEFLNYINPR LPGLLELEYE GFYRRGFFVT KKKYAVIDEE |
| 601 DKITTRGLEI VRRDWSEIAK ETQARVLEAI LKHGDVEEAV RIVKEVTEKL SRYEVPPEKL |
| 661 VIYEQITRDL RDYRATGPHV AVAKRLAARG IKIRPGTVIS YIVLKGPGRV GDRAIPFDEF |
| 721 DPAKHRYDAE YYIENQVLPA VERILRAFGY RKEDLRYQKT KQAGLGAWLK PKT |
| Sequence 24<br>Amino acid sequence of chimeric DNA polymerase GoZi<br>(SEQ ID NO: 24) |
| 1 MILDTDYITE DGKPVIRIFK KENGEFKIDY DRNFEPYIYA LLKDDSAIED VKKITAERHG |
| 61 TTVRVVRAEK VKKKFLGRPI EVWKLYFTHP QDVPAIRDKI KEHPAVVDIY EYDIPFAKRY |
| 121 LIDKGLIPME GDEELKMLAF DIETLYHEGE EFAEGPILMI SYADEEGARV ITWKNIDLPY |
| 181 VDVVSTEKEM IKRFLKVVKE KDPDVLITYN GDNFDFAYLK KRSEKLGVKF ILGREGSEPK |
| 241 IQRMGDRFAV EVKGRIHFDL YPVIRRTINL PTYTLEAVYE AIFGQPKEKV YAEEIAQAWE |
| 301 TGEGLERVAR YSMEDAKVTY ELGKEFFPME AQLSRLVGQS LWDVSRSSTG NLVEWFLLRK |
| 361 AYERNELAPN KPDERELARR RESYAGGYVK EPEKGLWENI VYLDYKSLYP SIIITHNVSP |
| 421 DTLNREGCRE YDVAPQVGHR FCKDFPGFIP SLLGDLLEER QKVKKKMKAT VDPIERKLLD |
| 481 YRQRAIKILA NSYYGYYGYA NARWYCRECA ESVTAWGRQY IETTMREIEE KFGFKVLYAD |
| 541 TDGFFATIPG ADAETVKKKA KEFLDYINAK LPGLLELEYE GFYKRGFFVT KKKYAVIDEE |
| 601 DKITTRGLEI VRRDWSEIAK ETQARVLEAI LKHGDVEEAV RIVKEVTEKL SKYEVPPEKL |
| 661 VIYEQITRDL KDYKATGPHV AVAKRLAARG IKIRPGTVIS YIVLKGSGRI GDRAIPFDEF |
| 721 DPAKHKYDAE YYIENQVLPA VERILRAFGY RKEDLRYQKT RQVGLGAWLK PKT |

TABLE 5-continued

Sequences

Sequence 25
Amino acid sequence of chimeric DNA polymerase ZiGo
(SEQ ID NO: 25)

```
  1 MILDADYITE DGKPVIRVFK KEKGEFKIDY DRDFEPYIYA LLKDDSAIED IKKITAERHG

 61 TTVRVTRAER VKKKFLGRPV EVWKLYFTHP QDVPAIRDKI REHPAVVDIY EYDIPFAKRY

121 LIDRGLIPME GDEELRMLAF DIETLYHEGE EFGEGPILMI SYADEEGARV ITWKNIDLPY

181 VESVSTEKEM IKRFLKVIQE KDPDVLITYN GDNFDFAYLK KRSETLGVKF ILGRDGSEPK

241 IQRMGDRFAV EVKGRIHFDL YPVIRRTINL PTYTLETVYE AIFGQPKEKV YAEEIARAWE

301 SGEGLERVAR YSMEDAKATY ELGKEFFPME AQLSRLVGQS LWDVSRSSTG NLVEWFLLRK

361 AYERNELAPN KPDERELARR AESYAGGYVK EPERGLWENI VYLDFRSLYP SIIITHNVSP

421 DTLNREGCEE YDVAPQVGHK FCKDFPGFIP SLLGDLLEER QKVKKKMKAT IDPIEKKLLD

481 YRQRAIKILA NSFYGYYGYA KARWYCKECA ESVTAWGRQY IETTIREIEE KFGFKVLYAD

541 TDGFFATIPG ADAETVKKKA KEFLNYINPR LPGLLELEYE GFYRRGFFVT KKKYAVIDEE

601 DKITTRGLEI VRRDWSEIAK ETQARVLEAI LKHGDVEEAV RIVKEVTEKL SRYEVPPEKL

661 VIYEQITRDL RDYRATGPHV AVAKRLAARG IKIRPGTVIS YIVLKGPGRV GDRAIPFDEF

721 DPAKHRYDAE YYIENQVLPA VERILRAFGY RKEDLRYQKT KQAGLGAWLK PKT
```

Amino acid sequences of additional chimeras of KOD and Pfu DNA polymerases.
Sequence 26
Amino acid sequence of chimeric DNA polymerase Kofu-II.
(SEQ ID NO: 26)

```
  1 MASAILDTDY ITEDGKPVIR IFKKENGEFK IEYDRTFEPY FYALLKDDSA IEEVKKITAE

 61 RHGTVVTVKR VEKVQKKFLG RPVEVWKLYF THPQDVPAIR DKIREHPAVI DIYEYDIPFA

121 KRYLIDKGLV PMEGDEELKM LAFDIETLYH EGEEFAEGPI LMISYADEEG ARVITWKNVD

181 LPYVDVVSTE REMIKRFLRV VKEKDPDVLI TYNGDNFDFA YLKKRCEKLG INFALGRDGS

241 EPKIQRMGDR FAVEVKGRIH FDLYPVIRRT INLPTYTLEA VYEAVFGQPK EKVYAEEITT

301 AWETGENLER VAKYSMEDAK ATYELGKEFL PMEIQLSRLV GQPLWDVSRS STGNLVEWFL

361 LRKAYERNEV APNKPSEEEY QRRLRESYTG GFVKEPEKGL WENIVYLDFR ALYPSIIITH

421 NVSPDTLNLE GCKNYDIAPQ VGHKFCKDIP GFIPSLLGHL LEERQKIKTK MKETQDPIEK

481 ILLDYRQKAI KLLANSFYGY YGYAKARWYC KECAESVTAW GRKYIELVWK ELEEKFGFKV

541 LYIDTDGLYA TIPGGESEEI KKKALEFVKY INSKLPGLLE LEYEGFYKRG FFVTKKRYAV

601 IDEEGKVITR GLEIVRRDWS EIAKETQARV LEALLKDGDV EKAVRIVKEV TEKLSKYEVP

661 PEKLVIHEQI TRDLKDYKAT GPHVAVAKRL AARGVKIRPG TVISYIVLKG SGRIGDRAIP

721 FDEFDPTKHK YDAEYYIENQ VLPAVERILR AFGYRKEDLR YQKTRQVGLS AWLKPKGT
```

Sequence 27
Amino acid sequence of chimeric DNA polymerase Pod-II.
(SEQ ID NO: 27)

```
  1 MASAILDVDY ITEEGKPVIR LFKKENGKFK IEHDRTFRPY IYALLRDDSK IEEVKKITGE

 61 RHGKIVRIVD VEKVEKKFLG KPITVWKLYL EHPQDVPTIR EKVREHPAVV DIFEYDIPFA

121 KRYLIDKGLI PMEGEEELKI LAFDIETLYH EGEEFGKGPI IMISYADENE AKVITWKNID

181 LPYVEVVSSE REMIKRFLRI IREKDPDIIV TYNGDSFDFP YLAKRAEKLG IKLTIGRDGS

241 EPKMQRIGDM TAVEVKGRIH FDLYHVITRT INLPTYTLEA VYEAIFGKPK EKVYADEIAK

301 AWESGENLER VARYSMEDAK VTYELGKEFL PMEAQLSRLI GQSLWDVSRS STGNLVEWFL

361 LRKAYERNEL APNKPDEKEL ARRRQSYEGG YVKEPERGLW ENIVYLDFRS LYPSIIITHN

421 VSPDTLNREG CKEYDVAPQV GHRFCKDFPG FIPSLLGDLL EERQKIKKKM KATIDPIERK
```

TABLE 5-continued

| Sequences |
|---|
| 481 LLDYRQRAIK ILANSYYGYY GYARARWYCK ECAESVTAWG REYITMTIKE IEEKYGFKVI |
| 541 YSDTDGFFAT IPGADAETVK KKAMEFLKYI NAKLPGALEL EYEGFYKRGF FVTKKKYAVI |
| 601 DEEGKITTRG LEIVRRDWSE IAKETQARVL ETILKHGDVE EAVRIVKEVI QKLANYEIPP |
| 661 EKLAIYEQIT RPLHEYKAIG PHVAVAKKLA AKGVKIKPGM VIGYIVLRGD GPISNRAILA |
| 721 EEYDPKKHKY DAEYYIENQV LPAVLRILEG FGYRKEDLRY QKTRQVGLTS WLNIKKS |
| Sequence 28<br>Amino acid sequence of chimeric DNA polymerase Kofu-III.<br>(SEQ ID NO: 28) |
| 1 MASAILDTDY ITEDGKPVIR IFKKENGEFK IEYDRTFEPY FYALLKDDSA IEEVKKITAE |
| 61 RHGTVVTVKR VEKVQKKFLG RPVEVWKLYF THPQDVPAIR DKIREHPAVI DIYEYDIPFA |
| 121 KRYLIDKGLV PMEGDEELKM LAFDIETLYH EGEEFAEGPI LMISYADEEG ARVITWKNVD |
| 181 LPYVDVVSTE REMIKRFLRV VKEKDPDVLI TYNGDNFDFA YLKKRCEKLG INFALGRDGS |
| 241 EPKIQRMGDR FAVEVKGRIH FDLYPVIRRT INLPTYTLEA VYEAVFGQPK EKVYAEEITT |
| 301 AWETGENLER VARYSMEDAK VTYELGKEFL PMEAQLSRLI GQSLWDVSRS STGNLVEWFL |
| 361 LRKAYERNEL APNKPDEKEL ARRRQSYEGG YVKEPEKGLW ENIVYLDFRA LYPSIIITHN |
| 421 VSPDTLNLEG CKNYDIAPQV GHKFCKDIPG FIPSLLGHLL EERQKIKTKM KETQDPIEKI |
| 481 LLDYRQKAIK LLANSFYGYY GYAKARWYCK ECAESVTAWG RKYIELVWKE LEEKFGFKVL |
| 541 YIDTDGLYAT IPGGESEEIK KKALEFLKYI NAKLPGALEL EYEGFYKRGF FVTKKKYAVI |
| 601 DEEGKITTRG LEIVRRDWSE IAKETQARVL EALLKDGDVE KAVRIVKEVT EKLSKYEVPP |
| 661 EKLVIHEQIT RDLKDYKATG PHVAVAKRLA ARGVKIRPGT VISYIVLKGS GRIGDRAIPF |
| 721 DEFDPTKHKY DAEYYIENQV LPAVERILRA FGYRKEDLRY QKTRQVGLSA WLKPKGT |
| Sequence 29<br>Amino acid sequence of chimeric DNA polymerase Pod-III.<br>(SEQ ID NO: 29) |
| 1 MASAILDVDY ITEEGKPVIR LFKKENGKFK IEHDRTFRPY IYALLRDDSK IEEVKKITGE |
| 61 RHGKIVRIVD VEKVEKKFLG KPITVWKLYL EHPQDVPTIR EKVREHPAVV DIFEYDIPFA |
| 121 KRYLIDKGLI PMEGEEELKI LAFDIETLYH EGEEFGKGPI IMISYADENE AKVITWKNID |
| 181 LPYVEVVSSE REMIKRFLRI IREKDPDIIV TYNGDSFDFP YLAKRAEKLG IKLTIGRDGS |
| 241 EPKMQRIGDM TAVEVKGRIH FDLYHVITRT INLPTYTLEA VYEAIFGKPK EKVYADEIAK |
| 301 AWESGENLER VAKYSMEDAK ATYELGKEFL PMEIQLSRLV GQPLWDVSRS STGNLVEWFL |
| 361 LRKAYERNEV APNKPSEEEY QRRLRESYTG GFVKEPERGL WENIVYLDFR SLYPSIIITH |
| 421 NVSPDTLNRE GCKEYDVAPQ VGHRFCKDFP GFIPSLLGDL LEERQKIKKK MKATIDPIER |
| 481 KLLDYRQRAI KILANSYYGY YGYARARWYC KECAESVTAW GREYITMTIK EIEEKYGFKV |
| 541 IYSDTDGFFA TIPGADAETV KKKAMEFVKY INSKLPGLLE LEYEGFYKRG FFVTKKRYAV |
| 601 IDEEGKVITR GLEIVRRDWS EIAKETQARV LETILKHGDV EEAVRIVKEV IQKLANYEIP |
| 661 PEKLAIYEQI TRPLHEYKAI GPHVAVAKKL AAKGVKIKPG MVIGYIVLRG DGPISNRAIL |
| 721 AEEYDPKKHK YDAEYYIENQ VLPAVLRILE GFGYRKEDLR YQKTRQVGLT SWLNIKKS |

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

Incorporation of References

All publications and patent documents cited in this application are incorporated by reference in their entirety to the same extent as if the contents of each individual publication or patent document were incorporated herein.

What is claimed is:

1. A DNA polymerase whose amino acid sequence contains, in order:

an N-terminal domain including a sequence that shows at least 90% identity with that sequence between residues 26 and 105 of SEQ ID NO: 16;

an exonuclease domain including a sequence that shows at least 90% identity with that sequence between residues 156 and 301 of SEQ ID NO: 16;

a palm and finger domain including a sequence that shows at least 90% identity with that sequence between residues 394 and 563 of SEQ ID NO: 16; and a thumb domain including a sequence that shows at least 90% identity with that sequence between residues 612 and 749 of SEQ ID NO: 16.

2. A kit comprising a DNA polymerase of claim 1.

3. A method of DNA synthesis using the DNA poiymerase of claim 1 comprising combining the DNA polymerase, template DNA, primer(s) and nucleotides and incubating under conditions for DNA synthesis.

4. A method of amplifying a DNA fragment using the DNA polymerase of claim 1 comprising combining the DNA polymerase, a DNA fragment, primer(s) and nucleotides and incubating under conditions for DNA amplification.

* * * * *